United States Patent
Kurimoto et al.

(10) Patent No.: US 8,969,362 B2
(45) Date of Patent: Mar. 3, 2015

(54) 9-SUBSTITUTED 8-OXOADENINE COMPOUND

(71) Applicants: Ayumu Kurimoto, Osaka (JP); Kazuki Hashimoto, Osaka (JP); Yoshiaki Isobe, Osaka (JP); Stephen Brough, Leicestershire (GB); Ian Millichip, Leicestershire (GB); Hiroki Wada, Nottinghamshire (GB); Roger Bonnert, Leicestershire (GB); Thomas Mcinally, Leicestershire (GB)

(72) Inventors: Ayumu Kurimoto, Osaka (JP); Kazuki Hashimoto, Osaka (JP); Yoshiaki Isobe, Osaka (JP); Stephen Brough, Leicestershire (GB); Ian Millichip, Leicestershire (GB); Hiroki Wada, Nottinghamshire (GB); Roger Bonnert, Leicestershire (GB); Thomas Mcinally, Leicestershire (GB)

(73) Assignees: AstraZeneca Aktiebolag, Soedertaelje (SE); Sumitomo Dainippon Pharma Co., Ltd., Osaka-shi (JP)

( * ) Notice: Subject to any disclaimer, the term of this patent is extended or adjusted under 35 U.S.C. 154(b) by 0 days.

(21) Appl. No.: 14/058,064

(22) Filed: Oct. 21, 2013

(65) Prior Publication Data
US 2014/0045837 A1   Feb. 13, 2014

Related U.S. Application Data

(63) Continuation of application No. 13/187,260, filed on Jul. 20, 2011, now Pat. No. 8,575,180, which is a continuation of application No. 10/593,691, filed as application No. PCT/JP2005/005401 on Mar. 24, 2005, now Pat. No. 8,012,964.

(30) Foreign Application Priority Data

Mar. 26, 2004   (JP) .................................. 2004-093672

(51) Int. Cl.
*A61K 31/522*   (2006.01)
*C07D 473/18*   (2006.01)
*A61K 31/5377*   (2006.01)

(52) U.S. Cl.
CPC ............ *C07D 473/18* (2013.01); *A61K 31/522* (2013.01); *A61K 31/5377* (2013.01)
USPC ..................... 514/263.37; 544/276

(58) Field of Classification Search
USPC .......... 544/118, 276, 277; 514/234.2, 263.22, 514/263.23, 263.37
See application file for complete search history.

(56) References Cited

U.S. PATENT DOCUMENTS

| | | | |
|---|---|---|---|
| 4,179,562 A | 12/1979 | Ponsford | |
| 4,689,338 A | 8/1987 | Gerster | |
| 4,698,348 A | 10/1987 | Gerster | |
| 4,714,701 A | 12/1987 | Beauchamp | |
| 4,912,112 A | 3/1990 | Seydel et al. | |
| 5,736,549 A | 4/1998 | Beasley et al. | |
| 5,994,361 A | 11/1999 | Penney et al. | |
| 6,028,076 A | 2/2000 | Hirota et al. | |
| 6,110,923 A | 8/2000 | Ely | |
| 6,329,381 B1 | 12/2001 | Kurimoto et al. | |
| 6,376,501 B1 | 4/2002 | Isobe et al. | |
| 6,448,236 B1 | 9/2002 | Monaghan | |
| 6,458,798 B1 | 10/2002 | Fujita et al. | |
| 6,630,478 B2 | 10/2003 | Diamond et al. | |

(Continued)

FOREIGN PATENT DOCUMENTS

| CA | 1220148 | 4/1987 |
|---|---|---|
| CN | 10239980 | 8/2008 |

(Continued)

OTHER PUBLICATIONS

Definition of Cancer. Sep. 18, 2004. <MedicineNet.com>.*

(Continued)

*Primary Examiner* — Golam M M Shameem
*Assistant Examiner* — Laura Daniel
(74) *Attorney, Agent, or Firm* — Finnegan, Henderson, Farabow, Garrett & Dunner LLP

(57) ABSTRACT

The present invention provides an 8-oxoadenine compound having immunomodulating activities such as an interferon inducing activity and useful as an antiviral agent and antiallergic agent, which is represented by the following formula (1):

(1)

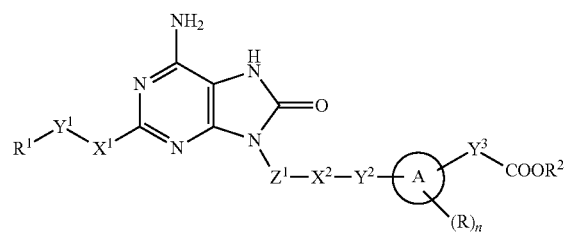

[wherein the ring A represents a 6-10 membered aromatic carbocyclic ring and the like, R represents a halogen atom, an alkyl group and the like, n represents an integer of 0-2, $Z^1$ represents alkylene, $X^2$ represents oxygen atom, sulfur atom, $SO_2$, $NR^5$, CO, $CONR^5$, $NR^5CO$ and the like, $Y^1$, $Y^2$ and $Y^3$ represent independently a single bond or an alkylene group, $X^1$ represents oxygen atom, sulfur atom, $NR^4$ ($R^4$ is hydrogen atom or an alkyl group) or a single bond, $R^2$ represents a substituted or unsubstituted alkyl group, $R^1$ represents hydrogen atom, hydroxy group, an alkoxy group, an alkoxycarbonyl group or a haloalkyl group]
or its pharmaceutically acceptable salt.

26 Claims, No Drawings

(56) References Cited

U.S. PATENT DOCUMENTS

| | | |
|---|---|---|
| 6,951,866 B2 | 10/2005 | Fujita et al. |
| 7,157,465 B2 | 1/2007 | Isobe et al. |
| 7,521,454 B2 | 4/2009 | Isobe et al. |
| 7,642,350 B2 | 1/2010 | Pryde |
| 8,012,964 B2 | 9/2011 | Kurimoto et al. |
| 8,138,172 B2 | 3/2012 | Cook et al. |
| 2002/0040032 A1 | 4/2002 | Glasky et al. |
| 2002/0068745 A1 | 6/2002 | Levy et al. |
| 2002/0128264 A1 | 9/2002 | Taylor |
| 2003/0105323 A1 | 6/2003 | Fujita et al. |
| 2003/0144283 A1 | 7/2003 | Coleman et al. |
| 2003/0187261 A1 | 10/2003 | Havlicek et al. |
| 2003/0191086 A1 | 10/2003 | Hanus et al. |
| 2003/0212092 A1 | 11/2003 | Heppner et al. |
| 2004/0019048 A1 | 1/2004 | Crooks et al. |
| 2004/0132748 A1 | 7/2004 | Isobe et al. |
| 2004/0204438 A1 | 10/2004 | Crooks et al. |
| 2004/0214192 A1 | 10/2004 | Hashida et al. |
| 2004/0229897 A1 | 11/2004 | Crooks et al. |
| 2005/0054590 A1 | 3/2005 | Averett |
| 2005/0119273 A1 | 6/2005 | Lipford et al. |
| 2006/0052403 A1 | 3/2006 | Isobe et al. |
| 2006/0252774 A1 | 11/2006 | Vatner |
| 2007/0190071 A1 | 8/2007 | Kurimoto et al. |
| 2007/0225303 A1 | 9/2007 | Ogita et al. |
| 2007/0249638 A1 | 10/2007 | Giorgio et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0281075 A1 | 11/2009 | Roughton et al. |
| 2009/0324551 A1 | 12/2009 | Carson et al. |
| 2009/0325877 A1 | 12/2009 | Grunt et al. |
| 2010/0068807 A1 | 3/2010 | Kaisho et al. |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2010/0280001 A1 | 11/2010 | Bonnert et al. |
| 2011/0046369 A1 | 2/2011 | Hashimoto et al. |
| 2011/0054168 A1 | 3/2011 | Kurimoto et al. |
| 2011/0136801 A1 | 6/2011 | Isobe et al. |

FOREIGN PATENT DOCUMENTS

| | | |
|---|---|---|
| EP | 1386923 | 2/2004 |
| EP | 1908480 | 4/2008 |
| GB | 1 375 162 | 11/1974 |
| JP | 8-165292 | 6/1996 |
| JP | 10-501533 | 1/1998 |
| JP | 10-507171 | 7/1998 |
| JP | 11-180981 | 7/1999 |
| JP | 11-180982 | 7/1999 |
| JP | 11-193282 | 7/1999 |
| JP | 2000-159767 | 6/2000 |
| JP | 2004137157 | 5/2004 |
| JP | 2005-089334 | 4/2005 |
| JP | 2007504232 | 3/2007 |
| JP | 4375901 | 12/2009 |
| WO | WO 98/01448 | 1/1998 |
| WO | WO-99/28321 | 6/1999 |
| WO | WO 0076519 | 12/2000 |
| WO | WO 02/04448 | 1/2002 |
| WO | WO 02/04449 | 1/2002 |
| WO | WO 02/04450 | 1/2002 |
| WO | WO 02/04451 | 1/2002 |
| WO | WO 02/04452 | 1/2002 |
| WO | WO 02/085905 | 10/2002 |
| WO | WO 2004/011481 | 2/2004 |
| WO | WO 2004/029054 | 4/2004 |
| WO | WO 2004075865 | 9/2004 |
| WO | WO 2004087049 | 10/2004 |
| WO | WO 2005025583 | 3/2005 |
| WO | WO 2005/092893 | 10/2005 |
| WO | WO 2005092892 | 10/2005 |
| WO | WO 2006/117670 | 11/2006 |
| WO | WO 2006/129784 | 12/2006 |
| WO | WO 2007/024707 | 3/2007 |
| WO | WO 2007/031726 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2007/093901 | 8/2007 |
| WO | WO 2008/004948 | 1/2008 |
| WO | WO 2008/071976 | 6/2008 |
| WO | WO 2008/114006 | 9/2008 |
| WO | WO 2008/114008 | 9/2008 |
| WO | WO 2009/067081 | 5/2009 |
| WO | WO 2009/078798 | 6/2009 |
| WO | WO 2010/018131 | 2/2010 |
| WO | WO 2010/018134 | 2/2010 |
| WO | WO 2010/033074 | 3/2010 |
| WO | WO 2010/133882 | 11/2010 |

OTHER PUBLICATIONS

Mayo Clinic: Prostate cancer prevention: Ways to reduce your risk. Sep. 23, 2011. <http://www.mayoclinic.com/health/prostate-cancer-prevention/MC00027>.*

WebMD: Allergic Rhinitis-Prevention. Jun. 30, 2011. < http://www.webmd.com/allergies/tc/allergic-rhinitis-prevention>.*

MayoClinic: HIV/AIDS. Aug. 11, 2012. <http://www.mayoclinic.com/health/hiv-aids/DS00005>.*

MayoClinic, Diseases and Conditions. 2014 < http://www.mayoclinic.org/diseases-conditions/index?letter=A>.*

MayClinic:Disease and Conditions: Milk Allergy. Aug. 11, 2011 < http://www.mayoclinic.org/diseases-conditions/milk-allergy/basics/treatment/con-20032147>.*

MayoClinic. Asthma: Treatments and drugs. 2014 < http://www.mayoclinic.org/diseases-conditions/asthma/basics/treatment/con-20026992>.*

Milgrom, Henry. The New England Journal of Medicine, 341:26, (1999) 1966-1973.*

Frew, Anthony. Journal of Allergy and Clinical Immunology, 111:2 (2003)S712-S719.*

International Preliminary Report on Patentability for PCT/JP2008/055088 from the Internation Bureau of WIPO, dated Sep. 22, 2009, Officer Masashi Honda.

E.A. Falco et al., "2,4-Diaminopyrimidines as Antimalarials. I. 5-Aryloxyl and 5-Alkoxyl Derivatives," Journal of the American Chemical Society, vol. 73, No. 8, pp. 3753-3758 (1951).

M. Tarkoy et al., "Nucleic-Acid Analogues with Constraint Conformational Flexibility in the Sugar-Phosphate Backbone ('Bicyclo-DNA')," Helvetica Chimica ACTA, vol. 76, No. 1, pp. 481-510 (1993).

M. Yoshimoto et al., "Correlation Analysis of Baker's Studies on Enzyme Inhibition. 2. Chymotrypsin, Trypsin, Thymidine Phosphorylase. Uridine Phosphorylase, Thymidylate Synthetase, Cytosine Nucleoside Deaminase, Dihydrofolate Reductase, Malate Dehydrogenase, Glutamate Dehydrogenase, Lactate Dehydrogenase, and Glyceraldehyde-phosphate Dehydrogenase," Journal of Medicinal Chemistry, vol. 19, No. 1, pp. 71-98 (1976).

M. Biffen et al., "Biological characterization of a novel class of toll-like receptor 7 agonists designed to have reduced systemic activity." *British Journal of Pharmacology*, vol. 166, pp. 573-586 (2012).

(56) References Cited

OTHER PUBLICATIONS

Office Action mailed from the Taiwan Patent Office for Taiwanese Patent Application No. 094109180, dated Feb. 16, 2012.
Office Action mailed from the Taiwan Patent Office for Taiwanese Patent Application No. 094109180, dated Feb. 10, 2011.
Office Action mailed from the Canadian Patent Office for Canadian Patent Application No. 2,559,036, dated May 2, 2012.
Office Action mailed from the Canadian Patent Office for Canadian Patent Application No. 2,559,036, dated Aug. 30, 2011.
Office Action mailed from the Korean Patent Office for Korean Patent Application No. 2006-7019791, dated May 18, 2012.
Official Action dated Jun. 26, 2012, issued by the Japanese Patent Office for the corresponding Japanese Application No. 2009-218640.
Hirota et al., J. Med. Chem, vol. 45, pp. 5419-5422 (2002).
Isobe et al., Bloorganic & Medicinal Chemistry, vol. 11, pp. 3641-3647 (2003).
Kurimoto et al., Bioorganic & Medicinal Chemistry, vol. 11, pp. 5501-5508 (2003).
Kurimoto et al., Bioorganic & Medicinal Chemistry, vol. 12, pp. 1091-1099 (2004).
Nov. 4, 2010 USPTO Notice of Allowance issued for U.S. Appl. No. 12/066,952.
Sep. 26, 2006 Office Action for Egypt Application PCT923/2006.
2008 PCT/JP2006/318603 IPER for U.S. Appl. No. 12/067,649.
Apr. 25, 2008 Office Action for Chinese Application 200580009706.3.
Mar. 25, 2009 New Zealand Examination Report for Application 549903.
Mar. 26, 2009 Office Action for Russian Application 2006137706.
Aug. 21, 2009 Office Action for Russian Application 2006137706.
Sep. 22, 2009 IPER for U.S. Appl. No. 12/532,007.
Nov. 17, 2009 Office Action for Japanese Application 2006-511501.
Jan. 14, 2010 New Zeal and Examination Report for Application 549903.
Jan. 15, 2010 Office Action for Malaysia Application PI20051334 in English.
Mar. 11, 2010 Office Action for U.S. Appl. No. 10/594,074.
Aoki et al., "Weekly Dosing of AZD8848/DSP-3025, A Novel TLR7 Agonist Anted rug, Demonstrates a Prolonged Period of Control Against Markers of Pulmonary Inflammation in an Allergen Challenge Model in the Mouse". ATS New Orleans, May 2010, Abstract 529 Poster, Pharmacology Research Laboratories, Dianippon Sumitomo Pharma Co., Ltd., Osaka, Japan, Bioscience AstraZenece R&D Charnwood, Loughborough, England.
Asthma, MDAdvice.com, http://www.mdadvice.com/topics/asthmalinfo/1.htm (downloaded Jun. 24, 2010.
Australian Office Action dated May 4, 2010 for Appl. No. 2005226359.
Bell et al., •AZD8848/DSP-3025, A Novel Potent TLR7 Agonist Antedrug, Demonstrates Negligible Systemic Activity and a Prolonged Period of Control After Cessation of Weekly Dosing in a Brown Norway Rat Ovalbumin Challenge Model, ATS New Orleans, May 2010, Abstract 291 Poster, Bioscience, AstraZeneca R&D Charnwood, Loughborough: England, Discovery DMPK, AslraZeneca R&D Charnwood, Loughborough, England, Pharmacology Research Laboratories, Dainippon Sumitomo Pharma Co., Ltd., Osaka, Japan.
Biffen et al., "Biological Activity of a Novel TLR7 Agonist Anted rug for the Treatment of Allergic Diseases". ATS New Orleans, May 2010, Abstract 649 Poster, Bioscience, AstraZeneca R&D Charnwood, Loughborough, England, Pharmacology Research Laboratories, Dainippon Sumitomo Pharma Co., Ltd., Osaka, Japan.
Chronic obstructive pulmonary disease, AllRefer.com, http :f/health.allrefer.com/health/chron ic_obstructive pulmonary_disease prevenlion. htmll (downloaded Jun. 24, 2010).
Drazen, J.M., "Surgery for Emphysema-Not for Everyone," New Eng. J. Med., vol. 345, No. 15, Ipp. 1126-1128 (2001).
Fridkin, SK, Vancomycin-Intermediate and -Resistant *Staphylococcus aureus*: What the Infectious Disease Specialist Needs to Know, Clinical Infectious Diseases, vol. 32, pp. 108-115 (2001).
Holy, A., et al., "9-(Aminoalkyl)-8-Hydroxyadenines: Preparation, Mechanism of Formation and Use in Affinity Chromatography of S-Adenosyl-Lhomocysteine Hydrolase," Inst. Org. Cham. and Biochem., Czechoslovak Academy of Sciences, vol. 51, pp. 459-477 (1986).
Ikeda et al., "AZD8848/DSP-3025, A Novel Potent TLR7 Agonist Anted rug, Demonstrates Efficacy Against Airway Obstruction and Other Inflammatory Endpoints in Guinea Pig Models of Rhinitis and Asthma with Acute and Weekly Dosing", Abstract 786 Poster, Pharmacology Research Laboratories, Dainippon Sumitomo Pharma Co., ltd., Osaka, Japan, Bioscience, AstraZeneca R&D Charnwood Loughborough, England, 2010.
TPO Office Action dated Feb. 10, 2011 and Taiwanese Search Report.
Isobe, Y., et al., "Synthesis and Biological Evaluation of Novel 9-Substituted-8-Hydroxyadenine Derivatives as Potent Interferon Inducers," J. Med. Chem., vol. 49, No. 6, pp. 2088-2095 (2006).
JP-9-347422 (priority document); Sumitomo Pharmaceuticals (1997).
JP-9-367449 (priority document); Sumitomo Pharmaceuticals (1997).
JP-9-367451 (priority document): Sumitomo Pharmaceuticals (1997).
Koro. M., "Pathways for aberrant angiogenesis in pancreatic cancer," Biomed Central, vol. 2, No. 8, pp. 1-8 (2003).
Krueger, R., et al., "Tilorone Hydrochloride: An Orally Active Antiviral Agent," Science, vol. 169, pp. 1213-1214 (1970).
Kurimoto, A., et al., "Prodrugs of 9-Benzyl-8-hydroxy-2-(2-hydroxyethylthio)adenine: Potent Interferon Inducing Agents in Monkeys," Chem. Pharm. Bull. vol. 52, No. 4, pp. 466-469 (2004).
Kurimoto, A., et al., "Synthesis and Biological Evaluation of 8-0xoadenine Derivatives as Tolllike Receptor 7 Agonists Introducing the Antedrug Concept," J. Med. Chem., vol. 53, No. 7, pp. 2964-2972 (2010).
Laino, C., In Small Study, Imaging Detects Lung Damage in People Exposed to Secondhand Smoke. Oncology Times, vol. 30, No. 2, pp. 15 2008.
Lee, J., et al., "Molecular basis for the immunostimulatory activity of guanine nucleoside analogs: Activation of Toll-like receptor 7," PNAS. vol. 100, No. 11 pp. 6646-6651 (2003).
Lee, J., et al., Activation of anti-hepatitis C virus responses via Toll-like receptor 7, PNAS, vol. 103, No. 6, pp. 1828-1833 (2006).
Matsui et al., Mechanisms of Inhibition of Type-2 Cytokines by Novel TLR7 Agonist Antedrugs•, ATS New Orleans, May 2010, Abstract 787 Poster, Pharmacology Research Laboratories, Dainippon Sumitomo Pharma Co., Ltd., Osaka, Japan, Bioscience, AstraZeneca R&D Charnwood, Loughborough, England.
Mayer, G. D., et al., "Tilorone Hydrochloride: Mode of Action," Science, vol. 169, pp. 1214-1215 (1970).
McInally et al., Identification of a Novel TLR7 Agonist Antedrug, Poster, Medicinal Chemistry, AstraZeneca R&D Charnwood, Loughborough, England, Chemistry Research Laboratories, Dainippon Sumitomo Pharma Co., Ltd., Osaka, Japan, EFMC-ISMC 201, Brussels, Belgium, Sep. 5-9, 2010.
Mogulkoc, N et al., "Pulmonary function in Idiopathic Pulmonary Fibrosis and Referral for Lung Transplantation," Am. J. Respir. Crit. Care Med., vol. 164, pp. 103-108 (2001).
Nichol, F.R., et al., "Stimulation of Murine Interferon by a Substituted Pyrimidine," Antimicro. Agents and Chemo., vol. 9, No. 3, (1976).
Nov. 18, 2010, Presentation by Tom McInally at RSC BMSC Inflammation meeting entitled "Identification and Pharmacology of Novel TLR7 Agonist Antedrugs."
Pakistani Office Action dated Sep. 3, 2009 for Appl. No. 291/2008.
Palmer, S., et al., "Highly drug-resistant HIV-1 clinical isolates are cross-resistant to many antiretroviral compounds in current clinical development," AIDS, vol. 13, pp. 661-667 (1999).
Reiter, M.J., et al., "Cytokine induction in mice by the immunomodulator imiquimod," J. Leukocyte Biol., vol. 55, pp. 234-240 (1994).
Respiratory Experts Call for Global Approach to Treat Chronic Disease, MedWire News, http://www.medwirenews.md/48/64443/Respi ratory/Respiratory_experts_cal 1 _for G lobal_Approach_to Treat_ChronicDisease.html, 2007.

(56) References Cited

OTHER PUBLICATIONS

Stringfellow, D. A., et al., "Antiviral and Interferon-Inducing Properties of 1,5-Diamino Anthraquinones," Antimicrobial Agents and Chemo., vol. 15, No. 1, pp. 111-118, (1979).

Tojo et al., "Synthesis and Biological Evaluation of a Novel TLR7 Agonist with an Antedrug CA2• Strategy", Poster, Chemistry Research Laboratories, Dainippon Sumitomo Pharma Co., Ltd., Osaka, Japan, Medicinal Chemistry, AstraZeneca R&D Charnwood, Loughborough, England, EFMC-ISMC 201, Brussels, Belgium, Sep. 5-9, 2010.

U.S. Appl. No. 60/937,726, filed Jun. 29, 2007 (priority document of US-2009/0047249-A1. U.S. Appl. No. 12/215,598.

USPTO Office Action dated Jun. 29, 2010 in U.S. Appl. No. 12/066,952.

USPTO Office Action dated Oct. 13, 2009 in U.S. Appl. No. 12/066,952.

USPTO Office Action dated Apr. 8, 2009 in U.S. Appl. No. 10/594,074.

USPTO Office Action dated Jul. 8, 2009 in U.S. Appl. No. 10/594,074.

Zalutsky, MR, "Targeted radiotherapy of brain tumours," British J. of Cancer, vol. 90, pp. 1469-1473 (2004).

Dvorakova, Journal of Medicinal Chemistry, vol. 39, No. 17 pp. 3263-3268 (1996).

Chavarot, Tetrahedron vol. 53, No. 40, pp. 13749-13756 (1997).

Itahara, ChemPhysChem, vol. 3, No. 4, pp. 378-379 (2002).

Spassova, Collection of Czechoslovak Chemical Communications, vol. 59, No. 5, pp. 1153-1174 (1994).

K. Eiho et al.. "Mechanism of long-lasting suppression against Th2 immune response in the ling by a novel antedrug TLR7 agonist," European Respiratory Society, Amsterdam, Sep. 24-28, 2011 (abstract and poster).

L. Greiff et al., "Repeated intranasal TLR7 stimulation reduces allergen responsiveness in allergic rhinitis," European Respiratory Society, Amsterdam, Sep. 24-28, 2011 (abstract and poster).

M. Biffen et al., "Novel TLR7 agonists for the treatment of allergic diseases," Toll 2011, Riva del Garda, Italy, May 4-7, 2011 (abstract).

* cited by examiner

9-SUBSTITUTED 8-OXOADENINE COMPOUND

This application is a continuation of U.S. application Ser. No. 13/187,260, filed on Jul. 20, 2011, now U.S. Pat. No. 8,575,180, which is a continuation of U.S. application Ser. No. 10/593,691, filed on Dec. 4, 2006, now U.S. Pat. No. 8,012,964, which is the National Stage under 35 USC §371 of International Application Number PCT/JP2005/005401, filed on Mar. 24, 2005, which claims priority under 35 USC §119 (a)-(d) of Application No. 2004-093672, filed in Japan on Mar. 26, 2004.

JOINT RESEARCH AGREEMENT

The subject matter claimed in this application was made as a result of activities undertaken within the scope of a joint research agreement dated Dec. 19, 2003 between AstraZeneca AB and Sumitomo Pharmaceuticals Co., Ltd. All of the rights and obligations of Sumitomo Pharmaceuticals Co., Ltd. as defined in the joint research agreement between AstraZeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct. 3, 2005. Dainippon Sumitomo Pharma Co., Ltd., has changed its name to Sumitomo Dainippon Pharma Co., Ltd.

TECHNICAL FIELD

The present invention relates to a novel adenine compound useful as a prophylactic or therapeutic agent for viral diseases, allergic diseases, etc.

BACKGROUND ART

Interferon is an endogenous protein having an important role in an immune system in mammals, and not only takes a partial role in a nonspecific defense mechanism in a living body but also strongly participates in a specific defense mechanism thereof. Actually, interferon has been used as an agent for treating viral diseases such as hepatitis B and hepatitis C in a clinical field. A low molecular weight organic compound (an interferon-inducing agent) which induces a biosynthesis of the said interferon has been developed as the next generation interferon therapy, including an imidazoquinoline derivative (refer to the patent document 1) and an adenine derivative (refer to the patent documents 2 and 3), and an imidazoquinoline derivative, Imiquimod has been used as an external antiviral agent for genital wart in a clinical field.

On the other hand, T-cell taking a central role in an immune response in a living body is classified into two groups, Th1-cell and Th2-cell, and in a living body of a patient suffering from an allergic disease, an excess amount of cytokines such as interleukin-4 (IL-4) and interleukin-5 (IL-5) is excreted from Th-2 cell, and thus a compound suppressing an immune response of Th2 cell can be expected as an agent for treating allergic diseases.

The above imidazoquinoline derivative and adenine derivative have been known as showing a suppressing activity of production of interleukin-4 (IL-4) and interleukin-5 (IL-5) as well as an inducing activity of interferon, and have been actually known to be effective to an allergic disease also in a model animal.

However, there is such a fear that systemic adverse effects based on the interferon inducing activity would be problem upon using such derivatives as an anti-allergic agent.

[Patent Document 1] U.S. Pat. No. 4,689,338
[Patent Document 2] WO 98/01448
[Patent Document 3] WO 99/28321

DISCLOSURE OF INVENTION

The problem to be solved by the present invention is to provide a novel 8-oxoadenine compound useful as an immuno-modulator and a therapeutic or prophylactic agent for allergic diseases, viral diseases and cancers comprising the said compound as an effective ingredient.

The present inventors have made extensive study for obtaining an immuno-modulator useful as a therapeutic or a prophylactic agent for allergic diseases such as asthma, viral diseases and cancers to find the 8-oxoadenine compound of the present invention. Namely, the compound of the present invention is an immuno-modulator having an immunoactivation effect such as an interferon inducing activity and also having a suppressing activity of production of a cytokine such as IL-4 and IL-5 originated from Th2-cell, and thus is effective as a therapeutic or prophylactic agent for allergic diseases, viral diseases and cancers.

The prevent invention has been completed on the basis of the above finding.

BEST MODE FOR CARRYING OUT THE INVENTION

Namely, the present invention is as follows:

[1] An 8-oxoadenine compound shown by the formula (1):

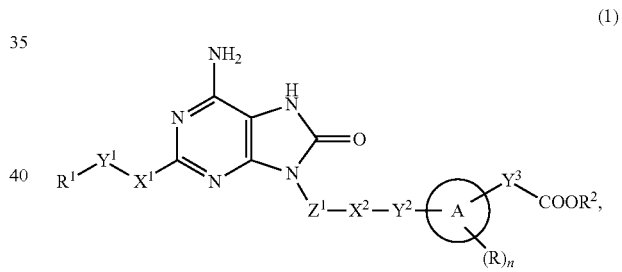

(1)

wherein ring A represents a 6-10 membered aromatic carbocyclic ring or a 5-10 membered heteroaromatic ring;

R represents a halogen atom, an alkyl group, a hydroxyalkyl group, a haloalkyl group, an alkoxy group, a hydroxyalkoxy group, a haloalkoxy group, amino group, an alkylamino group, a dialkylamino group, or a cyclic amino group;

n represents an integer of 0-2, and when n is 2, the Rs may be the same or different;

$Z^1$ represents a substituted or unsubstituted alkylene group or a substituted or unsubstituted cycloalkylene group;

$X^2$ represents oxygen atom, sulfur atom, $SO_2$, $NR^5$, CO, $CONR^5$, $NR^5CO$, $SO_2NR^5$, $NR^5SO_2$, $NR^5CONR^6$ or $NR^5CSNR^6$ (in which $R^5$ and $R^6$ are each independently hydrogen atom, a substituted or unsubstituted alkyl group, or a substituted or unsubstituted cycloalkyl group.);

$Y^1$, $Y^2$ and $Y^3$ represent each independently a single bond or an alkylene group;

$X^1$ represents oxygen atom, sulfur atom, $SO_2$, $NR^4$ (wherein $R^4$ is hydrogen atom or an alkyl group) or a single bond;

$R^2$ represents hydrogen atom, a substituted or unsubstituted alkyl group, a substituted or unsubstituted alkenyl group, a substituted or unsubstituted alkynyl group or a substituted or unsubstituted cycloalkyl group; and $R^1$ represents hydrogen atom, hydroxy group, an alkoxy group, an alkoxycarbonyl group, a haloalkyl group, a haloalkoxy group, a substituted or unsubstituted aryl group, a substituted or unsubstituted heteroaryl group or a substituted or unsubstituted cycloalkyl group, or its pharmaceutically acceptable salt.

[2] The 8-oxoadenine compound as described in the above [1], wherein ring A represents a 6-10 membered aromatic carbocyclic ring, or a 5-10 membered heteroaromatic ring containing 1-4 hetero atoms selected from 0-4 nitrogen atoms, 0-2 oxygen atoms and 0-2 sulfur atoms;

R represents a halogen atom, an alkyl group of 1-6 carbons, a hydroxyalkyl group of 1-6 carbon, a haloalkyl group of 1-6 carbons, an alkoxy group of 1-6 carbons, a hydroxyalkoxy group of 1-6 carbons, a haloalkoxy group of 1-6 carbons, amino group, an alkylamino group of 1-6 carbons, a dialkylamino group in which each alkyl moiety has 1-6 carbons, and a cyclic amino group, n is an integer of 0-2, and when n is 2, Rs may be the same or different;

$Z^1$ represents an alkylene group of 1-6 carbons or a cycloalkylene group of 3-8 carbons, which is optionally substituted by hydroxy group;

$X^2$ represents oxygen atom, sulfur atom, $SO_2$, $NR^5$, CO, $CONR^5$, $NR^5CO$, $SO_2NR^5$, $NR^5SO_2$, $NR^5CONR^6$ or $NR^5CSNR^6$ (in which $R^5$ and $R^6$ are independently hydrogen atom, a substituted or unsubstituted alkyl group of 1-6 carbons and a substituted or unsubstituted cycloalkyl group of 3-8 carbons, wherein the substituents of the alkyl group or cycloalkyl group are selected from a halogen atom, hydroxy group, an alkoxy group of 1-6 carbons, carboxy group, an alkoxycarbonyl group of 2-5 carbons, carbamoyl group, amino group, an alkylamino group of 1-6 carbons, a dialkylamino group in which each alkyl moiety has 1-6 carbons, a cyclic amino group, carboxy group and tetrazolyl group which may be substituted by an alkyl group of 1-6 carbons.);

$Y^1$, $Y^2$ and $Y^3$ represent independently a single bond or an alkylene group of 1-6 carbons;

$X^1$ represents oxygen atom, sulfur atom, $SO_2$, $NR^4$ (wherein $R^4$ represents hydrogen atom or an alkyl group), or a single bond;

$R^2$ represents a substituted or unsubstituted alkyl group of 1-6 carbons, a substituted or unsubstituted alkenyl group of 2-6 carbons, a substituted or unsubstituted alkynyl group of 2-6 carbons or a substituted or unsubstituted cycloalkyl group of 3-8 carbons (wherein the substituent in the alkyl group, the alkenyl group and the alkynyl group is selected from a halogen atom, hydroxy group, an alkoxy group of 1-6 carbons, an acyloxy group of 2-10 carbons, amino group, an alkylamino group of 1-6 carbons and a dialkylamino group in which each alkyl moiety has 1-6 carbons, and a cyclic amino group.);

$R^1$ represents hydrogen atom, hydroxy group, an alkoxy group of 1-6 carbons, an alkoxycarbonyl group of 2-5 carbons, a haloalkyl group of 1-6 carbons, a haloalkoxy group of 1-6 carbons, a substituted or unsubstituted aryl group of 6-10 carbons, a substituted or unsubstituted 5-10 membered heteroaryl group containing 1-4 hetero atoms selected from 0-4 nitrogen atoms, 0-2 oxygen atoms or 0-2 sulfur atoms or a substituted or unsubstituted cycloalkyl group of 3-8 carbons, and the said substituent in the aryl group, the heteroaryl group and the cycloalkyl group is selected from a halogen atom, hydroxy group, an alkyl group of 1-6 carbons, a haloalkyl group of 1-6 carbons, an alkoxy group of 1-6 carbons, a haloalkoxy group of 1-6 carbons, an alkylcarbonyl group of 2-5 carbons, amino group, an alkylamino group of 1-6 carbons and a dialkylamino group in which each alkyl moiety has 1-6 carbons, and the said cyclic amino group means a 4-7 membered saturated cyclic amino group containing 1-2 hetero atoms selected from 1-2 nitrogen atoms, 0-1 oxygen atom and 0-1 sulfur atom, which may be substituted with a halogen atom, hydroxy group, oxo group, an alkyl group of 1-6 carbons, an alkoxy group of 1-6 carbons, an alkylcarbonyl group of 2-5 carbons or an alkoxycarbonyl group of 2-5 carbons, in the formula (1), or its pharmaceutically acceptable salt.

[3] The 8-oxoadenine compound or its pharmaceutically acceptable salt as described in the above of the above [1] or [2], wherein $X^2$ in the formula (1) is oxygen atom, sulfur atom, $NR^5$, $SO_2$, $NR^5SO_2$ or $NR^5CONR^6$.

[4] The 8-oxoadenine compound or its pharmaceutically acceptable salt as described in any of the above [1] to [3], wherein $Y^3$ in the formula (1) is a single bond, methylene or ethylene.

[5] The 8-oxoadenine compound or its pharmaceutically acceptable salt as described in any of the above [1] to [4], wherein $Z^1$ in the formula (1) is a straight chained alkylene group of 1-6 carbons which may be substituted with hydroxy group.

[6] The 8-oxoadenine compound or its pharmaceutically acceptable salt as described in any of the above [1]-[5], wherein $X^1$ in the formula (1) is oxygen atom or sulfur atom.

[7] The 8-oxoadenine compound or its pharmaceutically acceptable salt as described in any of the above [1]-[6], wherein $Y^1$ in the formula (1) is a single bond or an alkylene group of 1-6 carbons.

[8] The 8-oxoadenine compound or its pharmaceutically acceptable salt as described in any of the above [1]-[7], wherein $R^1$ in the formula (1) is hydrogen atom, an alkoxycarbonyl group, hydroxy group, or an alkoxy group.

[9] The 8-oxoadenine compound or its pharmaceutically acceptable salt as described in any of the above [1]-[8], wherein a group shown by the formula (2) in the formula (1):

(2)

wherein ring A, R, n, $Y^3$ and $R^2$ have the same meaning as in the formula (1), is a group shown by the formula (3) or the formula (4):

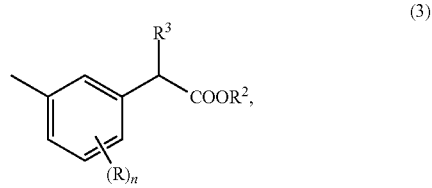

(3)

-continued

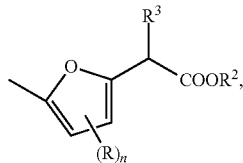
(4)

wherein R, n and $R^2$ have the same meaning as in the formula (1), and $R^3$ is hydrogen atom or an alkyl group.

[10] The 8-oxoadenine compound or its pharmaceutically acceptable salt as described in the above [9], wherein $R^2$ is methyl group or an alkyl group of 2-6 carbons substituted by a dialkylamino group or a cyclic amino group.

[11] The 8-oxoadenine compound or its pharmaceutically acceptable salt as described in the above [9] or [10], wherein $R^3$ is hydrogen atom.

[12] A pharmaceutical composition, comprising the 8-oxoadenine compound or its pharmaceutically acceptable salt described in any of the above [1]-[11] as an active ingredient.

[13] An immuno-modulator, comprising the 8-oxoadenine compound or its pharmaceutically acceptable salt described in any of the above [1]-[11] as an active ingredient.

[14] A therapeutic or prophylactic agent for viral diseases, cancers or allergic diseases, comprising the 8-oxoadenine compound or its pharmaceutically acceptable salt described in any of the above [1]-[11] as an active ingredient.

[15] A medicament for topical administration, comprising the 8-oxoadenine compound or its pharmaceutically acceptable salt described in any of the above [1]-[11] as an active ingredient.

[16] A use of the 8-oxoadenine compound or its pharmaceutically acceptable salt described in any of the above [1]-[11] as a medicament.

[17] A use of the 8-oxoadenine compound or its pharmaceutically acceptable salt described in any of the above [1]-[11] for manufacturing an immuno-modulator.

[18] A use of the 8-oxoadenine compound or its pharmaceutically acceptable salt described in any of the above [1]-[11] for manufacturing a therapeutic or prophylactic agent for viral diseases, cancers and allergic diseases.

[19] A method for modulating immune response which comprises administering to a patient, an effective amount of the 8-oxoadenine compound or its pharmaceutically acceptable salt described in any of the above [1]-[11].

[20] A method for treating or preventing viral diseases, cancers and allergic diseases which comprises administering to a patient, an effective amount of the 8-oxoadenine compound or its pharmaceutically acceptable salt described in any of the above [1]-[11].

[21] A process for preparing the 8-oxoadenine compound as described in any of the above [1]-[11] which comprises brominating a compound shown by the formula (10):

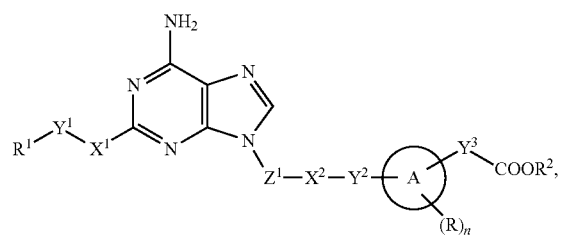
(10)

wherein ring A, n, R, $R^1$, $R^2$, $X^1$, $X^2$, $Y^1$, $Y^2$, $Y^3$ and $Z^1$ are the same defined in the above [1],
reacting the resultant with a metal alkoxide and then hydrolyzing, or hydrolyzing the resultant.

[22] A compound shown by the formula (10):

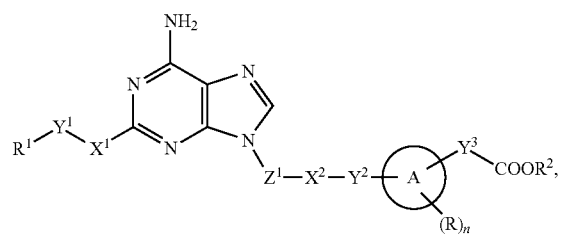
(10)

wherein ring A, n, R, $R^1$, $R^2$, $X^1$, $X^2$, $Y^1$, $Y^2$, $Y^3$ and $Z^1$ are the same defined in the above [1].

[23] A process for preparing an 8-oxoadenine compound as described in any of the above [1]-[11] which comprises deprotecting a compound shown by the formula (11):

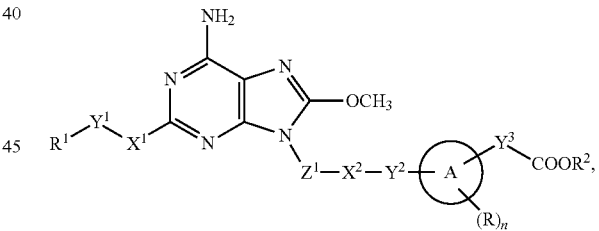
(11)

wherein ring A, n, R, $R^1$, $R^2$, $X^1$, $X^2$, $Y^1$, $Y^2$, $Y^3$ and $Z^1$ are the same defined in the above [1].

[24] A compound shown by the formula (11):

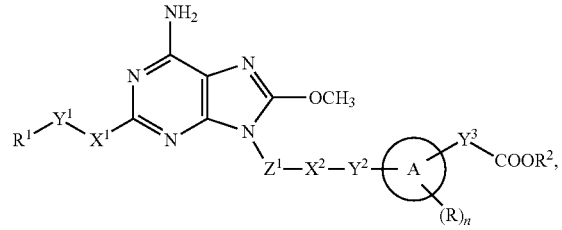
(11)

wherein Ring A, n, R, $R^1$, $R^2$, $X^1$, $X^2$, $Y^1$, $Y^2$, $Y^3$ and $Z^1$ are the same defined in the above [1].

[25] A compound or a pharmaceutically acceptable salt thereof selected from the group consisting of the following compounds:
2-Butoxy-8-oxo-9-[2-(3-methoxycarbonylphenoxy)ethyl]adenine,
2-Butoxy-8-oxo-9-[2-(3-methoxycarbonylmethylphenoxy)ethyl]adenine,
2-Butoxy-8-oxo-9-[2-(2-methoxycarbonylphenoxy)ethyl]adenine,
2-Butoxy-8-oxo-9-[2-(2-methoxycarbonylmethylphenoxy)ethyl]adenine,
2-Butoxy-8-oxo-9-[2-(4-methoxycarbonylphenoxy)ethyl]adenine,
2-Butoxy-8-oxo-9-[2-(4-methoxycarbonylmethylphenoxy)ethyl]adenine,
2-Butoxy-8-oxo-9-{2-[4-(2-methoxycarbonylethyl)phenoxy]ethyl}adenine,
2-Butoxy-8-oxo-9-[4-(3-methoxycarbonylbenzenesulfonamide)butyl]adenine,
2-Butoxy-8-oxo-9-[4-(3-methoxycarbonylmethylbenzenesulfonamide)butyl]adenine,
2-Butoxy-8-oxo-9-[4-(3-methoxycarbonylphenylaminocarbonylamino)butyl]adenine,
2-Butoxy-8-oxo-9-[4-(3-methoxycarbonylmethylphenylaminocarbonylamino)-butyl]adenine,
Methyl [3-({[2-(6-amino-2-butoxy-8-oxo-7,8-dihydro-9H-purin-9-yl)ethyl]amino}methyl)phenyl]acetate,
[3-({[2-(6-Amino-2-butoxy-8-oxo-7,8-dihydro-9H-purin-9-yl)ethyl]amino}methyl)phenyl]acetic acid,
Methyl 3-({[3-(6-amino-2-butoxy-8-oxo-7,8-dihydro-9H-purin-9-yl)propyl]amino}methyl)benzoate,
3-({[3-(6-Amino-2-butoxy-8-oxo-7,8-dihydro-9H-purin-9-yl)propyl]amino}methyl)benzoic acid,
Methyl 4-({[3-(6-amino-2-butoxy-8-oxo-7,8-dihydro-9H-purin-9-yl)propyl]amino}methyl)benzoate,
4-({[3-(6-Amino-2-butoxy-8-oxo-7,8-dihydro-9H-purin-9-yl)propyl]amino}methyl)benzoic acid,
Methyl (3-{[[3-(6-amino-2-butoxy-8-oxo-9H-purin-9-yl)propyl](2-morpholin-4-ylethyl)amino]methyl}phenyl)acetate,
Methyl [3-({[4-(6-amino-2-butoxy-8-oxo-7,8-dihydro-9H-purin-9-yl)butyl]amino}methyl)phenyl]acetate,
Ethyl 2-[2-(6-amino-2-butoxy-8-oxo-7,8-dihydro-9H-purin-9-yl)ethoxy]benzoate,
3-(Dimethylamino)propyl 2-[2-(6-amino-2-butoxy-8-oxo-7,8-dihydro-9H-purin-9-yl)ethoxy]benzoate,
Methyl 3-[4-({[4-(6-amino-2-butoxy-8-oxo-7,8-dihydro-9H-purin-9-yl)butyl]amino}sulfonyl)phenyl]propanoate,
3-[4-({[4-(6-Amino-2-butoxy-8-oxo-7,8-dihydro-9H-purin-9-yl)butyl]amino}sulfonyl)phenyl]propanoic acid,
Methyl (3-{[[4-(6-amino-2-butoxy-8-oxo-7,8-dihydro-9H-purin-9-yl)butyl](2-pyrrolidin-1-ylethyl)amino]sulfonyl}phenyl)acetate,
(3-{[[4-(6-Amino-2-butoxy-8-oxo-7,8-dihydro-9H-purin-9-yl)butyl](2-pyrrolidin-1-ylethyl)amino]sulfonyl}phenyl)acetic acid,
Methyl (3-{[[4-(6-amino-2-butoxy-8-oxo-7,8-dihydro-9H-purin-9-yl)butyl](2-methoxyethyl)amino]sulfonyl}phenyl)acetate,
(3-{[[4-(6-Amino-2-butoxy-8-oxo-7,8-dihydro-9H-purin-9-yl)butyl](2-methoxy-ethyl)amino]sulfonyl}phenyl)acetic acid,
Methyl (3-{[[4-(6-amino-2-butoxy-8-oxo-7,8-dihydro-9H-purin-9-yl)butyl](methyl)amino]sulfonyl}phenyl)acetate
(3-{[[4-(6-Amino-2-butoxy-8-oxo-7,8-dihydro-9H-purin-9-yl)butyl](methyl)amino]sulfonyl}phenyl)acetic acid,
Methyl [3-({[4-(6-amino-2-butoxy-8-oxo-7,8-dihydro-9H-purin-9-yl)butyl][3-(dimethylamino)-2,2-dimethylpropyl]amino}sulfonyl)phenyl]acetate,
[3-({[4-(6-Amino-2-butoxy-8-oxo-7,8-dihydro-9H-purin-9-yl)butyl][3-(dimethylamino)-2,2-dimethylpropyl]amino}sulfonyl)phenyl]acetic acid,
Methyl [3-({[3-(6-amino-2-butoxy-8-oxo-7,8-dihydro-9H-purin-9-yl)propyl]amino}sulfonyl)phenyl]acetate,
Methyl (3-{[[4-(6-amino-2-butoxy-8-oxo-7,8-dihydro-9H-purin-9-yl)butyl](2-hydroxy-2-methylpropyl)amino]sulfonyl}phenyl)acetate,
(3-{[[4-(6-Amino-2-butoxy-8-oxo-7,8-dihydro-9H-purin-9-yl)butyl](2-hydroxy-2-methylpropyl)amino]sulfonyl}phenyl)acetic acid,
Methyl [3-({[2-(6-amino-2-butoxy-8-oxo-7,8-dihydro-9H-purin-9-yl)ethyl]amino}sulfonyl)phenyl]acetate,
Methyl [3-({[4-(6-amino-2-butoxy-8-oxo-7,8-dihydro-9H-purin-9-yl)butyl][(2R)-2,3-dihydroxypropyl]amino}sulfonyl)phenyl]acetate,
[3-({[4-(6-Amino-2-butoxy-8-oxo-7,8-dihydro-9H-purin-9-yl)butyl][(2R)-2,3-dihydroxypropyl]amino}sulfonyl)phenyl]acetic acid,
Methyl 3-({[4-(6-amino-2-butoxy-8-oxo-7,8-dihydro-9H-purin-9-yl)butyl][3-(dimethylamino)-2,2-dimethylpropyl]amino}sulfonyl)benzoate,
3-({[4-(6-Amino-2-butoxy-8-oxo-7,8-dihydro-9H-purin-9-yl)butyl][3-(dimethyl-amino)-2,2-dimethylpropyl]amino}sulfonyl)benzoic acid,
Methyl (3-{[[4-(6-amino-2-butoxy-8-oxo-7,8-dihydro-9H-purin-9-yl)butyl](3-morpholin-4-ylpropyl)amino]methyl}phenyl)acetate,
(3-{[[4-(6-Amino-2-butoxy-8-oxo-7,8-dihydro-9H-purin-9-yl)butyl](3-morpholin-4-ylpropyl)amino]methyl}phenyl)acetic acid,
Methyl [3-({[4-(6-amino-2-butoxy-8-oxo-7,8-dihydro-9H-purin-9-yl)butyl][3-(dimethylamino)-2,2-dimethylpropyl]amino}methyl)phenyl]acetate,
[3-({[4-(6-Amino-2-butoxy-8-oxo-7,8-dihydro-9H-purin-9-yl)butyl][3-(dimethylamino)-2,2-dimethylpropyl]amino}methyl)phenyl]acetic acid,
Methyl [3-({[4-(6-amino-2-butoxy-8-oxo-7,8-dihydro-9H-purin-9-yl)butyl][3-(2-oxopyrrolidin-1-yl)propyl]amino}methyl)phenyl]acetate,
[3-({[4-(6-Amino-2-butoxy-8-oxo-7,8-dihydro-9H-purin-9-yl)butyl][3-(2-oxopyrrolidin-1-yl)propyl]amino}methyl)phenyl]acetic acid,
Methyl (3-{[[4-(6-amino-2-butoxy-8-oxo-7,8-dihydro-9H-purin-9-yl)butyl](2-morpholin-4-ylethyl)amino]methyl}phenyl)acetate,
(3-{[[4-(6-Amino-2-butoxy-8-oxo-7,8-dihydro-9H-purin-9-yl)butyl](2-morpholin-4-ylethyl)amino]methyl}phenyl)acetic acid,
Methyl (3-{[[3-(6-amino-2-butoxy-8-oxo-7,8-dihydro-9H-purin-9-yl)propyl](3-morpholin-4-ylpropyl)amino]methyl}phenyl)acetate,
Methyl [3-({[4-(6-amino-2-butoxy-8-oxo-7,8-dihydro-9H-purin-9-yl)butyl][2-(1H-tetrazol-5-yl)ethyl]amino}methyl)phenyl]acetate,
Methyl (3-{[2-(6-amino-2-butoxy-8-oxo-7,8-dihydro-9H-purin-9-yl)ethyl]thio}phenyl)acetate,
(3-{[2-(6-Amino-2-butoxy-8-oxo-7,8-dihydro-9H-purin-9-yl)ethyl]thio}phenyl)acetic acid,
Methyl (3-{[2-(6-amino-2-butoxy-8-oxo-7,8-dihydro-9H-purin-9-yl)ethyl]amino}phenyl)acetate,
Methyl (3-{[3-(6-amino-2-butoxy-8-oxo-7,8-dihydro-9H-purin-9-yl)propyl]amino}phenyl)acetate, (3-{[3-(6-Amino-2-butoxy-8-oxo-7,8-dihydro-9H-purin-9-yl)propyl]amino}phenyl)acetic acid,
Methyl [3-({[3-(6-amino-2-butoxy-8-oxo-7,8-dihydro-9H-purin-9-yl)propyl]amino}methyl)phenyl]acetate,
([3-({[3-(6-Amino-2-butoxy-8-methoxy-9H-purin-9-yl)propyl]amino}methyl)phenyl]acetic acid,
Methyl (3-{[[2-(6-amino-2-butoxy-8-oxo-7,8-dihydro-9H-purin-9-yl)ethyl] (2-methoxyethyl)amino]methyl}phenyl)acetate,
(3-{[[2-(6-Amino-2-butoxy-8-methoxy-9H-purin-9-yl)ethyl] (2-methoxyethyl)amino]methyl}phenyl)acetic acid,
Methyl (3-{[2-(6-amino-2-butoxy-8-oxo-7,8-dihydro-9H-purin-9-yl)ethyl]sulfonyl}phenyl)acetate,
Methyl (3-{[[2-(6-amino-2-butoxy-8-oxo-7,8-dihydro-9H-purin-9-yl)ethyl](methyl)amino]methyl}phenyl)acetate,
(3-{[[2-(6-Amino-2-butoxy-8-oxo-7,8-dihydro-9H-purin-9-yl)ethyl](methyl)amino]methyl}phenyl)acetic acid,
Methyl 4-[3-(6-amino-2-butoxy-8-oxo-7,8-dihydro-9H-purin-9-yl)-2-hydroxypropoxy]benzoate,
Methyl (3-{[[2-(6-amino-2-butoxy-8-oxo-7,8-dihydro-9H-purin-9-yl)ethyl] (2-hydroxyethyl)amino]methyl}phenyl)acetate,
Methyl (3-{[[4-(6-amino-2-butoxy-8-oxo-7,8-dihydro-9H-purin-9-yl)butyl] (2-hydroxyethyl)amino]methyl}phenyl)acetate,
2-Butoxy-8-oxo-9-[2-(3-hydroxycarbonylphenoxy)ethyl]adenine,
2-Butoxy-8-oxo-9-[2-(3-hydroxycarbonylmethylphenoxy)ethyl]adenine,
2-Butoxy-8-oxo-9-[2-(2-methoxycarbonylphenoxy)ethyl]adenine,
2-Butoxy-8-oxo-9-[2-(2-hydroxycarbonylmethylphenoxy)ethyl]adenine,
2-Butoxy-8-oxo-9-[2-(4-hydroxycarbonylphenoxy)ethyl]adenine,
2-Butoxy-8-oxo-9-[2-(4-methoxycarbonylmethylphenoxy)ethyl]adenine,
2-Butoxy-8-oxo-9-{2-[4-(2-hydroxycarbonylethyl)phenoxy]ethyl}adenine,
2-Butoxy-8-oxo-9-[4-(3-hydroxycarbonylbenzenesulfonamide)butyl]adenine,
2-Butoxy-8-oxo-9-[4-(3-hydroxycarbonylmethylbenzenesulfonamide)butyl]adenine,
2-Butoxy-8-oxo-9-[4-(3-hydroxycarbonylphenylaminocarbonylamino)butyl]adenine, and
2-Butoxy-8-oxo-9-[4-(3-hydroxycarbonylmethylphenylaminocarbonylamino)butyl]adenine.

The present invention is explained below further in details.

"Halogen atom" is exemplified by fluorine, chlorine, bromine and iodine, among which fluorine and chlorine are preferable.

"Alkyl group" is exemplified by a straight chained or branched alkyl group of 1-10 carbons, including specifically methyl group, ethyl group, propyl group, 1-methylethyl group, butyl group, 2-methylpropyl group, 1-methylpropyl group, 1,1-dimethylethyl group, pentyl group, 3-methylbutyl group, 2-methylbutyl group, 2,2-dimethylpropyl group, 1-ethylpropyl group, 1,1-dimethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, heptyl group, 1-methylhexyl group, 1-ethylpentyl group, octyl group, 1-methylheptyl group, 2-ethylhexyl group, nonyl group and decyl group, among which an alkyl group of 1-6 carbons is preferable and an alkyl group of 1-4 carbons is further preferable.

"Cycloalkyl group" is exemplified by a 3-8 membered monocyclic cycloalkyl group, including specifically cyclopropyl group, cyclobutyl group, cyclopentyl group, cyclohexyl group, cycloheptyl group and cyclooctyl group.

"Alkenyl group" is exemplified by a straight chained or branched alkenyl group of 2-8 carbons having 1-3 double bonds, including specifically ethenyl group, 1-propenyl group, 2-propenyl group, 1-methyl-ethenyl group, 1-butenyl group, 2-butenyl group, 3-butenyl group, 2-methyl-2-propenyl group, 1-pentenyl group, 2-pentenyl group, 4-pentenyl group, 3-methyl-2-butenyl group, 1-hexenyl group, 2-hexenyl group and 1-octenyl group, among which an alkenyl group of 2-4 carbons is preferable.

"Alkynyl group" is exemplified by a straight chained or branched alkynyl group of 2-8 carbons having 1 or 2 triple bonds, including specifically ethynyl group, 1-propynyl group, 2-propynyl group, 1-butynyl group, 2-butynyl group, 3-butynyl group, 1-methyl-2-propynyl group, 1-pentynyl group, 2-pentynyl group, 3-pentynyl group, 5-pentynyl group, 1-methyl-3-butynyl group, 1-hexynyl group, and 2-hexynyl group, among which an alkynyl group of 2-4 carbons is preferable.

"Alkylene" is exemplified by a straight chained or branched alkylene group of 1-6 carbons, including specifically methylene, ethylene, trimethylene, tetramethylene, pentamethylene, hexamethylene, methylmethylene, ethylmethylene, propylethylene, 1-methylethylene, 2-methylethylene, 1-methyltrimethylene, 2-methyltrimethylene, 2,2-dimethyltrimethylene, 2-methyltetramethylene and 3-methylpentamethylene.

"Cycloalkylene" is exemplified by a cycloalkylene of 3-8 carbons, which is a divalent group of a cycloalkane in the above mentioned cycloalkyl group, including specifically 1,2-cyclopropylene, 1,3-cyclobutylene, 1,2-cyclobutylene, 1,3-cyclopentylene, 1,2-cyclopentylene, 1,2-cyclohexylene, 1,3-cyclohexylene, 1,4-cyclohexylene, 1,4-cycloheptylene and 1,5-cyclooctylene.

"Alkoxy group" is exemplified by a straight chained or branched alkoxy group of 1-10 carbons, including specifically methoxy group, ethoxy group, propoxy group, 1-methylethoxy group, butoxy group, 2-methylpropoxy group, 1-methylpropoxy group, 1,1-dimethylethoxy group, pentoxy group, 3-methylbutoxy group, 2-methylbutoxy group, 2,2-dimethylpropoxy group, 1-ethylpropoxy group, 1,1-dimethylpropoxy group, hexyloxy group, 4-methylpentyloxy group, 3-methylpentyloxy group, 2-methylpentyloxy group, 1-methylpentyloxy group, 3,3-dimethylbutoxy group, 2,2-dimethylbutoxy group, 1,1-dimethylbutoxy group, 1,2-dimethylbutoxy group, heptyloxy group, 1-methylhexyloxy group, 1-ethylpentyloxy group, octyloxy group, 1-methylheptyloxy group, 2-ethylhexyloxy group, nonyloxy group and decyloxy group, among which an alkoxy group of 1-6 carbons is preferable, and an alkoxy group of 1-4 carbons is further preferable.

"Alkyl moiety" in "alkylcarbonyl group" is exemplified by the same as the above mentioned alkyl group. Preferable alkylcarbonyl group is a straight chained or branched alkylcarbonyl group of 2-5 carbons, including specifically acetyl group, propanoyl group, butanoyl group and 2-methylpropanoyl group.

"Alkoxy moiety" in "alkoxycarbonyl group" is exemplified by the same as the above mentioned alkoxy group. Preferable alkoxycarbonyl group is a straight chained or branched alkoxycarbonyl group of 2-5 carbons, including specifically methoxycarbonyl group, ethoxycarbonyl group, propoxycarbonyl group, 2-methylethoxycarbonyl group, butoxycarbonyl group and 2-methylpropoxycarbonyl group.

"Alkyl moiety" in "hydroxyalkyl group" is exemplified by the same as the above mentioned alkyl group. A hydroxyalkyl group includes specifically 2-hydroxyethyl group, 3-hydroxypropyl group, 4-hydroxybutyl group and 2-hydroxypropyl group.

"Haloalkyl group" is exemplified by an alkyl group substituted by the same or different, 1-9 halogen atoms, preferably 1-5 halogen atoms, including specifically trifluoromethyl group, 2,2,2-trifluoroethyl group, 2,2-difluoroethyl group and pentafluoroethyl group.

"Alkoxy moiety" in "hydroxyalkoxy group" is exemplified by the same as the above mentioned alkoxy group. A hydroxyalkoxy group includes specifically 2-hydroxyethoxy group, 3-hydroxypropoxy group, 4-hydroxybutoxy group and 2-hydroxypropoxy group.

"Haloalkoxy group" is exemplified by an alkoxy group substituted by the same or different, 1-9 halogen atoms, preferably 1-5 halogen atoms, including specifically trifluoromethoxy group, 2,2,2-trifluoroethoxy group, 2,2-difluoroethoxy group and pentafluoroethoxy group.

"Alkyl moiety" in "alkylamino group" is exemplified by the same as the above mentioned alkyl group as above. Preferable alkylamino group is a straight chained or branched alkylamino group of 1-4 carbons, including specifically methylamino group, ethylamino group, propylamino group, 2-methylethylamino group and butylamino group.

Two alkyl moieties in "dialkylamino group" may be the same or different, and the alkyl moiety is exemplified by the same as the above mentioned alkyl group. Preferable dialkylamino group is a straight chained or branched dialkylamino group in which each alkyl moiety has 1-4 carbons, including specifically dimethylamino group, diethylamino group, dipropylamino group, methylethylamino group, methylpropylamino group and ethylpropylamino group.

"Cyclic amino group" is exemplified by a saturated 4-7 membered cyclic amino group containing 1-2 hetero atoms selected from 1-2 nitrogen atoms, 0-1 oxygen atom and 0-1 sulfur atom, including specifically azetidinyl group, piperidinyl group, piperazinyl group, morpholino group and thiomorpholino group. The cyclic amino group may be substituted with a halogen atom, hydroxy group, oxo group, an alkyl group, an alkoxy group, an alkylcarbonyl group or an alkoxycarbonyl group.

"Aryl group" is exemplified by a 6-10 membered aryl group, including specifically phenyl group, 1-naphthyl group and 2-naphthyl group.

"Heteroaryl group" is exemplified by a 5-10 membered mono or bicyclic heteroaryl group containing 1-4 hetero atoms selected from 0-2 nitrogen atoms, 0-1 oxygen atom and 0-1 sulfur atom, including specifically furyl group, thienyl group, pyrrolyl group, pyridyl group, indolyl group, isoindolyl group, quinolyl group, isoquinolyl group, pyrazolyl group, imidazolyl group, pyrimidinyl group, pyrazinyl group, pyridazinyl group, thiazolyl group and oxazolyl group. The bonding site in the heteroaryl group is not specifically limited and it may be on any of the nitrogen or carbon atoms.

"6-10 Membered aromatic carbocyclic ring" shown by ring A in the formula (1) is exemplified by benzene ring and naphthalene ring.

"5-10 Membered heteroaromatic ring" shown by ring A is exemplified by a 5-10 membered monocyclic or bicyclic heteroaromatic ring containing 1-4 hetero atoms selected from 0-4 nitrogen atoms, 0-2 oxygen atoms and 0-2 sulfur atoms, including specifically pyrrole ring, furan ring, thiophene ring, pyrazole ring, imidazole ring, oxazole ring, thiazole ring, isoxazole ring, isothiazole ring, pyridine ring, pyridazine ring, pyrimidine ring, pyrazine ring, triazine ring, quinoline ring, isoquinoline ring, indole ring, benzofuran ring, benzothiophene ring, indazole ring, benzoisoxazole ring, benzoisothiazole ring, benzoimidazole ring, benzoxazole ring, benzothiazole ring, phthalazine ring, quinazoline ring and quinoxaline ring.

The bonding site in the heteroaromatic ring is not specifically limited and it may be on any of the nitrogen or carbon atoms. Preferable heterocyclic ring shown by ring A is pyridine ring, furan ring, thiophene ring, pyrrole ring, indole ring and oxazole ring, further preferable one is pyridine ring, furan ring and thiophene ring.

The group shown by the formula (2):

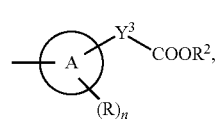

(2)

wherein ring A, R, n, $Y^3$ and $R^2$ are the same defined in the above, is preferably one selected from the group consisting of following formulas (3) to (9):

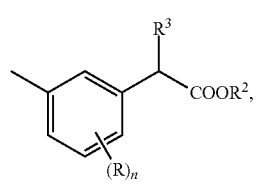

(3)

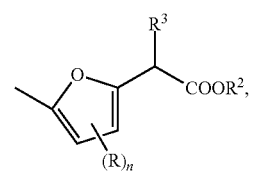

(4)

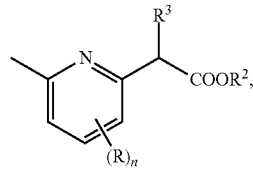

(5)

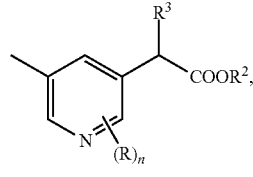

(6)

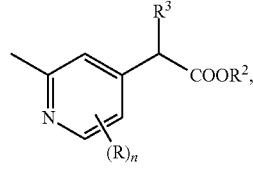

(7)

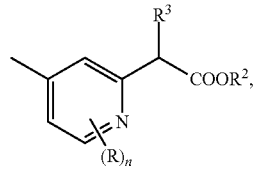

(8)

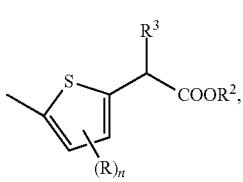

(9)

wherein n, R and $R^2$ have the same meaning as above, and $R^3$ is a hydrogen atom or an alkyl group, preferably hydrogen atom.

In the formula (1), R is preferably exemplified by a halogen atom such as fluorine atom and chlorine atom, an alkyl group of 1-4 carbons such as methyl group and ethyl group, an alkoxy group of 1-4 carbons such as methoxy group and ethoxy group, a haloalkyl group of 1-2 carbons such as trifluoromethyl group, difluoromethyl group and 2,2,2-trifluoroethyl group, a haloalkoxy group of 1-2 carbons such as trifluoromethoxy group, difluoromethoxy group and 2,2,2-trifluoroethoxy group, a dialkylamino group of 1-5 carbons such as dimethylamino group, diethylamino group, ethylmethylamino group and dipropylamino group, and a cyclic amino group such as morpholino group, piperidino group, piperazino group and pyrrolidino group, and the cyclic amino group may be substituted with a halogen atom, hydroxy group, an alkyl group, an alkoxy group, an alkylcarbonyl group or an alkoxycarbonyl group.

In the formula (1), n is preferably 0 or 1.

In the substituted or unsubstituted alkyl group, the substituted or unsubstituted alkenyl group, the substituted or unsubstituted alkynyl group and the substituted or unsubstituted cycloalkyl group shown by $R^2$ in the formula (1), the substituent is exemplified by a halogen atom, hydroxy group, an alkoxy group, an acyloxy group, amino group, an alkylamino group, a dialkylamino group and a cyclic amino group.

The acyloxy group is exemplified by acyloxy group of 2-10 carbons, including a substituted or unsubstituted alkylcarbonyloxy group of 2-5 carbons, a substituted or unsubstituted alkenylcarbonyloxy group of 2-5 carbons, a substituted or unsubstituted alkynylcarbonyloxy group of 2-5 carbons, a substituted or unsubstituted arylcarbonyloxy group and a substituted or unsubstituted heteroarylcarbonyloxy group. The alkyl, alkenyl and alkynyl in the above alkylcarbonyloxy group, alkenylcarbonyloxy group and alkynylcarbonyloxy group are exemplified by the same as the above mentioned alkyl group, alkenyl group and alkynyl group, respectively.

The substituent in the substituted alkylcarbonyloxy group, alkenylcarbonyloxy group and alkynylcarbonyloxy group is exemplified by a halogen atom, hydroxy group, an alkoxy group and an aryl group.

The aryl moiety in the above arylcarbonyloxy group is exemplified by the same as the above mentioned aryl group. The heteroaryl in the above heteroarylcarbonyloxy group is exemplified by the same as the above mentioned heteroaryl group. The substituent in the above substituted aryl group and heteroaryl group is exemplified by a halogen atom, hydroxy group, an alkoxy group, a haloalkyl group, a haloalkoxy group, an alkylcarbonyl group, amino group, an alkylamino group and a dialkylamino group.

The substituent in the substituted or unsubstituted alkyl group in the groups $R^5$ and $R^6$ in the formula (1) is exemplified by a halogen atom, hydroxy group, an alkoxy group, a carboxy group, an alkoxycarbonyl group, carbamoyl group, an alkylamino group, a dialkylamino group, a cyclic amino group, carboxy group and tetrazolyl group which may be substituted by an alkyl group, wherein the groups $R^5$ and $R^6$ may be substituted with one or more substituents, preferably 1-3 substituents.

The cyclic amino group includes specifically piperidino group, piperazino group, pyrrolidino group, morpholino group, thiomorpholino group, pyrrolidon-1-yl group and succinimide-1-yl group, 4-hydroxypiperidino group and 4-methylpiperidino group.

$R^2$ is preferably hydrogen atom, an alkyl group of 1-4 carbons, an acyloxyalkyl group, or an alkyl group of 1-6 carbons substituted by amino group, an alkylamino group, a dialkylamino group or a cyclic amino group. The acyloxyalkyl group is exemplified specifically by acetoxymethyl group, 1-acetoxyethyl group and benzoyloxymethyl group. Further preferably, $R^2$ is methyl group, or an alkyl group of 1-4 carbons substituted by amino group, an alkylamino group, a dialkylamino group or a cyclic amino group.

The compound in the formula (1) wherein $R^2$ represents hydrogen atom is also useful as the synthetic intermediate of the compound wherein $R^2$ represents except hydrogen atom. The compound in the formula (1) wherein $R^2$ represents hydrogen atom is also useful as a reagent for testing pharmacokinetics of the compound wherein $R^2$ represents except hydrogen atom because the former corresponds to a metabolite of the latter.

In the formula (1), $Y^2$ is preferably a single bond or a straight chained alkylene group of 1-4 carbons, including specifically methylene, ethylene, trimethylene and tetramethylene.

In the formula (1), $Y^3$ is preferably a single bond or a straight chained or branched alkylene of 1-4 carbons, including specifically methylene, ethylene, trimethylene, tetramethylene and methylmethylene.

In the formula (1), $X^2$ is preferably oxygen atom, $NHSO_2$, NHCONH and $NR^5$.

In the formula (1), $Z^1$ is preferably a straight chained or branched alkylene of 1-5 carbons, including specifically methylene, ethylene, trimethylene, tetramethylene and pentamethylene, 2-methylmethylene, 2-methylethylene, 1-methylethylene, 2-methylpropylene and 2,2-dimethylpropylene. Still further preferably $Z^1$ is ethylene, trimethylene and tetramethylene. The alkylene may be substituted by hydroxy group, oxo group, etc.

In the formula (1), when $X^1$ is $NR^4$, $R^4$ is preferably hydrogen atom and an alkyl group of 1-3 carbons, more preferably hydrogen atom and methyl group. $X^1$ is preferably oxygen atom and sulfur atom, more preferably oxygen atom.

In the formula (1), $Y^1$ is preferably alkylene of 1-6 carbons, including specifically methylene, ethylene, trimethylene, tetramethylene, pentamethylene and heptamethylene, more preferably a straight chained alkylene of 1-5 carbons.

In the formula (1), $R^1$ is preferably hydrogen atom, hydroxy group, a straight chained or branched alkoxy group of 1-4 carbons, a straight chained or branched alkoxycarbonyl group of 2-5 carbons, a haloalkyl group of 1 or 2 carbons, a haloalkoxy group of 1 or 2 carbons and a substituted or unsubstituted aryl group. The aryl group is preferably phenyl group.

The substituent in the substituted aryl group and the substituted heteroaryl group is exemplified by a halogen atom, hydroxy group, an alkyl group, an alkoxy group, a haloalkyl group, a haloalkoxy group, an alkylcarbonyl group, amino group, an alkylamino group and a dialkylamino group.

More preferably $R^1$ is hydrogen atom, hydroxy group, a straight chained or branched alkoxy group of 1-4 carbons and a straight chained or branched alkoxycarbonyl group of 2-5 carbons.

The above alkoxy group is specifically exemplified by methoxy group and ethoxy group. The above alkoxycarbonyl group is specifically exemplified by methoxycarbonyl group and ethoxycarbonyl group. The above haloalkyl group is specifically exemplified by trifluoromethyl group. The above haloalkoxy group is specifically exemplified by trifluoromethoxy group.

The adenine compound of the present invention, in accordance with the kind of the substituent includes all tautomers, geometrical isomers, stereoisomers, and a mixture thereof.

Namely, in a case where there are one or more asymmetrical carbons in the compound of the formula (1), there exist diastereomers and optical isomers, and mixtures of those diastereomers and optical isomers and separated ones are also included in the present invention.

Additionally, the adenine compound shown by the formula (1) and its tautomers are chemically equivalent, and the adenine compound of the present invention includes the tautomers. The tautomer is specifically a hydroxy compound shown by the formula (1'):

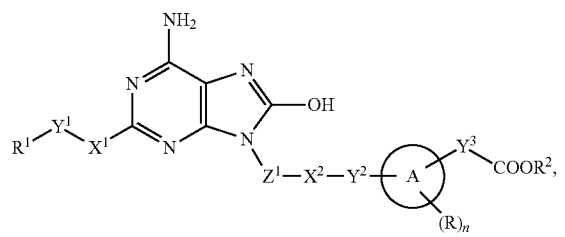

wherein ring A, n, R, $R^1$, $R^2$, $X^1$, $X^2$, $Y^1$, $Y^2$, $Y^3$ and $Z^1$ have the same meanings as above.

The pharmaceutically acceptable salt is exemplified by an acid salt and a base salt. The acid salt is, for example, an inorganic acid salt such as hydrochloride, hydrobromide, sulfate, hydroiodide, nitrate and phosphate, and an organic acid salt such as citrate, oxalate, acetate, formate, propionate, benzoate, trifluoroacetate, maleate, tartrate, methanesulfonate, benzenesulfonate and p-toluenesulfonate, and the base salt is exemplified by an inorganic base salt such as sodium salt, potassium salt, calcium salt, magnesium salt and ammonium salt, and an organic base salt such as triethylammonium salt, triethanolammonium salt, pyridinium salt and diisopropylammonium salt, and further a basic or acidic amino acid salt such as arginine salt, aspartic acid salt and glutamic acid salt. The compound shown by the formula (1) may be hydrate and a solvate such as ethanolate.

The compound shown by the formula (1) can be prepared by the following methods. The starting compounds not disclosed in the below can be prepared by a similar method to the following method or by a known method or its similar method.

Preparation Method 1

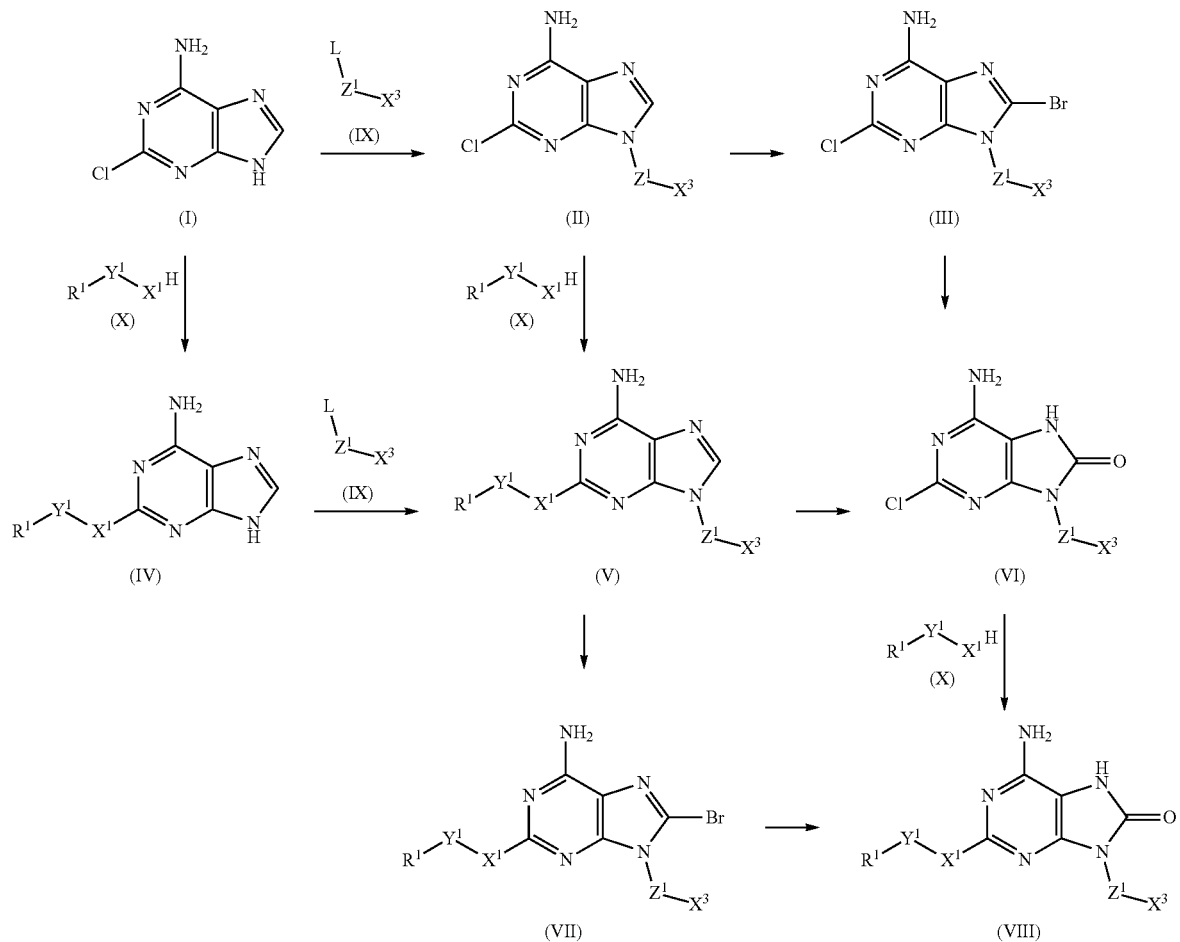

wherein L represents a leaving group, and $R^1$, $Y^1$, $X^1$ and $Z^1$ have the same meanings as above, and $X^3$ is a group shown by the following formula:

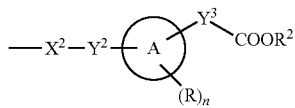

(wherein ring A, n, R, $R^2$, $X^2$, $Y^2$ and $Y^3$ have the same meanings as above), a leaving group, amino group, hydroxy group, mercapto group, carboxy group or sulfonic acid group.

The compound (II) can be obtained by reacting the compound (I) with the compound (IX) in the presence of a base.

As the base, use can be made of an alkali metal carbonate such as sodium carbonate and potassium carbonate, an alkaline earth metal carbonate such as calcium carbonate, a metal hydroxide such as sodium hydroxide and potassium hydroxide, a metal hydrogenate such as sodium hydride, a metal alkoxide such as potassium t-butoxide. As the solvent, use can be made of a halogenated hydrocarbon such as carbon tetrachloride, chloroform and methylene chloride, an ether such as diethyl ether, tetrahydrofuran and 1,4-dioxane, and an aprotic solvent such as dimethylformamide, dimethyl sulfoxide and acetonitrile. The reaction temperature is selected from a range of about 0° C. to around the boiling point of the solvent.

The compound (III) can be obtained by brominating the compound (II). As the brominating agent, use can be made of bromine, hydroperbromic acid and N-bromosuccinimide. In this reaction, a reaction auxiliary such as sodium acetate may be added. As the solvent, use can be made of a halogenated hydrocarbon such as carbon tetrachloride, methylene chloride and dichloroethane, ether such as diethyl ether, acetic acid and carbon disulfide. The reaction temperature is selected from a range of about 0° C. to around the boiling point of the solvent.

The compound (VI) can be obtained by reacting the compound (III) with a metal alkoxide such as sodium methoxide, followed by treating under acidic conditions.

As the solvent on reacting with the metal alkoxide, use is made of an ether such as diethyl ether, tetrahydrofuran and 1,4-dioxane, an aprotic solvent such as dimethylformamide and an alcohol such as methanol corresponding to the metal alkoxide used. The reaction temperature is selected from a range of room temperature to around the boiling point of the solvent.

As the acid to be used in the acid treatment, use can be made of an inorganic acid such as hydrochloric acid, hydrobromic acid and sulfuric acid and an organic acid such as trifluoroacetic acid. As the solvent, use is made of ether such as diethyl ether and tetrahydrofuran, an aprotic solvent such as dimethylformamide and acetonitrile and an alcohol such as methanol and ethanol. The reaction temperature is selected from a range of room temperature to around the boiling point of the solvent.

The compound (VIII) can be obtained by reacting the compound (VI) with the compound (X).

In a case where $X^1$ is $NR^4$, the reaction is conducted in the presence or absence of a base. As the base, use can be made of an alkali metal carbonate such as sodium carbonate and potassium carbonate, an alkaline earth metal carbonate such as calcium carbonate, a metal hydroxide such as sodium hydroxide and potassium hydroxide and an organic base such as triethylamine, diisopropylethylamine and 4-dimethylamino pyridine. As the solvent, use can be made of an ether such as tetrahydrofuran, 1,4-dioxane and diglyme, an alcohol such as propanol and butanol and an aprotic solvent such as dimethylformamide. The reaction temperature is selected from a range of about 50° C. to about 200° C. The reaction may be carried out in the absence of a solvent.

In a case where $X^1$ is oxygen atom or sulfur atom, the reaction is conducted in the presence of a base. As the base, use can be made of an alkali metal such as sodium and potassium and an alkali metal hydride such as sodium hydride. As the solvent, use can be made of an ether such as tetrahydrofuran, 1,4-dioxane and diglyme, and an aprotic solvent such as dimethylformamide and dimethyl sulfoxide. The reaction may be carried out in the absence of a solvent. The reaction temperature is selected from a range of about 50° C. to about 200° C.

In a case where $X^1$ is $SO_2$, an intermediate wherein the corresponding $X^1$ is sulfur atom is oxidized by oxone (registered trade mark) or m-chloroperbenzoic acid (mCPBA).

In the process of preparing the compound (VIII) from the compound (I), the compound (V) can also be synthesized from the compound (II) by the same method as above, or the compound (VIII) can also be obtained by synthesizing the compound (V) from the compound (I) through the compound (IV) and converting the resultant to the compound (VII) which is then converted to the object.

Preparation Method 2

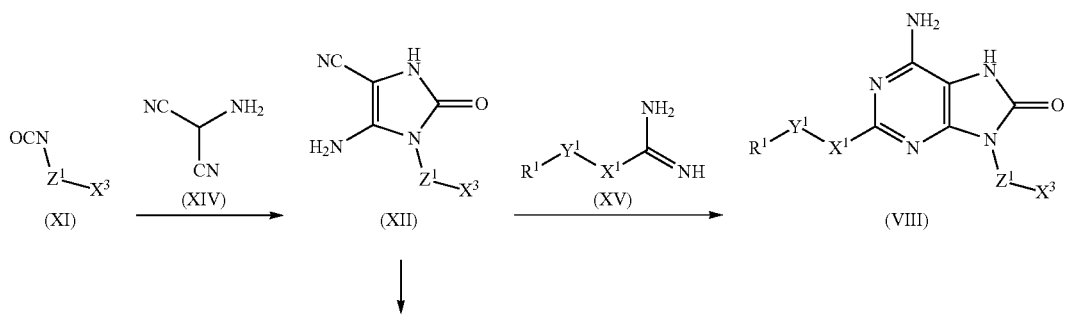

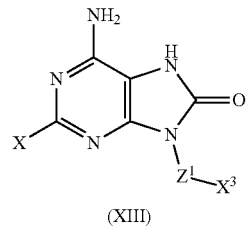

(XIII)

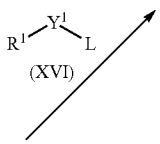

(XVI)

wherein L is a leaving group, $R^1$, $Y^1$, $X^1$ and $Z^1$ have the same meanings as above, X is amino group, hydroxy group or mercapto group, and $X^3$ is a group shown by the following formula:

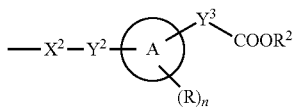

(wherein ring A, n, R, $R^2$, $X^2$, $Y^2$ and $Y^3$ have the same meanings as above), a leaving group, amino group, hydroxy group, mercapto group, carboxy group or sulfonic acid group.

The compound (XII) can be obtained by reacting the compound (XI) with the compound (XIV) in the presence of a base.

As the base, use can be made of an alkali metal carbonate such as sodium carbonate and potassium carbonate, an alkaline earth metal carbonate such as calcium carbonate, a metal hydroxide such as sodium hydroxide and potassium hydroxide, an organic base such as triethylamine, diisopropylethylamine, pyridine and 4-dimethylaminopyridine, a metal alkoxide such as sodium methoxide. As the solvent, use can be made of a halogenated hydrocarbon such as methylene chloride, an ether such as diethyl ether, tetrahydrofuran and 1,4-dioxane, an alcohol such as methanol and ethanol, and an aprotic solvent such as dimethylformamide, dimethyl sulfoxide and acetonitrile. The reaction temperature is selected from a range of about 0° C. to around the boiling point of the solvent.

The compound (VIII) can be obtained by reacting the compound (XII) with the compound (XV) in the presence or absence of a base.

As the base, use can be made of an inorganic base including an alkali metal carbonate such as sodium carbonate and potassium carbonate, an alkaline earth metal carbonate such as calcium carbonate, a metal hydroxide such as sodium hydroxide and potassium hydroxide, an organic base such as triethylamine, diisopropylethylamine, pyridine and 4-dimethylaminopyridine, a metal alkoxide such as sodium methoxide. As the solvent, use can be made of an ether such as tetrahydrofuran, 1,4-dioxane and diglyme, an alcohol such as methanol and ethanol, and an aprotic solvent such as toluene, dimethylformamide and dimethyl sulfoxide. The reaction may be carried out in the absent of a solvent. The reaction temperature is selected from a range of room temperature to around the boiling point of the solvent.

In the process for preparing the compound (VIII) from the compound (XII), the compound (VIII) can also be obtained by synthesizing the compound (XIII) and then reacting it with the compound (XVI).

In a case where X is amino group, the compound (XIII) can be obtained by reacting the compound (XII) with guanidine in the presence or absence of a base.

As the base, use can be made of an alkali metal carbonate such as sodium carbonate and potassium carbonate, an alkaline earth metal carbonate such as calcium carbonate, a metal hydroxide such as sodium hydroxide and potassium hydroxide, an organic base such as triethylamine, diisopropylethylamine, pyridine and 4-dimethylaminopyridine, a metal alkoxide such as sodium methoxide.

As the solvent, use can be made of an ether such as tetrahydrofuran, 1,4-dioxane and diglyme, an alcohol such as methanol and ethanol, and an aprotic solvent such as toluene, dimethylformamide and dimethyl sulfoxide. The reaction may be carried out in the absence of a solvent. The reaction temperature is selected from a range of room temperature to around the boiling point of the solvent.

In a case where X is hydroxy group, the compound (XIII) can be obtained by reacting the compound (XII) with urea in the presence or absence of a base. As the base, use can be made of an alkali metal carbonate such as sodium carbonate and potassium carbonate, an alkaline earth metal carbonate such as calcium carbonate, a metal hydroxide such as sodium hydroxide and potassium hydroxide, an organic base such as triethylamine, diisopropylethylamine, pyridine and 4-dimethylaminopyridine, and a metal alkoxide such as sodium methoxide.

As the solvent, use can be made of an ether such as tetrahydrofuran, 1,4-dioxane and diglyme, an alcohol such as methanol and ethanol, and an aprotic solvent such as toluene, dimethylformamide and dimethyl sulfoxide. The reaction may be carried out in the absence of a solvent. The reaction temperature is selected from a range of room temperature to around the boiling point of the solvent.

In a case where X is mercapto group, the compound (XIII) can be obtained by reacting the compound (XII) with benzoylisothiocyanate in the presence or absence of a base, followed by cyclization. In the reaction with benzoylisothiocyanate, as the base, use can be made of an alkali metal carbonate such as sodium carbonate and potassium carbonate, an alkaline earth metal carbonate such as calcium carbonate and an organic base such as triethylamine, diisopropylethylamine, pyridine and 4-dimethylaminopyridine. As the solvent, use can be made of a halogenated hydrocarbon such as methylene chloride, an ether such as tetrahydrofuran and 1,4-dioxane and an aprotic solvent such as dimethylformamide and dimethyl sulfoxide. The reaction temperature is selected from a range of 0° C. to around the boiling point of the solvent.

In the cyclization reaction, as the base, use can be made of an alkali metal hydroxide such as sodium hydroxide and potassium hydroxide and a metal alkoxide such as sodium methoxide and potassium t-butoxide. As the solvent, use can be made of an ether such as tetrahydrofuran, an alcohol such as ethanol and 2-propanol and an aprotic solvent such as dimethylformamide and dimethyl sulfoxide. The reaction temperature is selected from a range of around room temperature to around the boiling point of the solvent.

The compound (VIII) can be obtained by reacting the compound (XIII) with the compound (XVI) in the presence of a base. As the base, use can be made of an alkali metal carbonate such as sodium carbonate and potassium carbonate, an alkaline earth metal carbonate such as calcium carbonate, a metal hydroxide such as sodium hydroxide and potassium hydroxide, a metal hydrogenate such as sodium hydride, an organic base such as triethylamine, diisopropylethylamine, pyridine and 4-dimethylaminopyridine and a metal alkoxide such as potassium t-butoxide. As the solvent, use can be made of a halogenated hydrocarbon such as carbon tetrachloride, chloroform and methylene chloride, an ether such as diethyl ether, tetrahydrofuran and 1,4-dioxane and an aprotic solvent such as dimethylformamide, dimethyl sulfoxide and acetonitrile. The reaction temperature is selected from a range of about 0° C. to around the boiling point of the solvent.

Preparation Method 3

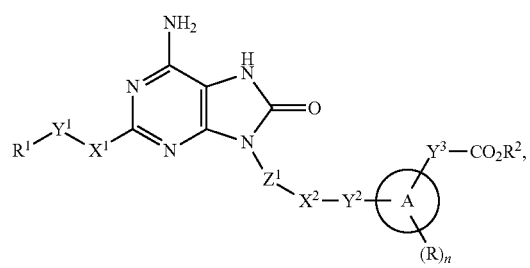

(XVIII)

wherein ring A, n, R, $R^1$, $R^2$, $X^1$, $X^2$, $Y^1$, $Y^2$, $Y^3$ and $Z^1$ have the same meanings as above.

In a case where $X^3$ is a leaving group, amino group, hydroxy group, mercapto group, carboxy group or sulfonic acid group in the above formula (II) to (XVI), each of them can be respectively converted to the compound (XVIII) according to a method known to the skilled artisan or similar thereto. Those methods are, for example, disclosed in "Comprehensive Organic Transformations, R. C. Lalock (VCH Publishers, Inc. 1989)". Those methods are concretely explained below.

(1) A Case where $X^3$ is a Leaving Group

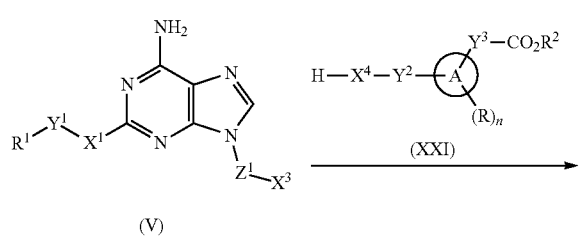

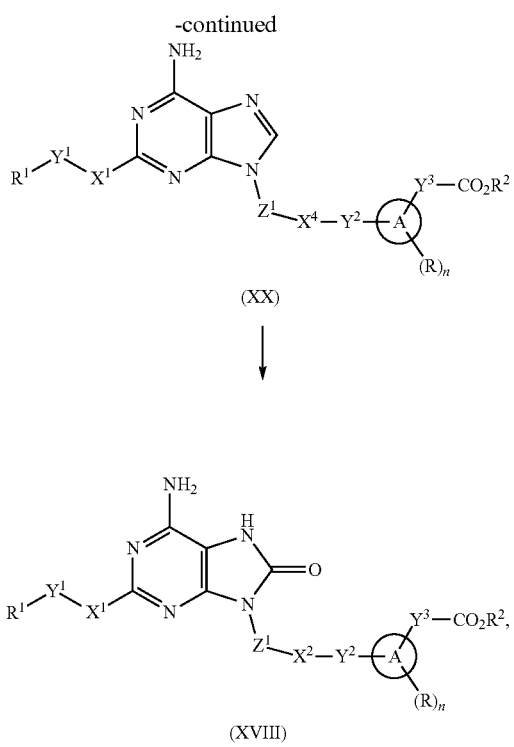

wherein ring A, n, R, $R^1$, $R^2$, $X^1$, $X^2$, $Y^1$, $Y^2$, $Y^3$ and $Z^1$ have the same meanings as above, and $X^4$ is oxygen atom, sulfur atom or $NR^5$.

The compound (XX) can be obtained by reacting the compound (V) (wherein $X^3$ is a leaving group) with the compound (XXI).

In case where $X^4$ is $NR^5$, the reaction is conducted in the presence or absence of a base. As the base, use can be made of an alkali metal carbonate such as sodium carbonate and potassium carbonate, an alkaline earth metal carbonate such as calcium carbonate, a metal hydroxide such as sodium hydroxide and potassium hydroxide and an organic base such as triethylamine, diisopropylethylamine and 4-dimethylaminopyridine. As the solvent, use can be made of an ether such as tetrahydrofuran and 1,4-dioxane and diglyme, an alcohol such as propanol and butanol and an aprotic solvent such as dimethylformamide, dimethyl sulfoxide or acetonitrile. The reaction may also be carried out in the absence of a solvent. The reaction temperature is selected from a range of room temperature to around the boiling point of the solvent.

In case where $X^4$ is oxygen atom or sulfur atom, the reaction is conducted in the presence of a base. As the base, use can be made of an alkali metal such as sodium or potassium or a alkali metal hydride such as sodium hydride. As the solvent, use can be made of an ether such as tetrahydrofuran and 1,4-dioxane and diglyme and an aprotic solvent such as dimethylformamide or dimethyl sulfoxide. The reaction may also be carried out in the absence of a solvent. The reaction temperature is selected from a range of room temperature to around the boiling point of the solvent.

(2) A Case where $X^3$ is Amino Group i) A Case where $X^2$ is $NR^5CO$, $NR^5SO_2$, $NR^5CONR^6$ or $NR^5CSNR^6$

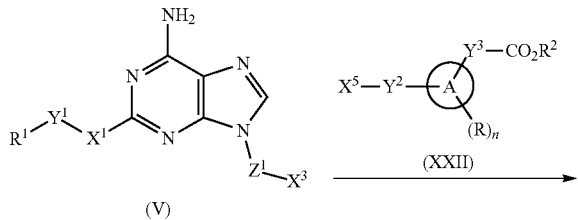

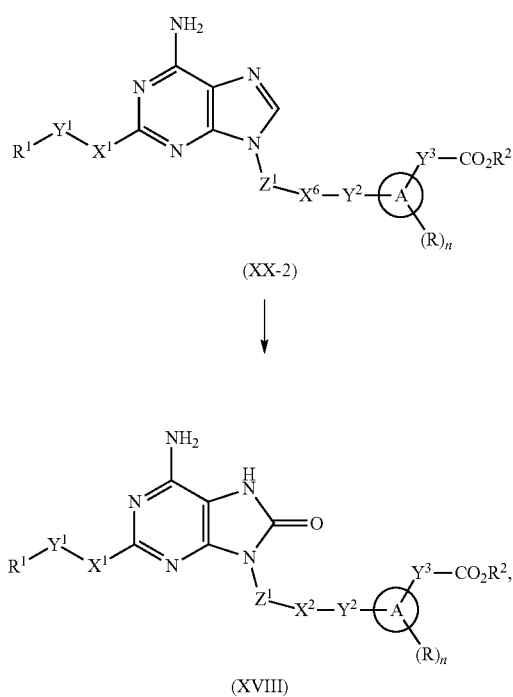

wherein ring A, n, R, $R^1$, $R^2$, $X^1$, $X^2$, $Y^1$, $Y^2$, $Y^3$ and $Z^1$ have the same meanings as above, $X^5$ is COCl, $SO_2Cl$, NCO or NCS, and $X^6$ is $NR^5CO$, $NR^5SO_2$, $NR^5CONR^6$ or $NR^5CSNR^6$.

The compound (XX) can be obtained by reacting the compound (V) (wherein $X^3$ is amino group) with the compound (XXII) in the presence or absence of a base. As the base, use can be made of an alkali metal carbonate such as sodium carbonate and potassium carbonate, an alkaline earth metal carbonate such as calcium carbonate and an organic base such as triethylamine, diisopropylethylamine and 4-dimethylaminopyridine. As the solvent, use can be made of a halogenated hydrocarbon such as carbon tetrachloride, chloroform and methylene chloride, an ether such as diethyl ether, tetrahydrofuran and 1,4-dioxane and an aprotic solvent such as toluene and xylene. The reaction temperature is selected from a range of about 0° C. to around the boiling point of the solvent.

ii) A Case where $X^2$ is $NR^5$

The compound (XIX-2) or the compound (XIX-3) which corresponds to the compound of formula (1) can be obtained by the following process.

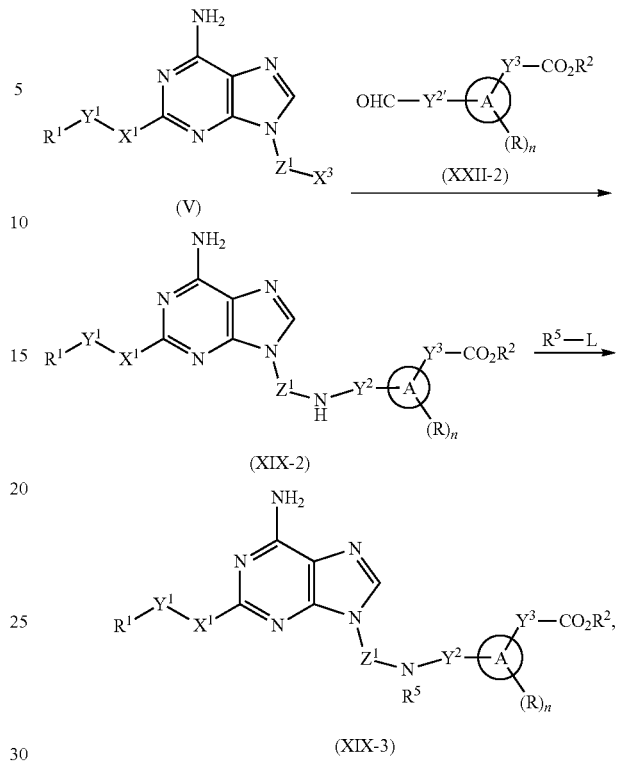

wherein ring A, n, R, $R^1$, $R^2$, $R^5$, $X^1$, $X^2$, $Y^1$, $Y^2$, $Y^3$, $Z^1$ and L have the same meanings as above, and $Y^{2'}$ is combined with methylene to represent $Y^2$.

The compound (XIX-2) can be obtained by reacting the compound (V) with the aldehyde compound (XXII-2) using a reducing agent such as sodium borohydride ($NaBH_4$) in a solvent such as methanol. When $R^5$ is except hydrogen atom, the compound (XIX-3) can be obtained by reacting the compound (XIX-2) with alkylating reagent such as a halogenated alkyl reagent in the presence of a base such as potassium carbonate in a solvent such as acetonitrile or dimethylformamide.

The compound (XIX-2) or the compound (XIX-3) can be also obtained in the following process.

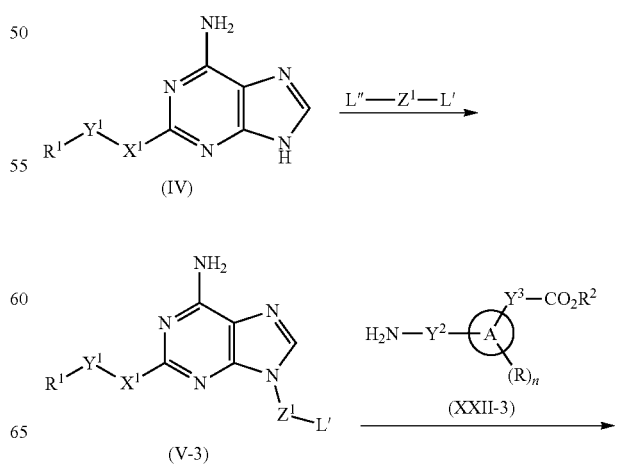

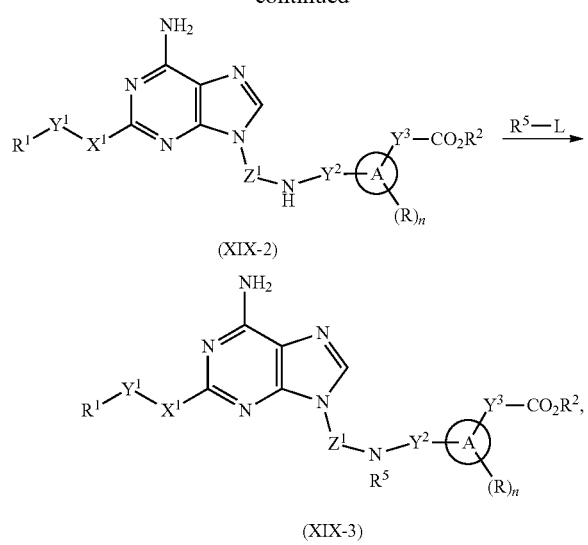

(XIX-2)

(XIX-3)

wherein ring A, n, R, $R^1$, $R^2$, $R^5$, $X^1$, $X^2$, $Y^1$, $Y^2$, $Y^3$, $Z^1$ and L have the same meanings as above, and L' and L" is the same or different, and is a leaving group.

The compound (V-3) can be obtained by reacting the compound (IV) with the compound shown as L"-$Z^1$-L' such as alkylene dihalide in the presence of a base such as potassium carbonate in the solvent such as dimethylformamide. The compound (XIX-2) can be obtained by reacting the compound (V-3) with the compound (XXII-3) under the same condition. The compound (XIX-2) is converted to the compound (XIX-3) wherein $R^5$ is the group except hydrogen in the same manner as mentioned above.

The compound (XIX-3) can be also obtained by the following process.

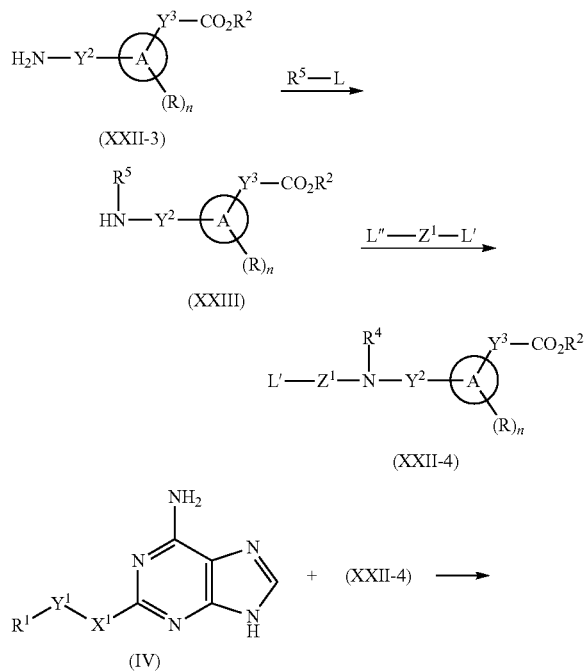

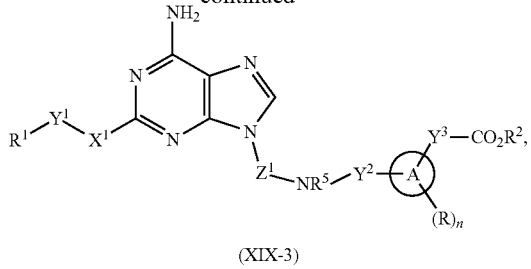

(XIX-3)

wherein ring A, n, R, $R^1$, $R^2$, $R^5$, $X^1$, $X^2$, $Y^1$, $Y^2$, $Y^3$, L' and L" have the same meanings as above.

The compound (XXII-4) can be obtained by alkylating the compound (XXII-3) in the two-steps process. The compound (XIX-3) can be obtained by condensing the compound (XXII-4) with the compound (IV) in the presence of a base such as potassium carbonate in a solvent such as dimethylformamide. In the case of the compound (XIX-3) wherein $R^5$ represent hydrogen atom, the compound (XXII-4) can be obtained by reacting the compound (XXII-3) with the compound shown as L"-$Z^1$-L' such as alkylene dihalide.

The amino group in the compound (V) can be protected if necessary, and the protecting group of the amino group can be deprotected to give the compound (V) wherein $X^3$ represents amino group. For example, the compound (V-1) can be obtained by reacting the compound (IV) with the compound (IX-2) in the presence of a base such as potassium carbonate in a solvent such as dimethylformamide. The obtained compound can be treated with hydrazine in a solvent such as ethanol to give the compound (V-2), namely the compound (V) wherein $X^3$ represents amino group.

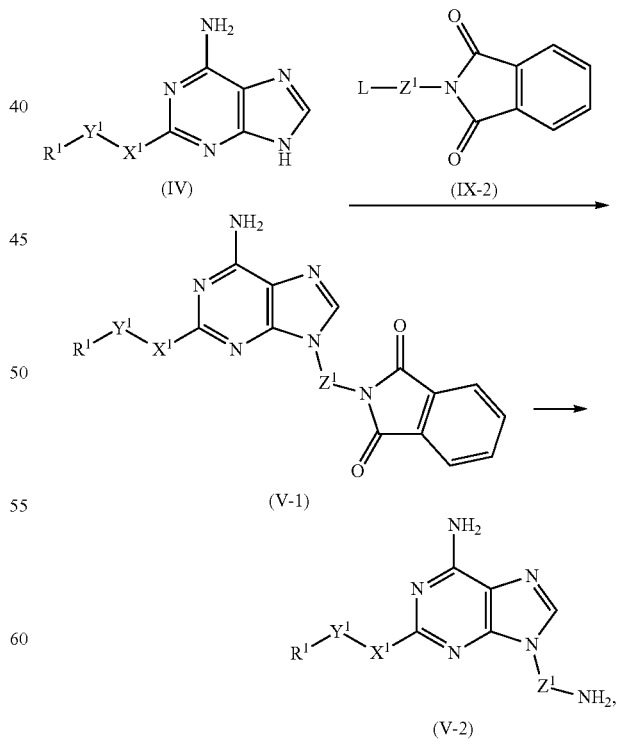

wherein $R^1$, $X^1$, $Y^1$, $Z^1$ and L have the same meanings as above.

(3) A Case where $X^3$ is Carboxy Group or Sulfonic Acid Group

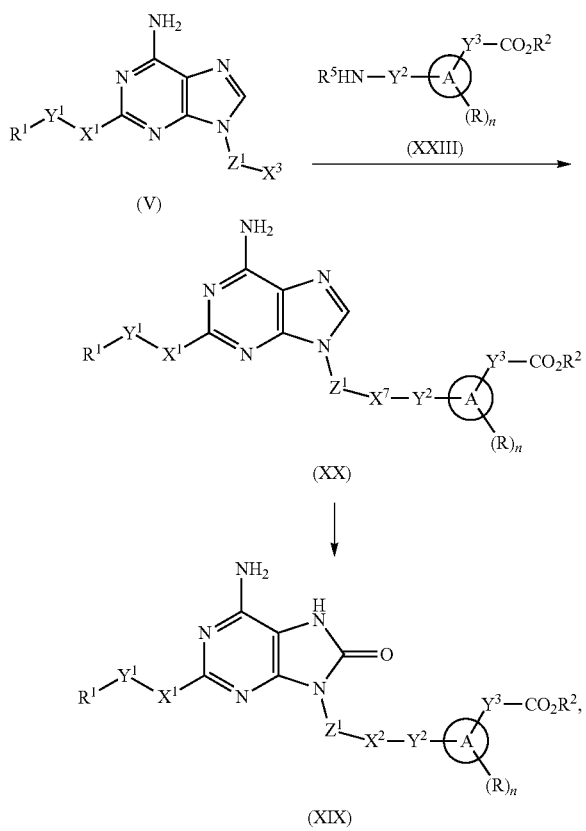

wherein ring A, n, R, $R^1$, $R^2$, $R^5$, $X^1$, $X^2$, $Y^1$, $Y^2$, $Y^3$ and $Z^1$ have the same meanings as above, and $X^7$ is $CONR^5$ or $SO_2NR^5$.

The compound (XX) can be obtained by converting the compound (V) wherein $X^3$ is carboxy group or sulfonic acid group to an acid halide compound and then reacting it with the compound (XXIII) in the presence or absence of a base. As the halogenating agent, use can be made of thionyl chloride, phosphoryl chloride, phosphorus pentachloride and phosphorus trichloride. As the solvent, use can be made of a halogenated hydrocarbon such as carbon tetrachloride, chloroform and methylene chloride, an ether such as diethyl ether, tetrahydrofuran and 1,4-dioxane and an aprotic solvent such as toluene and xylene. The reaction temperature is selected from a range of about 0° C. to around the boiling point of the solvent. As the base, use can be made of an alkali metal carbonate such as sodium carbonate and potassium carbonate, an alkaline earth metal carbonate such as calcium carbonate and an organic base such as triethylamine, diisopropylethylamine and 4-dimethylaminopyridine.

Each step described in the preparation method 3 can be conducted with the use of any of the compounds in the preparation method 1 or 2 as a starting material, so far as it does not hinder the preparation steps after the present preparation step, and can be conducted by any of the reaction scheme described in the preparation method 1 or 2. Further, in the preparation method 3, the compound of the formula (XX) can be converted to the compound of the formula (XIX) by the method described in the preparation method 1.

Preparation Method 4

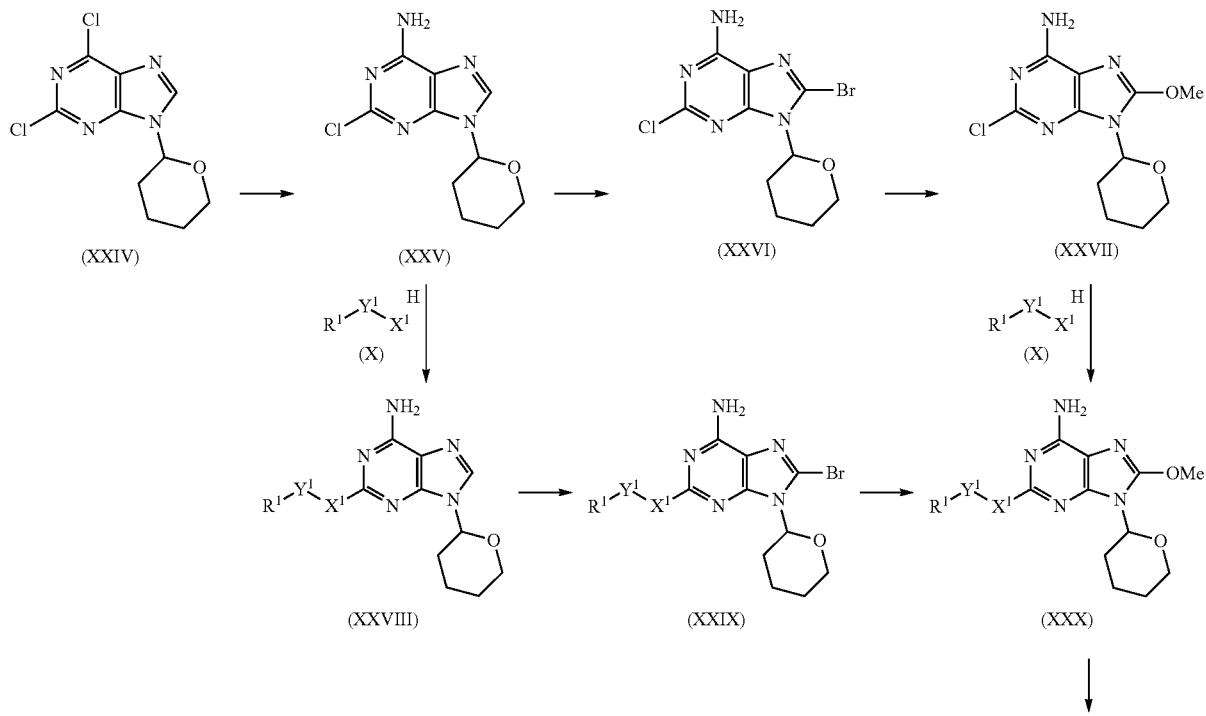

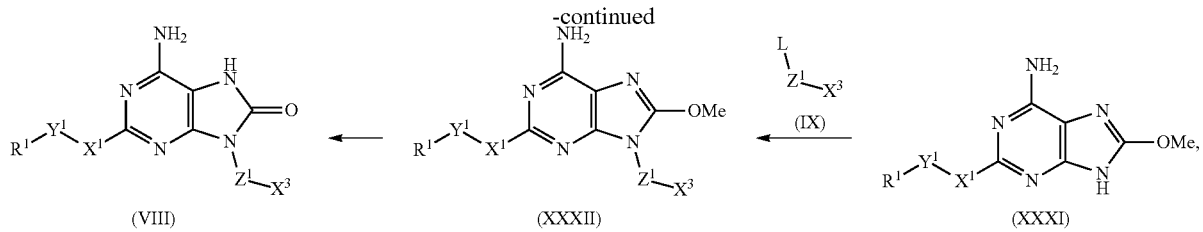

(VIII) (XXXII) (XXXI)

wherein L is a leaving group, and $R^1$, $Y^1$, $X^1$, $Z^1$ and $X^3$ have the same meanings as above.

The compound (XXV) can be obtained by reacting the compound (XXIV) with ammonia in an aqueous solution, an organic solvent or a mixture of water and an organic solvent.

The organic solvent includes an alcohol such as methanol, ethanol, propanol, and butanol, an ether such as tetrahydrofuran, 1,4-dioxane and diglyme, an aprotic solvent such as acetonitrile. The reaction temperature is selected from, for instance, around room temperature to 200° C. A reaction vessel such as an autoclave may optionally be used in the reaction.

The compound (XXVI) can be obtained in the same manner as the synthesis of the compound (III) using the compound (XXV).

The compound (XXVII) can be obtained by reacting the compound (XXVI) with sodium methoxide.

As the organic solvent, use is made of an ether such as diethyl ether, tetrahydrofuran and 1,4-dioxane, an aprotic solvent such as dimethylformamide and an alcohol such as methanol.

The reaction temperature is selected from, for instance, a range of room temperature to around the boiling point of the solvent.

Further, the compound (XXVII) can be obtained by treating the compound (XXVI) with an aqueous alkaline solution containing methanol.

As the aqueous alkaline solution, use is made of an aqueous solution of an alkali metal hydroxide such as sodium hydroxide and potassium hydroxide solution. The reaction temperature is selected from, for instance, a range of room temperature to around the boiling point of the solvent.

The compound (XXX) can be obtained in the same manner as the synthesis of the compound (VIII) using the compound (XXVII) in the preparation method 1.

Additionally, in the step from the compound (XXV) to the compound (XXX), the compound (XXVIII) is prepared by the same method as above, and it is converted into the compound (XXIX). The compound (XXX) can also be obtained from the compound (XXIX).

The compound (XXXI) can be obtained by treating the compound (XXX) with trifluoroacetic acid in the solvent such as methanol.

The compound (XXXII) can be prepared using the compound (XXXI) in the same manner as the synthesis of the compound (II) from the compound (I), or the synthesis of the compound (V) from the compound (IV) in the preparation method 1.

The compound (VIII) can be obtained by acid treatment of the compound (XXXII).

As the acid, use can be made of, for instance, an inorganic acid such as hydrochloric acid, hydrobromic acid and sulfuric acid, and an organic acid such as trifluoroacetic acid.

As the solvent, use can be made of, for instance, water, and a mixture of water and an organic solvent. The organic solvent is exemplified by an ether such as diethyl ether and tetrahydrofuran, an aprotic solvent such as dimethylformamide and acetonitrile and an alcohol such as methanol and ethanol. The reaction temperature is selected from, for instance, a range from room temperature to around the boiling point of the solvent.

The compound (XXXII) wherein $X^3$ represents a leaving group, amino group, hydroxy group, mercapto group, carboxy group or sulfonic acid group can be converted into the compound (XVIII-2):

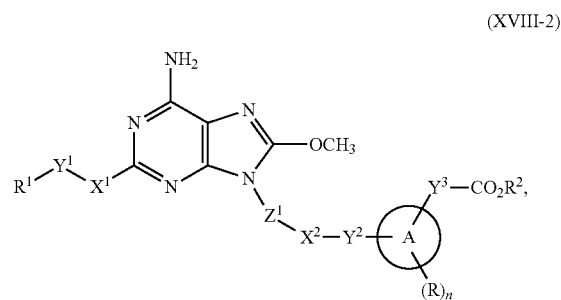

(XVIII-2)

wherein ring A, n, R, $R^1$, $R^2$, $X^1$, $X^2$, $Y^1$, $Y^2$, $Y^3$ and $Z^1$ have the same meanings as above, by using a method described in the above mentioned preparation method 3. And then, the compound (XVIII-2) is subjected to deprotection of the methoxy group by the acid treatment mentioned above to prepare the compound (XVIII):

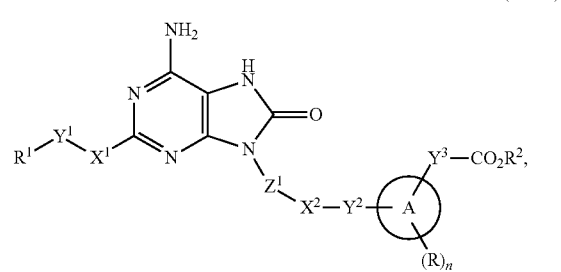

(XVIII)

wherein ring A, n, R, $R^1$, $R^2$, $X^1$, $X^2$, $Y^1$, $Y^2$, $Y^3$ and $Z^1$ have the same meanings as above.

The compound (XXXII) can also be subjected to deprotection of the methoxy group by the above mentioned acid treatment to give the 8-oxo-compound (VIII), and then the compound (VIII) is converted into the compound (XVIII) by using the preparation method 3.

In a case where the adenine compound of the present invention, its intermediate or the starting compound contains a functional group, a reaction for increasing a carbon atom, a reaction for introducing a substituent or a reaction for conversion of the functional group can be conducted optionally according to a manner conventional to the skilled artisan in an appropriate step, namely in an intermittent step in each of the preparation methods described in the preparation method 1 or 2. For this purpose, the methods described in "JIKKEN KAGAKU-KOZA (edited by NIHON KAGAKU-KAI, MARUZEN)", or "Comprehensive Organic Transformation, R. C. Lalock (VCH Publishers, Inc. 1989)" can be used. The reaction for increasing a carbon atom includes a method comprising converting an ester group to hydroxymethyl group using a reducing agent such as aluminum lithium hydride, introducing a leaving group and then introducing a cyano group. The reacting for conversion of a functional group includes a reaction for conducting acylation or sulfonylation using an acid halide, a sulfonyl halide, etc., a reaction for reacting an alkylation agent such as a halogenated alkyl, a hydrolysis reaction, a reaction for C—C bond formation such as Friedel-Crafts reaction and Wittig reaction, and oxidation reaction, a reducing reaction, etc.

In a case where the compound of the present invention or its intermediate contains a functional group such as amino group, carboxy group, hydroxy group and oxo group, a technology of protection and de-protection can optionally be used. A preferable protecting group, a protection method and a deprotection method are described in details in "Protective Groups in Organic Synthesis 2nd Edition (John Wiley & Sons, Inc.; 1990)", etc.

The compound (1) of the present invention and the intermediate compound for production thereof can be purified by a method known to the skilled artisan. For instance, purification can be conducted by column chromatography (e.g. silica gel column chromatography or ion exchange chromatography) or recrystallization. As the recrystallization solvent, for instance, use can be made of an alcohol such as methanol, ethanol and 2-propanol, an ether such as diethyl ether, an ester such as ethyl acetate, an aromatic hydrocarbon such as benzene and toluene, a ketone such as acetone, a hydrocarbon such as hexane, an aprotic solvent such as dimethylformamide and acetonitrile, water and a mixture of two or more thereof. As other purification method, use can be made of those described in "JIKKEN KAGAKU-KOZA (edited by NIHON KAGAKU-KAI, MARUZEN) Vol. 1", etc.

In a case where the compound of the formula (1) of the present invention contains one or more asymmetric carbons, its production can be conducted by using the starting material containing those asymmetric carbons or by introducing the asymmetric carbons during the production steps. For instance, in a case of an optical isomer, it can be obtained by using an optically active starting material or by conducting an optical resolution at a suitable stage of the production steps. The optical resolution method can be conducted by a diastereomer method comprising allowing the compound of the formula (1) or its intermediate to form a salt with an optically active acid (e.g. a monocarboxylic acid such as mandelic acid, N-benzyloxy alanine and lactic acid, a dicarboxylic acid such as tartaric acid, o-diisopropylidene tartrate and malic acid, a sulfonic acid such as camphor sulfonic acid and bromocamphor sulfonic acid) in an inert solvent (e.g. an alcohol such as methanol, ethanol, and 2-propanol, an ether such as diethyl ether, an ester such as ethyl acetate, a hydrocarbon such as toluene, an aprotic solvent such as acetonitrile and a mixture of two or more thereof).

In a case where the compound of the formula (1) or its intermediate contains a functional group such as carboxylic group, the object can be attained also by forming a salt with an optically active amine (e.g. an organic amine such as α-phenethylamine, quinine, quinidine, cinchonidine, cinchonine and strychinene).

The temperature for formation of the salt is selected from room temperature to the boiling point of the solvent. In order to increase optical purity, the temperature is preferably once increased up to the boiling point of the solvent. Upon recovering the salt formed by filtration, the yield can be increased optionally by cooling. An amount of the optical active acid or amine is about 0.5 to about 2.0 equivalent, preferably around 1 equivalent, relative to the substrate. An optically active salt with highly optical purity can be obtained optionally by recrystallization from an inert solvent (e.g. an alcohol such as methanol, ethanol and 2-propanol, an ether such as diethyl ether, an ester such as ethyl acetate, a hydrocarbon such as toluene, an aprotic solvent such as acetonitrile and a mixture of two or more thereof). If necessary, the optically resoluted salt can be converted into a free form by treating with an acid or a base by the conventional method.

The 8-oxoadenine compound and its pharmaceutically acceptable salt of the present invention is useful as an immuno-modulator and thus useful as a therapeutic and prophylactic agent for diseases associated with an abnormal immune response (e.g. autoimmune diseases and allergic diseases) and various infections and cancers which are required for activation of an immune response. For instance, the 8-oxoadenine compound and its pharmaceutically acceptable salt is useful as a therapeutic and prophylactic agent for the diseases mentioned in the following (1)-(8).

(1) Respiratory diseases: asthma, including bronchial, allergic, intrinsic, extrinsic, exercise-induced, drug-induced (including NSAID such as aspirin and indomethacin) and dust-induced asthma; intermittent and persistent and of all severities, and other causes of airway hyper-responsiveness; chronic obstructive pulmonary disease (COPD); bronchitis including infectious and eosinophilic bronchitis; emphysema; bronchiectasis; cystic fibrosis; sarcoidosis; farmer's lung and related diseases; hypersensitivity pneumonitis; lung fibrosis including cryptogenic fibrosing alveolitis, idiopathic interstitial pneumonias, fibrosis complicating antineoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

(2) (Skin) psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

(3) (Eyes) blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

(4) (Genitourinary) nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

(5) (Allograft rejection) acute and chronic following, for example, transplantation of kidney, heart, liver, lung, bone marrow, skin or cornea or following blood transfusion; or chronic graft versus host disease.

(6) Other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome, Sazary syndrome.

(7) (Oncology) treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes.

(8) (Infectious diseases) virus diseases such as genital warts, common warts, plantar warts, hepatitis B, hepatitis C, herpes simplex virus, molluscum contagiosum, variola, HIV, CMV, VZV, rhinovirus, adenovirus, coronavirus, influenza, para-influenza; bacterial diseases such as tuberculosis and *mycobacterium avium*, leprosy; other infectious diseases, such as fungal diseases, *chlamydia, candida, aspergillus*, cryptococcal meningitis, *pneumocystis carnii*, cryptosporidiosis, histoplasmosis, toxoplasmosis, trypanosome infection, leishmaniasis.

The 8-oxoadenine compounds or pharmaceutically acceptable salt thereof can also be used as vaccine adjuvant.

The 8-oxoadenine compound of the present invention, or its pharmaceutically acceptable salt shows an interferon inducing activity and/or a suppressing activity of the production of IL-4 and IL-5, and thus shows an effect as a medicament having an immunomodulating activity specific against type 1 helper T-cell (Th1 cell)/type 2 helper T-cell (Th2 cell), namely, preferably useful as a prophylactic or therapeutic agent for asthma caused by Th2 cell, and allergic diseases such as allergic rhinitis, allergic conjunctivitis and atopic dermatosis. Additionally, due to its an immuno activating activity such as interferon α and interferon γ inducing activity, it is useful as a prophylactic or therapeutic agent for cancer, a viral disease caused by infection with virus such as hepatitis B virus, hepatitis C virus, HIV and human papilloma virus (HPV), infections by bacteria and dermatosis such as psoriasis.

The compound of the present invention has no limitation as to its administration formulation and is administered orally or parenterally. The preparation for oral administration can be exemplified by capsules, powders, tablets, granules, fine-grain, syrups, solutions, suspensions, etc., and the preparation for parenteral administration can be exemplified by injections, drips, eye-drops, intrarectal preparations, inhalations, sprays (e.g. sprays, aerosols, liquids/suspensions for cartridge spray for inhalators or insufflators), lotions, gels, ointments, creams, transdermal preparations, transmucosa preparations, collunariums, ear drops, tapes, transdermal patches, cataplasms, powders for external application, and the like. Those preparations can be prepared by so-far known manners, and acceptable conventional carriers, fillers, binders, lubricants, stabilizers, disintegrants, buffering agents, solubilizing agents, isotonic agents, surfactants, antiseptics, perfumes, and so on can be used. Two or more pharmaceutical carriers can be appropriately used.

A liquid preparation such as emulsions and syrups, among the preparations for oral administration, can be prepared by using additives including water; a sugar such as sucrose, sorbitol and fructose; a glycol such as polyethylene glycol and propylene glycol; an oil such as sesame oil, olive oil and soybean oil; an antiseptic such as p-hydroxybenzoic acid ester; a flavor such as strawberry flavor and peppermint flavor. The solid preparation such as capsules, tablets, powders and granules can be prepared by using a filler such as lactose, glucose, sucrose and mannitol; a disintegrant such as starch and sodium alginate; a lubricant such as magnesium stearate and talc; a binder such as polyvinyl alcohol, hydroxypropyl cellulose and gelatin; a surfactant such as a fatty acid ester; a plasticizer such as glycerin.

The liquid preparation such as injections, drips, eye-drops and ear drops, among the preparations for parenteral administration, can be prepared preferably as a sterilized isotonic liquid preparation. For instance, injections can be prepared by using an aqueous medium such as a salt solution, a glucose solution or a mixture of a salt solution and a glucose solution. The preparation for intrarectal administration can be prepared by using a carrier such as cacao butter usually in the form of suppository.

The ointments, creams and gels contain the compound of the present invention usually in an amount of 0.01-10 w/w %, and there may be incorporated a thickening agent suitable to an aqueous or oily base and/or a gelling agent and/or a solvent. The base is exemplified by water and/or oil such as liquid paraffin, a vegetable oil such as arachis oil and castor oil, a solvent such as polyethylene glycol, and so on. The thickening agent and gelling agent are exemplified by soft paraffin, aluminum stearate, cetostearic alcohol, polyethylene glycol, sheep fat, beeswax, carboxypolymethylene and cellulose derivatives and/or glyceryl monostearate and/or nonionic emulsifiers.

The lotions contain the compound of the present invention usually in an amount of 0.01-10 w/w %, and it may be prepared with the use of an aqueous or oily base, it may contain generally emulsifiers, stabilizers, dispersing agents, precipitation inhibitors and also thickening agents.

Powders for external use contain the compound of the present invention usually an amount of 0.01-10 w/w %, and it may be formulated using a suitable powdery base such as talc, lactose and starch.

The drips may be formulated by using an aqueous or non-aqueous base, and may contain dispersing agents, solubilizing agents, precipitation inhibitors or antiseptics.

The sprays may be formulated into an aqueous solution or suspension using a suitable liquid propellant, or into an aerosol distributed from a pressured package such as a metered-dose inhaler.

The aerosols suitable to inhalation may be a suspension or aqueous solution, and they contain generally the compound of the present invention and a suitable propellant such as fluorocarbon, hydrogen-containing chlorofluorocarbon and a mixture thereof, particularly hydrofluoroalkane, specifically 1,1,1,2-tetrafluoroethane, 1,1,1,2,3,3,3-heptafluoro-n-propane or a mixture thereof. The aerosols may contain optionally additional excipients well known in the art such as a surfactant, (e.g., oleic acid or lecitin) and a co-solvent such as ethanol.

The gelatin capsules or cartridges used for inhalator or insufflator may be formulated by using a powdery mixture of the compounds used in the present invention and a powdery base such as lactose and starch. They contain the compound of the present invention usually in an amount of 20 µg-10 mg. The compound of the present invention may be administered without using excipients such as lactose as an alternative method.

The 8-oxoadenine compound of the present invention is preferably parenterally administered as a preparation for topical administration. The suitable preparation is exemplified by ointments, lotions, creams, gels, tapes, transdermal patches, cataplasms, sprays, aerosols, aqueous solutions/suspensions for cartridge spray for inhalators or insufflators, eye-drops, ear drops, nasal drops, powders for external administrations and so on.

A ratio of the active compound of the present invention in the preparation for topical administration of the present invention is, though depending upon the formulation, generally 0.001-10 wt %, preferably 0.005-1%. The ratio used in powders for inhalation or insufflation is 0.1-5%.

In a case of aerosols, the compound of the present invention is preferably contained in an amount of 20-2000 µg, more preferably about 20 µg-500 µg per each a measured amount or one sprayed amount. The dosage is once or several times per day, for instance, 2, 3, 4 or 8 times, and one to three units are administered per each time.

The 8-oxoadenine compound of the present invention, preferably the compound (I) wherein $R^2$ is except hydrogen atom, its tautomer or its pharmaceutically acceptable salt can show the pharmaceutical activity at the site administered in a case of topical administration, and further they are useful as a pharmaceutical preparation for topical administration characterized by showing no systemic pharmacological activity because the compounds are converted by an enzyme in vivo into different compounds (degraded compounds) having only a substantially reduced medical effect. The medical effect used here means a pharmacological activity of the compound, including specifically an interferon inducing activity, and a suppressing activity of the production IL-4 and/or IL-5.

The medical effect of the degraded compound is preferably 10 times, more preferably 100 times, still more preferably 1000 times reduced comparing with that of the parent compound.

The pharmacological activity can be measured by any of conventional evaluation methods, preferably by an in vitro evaluation method. Specific examples of the methods are one described in Method in ENZYMOLOGY (Academic Press), a method using commercially available ELISA kits (e.g. AN'ALYSA (immunoassay System)) and a method described in examples of the present specification.

For instance, by measuring interferon inducing activity with bioassay using cells of mouse spleen, the amount of each interferon induction (IU/ml at the same concentration of the parent compound (the compound of the present invention) and the degraded compound can be compared.

As the pharmacological activity, the activity in vivo caused by interferon inducing activity, etc. is illustrated. Said activity in vivo includes immune activating activity, influenza-like symptom, etc. The immune activating activity includes induction of cytotoxic activity such as natural killer (NK) cells, etc. The influenza-like symptom includes fever, etc. The fever means elevation in body temperature of a mammalian, for example, in a case of human, the fever means that the body temperature increases more than normal temperature.

The topical administration is not limited as to the administration method, and the administration is conducted in a case of administration via nasal cavity, alveolus or air way, by aeration or inhalation, in a case of administration to skin, by spreading on the skins, and in a case of administration to eye, by eye dropping, etc. Preferable administration is aeration and inhalation.

It can be confirmed that when the pharmaceutical composition for topical administration of the present invention is administered topically, the compound of the present invention therein is converted to a degraded compound in the blood, etc. in human or animal for example, by its half life in the serum or in lever S9 in vitro. The test method to determine the half life of the compound of the present invention in vitro is known.

In the vitro measuring test, the compound of the present invention is metabolized in liver S9 and its half life is preferably not longer than 60 minutes, more preferably not longer than 30 minutes, and still more preferably not longer than 10 minutes.

Further, the compound of the present invention is metabolized in serum, and its half life is preferably not longer than 60 minutes, more preferably not longer than 30 minutes, and still more preferably not longer than 10 minutes.

As the degraded compound, the compound of the formula (1) wherein $R^2$ is a hydrogen atom is exemplified, when the parent compound is the compound of the formula (1) wherein $R^2$ is a group except hydrogen atom.

The method for measuring the half life in liver S9 is as follows. Namely, the compound of the present invention is added to a liver S9 solution and incubated at 37±0.5° C. for 5 minutes to 2 hours. By quantitative analyzing at the definite interval the amount of the compound of the present invention remaining in the lever S9 solution with HPLC (high performance liquid chromatography), etc., the constant of quenching velocity calculated and the half life is calculated. The specific method is described in the Example.

The liver S9 solution used here means product obtained by homogenizing a liver of a mammal in an aqueous solution such as a physiological saline solution, a sucrose solution and a KCl solution and then by recovering the supernatant upon centrifugation at 9000×g. The aqueous solution is used usually in an amount of 2 to 4 times as much as the liver. The mammal includes human, dog, rabbit, guinea pig, mouse and rat. The liver S9 can be used optionally after dilution with a buffering solution.

The measuring method for the half life in serum of the present invention is as follows. Namely, the compound of the present invention is a serum solution and incubated at 37±0.5° C. for 5 minutes to 2 hours. By quantitative analyzing at the definite interval the amount of the compound of the present invention remaining in the serum solution with HPLC (high performance liquid chromatograph), etc., the constant of quenching velocity calculated and the half life is calculated.

The serum used here means a supernatant fraction obtained by leaving hemocytes and blood coagulation factor from blood by centrifugation, etc. and it may be used after dilution with a buffering solution.

The invention further relates to combination therapies wherein a compound of formula (1) or a pharmaceutically acceptable salt or a pharmaceutical composition or formulation comprising a compound of formula (1) is administered concurrently or sequentially or as a combined preparation with another therapeutic agent or agents, for the treatment of one or more of the conditions listed.

In particular, for the treatment of the inflammatory diseases, COPD, asthma and allergic rhinitis, the compounds of the invention may be combined with agents such as tumour necrosis factor alpha (TNF-a ) inhibitors such as anti-TNF monoclonal antibodies (for example Remicade, CDP-870 and adalimumab) and TNF receptor immunoglobulin molecules (such as Enbrel); non-selective cyclo-oxygenase (COX)-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocortico steroids (whether administered by topical, oral, intramuscular, intravenous, or intra-articular routes); methotrexate, lefunomide; hydroxychloroquine, d-penicillamine, auranofin or other parenteral or oral gold preparations.

The present invention still further relates to combination therapies of a compound of the invention together with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY×1005.

The present invention still further relates to combination therapies of a compound of the invention together with a receptor antagonist for leukotrienes (LT) B4, LTC4, LTD4, and LTE4 selected from the group consisting of phenothiazin compound such as L-651,392; amidino compounds such as CGS-25019; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to combination therapies of a compound of the invention together with a phosphodiesterase (PDE) inhibitor such as the methylxanthanines including theophylline and aminophylline; and selective PDE isoenzyme inhibitors including PDE4 inhibitors and inhibitors of isoform PDE4D, and inhibitors of PDE5.

The present invention still further relates to combination therapies of a compound of the invention together with histamine type 1 receptor antagonists such as cetirizine, loratadine, desloratadine, fexofenadine, acrivastine, terfenadine, astemizole, azelastine, levocabastine, chlorpheniramine, promethazine, cyclizine, and mizolastine, which is applied orally, topically or parenterally.

The present invention still further relates to combination therapies of a compound of the invention together with a gastroprotective histamine type 2 receptor antagonist.

The present invention still further relates to combination therapies of a compound of the invention with antagonists of the histamine type 4 receptor.

The present invention still further relates to combination therapies of a compound of the invention together with an alpha-1/alpha-2 adrenoceptor agonist, vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride.

The present invention still further relates to combination therapies of a compound of the invention together with anticholinergic agents including muscarinic receptor (M1, M2 and M3) antagonists such as atropine, hyoscine, glycopyrrolate, ipratropium bromide; tiotropium bromide; oxitropium bromide; pirenzepine; and telenzepine.

The present invention still further relates to combination therapies of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present invention still further relates to combination therapies of a compound of the invention together with a chromone, including sodium cromoglycate and nedocromil sodium.

The present invention still further relates to combination therapies of a compound of the invention together with an insulin-like growth factor type I (IGF-1) mimetic.

The present invention still further relates to combination therapies of a compound of the invention together with an inhaled glucocorticoid, such as flunisolide, triamcinolone acetonide, beclomethasone dipropionate, budesonide, fluticasone propionate, ciclesonide, and mometasone furoate.

The present invention still further relates to combination therapies of a compound of the invention together with an inhibitor of matrix metalloproteases (MMPs), i.e., stromelysin, collagenase, gelatinase, aggrecanase; especially collagenase-1 (MMP-1), collagenase-2 (MMP-8), collagenase-3 (MMP-13), stromelysin-1 (MMP-3), stromelysin-2 (MMP-10), stromelysin-3 (MMP-11), MMP-9 and MMP-12.

The present invention still further relates to combination therapies of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX3CR1 (for the C—X3-C family).

The present invention still further relates to combination therapies of a compound of the invention together with a cytokine or a modulator of cytokine function including agents which act on cytokine signalling pathways, such as alpha-, beta-, and gamma-interferon; interleukins (IL) including IL1 to 15, and interleukin antagonists or inhibitors.

The present invention still further relates to combination therapies of a compound of the invention together with an immunoglobulin (Ig), an Ig preparation, or an antagonist or antibody modulating Ig function such as anti-IgE (omalizumab).

The present invention still further relates to combination therapies of a compound of the invention together with thalidomide and derivatives, or systemic or topically-applied anti-inflammatory agents such as retinoids, dithranol, and calcipotriol.

The present invention still further relates to combination therapies of a compound of the invention together with an antibacterial agent including penicillin derivatives, tetracyclines, macrolides, beta-lactams, fluoroquinolones, and inhaled aminoglycosides; and antiviral agents including acyclovir, famciclovir, valaciclovir, ganciclovir, cidofovir, amantadine, rimantadine, ribavirin; zanamavirand oseltamavir; protease inhibitors such as indinavir, nelfinavir, ritonavir, and saquinavir; nucleoside reverse transcriptase inhibitors such as didanosine, lamivudine, stavudine, zalcitabine and zidovudine; non-nucleoside reverse transcriptase inhibitors such as nevirapine and efavirenz.

The present invention still further relates to combination therapies of a compound of the invention together with agents used for treatment of cancer. Suitable agents to be used in the combination therapies include:

(i) antiproliferative/antineoplastic drugs and combinations thereof, which are used as an anticancer agent, such as alkylating agents (for example cis platin, carboplatin, cyclophosphamide, nitrogen mustard, melphalan, chlorambucil, busulphan and nitrosoureas); antimetabolites (for example fluoropyrimidines like 5-fluorouracil and tegafur, antifolates such as raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti erbb2 antibody trastuzumab and the anti erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti vascular endothelial cell growth factor antibody bevacizumab, compounds disclosed in WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as combretastatin A4 and compounds disclosed in WO 99/02166, WO00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

The compounds of the present invention are illustrated in the following Tables 1 to 29, but should not be limited to these compounds. In these Tables, the compounds of the present invention are shown in a form of 8-hydroxy type for convenience and it is not different from 8-oxo type.

TABLE 1

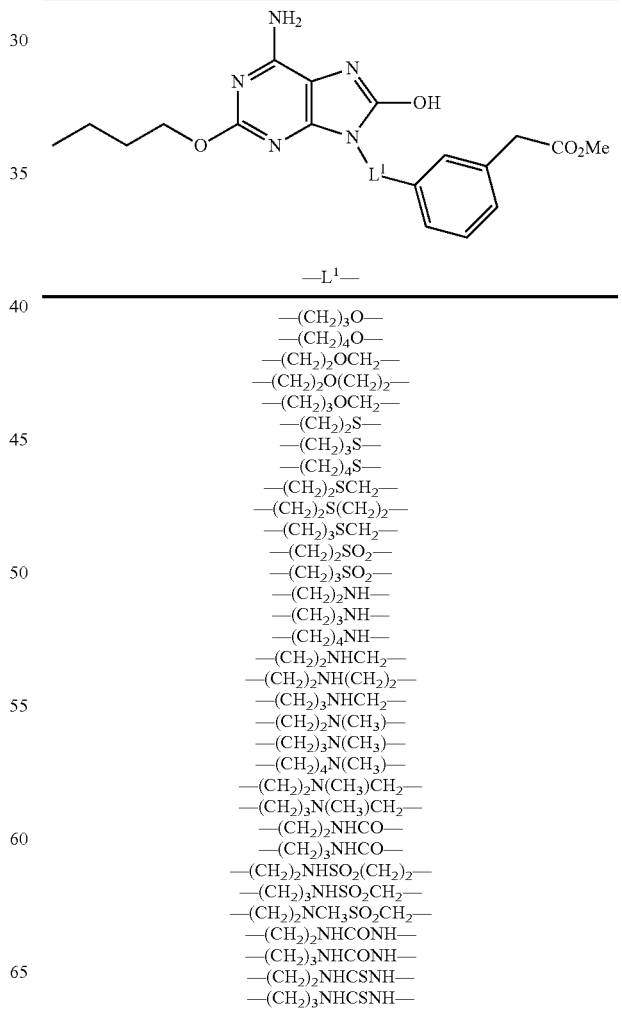

| $-L^1-$ |
|---|
| $-(CH_2)_3O-$ |
| $-(CH_2)_4O-$ |
| $-(CH_2)_2OCH_2-$ |
| $-(CH_2)_2O(CH_2)_2-$ |
| $-(CH_2)_3OCH_2-$ |
| $-(CH_2)_2S-$ |
| $-(CH_2)_3S-$ |
| $-(CH_2)_4S-$ |
| $-(CH_2)_2SCH_2-$ |
| $-(CH_2)_2S(CH_2)_2-$ |
| $-(CH_2)_3SCH_2-$ |
| $-(CH_2)_2SO_2-$ |
| $-(CH_2)_3SO_2-$ |
| $-(CH_2)_2NH-$ |
| $-(CH_2)_3NH-$ |
| $-(CH_2)_4NH-$ |
| $-(CH_2)_2NHCH_2-$ |
| $-(CH_2)_2NH(CH_2)_2-$ |
| $-(CH_2)_3NHCH_2-$ |
| $-(CH_2)_2N(CH_3)-$ |
| $-(CH_2)_3N(CH_3)-$ |
| $-(CH_2)_4N(CH_3)-$ |
| $-(CH_2)_2N(CH_3)CH_2-$ |
| $-(CH_2)_3N(CH_3)CH_2-$ |
| $-(CH_2)_2NHCO-$ |
| $-(CH_2)_3NHCO-$ |
| $-(CH_2)_2NHSO_2(CH_2)_2-$ |
| $-(CH_2)_3NHSO_2CH_2-$ |
| $-(CH_2)_2NCH_3SO_2CH_2-$ |
| $-(CH_2)_2NHCONH-$ |
| $-(CH_2)_3NHCONH-$ |
| $-(CH_2)_2NHCSNH-$ |
| $-(CH_2)_3NHCSNH-$ |

TABLE 1-continued

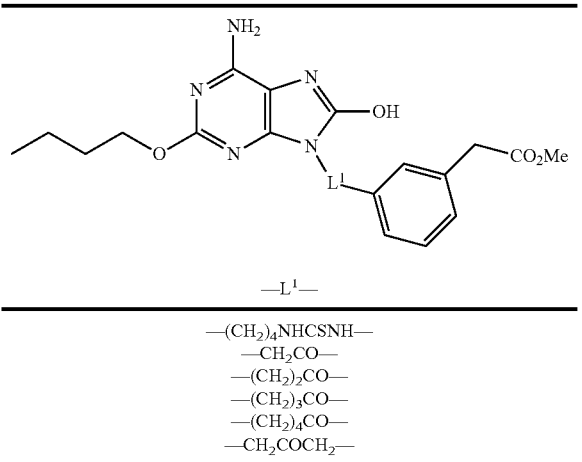

—L¹—

—(CH$_2$)$_4$NHCSNH—
—CH$_2$CO—
—(CH$_2$)$_2$CO—
—(CH$_2$)$_3$CO—
—(CH$_2$)$_4$CO—
—CH$_2$COCH$_2$—

TABLE 2

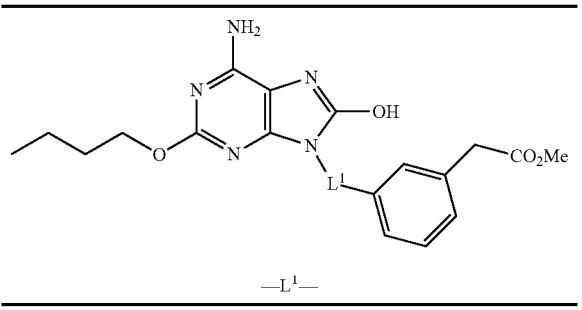

—L¹—

—(CH$_2$)$_4$SO$_2$—
—(CH$_2$)$_2$SO$_2$CH$_2$—
—(CH$_2$)$_2$SO$_2$(CH$_2$)$_2$—
—(CH$_2$)$_3$SO$_2$CH$_2$—
—(CH$_2$)$_2$SO$_2$NH—
—(CH$_2$)$_3$SO$_2$NH—
—(CH$_2$)$_4$SO$_2$NH—
—(CH$_2$)$_2$SO$_2$NHCH$_2$—
—(CH$_2$)$_2$SO$_2$NH(CH$_2$)$_2$—
—(CH$_2$)$_3$SO$_2$NHCH$_2$—
—(CH$_2$)$_2$SO$_2$N(CH$_3$)—
—(CH$_2$)$_3$SO$_2$N(CH$_3$)—
—(CH$_2$)$_2$SO$_2$N(CH$_3$)CH$_2$—
—(CH$_2$)$_3$SO$_2$N(CH$_3$)CH$_2$—
—(CH$_2$)$_4$NHCO—
—(CH$_2$)$_2$NHCOCH$_2$—
—(CH$_2$)$_3$NHCOCH$_2$—
—(CH$_2$)$_2$N(CH$_3$)CO—
—(CH$_2$)$_3$N(CH$_3$)CO—
—(CH$_2$)$_4$N(CH$_3$)CO—
—(CH$_2$)$_3$N(CH$_3$)COCH$_2$—
—(CH$_2$)$_2$NHCO$_2$CH$_2$—
—(CH$_2$)$_2$NHSO$_2$—
—(CH$_2$)$_3$NHSO$_2$—
—(CH$_2$)$_2$N(CH$_3$)SO$_2$—
—(CH$_2$)$_3$N(CH$_3$)SO$_2$—
—(CH$_2$)$_4$N(CH$_3$)SO$_2$—
—(CH$_2$)$_2$NHSO$_2$CH$_2$—
—CH$_2$CO(CH$_2$)$_2$—
—(CH$_2$)$_2$COCH$_2$—
—(CH$_2$)$_2$CO(CH$_2$)$_2$—
—CH$_2$CONH—
—(CH$_2$)$_2$CONH—
—(CH$_2$)$_3$CONH—
—CH$_2$CONHCH$_2$—
—(CH$_2$)$_2$CONHCH$_2$—
—CH$_2$CON(CH$_3$)—
—(CH$_2$)$_2$CON(CH$_3$)—
—(CH$_2$)$_3$CON(CH$_3$)—
—CH$_2$CON(CH$_3$)CH$_2$—

TABLE 2-continued

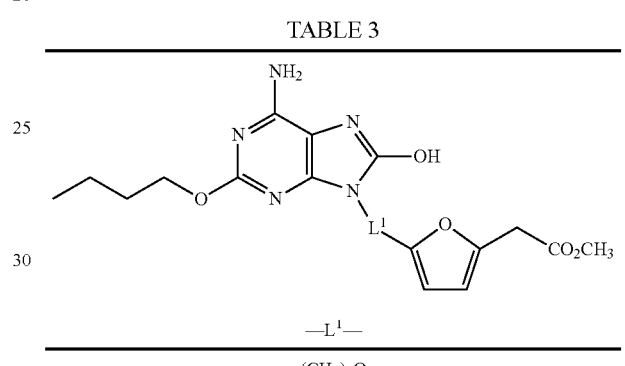

—L¹—

—CH$_2$CON(CH$_3$)(CH$_2$)$_2$—
—(CH$_2$)$_2$CON(CH$_3$)CH$_2$—

TABLE 3

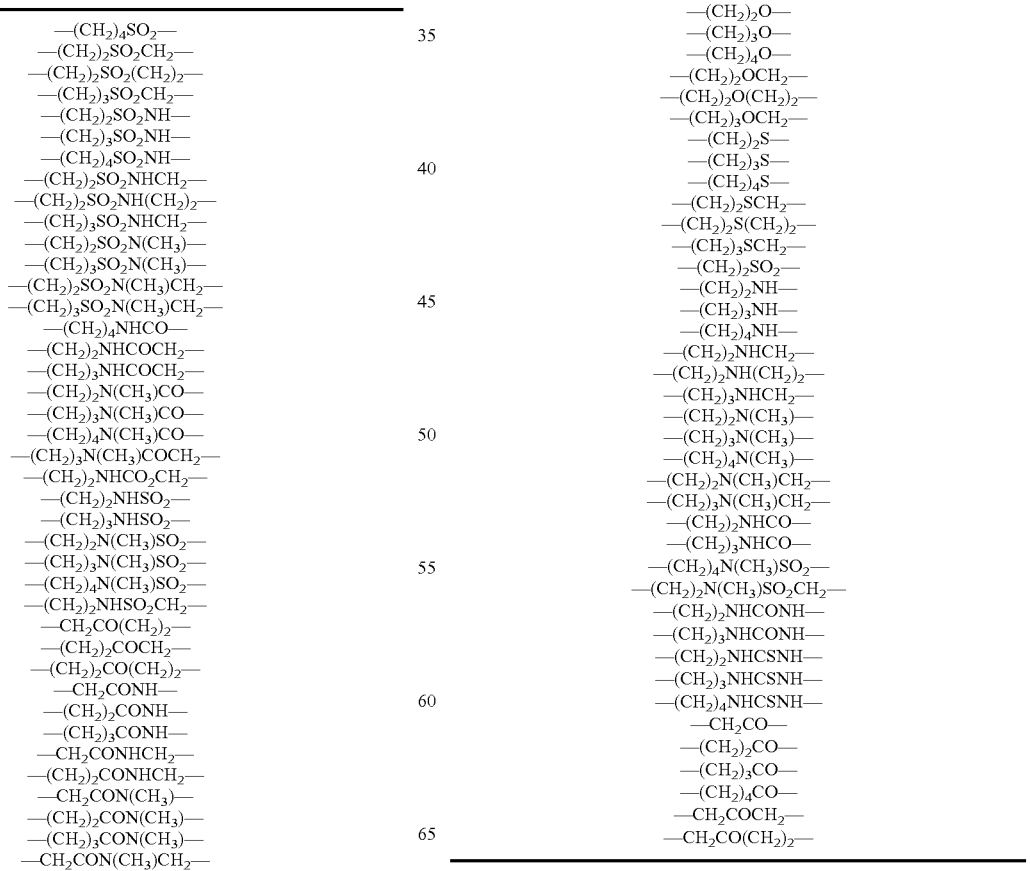

—L¹—

—(CH$_2$)$_2$O—
—(CH$_2$)$_3$O—
—(CH$_2$)$_4$O—
—(CH$_2$)$_2$OCH$_2$—
—(CH$_2$)$_2$O(CH$_2$)$_2$—
—(CH$_2$)$_3$OCH$_2$—
—(CH$_2$)$_2$S—
—(CH$_2$)$_3$S—
—(CH$_2$)$_4$S—
—(CH$_2$)$_2$SCH$_2$—
—(CH$_2$)$_2$S(CH$_2$)$_2$—
—(CH$_2$)$_3$SCH$_2$—
—(CH$_2$)$_2$SO$_2$—
—(CH$_2$)$_2$NH—
—(CH$_2$)$_3$NH—
—(CH$_2$)$_4$NH—
—(CH$_2$)$_2$NHCH$_2$—
—(CH$_2$)$_2$NH(CH$_2$)$_2$—
—(CH$_2$)$_3$NHCH$_2$—
—(CH$_2$)$_2$N(CH$_3$)—
—(CH$_2$)$_3$N(CH$_3$)—
—(CH$_2$)$_4$N(CH$_3$)—
—(CH$_2$)$_2$N(CH$_3$)CH$_2$—
—(CH$_2$)$_3$N(CH$_3$)CH$_2$—
—(CH$_2$)$_2$NHCO—
—(CH$_2$)$_3$NHCO—
—(CH$_2$)$_4$N(CH$_3$)SO$_2$—
—(CH$_2$)$_2$N(CH$_3$)SO$_2$CH$_2$—
—(CH$_2$)$_2$NHCONH—
—(CH$_2$)$_3$NHCONH—
—(CH$_2$)$_2$NHCSNH—
—(CH$_2$)$_3$NHCSNH—
—(CH$_2$)$_4$NHCSNH—
—CH$_2$CO—
—(CH$_2$)$_2$CO—
—(CH$_2$)$_3$CO—
—(CH$_2$)$_4$CO—
—CH$_2$COCH$_2$—
—CH$_2$CO(CH$_2$)$_2$—

TABLE 4

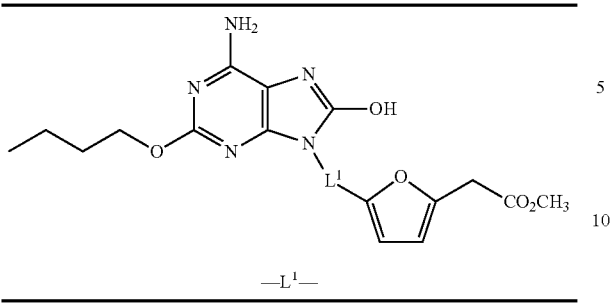

—L¹—

—(CH₂)₃SO₂—
—(CH₂)₄SO₂—
—(CH₂)₂SO₂CH₂—
—(CH₂)₂SO₂(CH₂)₂—
—(CH₂)₃SO₂CH₂—
—(CH₂)₂SO₂NH—
—(CH₂)₃SO₂NH—
—(CH₂)₄SO₂NH—
—(CH₂)₂SO₂NHCH₂—
—(CH₂)₂SO₂NH(CH₂)₂—
—(CH₂)₃SO₂NHCH₂—
—(CH₂)₂SO₂N(CH₃)—
—(CH₂)₃SO₂N(CH₃)—
—(CH₂)₄SO₂N(CH₃)—
—(CH₂)₂SO₂N(CH₃)CH₂—
—(CH₂)₃SO₂N(CH₃)CH₂—
—(CH₂)₄NHCO—
—(CH₂)₂NHCOCH₂—
—(CH₂)₃NHCOCH₂—
—(CH₂)₂N(CH₃)CO—
—(CH₂)₃N(CH₃)CO—
—(CH₂)₄N(CH₃)CO—
—(CH₂)₃N(CH₃)COCH₂—
—(CH₂)₂NHCO₂CH₂—
—(CH₂)₂NHSO₂—
—(CH₂)₃NHSO₂—
—(CH₂)₄NHSO₂—
—(CH₂)₂NHSO₂CH₂—
—(CH₂)₂NHSO₂(CH₂)₂—
—(CH₂)₃NHSO₂CH₂—
—(CH₂)₂N(CH₃)SO₂—
—(CH₂)₃N(CH₃)SO₂—
—(CH₂)₂COCH₂—
—CH₂CONH—
—(CH₂)₂CONH—
—(CH₂)₃CONH—
—CH₂CONHCH₂—
—(CH₂)₂CONHCH₂—
—CH₂CON(CH₃)—
—(CH₂)₂CON(CH₃)—
—(CH₂)₃CON(CH₃)—
—CH₂CON(CH₃)CH₂—
—CH₂CON(CH₃)(CH₂)₂—
—(CH₂)₂CON(CH₃)CH₂—

TABLE 5

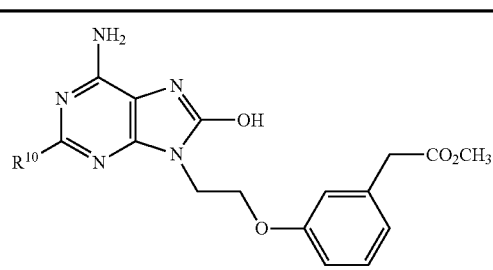

—R¹⁰—

—O(CH₂)₂CH₃
—O(CH₂)₄CH₃

TABLE 5-continued

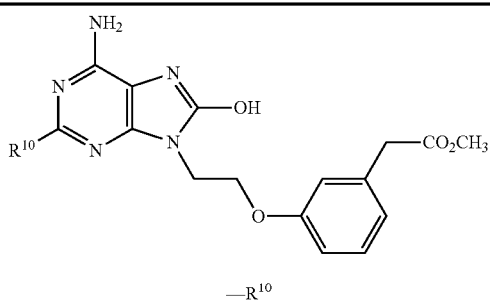

—R¹⁰—

—O(CH₂)₂OH
—O(CH₂)₃OH
—O(CH₂)₂OCH₃
—O(CH₂)₂OCH₂CH₃
—O(CH₂)₃OCH₃
—O(CH₂)₃CF₃

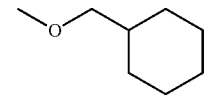

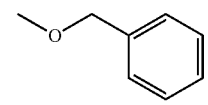

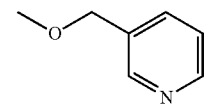

—S(CH₂)₂CH₃
—S(CH₂)₃CH₃
—S(CH₂)₂OH
—S(CH₂)₃OH
—S(CH₂)₄OH
—S(CH₂)₂OCH₃
—S(CH₂)₂OCH₂CH₃
—S(CH₂)₃OCH₃
—(CH₂)₃CH₃
—(CH₂)₂CO₂CH₃
—NH(CH₂)₂CH₃
—NH(CH₂)₃CH₃
—NH(CH₂)₂OCH₃
—NH(CH₂)₃OCH₃
—NCH₃(CH₂)₂CH₃
—NCH₃(CH₂)₃CH₃
—NCH₃(CH₂)₂OCH₃
—NCH₃(CH₂)₃OCH₃

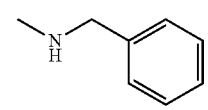

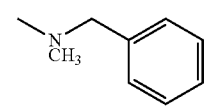

TABLE 6

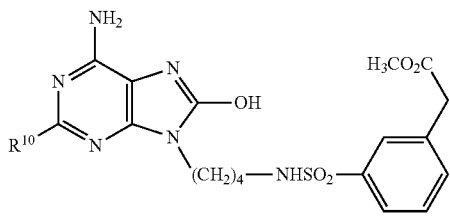

—R¹⁰

—O(CH₂)₂CH₃
—O(CH₂)₄CH₃
—O(CH₂)₂OH
—O(CH₂)₃OH
—O(CH₂)₂OCH₃
—O(CH₂)₂OCH₂CH₃
—O(CH₂)₃OCH₃
—O(CH₂)₃CF₃

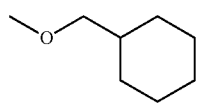

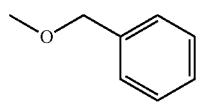

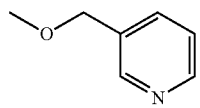

—S(CH₂)₂CH₃
—S(CH₂)₃CH₃
—S(CH₂)₂OH
—S(CH₂)₃OH
—S(CH₂)₄OH
—S(CH₂)₂OCH₃
—S(CH₂)₂OCH₂CH₃
—S(CH₂)₃OCH₃
—(CH₂)₃CH₃
—(CH₂)₂CO₂CH₃
—NH(CH₂)₂CH₃
—NH(CH₂)₃CH₃
—NH(CH₂)₂OCH₃
—NH(CH₂)₃OCH₃
—NCH₃(CH₂)₂CH₃
—NCH₃(CH₂)₃CH₃
—NCH₃(CH₂)₂OCH₃
—NCH₃(CH₂)₃OCH₃

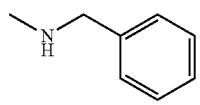

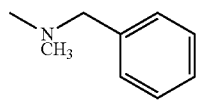

TABLE 7

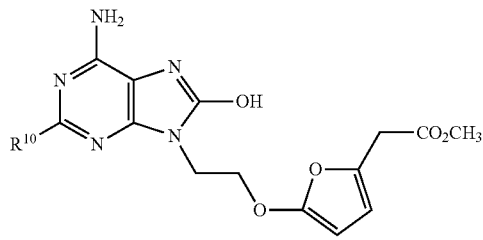

—R¹⁰

—O(CH₂)₂CH₃
—O(CH₂)₃CH₃
—O(CH₂)₂OH
—O(CH₂)₃OH
—O(CH₂)₂OCH₃
—O(CH₂)₂OCH₂CH₃
—O(CH₂)₃OCH₃
—O(CH₂)₃CF₃

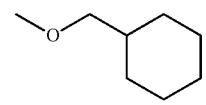

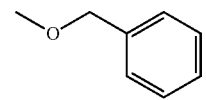

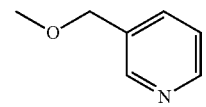

—S(CH₂)₂CH₃
—S(CH₂)₃CH₃
—S(CH₂)₂OH
—S(CH₂)₃OH
—S(CH₂)₄OH
—S(CH₂)₂OCH₃
—S(CH₂)₂OCH₂CH₃
—S(CH₂)₃OCH₃
—(CH₂)₃CH₃
—(CH₂)₂CO₂CH₃
—NH(CH₂)₂CH₃
—NH(CH₂)₃CH₃
—NH(CH₂)₂OCH₃
—NH(CH₂)₃OCH₃
—NCH₃(CH₂)₂CH₃
—NCH₃(CH₂)₃CH₃
—NCH₃(CH₂)₂OCH₃
—NCH₃(CH₂)₃OCH₃

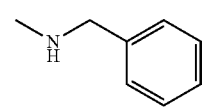

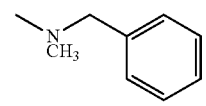

TABLE 8

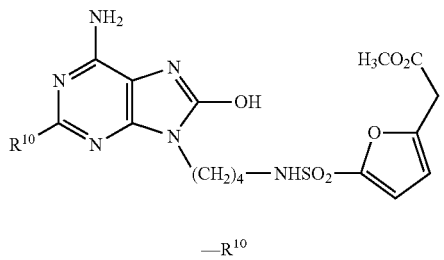

—R10

—O(CH₂)₂CH₃
—O(CH₂)₃CH₃
—O(CH₂)₂OH
—O(CH₂)₃OH
—O(CH₂)₂OCH₃
—O(CH₂)₂OCH₂CH₃
—O(CH₂)₃OCH₃
—O(CH₂)₃CF₃

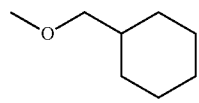

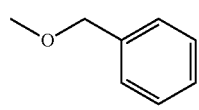

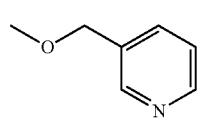

—S(CH₂)₂CH₃
—S(CH₂)₃CH₃
—S(CH₂)₂OH
—S(CH₂)₃OH
—S(CH₂)₄OH
—S(CH₂)₂OCH₃
—S(CH₂)₂OCH₂CH₃
—S(CH₂)₃OCH₃
—(CH₂)₃CH₃
—(CH₂)₂CO₂CH₃
—NH(CH₂)₂CH₃
—NH(CH₂)₃CH₃
—NH(CH₂)₂OCH₃
—NH(CH₂)₃OCH₃
—NCH₃(CH₂)₂CH₃
—NCH₃(CH₂)₃CH₃
—NCH₃(CH₂)₂OCH₃
—NCH₃(CH₂)₃OCH₃

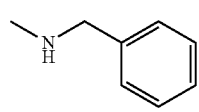

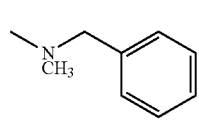

TABLE 9

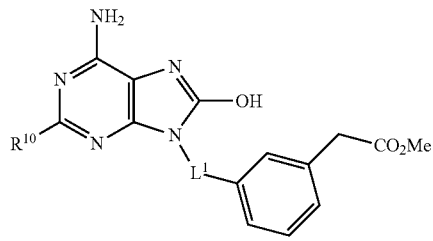

| —R10 | —L¹— |
|---|---|
| —O(CH₂)₂OCH₃ | —(CH₂)₃O— |
| —S(CH₂)₃CH₃ | —(CH₂)₄O— |
| —S(CH₂)₂OH | —(CH₂)₂OCH₂— |
| —(CH₂)₂CO₂CH₃ | —(CH₂)₃OCH₂— |
| —O(CH₂)₃CF₃ | —(CH₂)₂S— |
| —S(CH₂)₂OCH₃ | —(CH₂)₃S— |
| —NH(CH₂)₂OCH₃ | —(CH₂)₄S— |
| —NCH₃(CH₂)₂OCH₃ | —(CH₂)₂SCH₂— |
| —O(CH₂)₃OH | —(CH₂)₂S(CH₂)₂— |
| —S(CH₂)₃CF₃ | —(CH₂)₃SCH₂— |
| (benzyl methylamine) | —(CH₂)₂O(CH₂)₂— |
| —(CH₂)₂CO₂CH₃ | —(CH₂)₂SO₂— |

TABLE 10

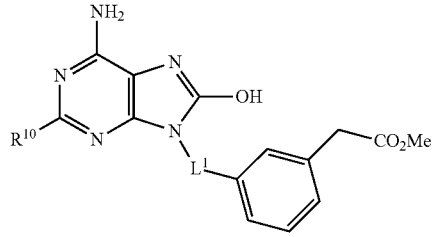

| —R10 | —L¹— |
|---|---|
| —O(CH₂)₂OCH₃ | —(CH₂)₃SO₂— |
| —S(CH₂)₃CH₃ | —(CH₂)₄SO₂— |
| —S(CH₂)₂OH | —(CH₂)₂SO₂CH₂— |
| —(CH₂)₂CO₂CH₃ | —(CH₂)₃SO₂CH₂— |
| —O(CH₂)₃CF₃ | —(CH₂)₂SO₂NH— |
| —S(CH₂)₂OCH₃ | —(CH₂)₃SO₂NH— |
| —NH(CH₂)₂OCH₃ | —(CH₂)₄SO₂NH— |
| —NCH₃(CH₂)₂OCH₃ | —(CH₂)₂SO₂NHCH₂— |
| —O(CH₂)₃OH | —(CH₂)₂SO₂NH(CH₂)₂— |
| —S(CH₂)₃CF₃ | —(CH₂)₃SO₂NHCH₂— |
| (benzyl methylamine) | —(CH₂)₂SO₂(CH₂)₂— |
| —(CH₂)₂CO₂CH₃ | —(CH₂)₂SO₂NCH₃— |

TABLE 11

[Structure: adenine with 8-OH, 9-N substituted with L¹-phenyl-CH₂CO₂Me, 2-position R¹⁰]

| —R¹⁰ | —L¹— |
|---|---|
| —O(CH₂)₂OCH₃ | —(CH₂)₃SO₂NCH₃— |
| —S(CH₂)₃CH₃ | —(CH₂)₄SO₂NCH₃— |
| —S(CH₂)₂OH | —(CH₂)₂SO₂NCH₃CH₂— |
| —(CH₂)₂CO₂CH₃ | —(CH₂)₂NH— |
| —O(CH₂)₃CF₃ | —(CH₂)₃NH— |
| —S(CH₂)₂OCH₃ | —(CH₂)₄NH— |
| —NH(CH₂)₂OCH₃ | —(CH₂)₂NHCH₂— |
| —NCH₃(CH₂)₂OCH₃ | —(CH₂)₂NH(CH₂)₂— |
| —O(CH₂)₃OH | —(CH₂)₃NHCH₂— |
| —S(CH₂)₃CF₃ | —(CH₂)₂NCH₃— |
| —NH-CH₂-C₆H₅ (N-methylbenzylamine) | —(CH₂)₃SO₂NHCH₂— |
| —(CH₂)₂CO₂CH₃ | —(CH₂)₃NCH₃— |

TABLE 12

[Same core structure]

| —R¹⁰ | —L¹— |
|---|---|
| —O(CH₂)₂OCH₃ | —(CH₂)₄NCH₃— |
| —S(CH₂)₃CH₃ | —(CH₂)₂N(CH₃)CH₂— |
| —S(CH₂)₂OH | —(CH₂)₃N(CH₃)CH₂— |
| —(CH₂)₂CO₂CH₃ | —(CH₂)₃NHCO— |
| —O(CH₂)₃CF₃ | —(CH₂)₄NHCO— |
| —S(CH₂)₂OCH₃ | —(CH₂)₂NHCOCH₂— |
| —NH(CH₂)₂OCH₃ | —(CH₂)₃NHCOCH₂— |
| —NCH₃(CH₂)₂OCH₃ | —(CH₂)₂N(CH₃)CO— |
| —O(CH₂)₃OH | —(CH₂)₃N(CH₃)CO— |
| —S(CH₂)₃CF₃ | —(CH₂)₄N(CH₃)CO— |
| —NH-CH₂-C₆H₅ (N-methylbenzylamine) | —(CH₂)₂NHCO— |
| —(CH₂)₂CO₂CH₃ | —(CH₂)₃N(CH₃)COCH₂— |

TABLE 13

[Same core structure]

| —R¹⁰ | —L¹— |
|---|---|
| —O(CH₂)₂OCH₃ | —(CH₂)₂NCOOCH₂— |
| —S(CH₂)₃CH₃ | —(CH₂)₂NHSO₂— |
| —S(CH₂)₂OH | —(CH₂)₃NHSO₂— |
| —(CH₂)₂CO₂CH₃ | —(CH₂)₂NHSO₂(CH₂)₂— |
| —O(CH₂)₃CF₃ | —(CH₂)₂NHSO₂CH₂— |
| —S(CH₂)₂OCH₃ | —(CH₂)₂N(CH₃)SO₂— |
| —NH(CH₂)₂OCH₃ | —(CH₂)₃N(CH₃)SO₂— |
| —NCH₃(CH₂)₂OCH₃ | —(CH₂)₄N(CH₃)SO₂— |
| —O(CH₂)₃OH | —(CH₂)₂N(CH₃)SO₂CH₂— |
| —S(CH₂)₃CF₃ | —(CH₂)₂NHCONH— |
| —NH-CH₂-C₆H₅ (N-methylbenzylamine) | —(CH₂)₂NHSO₂CH₂— |
| —(CH₂)₂CO₂CH₃ | —(CH₂)₃NHCONH— |

TABLE 14

[Same core structure]

| —R¹⁰ | —L¹— |
|---|---|
| —O(CH₂)₂OCH₃ | —(CH₂)₂NHCSNH— |
| —S(CH₂)₃CH₃ | —(CH₂)₃NHCSNH— |
| —S(CH₂)₂OH | —(CH₂)₄NHCSNH— |
| —(CH₂)₂CO₂CH₃ | —(CH₂)₂CO— |
| —O(CH₂)₃CF₃ | —(CH₂)₃CO— |
| —S(CH₂)₂OCH₃ | —(CH₂)₄CO— |
| —NH(CH₂)₂OCH₃ | —CH₂COCH₂— |
| —NCH₃(CH₂)₂OCH₃ | —CH₂CO(CH₂)₂— |
| —O(CH₂)₃OH | —(CH₂)₂COCH₂— |
| —S(CH₂)₃CF₃ | —(CH₂)₂CO(CH₂)₂— |
| —NH-CH₂-C₆H₅ (N-methylbenzylamine) | —CH₂CO— |
| —(CH₂)₂CO₂CH₃ | —CH₂CONH— |

TABLE 15

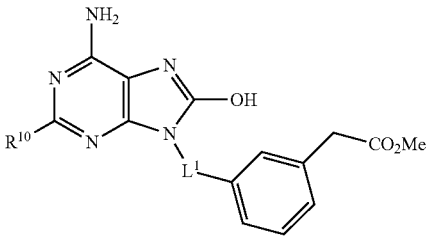

| —R10 | —L1— |
|---|---|
| —O(CH2)2OCH3 | —(CH2)2CONH— |
| —S(CH2)3CH3 | —(CH2)3CONH— |
| —S(CH2)2OH | —CH2CONHCH2— |
| —(CH2)2CO2CH3 | —(CH2)2CONHCH2— |
| —O(CH2)3CF3 | —CH2CON(CH3)— |
| —S(CH2)2OCH3 | —(CH2)2CON(CH3)— |
| —NH(CH2)2OCH3 | —(CH2)3CON(CH3)— |
| —NCH3(CH2)2OCH3 | —CH2CON(CH3)CH2— |
| —O(CH2)3OH | —CH2CON(CH3)(CH2)2— |
| —S(CH2)3CF3 | —(CH2)2CON(CH3)CH2— |
| 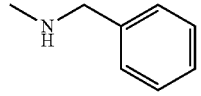 | —(CH2)3CONH— |

TABLE 16

| —R10 | —L1— |
|---|---|
| —O(CH2)2OCH3 | —(CH2)3O— |
| —S(CH2)3CH3 | —(CH2)4O— |
| —S(CH2)2OH | —(CH2)2OCH2— |
| —(CH2)2CO2CH3 | —(CH2)3OCH2— |
| —O(CH2)3CF3 | —(CH2)2S— |
| —S(CH2)2OCH3 | —(CH2)3S— |
| —NH(CH2)2OCH3 | —(CH2)4S— |
| —NCH3(CH2)2OCH3 | —(CH2)2SCH2— |
| —O(CH2)3OH | —(CH2)2S(CH2)2— |
| —S(CH2)3CF3 | —(CH2)3SCH2— |
| 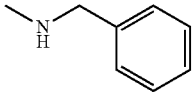 | —(CH2)2O(CH2)2— |
| —(CH2)2CO2CH3 | —(CH2)2SO2— |

TABLE 17

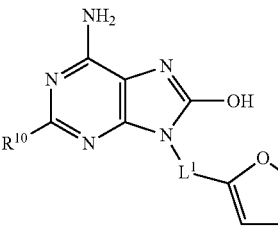

| —R10 | —L1— |
|---|---|
| —O(CH2)2OCH3 | —(CH2)3SO2— |
| —S(CH2)3CH3 | —(CH2)4SO2— |
| —S(CH2)2OH | —(CH2)2SO2CH2— |
| —(CH2)2CO2CH3 | —(CH2)3SO2CH2— |
| —O(CH2)3CF3 | —(CH2)2SO2NH— |
| —S(CH2)2OCH3 | —(CH2)3SO2NH— |
| —NH(CH2)2OCH3 | —(CH2)4SO2NH— |
| —NCH3(CH2)2OCH3 | —(CH2)2SO2NHCH2— |
| —O(CH2)3OH | —(CH2)2SO2NH(CH2)2— |
| —S(CH2)3CF3 | —(CH2)3SO2NHCH2— |
|  | —(CH2)2SO2(CH2)2— |
| —(CH2)2CO2CH3 | —(CH2)2SO2NCH3— |

TABLE 18

| —R10 | —L1— |
|---|---|
| —O(CH2)2OCH3 | —(CH2)3SO2NCH3— |
| —S(CH2)3CH3 | —(CH2)4SO2NCH3— |
| —S(CH2)2OH | —(CH2)2SO2NCH3CH2— |
| —(CH2)2CO2CH3 | —(CH2)2NH— |
| —O(CH2)3CF3 | —(CH2)3NH— |
| —S(CH2)2OCH3 | —(CH2)4NH— |
| —NH(CH2)2OCH3 | —(CH2)2NHCH2— |
| —NCH3(CH2)2OCH3 | —(CH2)2NH(CH2)2— |
| —O(CH2)3OH | —(CH2)3NHCH2— |
| —S(CH2)3CF3 | —(CH2)2NCH3— |
| | —(CH2)3SO2NHCH2— |
| —(CH2)2CO2CH3 | —(CH2)3NCH3— |

TABLE 19

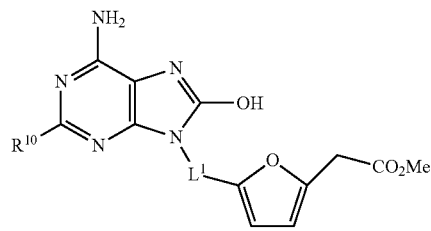

| —R$^{10}$ | —L$^{1}$— |
|---|---|
| —O(CH$_2$)$_2$OCH$_3$ | —(CH$_2$)$_4$NCH$_3$— |
| —S(CH$_2$)$_3$CH$_3$ | —(CH$_2$)$_2$N(CH$_3$)CH$_2$— |
| —S(CH$_2$)$_2$OH | —(CH$_2$)$_3$N(CH$_3$)CH$_2$— |
| —(CH$_2$)$_2$CO$_2$CH$_3$ | —(CH$_2$)$_3$NHCO— |
| —O(CH$_2$)$_3$CF$_3$ | —(CH$_2$)$_4$NHCO— |
| —S(CH$_2$)$_2$OCH$_3$ | —(CH$_2$)$_2$NHCOCH$_2$— |
| —NH(CH$_2$)$_2$OCH$_3$ | —(CH$_2$)$_3$NHCOCH$_2$— |
| —NCH$_3$(CH$_2$)$_2$OCH$_3$ | —(CH$_2$)$_2$N(CH$_3$)CO— |
| —O(CH$_2$)$_3$OH | —(CH$_2$)$_3$N(CH$_3$)CO— |
| —S(CH$_2$)$_3$CF$_3$ | —(CH$_2$)$_4$N(CH$_3$)CO— |
| 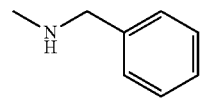 | —(CH$_2$)$_2$NHCO— |
| —(CH$_2$)$_2$CO$_2$CH$_3$ | —(CH$_2$)$_3$N(CH$_3$)COCH$_2$— |

TABLE 21

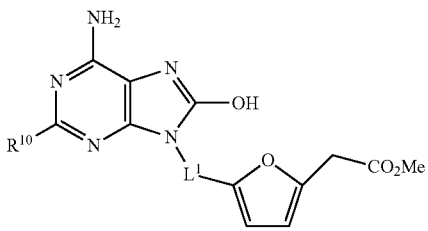

| —R$^{10}$ | —L$^{1}$— |
|---|---|
| —O(CH$_2$)$_2$OCH$_3$ | —(CH$_2$)$_2$NHCSNH— |
| —S(CH$_2$)$_3$CH$_3$ | —(CH$_2$)$_3$NHCSNH— |
| —S(CH$_2$)$_2$OH | —(CH$_2$)$_4$NHCSNH— |
| —(CH$_2$)$_2$CO$_2$CH$_3$ | —(CH$_2$)$_2$CO— |
| —O(CH$_2$)$_3$CF$_3$ | —(CH$_2$)$_3$CO— |
| —S(CH$_2$)$_2$OCH$_3$ | —(CH$_2$)$_4$CO— |
| —NH(CH$_2$)$_2$OCH$_3$ | —CH$_2$OCH$_2$— |
| —NCH$_3$(CH$_2$)$_2$OCH$_3$ | —CH$_2$CO(CH$_2$)$_2$— |
| —O(CH$_2$)$_3$OH | —(CH$_2$)$_2$COCH$_2$— |
| —S(CH$_2$)$_3$CF$_3$ | —(CH$_2$)$_2$CO(CH$_2$)$_2$— |
| 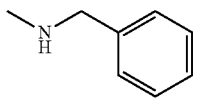 | —CH$_2$CO— |
| —(CH$_2$)$_2$CO$_2$CH$_3$ | —CH$_2$CONH— |

TABLE 20

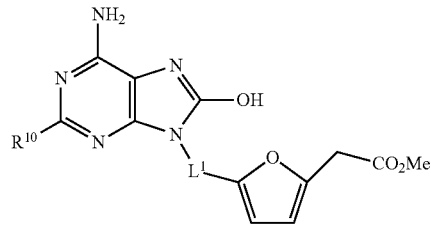

| —R$^{10}$ | —L$^{1}$— |
|---|---|
| —O(CH$_2$)$_2$OCH$_3$ | —(CH$_2$)$_2$NHCOOCH$_2$— |
| —S(CH$_2$)$_3$CH$_3$ | —(CH$_2$)$_2$NHSO$_2$— |
| —S(CH$_2$)$_2$OH | —(CH$_2$)$_3$NHSO$_2$— |
| —(CH$_2$)$_2$CO$_2$CH$_3$ | —(CH$_2$)$_2$NHSO$_2$(CH$_2$)$_2$— |
| —O(CH$_2$)$_3$CF$_3$ | —(CH$_2$)$_3$NHSO$_2$CH$_2$— |
| —S(CH$_2$)$_2$OCH$_3$ | —(CH$_2$)$_2$N(CH$_3$)SO$_2$— |
| —NH(CH$_2$)$_2$OCH$_3$ | —(CH$_2$)$_3$N(CH$_3$)SO$_2$— |
| —NCH$_3$(CH$_2$)$_2$OCH$_3$ | —(CH$_2$)$_4$N(CH$_3$)SO$_2$— |
| —O(CH$_2$)$_3$OH | —(CH$_2$)$_2$N(CH$_3$)SO$_2$CH$_2$— |
| —S(CH$_2$)$_3$CF$_3$ | —(CH$_2$)$_2$NHCONH— |
| 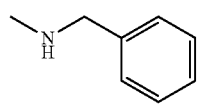 | —(CH$_2$)$_2$NHSO$_2$CH$_2$— |
| —(CH$_2$)$_2$CO$_2$CH$_3$ | —(CH$_2$)$_3$NHCONH— |

TABLE 22

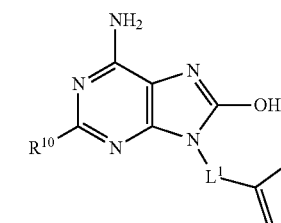

| —R$^{10}$ | —L$^{1}$— |
|---|---|
| —O(CH$_2$)$_2$OCH$_3$ | —(CH$_2$)$_2$CONH— |
| —S(CH$_2$)$_3$CH$_3$ | —(CH$_2$)$_3$CONH— |
| —S(CH$_2$)$_2$OH | —CH$_2$CONHCH$_2$— |
| —(CH$_2$)$_2$CO$_2$CH$_3$ | —(CH$_2$)$_2$CONHCH$_2$— |
| —O(CH$_2$)$_3$CF$_3$ | —CH$_2$CON(CH$_3$)— |
| —S(CH$_2$)$_2$OCH$_3$ | —(CH$_2$)$_2$CON(CH$_3$)— |
| —NH(CH$_2$)$_2$OCH$_3$ | —(CH$_2$)$_3$CON(CH$_3$)— |
| —NCH$_3$(CH$_2$)$_2$OCH$_3$ | —CH$_2$CON(CH$_3$)CH$_2$— |
| —O(CH$_2$)$_3$OH | —CH$_2$CON(CH$_3$)(CH$_2$)$_2$— |
| —S(CH$_2$)$_3$CF$_3$ | —(CH$_2$)$_2$CON(CH$_3$)CH$_2$— |
| 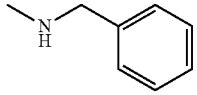 | —(CH$_2$)$_3$CONH— |

TABLE 23

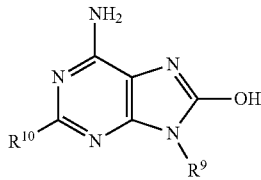

| —R¹⁰ | —R⁹ |
|---|---|
| —O(CH₂)₃CH₃ | —(CH₂)₃SO₂-C₆H₄-(CH₂)₂CO₂CH₃ |
| —O(CH₂)₂OCH₃ | —(CH₂)₄SO₂-C₆H₄-CO₂Et |
| —S(CH₂)₂OH | —(CH₂)₂SO₂CH₂-(pyridyl)-CH₂CO₂CH₃ |
| —NH-CH₂-C₆H₅ | —(CH₂)₂SO₂(CH₂)₂-(thienyl)-CH₂CO₂Pr |
| —(CH₂)₂CO₂CH₃ | —(CH₂)₃SO₂CH₂-(N-Me-pyrrolyl)-CH₂CO₂CH₃ |
| —O(CH₂)₃CH₃ | —(CH₂)₂SO₂NH-C₆H₄-CH₂CO₂Et |
| —O(CH₂)₃CH₃ | —(CH₂)₃SO₂NH-C₆H₄-CH₂CO₂CH₃ |
| —O(CH₂)₂OCH₃ | —(CH₂)₄SO₂NH-(pyridyl)-CH₂CO₂CH₃ |
| —S(CH₂)₂OH | —(CH₂)₂SO₂NHCH₂-(oxazolyl)-CH₂CO₂CH₃ |
| —NH-CH₂-C₆H₅ | —(CH₂)₂SO₂NH(CH₂)₂-(indolyl)-CO₂CH₃ |
| —(CH₂)₂CO₂CH₃ | —(CH₂)₃SO₂NHCH₂-(furyl)-CH₂CO₂CH₃ |

TABLE 23-continued

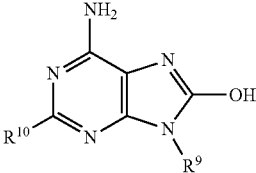

| —R10 | —R9 |
|---|---|
| —O(CH2)3CH3 | —(CH2)2SO2N(CH3)— [naphthyl]—CH2CO2CH3 |

TABLE 24

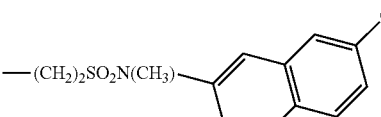

| —R10 | —R9 |
|---|---|
| —O(CH2)3CH3 | —(CH2)3O—[phenyl]—(CH2)2CO2CH3 |
| —O(CH2)2OCH3 | —(CH2)4O—[phenyl]—CO2Et |
| —S(CH2)2OH | —(CH2)2OCH2—[pyridyl]—CH2CO2CH3 |
| —NH-benzyl | —(CH2)2O(CH2)2—[thienyl]—CH2CO2Pr |
| —(CH2)2CO2CH3 | —(CH2)3OCH2—[N-Me pyrrolyl]—CH2CO2CH3 |
| —O(CH2)3CH3 | —(CH2)2S—[phenyl]—CO2Et |
| —O(CH2)3CH3 | —(CH2)3S—[phenyl]—CH2CO2CH3 (with H3CO2C) |
| —O(CH2)2OCH3 | —(CH2)4S—[pyridyl]—CH2CO2CH3 |

TABLE 24-continued

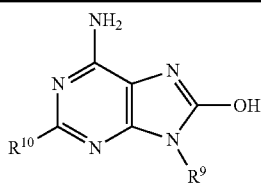

| —R10 | —R9 |
|---|---|
| —S(CH2)2OH | —(CH2)SCH2—[oxazolyl]—CH2CO2CH3 |
| —NH-benzyl | —(CH2)2S(CH2)2—[indolyl]—CO2CH3 |
| —(CH2)2CO2CH3 | —(CH2)3SCH2—[furyl]—CH2CO2CH3 |
| —O(CH2)3CH3 | —(CH2)2SO2—[naphthyl]—CH2CO2CH3 |

TABLE 25

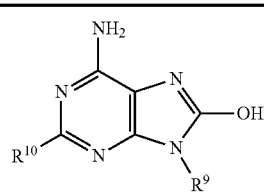

| —R10 | —R9 |
|---|---|
| —O(CH2)3CH3 | —(CH2)3SON(CH3)—[phenyl]—(CH2)2CO2CH3 |

TABLE 25-continued

Structure: 6-amino-8-hydroxy-purine with R10 at 2-position and R9 at 9-position.

| —R10 | —R9 |
|---|---|
| —O(CH2)2OCH3 | —(CH2)4SO2N(CH3)-(3-ethoxycarbonylphenyl) |
| —S(CH2)2OH | —(CH2)2SO2N(CH3)CH2-(pyridin-3-yl-5-CH2CO2CH3) |
| —NH-CH2-phenyl (benzylamino) | —(CH2)3SO2NHCH2-(thiophen-2-yl-5-CH2CO2Pr) |
| —(CH2)2CO2CH3 | —(CH2)2NH-(1-methylpyrrol-2-yl-5-CH2CO2CH3) |
| —O(CH2)3CH3 | —(CH2)3NH-(4-(CO2Et-CH2)phenyl) |
| —O(CH2)3CH3 | —(CH2)4NH-(2-(H3CO2C-CH2)phenyl) |

TABLE 25-continued

| —R10 | —R9 |
|---|---|
| —O(CH2)2OCH3 | —(CH2)2NHCH2-(pyridin-2-yl-4-CH2CO2CH3) |
| —S(CH2)2OH | —(CH2)2NH(CH2)2-(oxazol-5-yl-2-CH2CO2CH3) |
| —NH-CH2-phenyl (benzylamino) | —(CH2)3NHCH2-(indol-6-yl-2-CO2CH3) |
| —(CH2)2CO2CH3 | —(CH2)2N(CH3)-(furan-5-yl-3-CH2CO2CH3) |
| —O(CH2)3CH3 | —(CH2)3N(CH3)-(naphthalen-6-yl-2-CH2CO2CH3) |

TABLE 26

Structure: 6-amino-8-hydroxy-purine with R10 at 2-position and R9 at 9-position.

| —R10 | —R9 |
|---|---|
| —O(CH2)3CH3 | —(CH2)4N(CH3)-(3-((CH2)2CO2CH3)phenyl) |
| —O(CH2)2OCH3 | —(CH2)2N(CH3)CH2-(3-CO2Et-phenyl) |
| —S(CH2)2OH | —(CH2)3N(CH3)CH2-(pyridin-3-yl-5-CH2CO2CH3) |
| —NH-CH2-phenyl (benzylamino) | —(CH2)2NHCO-(thiophen-2-yl-5-CH2CO2Pr) |

TABLE 26-continued
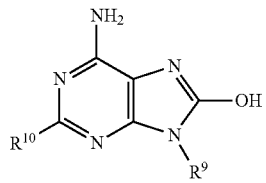
| —R[10] | —R[9] |
|---|---|
| —(CH$_2$)$_2$CO$_2$CH$_3$ | 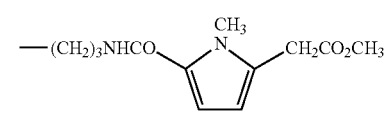 |
| —O(CH$_2$)$_3$CH$_3$ | 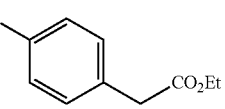 |
| —O(CH$_2$)$_3$CH$_3$ | 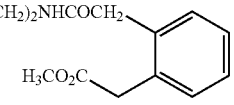 |
| —O(CH$_2$)$_2$OCH$_3$ | 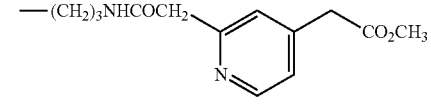 |
| —S(CH$_2$)$_2$OH | 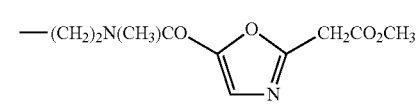 |
| 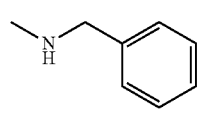 | 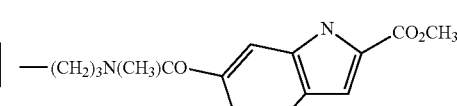 |
| —(CH$_2$)$_2$CO$_2$CH$_3$ | 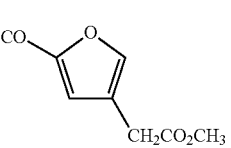 |
| —O(CH$_2$)$_3$CH$_3$ | 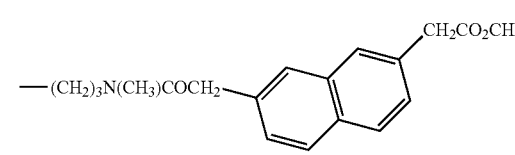 |

TABLE 27

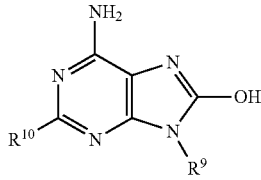

| —R¹⁰ | —R⁹ |
|---|---|
| —O(CH₂)₃CH₃ | —(CH₂)₂NHCOO-C₆H₄-(CH₂)₂CO₂CH₃ (meta) |
| —O(CH₂)₂OCH₃ | —(CH₂)₂NHSO₂-C₆H₄-CO₂Et (meta) |
| —S(CH₂)₂OH | —(CH₂)₃NHSO₂-(pyridyl)-CH₂CO₂CH₃ |
| —NH-CH₂-C₆H₅ | —(CH₂)₂NHSO₂-(thienyl)-CH₂CO₂Pr |
| —(CH₂)₂CO₂CH₃ | —(CH₂)₂NHSO₂(CH₂)₂-(N-methylpyrrolyl)-CH₂CO₂CH₃ |
| —O(CH₂)₃CH₃ | —(CH₂)₃NHSO₂CH₂-C₆H₄-CO₂Et (para) |
| —O(CH₂)₃CH₃ | —(CH₂)₂N(CH₃)SO₂-C₆H₄-CH₂CO₂CH₃ (ortho) |
| —O(CH₂)₂OCH₃ | —(CH₂)₃N(CH₃)SO₂-(pyridyl)-CH₂CO₂CH₃ |
| —S(CH₂)₂OH | —(CH₂)₄N(CH₃)SO₂-(oxazolyl)-CH₂CO₂CH₃ |
| —NH-CH₂-C₆H₅ | —(CH₂)₂N(CH₃)SO₂CH₂-(indolyl)-CO₂CH₃ |
| —(CH₂)₂CO₂CH₃ | —(CH₂)₂NHCONH-(furyl)-CH₂CO₂CH₃ |

TABLE 27-continued

Structure: 6-amino-8-hydroxy-purine with R10 at position 2 and R9 at position 9

| —R10 | —R9 |
|---|---|
| —O(CH2)3CH3 | —(CH2)3NHCONH-(naphthalen-2-yl)-CH2CO2CH3 |

TABLE 28

Structure: 6-amino-8-hydroxy-purine with R10 at position 2 and R9 at position 9

| —R10 | —R9 |
|---|---|
| —O(CH2)3CH3 | —(CH2)2NHCSNH-(3-substituted phenyl)-(CH2)2CO2CH3 |
| —O(CH2)2OCH3 | —(CH2)3NHCSNH-(3-substituted phenyl)-CO2Et |
| —S(CH2)2OH | —(CH2)4NHCSNH-(pyridin-3-yl)-CH2CO2CH3 |
| —NH-CH2-phenyl | —CH2CO-(thiophene-2,5-diyl)-CH2CO2Pr |
| —(CH2)2CO2CH3 | —(CH2)2CO-(N-methylpyrrole-2,5-diyl)-CH2CO2CH3 |
| —O(CH2)3CH3 | —(CH2)3O-(phenyl-1,4-diyl)-CO2Et |
| —O(CH2)3CH3 | —(CH2)4O-(phenyl-1,2-diyl with H3CO2C-CH2-)-  |
| —O(CH2)2OCH3 | —CH2COCH2-(pyridin-2,4-diyl)-CH2CO2CH3 |

TABLE 28-continued

Structure: 6-amino-8-hydroxy-purine with R10 at position 2 and R9 at position 9

| —R10 | —R9 |
|---|---|
| —S(CH2)2OH | —CH2CO(CH2)2-(oxazole-2,5-diyl)-CH2CO2CH3 |
| —NH-CH2-phenyl | —(CH2)2COCH2-(indole-2,6-diyl)-CO2CH3 |
| —(CH2)2CO2CH3 | —(CH2)2CO(CH2)2-(furan-2,4-diyl)-CH2CO2CH3 |
| —O(CH2)3CH3 | —CH2CONH-(naphthalen-2,6-diyl)-CH2CO2CH3 |

TABLE 29

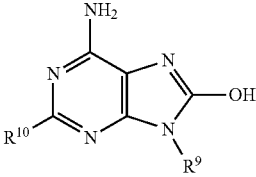

| —R10 | —R9 |
|---|---|
| —O(CH2)3CH3 | —(CH2)2CONH-(3-substituted phenyl)-(CH2)2CO2CH3 |

TABLE 29-continued

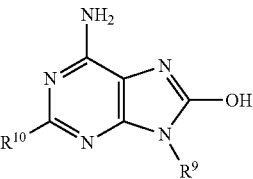

| —R¹⁰ | —R⁹ |
|---|---|
| —O(CH₂)₂OCH₃ | —(CH₂)₃CONH-C₆H₄-CO₂Et |
| —S(CH₂)₂OH | —CH₂CONHCH₂-(pyridyl)-CH₂CO₂CH₃ |
| PhCH₂NH— | —(CH₂)₃CONH-(thienyl)-CH₂CO₂Pr |
| —(CH₂)₂CO₂CH₃ | —(CH₂)₂CONHCH₂-(N-CH₃-pyrrolyl)-CH₂CO₂CH₃ |
| —O(CH₂)₃CH₃ | —CH₂CON(CH₃)-C₆H₄-CO₂Et |
| —O(CH₂)₃CH₃ | —(CH₂)₂CON(CH₃)-C₆H₄-CO₂CH₃ |
| —O(CH₂)₂OCH₃ | —(CH₂)₃CON(CH₃)-(pyridyl)-CO₂CH₃ |
| —S(CH₂)₂OH | —CH₂CON(CH₃)CH₂-(oxazolyl)-CH₂CO₂CH₃ |
| PhCH₂NH— | —CH₂CON(CH₃)(CH₂)₂-(indolyl)-CO₂CH₃ |
| —(CH₂)₂CO₂CH₃ | —(CH₂)₂CON(CH₃)CH₂-(furyl)-CH₂CO₂CH₃ |
| —O(CH₂)₃CH₃ | —CH₂CONH-(naphthyl)-CH₂CO₂CH₃ |

In the following, the present invention is further explained in details referring to Examples, Comparison Examples and Reference Examples, but the present invention is not limited thereto. In the following examples, chemical structures are for convenience shown in a form of 8-hydroxy type and it is not differentiated from 8-oxo type.

When otherwise stated, the organic solvent was dried over magnesium sulfate.

RPHPLC means preparative reverse phase HPLC using Waters Symmetry C8, Xterra or Gemini columns and using, as a mobile phase, acetonitrile and either aqueous solution of ammonium acetate or ammonia or trifluoroacetic acid. The column chromatography was conducted with the use of silica gel.

EXAMPLE 1

Synthesis of 2-butoxy-8-oxo-9-[2-(3-methoxycarbonylphenoxy)ethyl]adenine

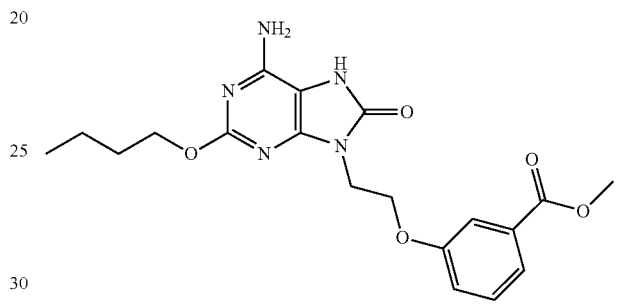

To 2-butoxy-9-[2-(3-methoxycarbonylphenoxy)ethyl]adenine (400 mg, 1.04 mmol) in chloroform (10 mL) obtained in Reference Example 2 was added sodium acetate (283 mg, 1.56 mmol), and bromine (78 μl, 1.56 mmol) was dropped under ice-cooling thereto, and the mixture was stirred at room temperature for 3 hours. To the reaction mixture were added saturated sodium hydrogen carbonate (1 ml) and saturated sodium thiosulfate (2 ml) and stirred for 10 minutes. The reaction solution was diluted with water and extracted with chloroform (methanol 5%).

The organic layer was washed with water, saturated brine, dried over sodium sulfate and concentrated under reduced pressure. The residue was purified by silica gel chromatography to give a bromo compound. To the obtained bromo compound were added methanol (10 ml) and 2.5N sodium hydroxide (16 ml), and the mixture was stirred at 85° C. for 1.5 hours. The reaction mixture was diluted with water and acidified with concentrated hydrochloric acid, and concentrated under reduced pressure. To the residue was added water, and the precipitate was collected by filtration. Methanol (15 ml) and concentrated sulfuric acid (300 μl) were added thereto and the resultant was heated at 85° C. for 2.5 hours. The reaction solution was concentrated under reduced pressure and diluted with water, and the resultant was neutralized with saturated sodium hydrogencarbonate. The precipitated solid was collected by filtration to give 215 mg (0.54 mmol) of the titled compound as a white solid. Yield: 52%.

¹H NMR (DMSO-d₆) δ 9.89 (1H, brs), 7.53 (1H, dd, J=2.4, 8.2 Hz), 7.40 (1H, dd, J=7.8, 8.2 Hz), 7.36 (1H, dd, J=1.6. 2.4 Hz), 7.19 (1H, dd, J=1.6, 7.8 Hz), 6.43 (2H, brs), 4.36-4.34 (2H, m), 4.08-4.04 (4H, m), 3.82 (3H, s), 1.63-1.60 (2H, m), 1.40-1.35 (2H, m), 0.89 (3H, t, J=7.4 Hz).

EXAMPLE 2

Synthesis of 2-butoxy-8-oxo-9-[2-(3-methoxycarbonylmethylphenoxy)ethyl]adenine

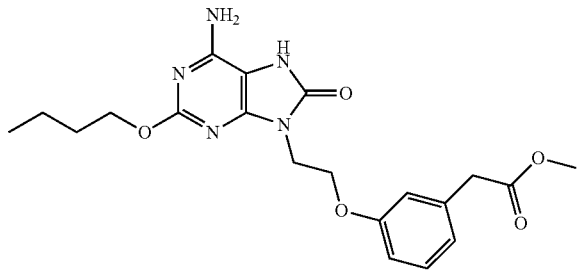 [SMILES: CCCCOc1nc(N)c2[nH]c(=O)n(CCOc3cccc(CC(=O)OC)c3)c2n1]

From 2-butoxy-9-[2-(3-methoxycarbonylmethylphenoxy)ethyl]adenine 160 mg (0.40 mmol) obtained in Reference Example 3 by the same manner to Example 1, the titled compound was obtained as a white solid in an amount of 49 mg (0.12 mmol). Yield: 29%.

$^1$H NMR (DMSO-$d_6$) δ 9.90 (1H, s), 7.20 (1H, td, J=1.5, 7.4 Hz), 6.84-6.81 (3H, m), 6.43 (2H, brs), 4.24 (2H, t, J=5.8 Hz), 4.12 (2H, t, J=6.6 Hz), 4.03 (2H, t, J=5.8 Hz), 3.61 (2H, s), 3.59 (3H, s), 1.66-1.61 (2H, m), 1.39-1.35 (2H, m), 0.90 (3H, t, J=7.4 Hz).

EXAMPLE 2-1

Methyl [3-({[2-(6-amino-2-butoxy-8-oxo-7,8-dihydro-9H-purin-9-yl)ethyl]amino}methyl)phenyl]acetate

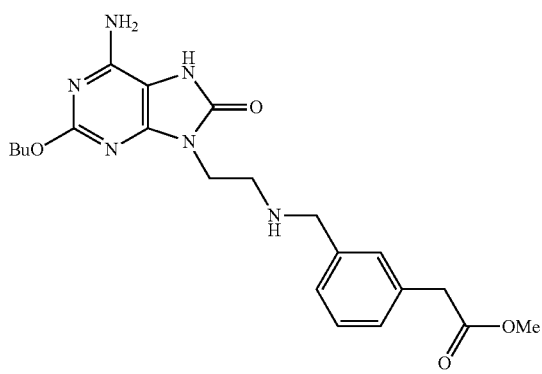

(i) 2-Chloro-9-(tetrahydro-2H-pyran-2-yl)-9H-purine-6-amine

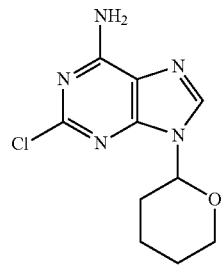 [SMILES: Nc1nc(Cl)nc2c1ncn2C1CCCCO1]

2,6-dichloro-9-(tetrahydro-2H-pyran-2-yl)-9H-purine (55 g) was dissolved in 7N ammonia-methanol solution, and heated in a sealed flask at 100° C. for 6 hours. The reaction mixture was cooled to room temperature, followed by standing overnight and filtration to give the titled compound. Yield: 40 g (80%).

$^1$H NMR δ (CDCl$_3$) 8.02 (1H, s), 5.94 (2H, bs), 5.71 (1H, dd), 4.15-4.22 (1H, m), 3.75-3.82 (1H, m), 1.27-2.12 (6H, m).

(ii) 2-butoxy-9-(tetrahydro-2H-pyran-2-yl)-9H-purine-6-amine

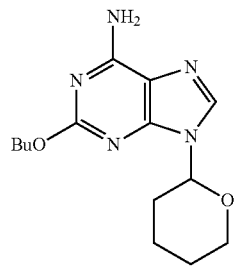

The compound (40 g) obtained in the step (i) was dissolved in 19% sodium butoxide-butanol solution, and heated under reflux for 6 hours. The obtained suspension was cooled to room temperature, diluted with water and extracted with diethyl ether. The organic layer was washed with water, dried and concentrated under reduced pressure. The residue was dissolved in a mixed solvent of isohexane and diethyl ether to crystallize. The resulting crystals were collected by filtration to give the titled compound. Yield: 19 g (64%).

$^1$H NMR δ (CDCl$_3$) 7.87 (1H, s), 5.56-5.68 (3H, m), 4.31-4.35 (2H, t), 4.14-4.17 (1H, m), 3.76-3.80 (1H, m), 1.49-2.08 (10H, m), 0.98 (3H, t).

(iii) 8-bromo-2-butoxy-9-(tetrahydro-2H-pyran-2-yl)-9H-purine-6-amine

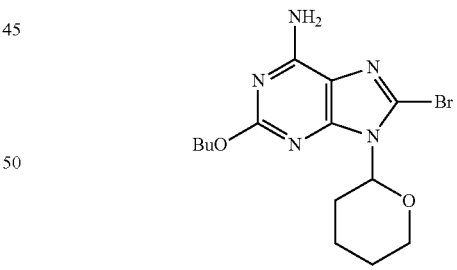

The compound obtained in the above step (ii) (30 g) was dissolved in dichloromethane (200 ml), and under stirring at room temperature, N-bromosuccinimide (27 g) was slowly added, followed by stirring at room temperature overnight. A 20% aqueous sodium thiosulfate solution was added, and the separated aqueous layer was extracted with dichloromethane, and the organic layer was washed with an aqueous saturated sodium hydrogencarbonate solution and saturated brine and concentrated under reduced pressure. The residue was dissolved in ethyl acetate, washed with water and saturated brine, and dried. The obtained solution was filtered through a silica gel and concentrated under reduced pressure. The residue was dissolved in a mixed solvent of isohexane and diethy ether to crystallize, which was then collected by filtration to give 26 g of a product. The filtrate was concentrated and the residue was purified by column chromatography (ethylacetate: isohexane) to give a product 2.5 g. As the combined products, the titled compound was obtained totally 28.5 g (75%) as a yellow solid. mp 148-150° C.

¹H NMR δ (CDCl₃) 5.59-5.64 (3H, m), 4.32 (2H, m), 4.17 (1H, m), 3.74 (1H, m), 3.08 (1H, m), 2.13 (1H, d), 1.48-1.83 (8H, m), 0.98 (3H, t).

(iv) 2-Butoxy-8-methoxy-9-(tetrahydro-2H-pyran-2-yl)-9H-purine-6-amine

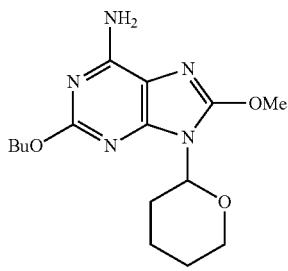

Under nitrogen atmosphere, to methanol (400 ml) was added sodium (3.7 g). To the obtained solution was added the compound obtained in the step (iii) (28.5 g) and the mixture was heated at 65° C. for 9 hours. The reaction solution was concentrated under reduced pressure and water (500 ml) was added thereto. The separated aqueous layer was extracted with ethyl acetate and washed with saturated brine, followed by concentration. The residue was crystallized from diethyl ether to give the titled compound. Yield: 14.2 g (98%).

¹H NMR δ (CDCl₃) 5.51 (1H dd), 5.28 (2H, bs), 4.29 (2H, t), 4.11-4.14 (4H, m), 3.70 (1H, m), 2.76-2.80 (1H, m), 2.05 (1H, d), 1.47-1.81 (8H, m), 0.97 (3H, t).

(v) 2-Butoxy-8-methoxy-9H-purin-6-amine trifluoroacetate

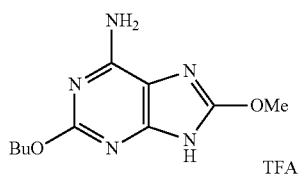

The compound (24 g) obtained in the step (iv) was dissolved in methanol (300 ml) and trifluoroacetic acid (30 ml) was added thereto, and the mixture was stirred at room temperature for 72 hours and concentrated under reduced pressure. A mixture of methanol and ethyl acetate was added thereto to precipitate the titled compound as a white solid. Yield: 21 g (80%).

¹H NMR δ (CD₃OD) 4.48 (2H, t), 4.15 (3H, s), 1.80 (2H, quintet), 1.50 (2H, sextet), 0.99 (3H, t).

(vi) 2-[2-(6-Amino-2-butoxy-8-methoxy-9H-purin-9-yl)ethyl]-1H-isoindol-1,3(2H)-dione

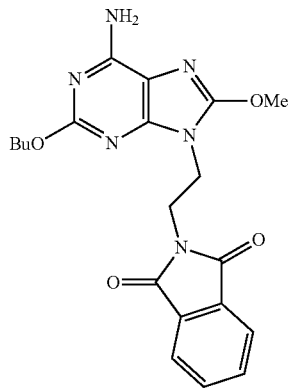

In dimethylformamide, a mixture of the compound obtained in the step (v) (3 g) and potassium carbonate (3.54 g) was stirred at 60° C. for 1 hour. The resultant was cooled to room temperature, and 2-(2-bromoethyl)-1H-isoindol-1,3(2H)-dione (2.60 g) was added and stirred at room temperature overnight. Ethyl acetate and water were added thereto and the organic layer was separated, washed with saturated brine, dried and concentrated under reduced pressure. The residue was purified by column chromatography (methanol: dichloromethane) to give the titled compound. Yield: 2.6 g (74%); MS APCI+ve 412 (M+H).

(vii) 9-(2-Aminoethyl)-butoxy-8-methoxy-9H-purin-6-amine

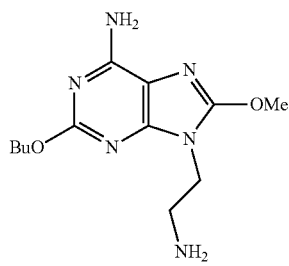

The compound obtained in the step (vi) (1 g) was dissolved in ethanol (10 ml), and hydrazine monohydrate (1 ml) was added thereto. The mixture was heated under reflux for 2 hours. The resultant was cooled to room temperature and concentrated under reduced pressure, and the residue was suspended in dichloromethane (10 ml) and stirred for 1 hour. The suspension was filtered, washed with dichloromethane, and the filtrate was concentrated under reduced pressure to give the titled compound. Yield: 700 mg (99%); MS APCI+ve 282 (M+H).

¹H NMR δ (DMSO d₆) 6.76 (2H, brs), 4.10-4.18 (2H, m), 4.04 (3H, s), 3.81 (2H, t), 2.82 (2H, t), 1.62-1.69 (2H, m), 1.34-1.46 (2H, m), 0.92 (3H, t).

(viii) Methyl [3-({[2-(6-amino-2-butoxy-8-methoxy-9H-purin-9-yl)ethyl]amino}methyl)phenyl]acetate

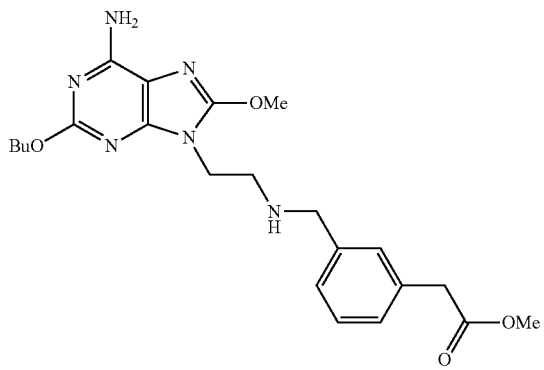

The compound obtained in the step (vii) (200 mg) and methyl (3-formylphenyl)acetate (133 mg) were dissolved in methanol (5 ml) and the mixture was stirred at room temperature for 4 hours. Sodium borohydride (32 mg) was added and the mixture was stirred at room temperature overnight. To the reaction solution were added dichloromethane (100 ml) and water (100 ml) and the organic layer was separated, washed with water and saturated brine and dried. To the obtained solution was added polymer supported aldehyde resin (300 mg) and the mixture was agitated at room temperature overnight. The resin was removed by filtration and the filtrate was concentrated under reduced pressure to give the titled compound 200 mg. The product was used in the next reaction without further purification. MS APCI+ve 444 (M+H).

(ix) Methyl [3-({[2-(6-amino-2-butoxy-8-oxo-7,8-dihydro-9H-purin-9-yl)ethyl]amino}methyl)phenyl]acetate

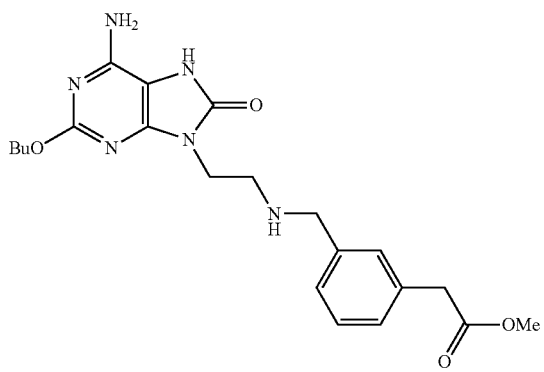

To the compound obtained in the step (viii) solution (200 mg) in methanol (5 ml) was added 4N hydrochloric acid-dioxane (1 ml). The mixture was stirred at room temperature overnight and concentrated under reduced pressure. To the residue were added water (3 ml) and an aqueous saturated sodium hydrogen carbonate solution (3 ml) and extracted with dichloromethane and ethyl acetate. The organic layer was dried and concentrated under reduced pressure and purified by column chromatography (methanol: dichloromethane). Crystallization from dichloromethane/acetonitrile gave the titled compound as a white powder. Yield: 50 mg (15%); MS APCI+ve 429 (M+H).

$^1$H NMR δ (DMSO d$_6$) 10.34 (1H, brs), 9.04 (2H, brs), 7.31-7.41 (4H, m), 4.21 (2H, m), 4.14 (2H, t), 4.05 (2H, brt), 3.69 (3H, s), 3.62 (2H, s), 3.30 (2H, m), 1.58-1.68 (2H, m), 1.31-1.44 (2H, m), 0.91 (3H, t).

EXAMPLE 2-2

[3-({[2-(6-Amino-2-butoxy-8-oxo-7,8-dihydro-9H-purin-9-yl)ethyl]amino}methyl)phenyl]acetic acid

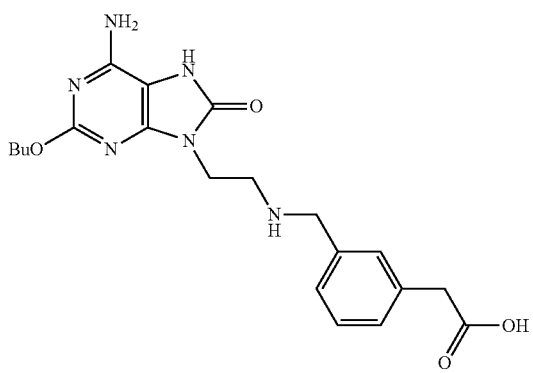

To the compound obtained in Example 1 solution (30 mg) in methanol (1 ml) was added 5N aqueous sodium hydroxide solution (1 ml) and the mixture was stirred at room temperature for 6 hours, followed by concentration under reduced pressure. Water was added thereto and the resultant was neutralized with acetic acid. The precipitated solid was collected by filtration to give the titled compound. Yield: 9 mg (31%); MS APCI+ve 415 (M+H).

$^1$H NMR δ (DMSO d$_6$) 6.89-7.02 (4H, m), 6.69 (2H, brs), 4.12 (2H, t), 3.73 (2H, t, J), 3.57 (2H, s), 3.16 (2H, s), 2.79 (2H, t), 1.57-1.65 (2H, m), 1.34-1.41 (2H, m), 0.91 (3H, t).

EXAMPLE 2-3

Methyl 3-({[3-(6-amino-2-butoxy-8-oxo-7,8-dihydro-9H-purin-9-yl)propyl]amino}methyl)benzoate

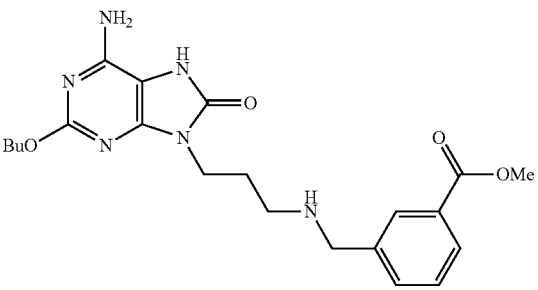

(i) 3-[2-(6-Amino-2-butoxy-8-methoxy-9H-purin-9-yl)propyl]-1H-isoindol-1,3(2H)-dione

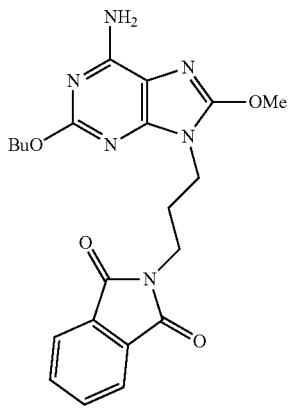

Using the compound obtained in Example 1 step (v) and 2-(3-bromopropyl)-1H-isoindole-1,3(2H)-dione, the titled compound was obtained by the same manner to Example 2-1 (vi). Yield: 2 g (55%).

$^1$H NMR δ (DMSO d$_6$) 7.83 (4H, m), 6.73 (2H, brs), 4.06 (2H, t,), 4.01 (3H, s), 3.89 (2H, t), 3.58 (2H, t), 2.07-2.14 (2H, m), 1.55-1.62 (2H, m), 1.31-1.40 (2H, m), 0.90 (3H, t).

(ii) 9-(3-Aminopropyl)-2-butoxy-8-methoxy-9H-purine-6-amine

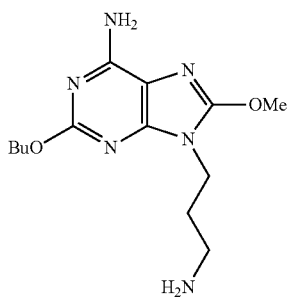

The titled compound was obtained by using the compound obtained in the step (i) by the same manner to Example 2-1 step (vii). Yield: 400 mg (50%).

$^1$H NMR δ (DMSO d$_6$) 6.77 (2H, brs), 4.16 (2H, t), 4.05 (3H, s), 3.89 (2H, t), 2.46-2.52 (2H, m), 1.61-1.76 (4H, m), 1.35-1.45 (2H, m), 0.92 (3H, t).

(iii) Methyl 3-({[3-(6-amino-2-butoxy-8-methoxy-9H-purin-9-yl)propyl]amino}methyl)benzoate

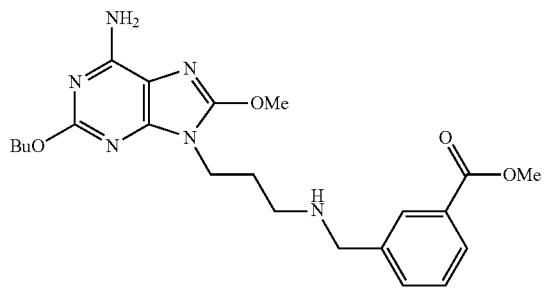

The titled compound was obtained by using the compound obtained in the step (ii) by the similar manner to Example 2-1 step (viii). This product was used in the next reaction without further purification. Yield: 250 mg (60%); MS APCI+ve 444 (M+H).

(iv) Methyl 3-({[3-(6-amino-2-butoxy-8-oxo-7,8-dihydro-9H-purin-9-yl)propyl]amino}methyl)benzoate

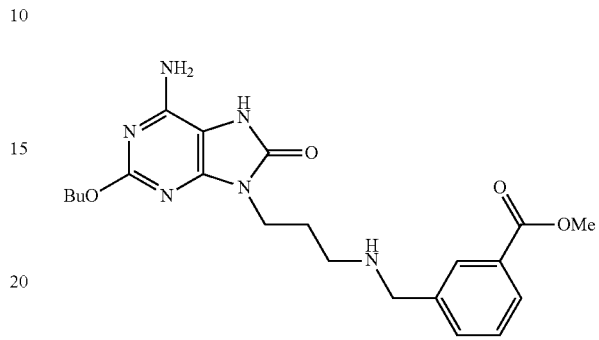

The titled compound was obtained by using the compound obtained in the step (iii) by the similar manner to Example 2-1 step (ix). Yield: 176 mg (43%); m.p. 214-218° C., MS APCI+ve 429 (M+H).

$^1$H NMR δ (DMSO d$_6$) 9.90 (1H, brs), 7.92 (1H, s), 7.80-7.82 (1H, m), 7.57-7.59 (1H, m), 7.41-7.45 (1H, m), 6.41 (2H, brs), 4.10 (2H, t), 3.74 (3H, s), 3.70-3.72 (4H, m), 2.46-2.55 (2H, m), 1.76-1.90 (2H, m), 1.56-1.63 (2H, m), 1.30-1.40 (2H, m), 0.89 (3H, t).

EXAMPLE 2-4

3-({[3-(6-Amino-2-butoxy-8-oxo-7,8-dihydro-9H-purin-9-yl)propyl]amino}methyl)benzoic acid

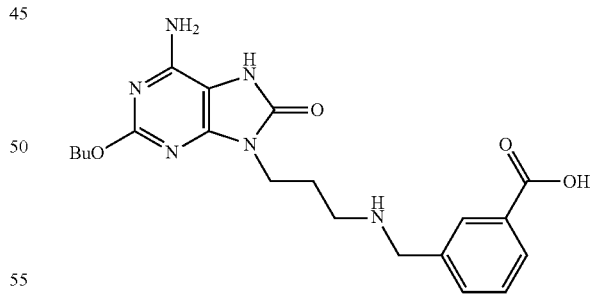

The titled compound was obtained by using the compound obtained in Example 2-3 by the similar manner to Example 2-2. Yield: 64 mg (33%); MS APCI+ve 415 (M+H).

$^1$H NMR δ (CD$_3$OD) 7.89 (1H, s), 7.83-7.86 (1H, m), 7.27-7.39 (2H, m), 4.25 (2H, t), 3.91 (2H, t), 3.78 (2H, s), 2.62 (2H, t), 1.96-2.03 (2H, m), 1.68-1.75 (2H, m), 1.42-1.52 (2H, m), 0.98 (3H, t).

EXAMPLE 2-5

Methyl 4-({[3-(6-amino-2-butoxy-8-oxo-7,8-dihydro-9H-purin-9-yl)propyl]amino}methyl)benzoate

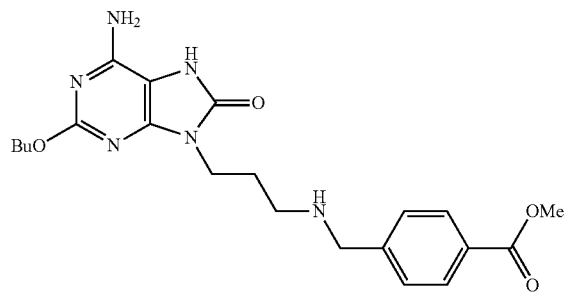

(i) Methyl 4-({[3-(6-amino-2-butoxy-8-methoxy-9H-purin-9-yl)propyl]amino}methyl)benzoate

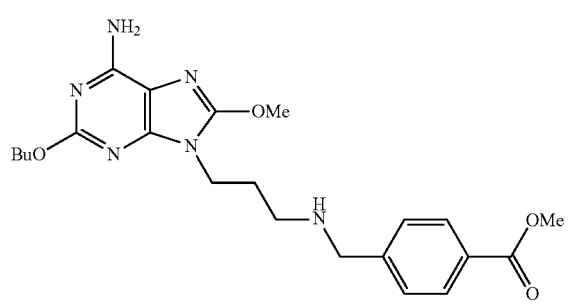

The titled compound was obtained by using the compound obtained in Example 2-3 step (ii) and methyl 4-formylbenzoate by the similar manner to Example 2-3 step (i). Yield: 90 mg; MS APCI+ve 444 (M+H).

(ii) Methyl 4-({[3-(6-amino-2-butoxy-8-oxo-7,8-dihydro-9H-purin-9-yl)propyl]amino}methyl)benzoate

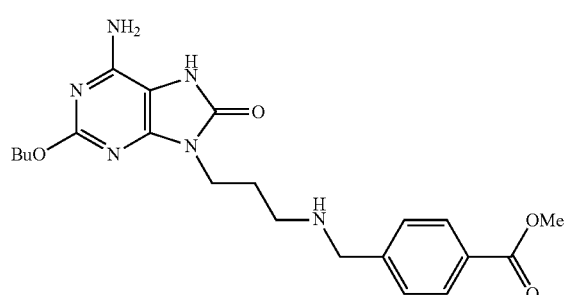

The titled compound was obtained by using the compound obtained in the step (i) by the similar manner to Example 2-1 step (ix). Yield: 6 mg (11%); MS APCI+ve 429 (M+H).
$^1$H NMR δ (DMSO d$_6$) 7.87-7.89 (2H, m), 7.43-7.46 (2H, m), 6.43 (2H, brs), 4.10 (2H, t), 3.84 (3H, s), 3.71-3.74 (4H, m), 2.44-2.50 (2H, m), 1.76-1.83 (2H, m), 1.56-1.64 (2H, m), 1.30-1.40 (2H, m), 0.89 (3H, t).

EXAMPLE 2-6

4-({[3-(6-Amino-2-butoxy-8-oxo-7,8-dihydro-9H-purin-9-yl)propyl]amino}methyl)benzoic acid

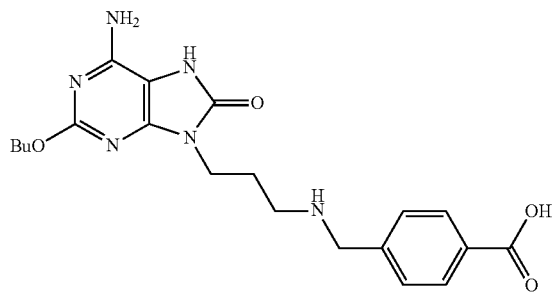

The titled compound was obtained by using the compound obtained in Example 2-5 by the similar manner to Example 2-2. Yield: 2.6 mg (50%); MS APCI+ve 415 (M+H).
$^1$H NMR δ (CD$_3$OD) 7.90-7.93 (2H, m), 7.29-7.32 (2H, m), 4.24-4.26 (2H, m), 3.85-3.93 (2H, m), 3.75 (2H, s), 2.58-2.62 (2H, m), 1.95-2.03 (2H, m), 1.69-1.78 (2H, m), 1.40-1.52 (2H, m), 0.99 (3H, t).

EXAMPLE 2-7

Methyl (3-{[[3-(6-amino-2-butoxy-8-oxo-9H-purin-9-yl)propyl](2-morpholin-4-ylethyl)amino]methyl}phenyl)acetate

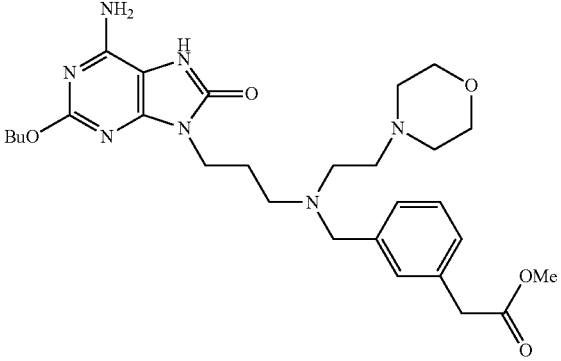

(i) Methyl [3-({[3-(6-amino-2-butoxy-8-methoxy-9H-purin-9-yl)propyl]amino}methyl)phenyl]acetate

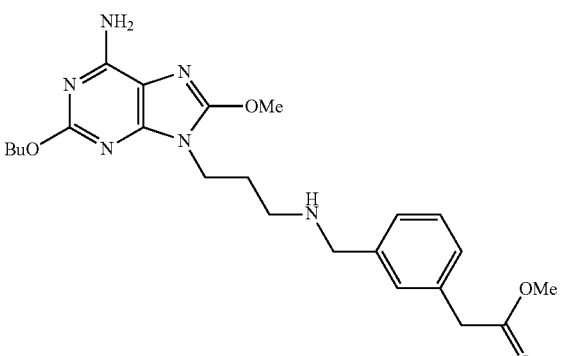

The titled compound was obtained by using the compound obtained in Example 2-3 step (ii) and methyl (3-formylphenyl)acetate by the similar manner to Example 2-1 step (viii).

Yield: 270 mg (61%); MS APCI+ve 458 (M+H).

(ii) Methyl (3-{[[3-(6-amino-2-butoxy-8-methoxy-9H-purin-9-yl)propyl](2-morpholin-4-ylethyl)amino]methyl}phenyl)acetate

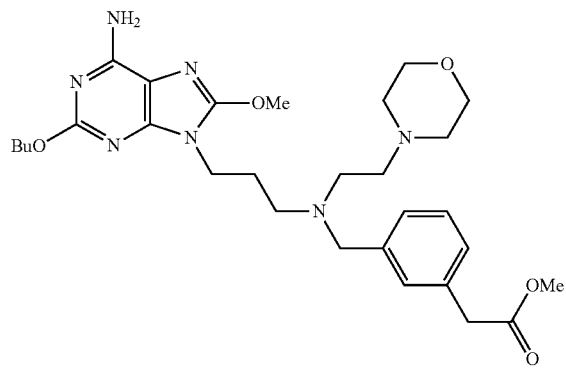

The compound obtained in the step (i) (80 mg) was dissolved in acetonitrile (3 ml) and potassium carbonate (58 mg) was added. The resultant was stirred at room temperature for 10 minutes and 4-(2-chloroethyl)morpholine hydrochloride (39 mg) was added thereto, followed by stirring at 60° C. overnight. The reaction solution was concentrated under reduced pressure and purified by RPHPLC to give the titled compound. MS APCI+ve 571 (M+H).

(iii) Methyl (3-{[[3-(6-amino-2-butoxy-8-oxo-7,8-dihydro-9H-purin-9-yl)propyl](2-morpholin-4-ylethyl)amino]methyl}phenyl)acetate

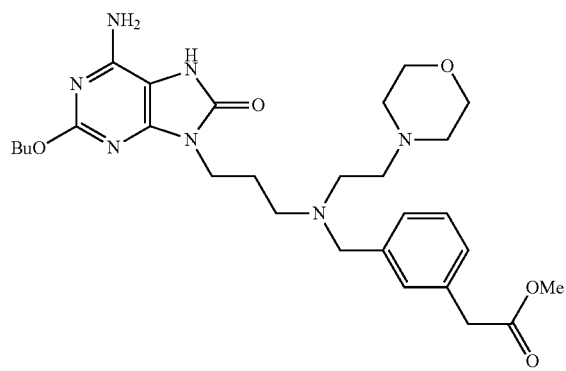

The titled compound was obtained by using the compound obtained in the step (ii) by the similar manner to Example 2-1 step (ix). Yield: 4 mg (11%); MS APCI+ve 557 (M+H).

$^1$H NMR δ (CD$_3$OD) 7.12-7.25 (4H, m), 4.26 (2H, t), 3.88 (2H, t,), 3.61-3.67 (13H, m), 2.42-2.63 (10H, m), 1.91-2.01 (2H, m), 1.67-1.78 (2H, m), 1.42-1.52 (2H, m), 0.98 (3H, t).

EXAMPLE 2-8

Methyl [3-({[4-(6-amino-2-butoxy-8-oxo-7,8-dihydro-9H-purin-9-yl)butyl]amino}methyl)phenyl]acetate

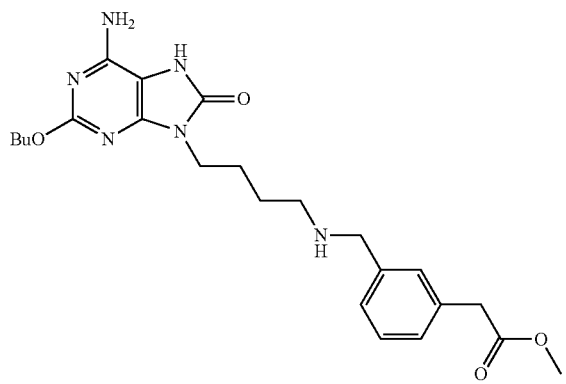

(i) 4-[2-(6-Amino-2-butoxy-8-methoxy-9H-purin-9-yl)butyl]-1H-isoindole-1,3(2H)-dione

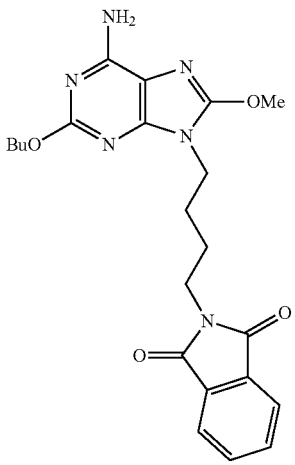

The titled compound was obtained by using the compound obtained in Example 2-1 step (v) and 2-(4-bromobutyl)-1H-isoindole-1,3(2H)-dione by the similar manner to Example 2-1 step (vi). Yield: 1.1 g (88%); MS APCI+ve 440 (M+H).

(ii) 9-(4-Aminobutyl)-2-butoxy-8-methoxy-9H-purin-6-amine

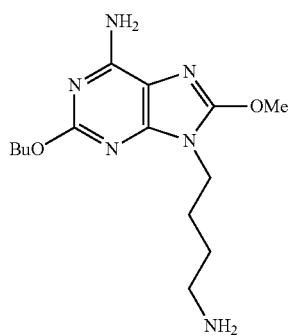

The titled compound was obtained by using the compound obtained in the step (i) by the similar manner to Example 2-1 step (vii). Yield: 720 mg (94%); MS APCI+ve 310 (M+H).

(iii) Methyl [3-({[4-(6-amino-2-butoxy-8-methoxy-9H-purin-9-yl)butyl]amino}methyl)phenyl]acetate

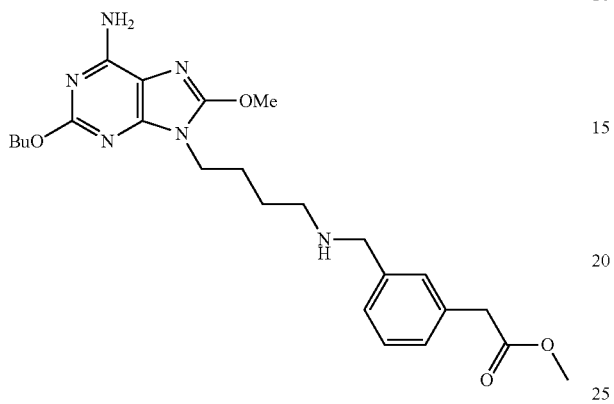

The titled compound was obtained by using the compound obtained in the step (ii) and methyl (3-formylphenyl)acetate, by the similar manner to Example 2-1 step (viii). Yield: 200 mg (42%); MS APCI+ve 472 (M+H).

(iv) Methyl [3-({[4-(6-amino-2-butoxy-8-oxo-7,8-dihydro-9H-purin-9-yl)butyl]amino}methyl)phenyl]acetate

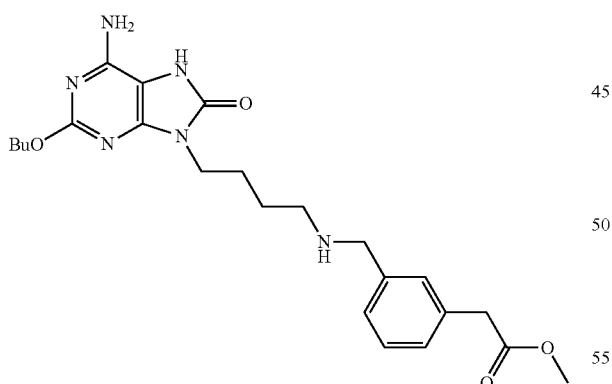

The titled compound was obtained by using the compound obtained in the step (iii) by the similar manner to Example 2-1 step (ix). Yield: 87 mg (45%); MS APCI+ve 457 (M+H).

¹H NMR δ (DMSO d₆) 7.08-7.26 (4H, m), 6.40 (2H, brs), 4.13 (2H, t), 3.59-3.68 (9H, m), 2.46-2.51 (2H, m), 1.58-1.70 (4H, m), 1.31-1.44 (4H, m), 0.91 (3H, t).

EXAMPLE 2-9

Ethyl 2-[2-(6-amino-2-butoxy-8-oxo-7,8-dihydro-9H-purin-9-yl)ethoxy]benzoate

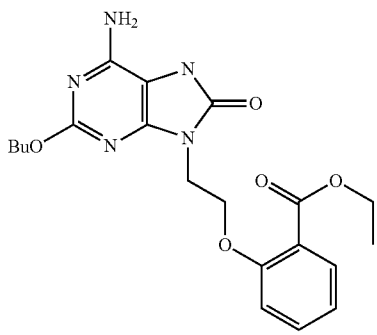

(i) Methyl 2-[2-(6-amino-2-butoxy-8-methoxy-9H-purin-9-yl)ethoxy]benzoate

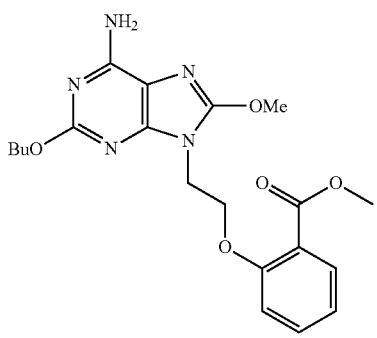

The compound obtained in Example 2-1 step (v) was dissolved in dimethylformamide (50 ml), and potassium carbonate (3.52 g) and methyl 2-(2-bromoethoxy)benzoate (2.2 g) were added thereto. The mixture was stirred at room temperature for 96 hours and partitioned between ethyl acetate and 2M hydrochloric acid. The organic layer was dried and concentrated under reduced pressure. The residue was dissolved in methanol and purified by RPHPLC to give the titled compound. Yield: 0.768 g (22%).

(ii) Methyl 2-[2-(6-amino-2-butoxy-8-oxo-7,8-dihydro-9H-purin-9-yl)ethoxy]benzoate

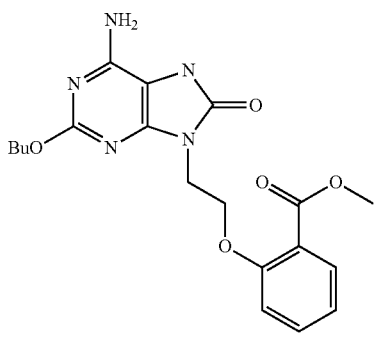

The compound obtained in the step (i) (0.76 g) was dissolved in methanol (10 ml) and hydrochloric acid (20 ml) was added thereto. The mixture was stirred at room temperature for 18 hours and concentrated under reduced pressure to give the titled compound. Yield: 0.562 g (16%).

$^1$H NMR δ (DMSO d$_6$) 7.56 (1H, d), 7.48 (1H, t), 7.17 (1H, d), 7.00 (1H, t), 6.40 (2H, s), 4.36 (2H, t), 4.10 (2H, t), 4.06 (2H, t), 3.62 (3H, s), 1.61 (2H, tt), 1.36 (2H, m), 0.90 (3H, t).

(iii) 2-[2-(6-Amino-2-butoxy-8-oxo-7,8-dihydro-9H-purin-9-yl)ethoxy]benzoic acid

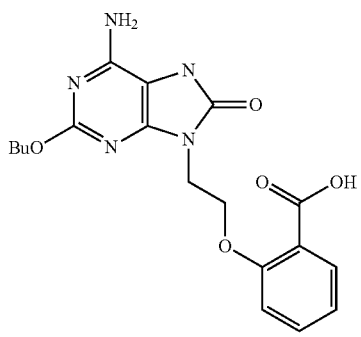

The compound obtained in the step (ii) (0.77 g) was dissolved in tetrahydrofuran (7 ml) and methanol (2.3 ml) and 1M lithium hydroxide (2.3 ml) was added thereto and the mixture was stirred at room temperature for 16 hours. The reaction solution was concentrated under reduced pressure and diluted with 2M hydrochloric acid and the resulting white precipitate was collected by filtration, and dried to give the titled compound as a solid, 0.65 g. The product was used in the next reaction without further purification.

(iv) Ethyl 2-[2-(6-amino-2-butoxy-8-oxo-7,8-dihydro-9H-purin-9-yl)ethoxy]benzoate

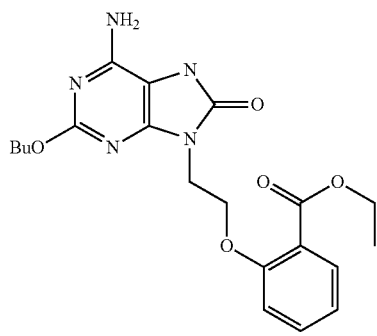

The compound obtained in the step (iii) (50 mg) was dissolved in dichloromethane (5 ml) and ethanol (0.008 ml), 4-pyrrolidin-1-ylpyridine (2 mg) and 1-(3-dimethylaminopropyl)-3-ethylcarbodiimide iodine methyl (42 mg) were added thereto. The resultant was stirred at room temperature for 12 hours, and to the reaction solution was added 2 M hydrochloric acid. The organic layer was separated and concentrated under reduced pressure. The residue was dissolved in ethanol and purified by RPHPLC to give the titled compound. Yield: 5.6 mg (10%).

$^1$H NMR δ (DMSO d$_6$) 7.54 (1H, d), 7.48 (1H, t), 7.17 (1H, d), 7.01 (1H, t), 6.39 (2H, s), 4.36 (2H, t), 4.11 (2H, t), 4.05 (2H, q), 1.61 (2H, tt), 1.37 (m), 1.18 (3H, t), 0.90 (3H, t).

EXAMPLE 2-10

3-(Dimethylamino)propyl 2-[2-(6-amino-2-butoxy-8-oxo-7,8-dihydro-9H-purin-9-yl)ethoxy]benzoate

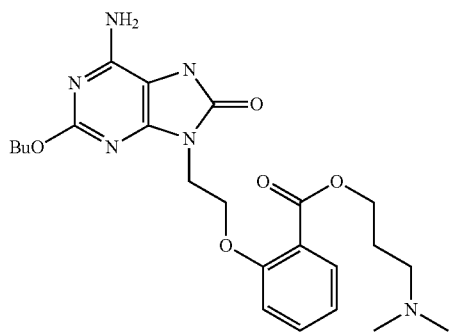

The compound obtained in Example 2-9 step (iii) (50 mg) was dissolved in dichloromethane (5 ml), and thereto were added 3-(dimethylamino)propane-1-ol (0.016 ml), 4-pyrrolidin-1-ylpyridine (2 mg) and 1-(3-dimethylaminopropyl)-3-ethylcarbodiimide iodine methyl (42 mg). The mixture was stirred at room temperature for 96 hours and applied to a cartridge of SCX resin. The resin was washed with acetonitrile and the fractions were collected by application of 10% aqueous ammonium solution-acetonitrile, and purified by RPHPLC to give the titled compound. Yield: 8.9 mg (14%).

$^1$H NMR δ (DMSO d$_6$) 7.57 (1H, d), 7.48 (1H, t), 7.18 (1H, d), 7.01 (1H, t), 6.40 (2H, s), 4.36 (2H, t), 4.09 (2H, t), 4.06 (2H, m), 4.04 (2H, m), 2.24 (2H, t), 2.11 (6H, s), 1.69 (2H, m), 1.59 (2H, m), 1.38 (1H, m), 0.90 (3H, t).

EXAMPLE 2-11

Methyl 3-[4-({[4-(6-amino-2-butoxy-8-oxo-7,8-dihydro-9H-purin-9-yl)butyl]amino}sulfonyl)phenyl]propanoate

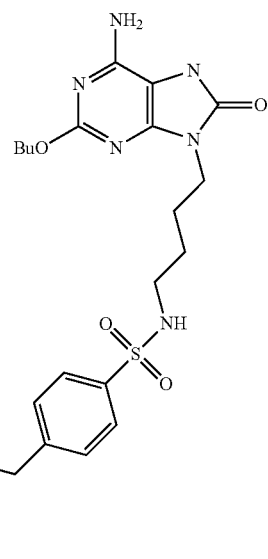

The compound obtained in Example 2-8 step (ii) (308 mg), methyl 3-[4-(chlorosulfonyl)phenyl]propanoate (263 mg) and triethylamine (0.284 ml) were mixed under stirring at 60° C. for 1 hour, and then cooled. After concentration under reduced pressure, the residue was purified by RPHPLC. The resulting white substance was dissolved in methanol, and 4M hydrochloric acid-dioxane was added thereto. The mixture was stirred at room temperature overnight and then concentrated under reduced pressure to give the titled compound as a white solid. Yield: 124 mg (24%); mp 150-152° C., MS APCI+ve 521 (M+H).

$^1$H NMR δ (DMSO d$_6$) 10.30-10.24 (1H, m), 7.66 (2H, d), 7.51 (1H, t), 7.42 (2H, d), 4.21 (2H, t), 3.63 (2H, t), 3.58 (3H, s), 2.96-2.86 (2H, m), 2.80-2.60 (4H, m), 1.72-1.53 (4H, m), 1.48-1.23 (4H, m), 0.99-0.78 (5H, m).

EXAMPLE 2-12

3-[4-({[4-(6-Amino-2-butoxy-8-oxo-7,8-dihydro-9H-purin-9-yl)butyl]amino}sulfonyl)phenyl]propionic acid

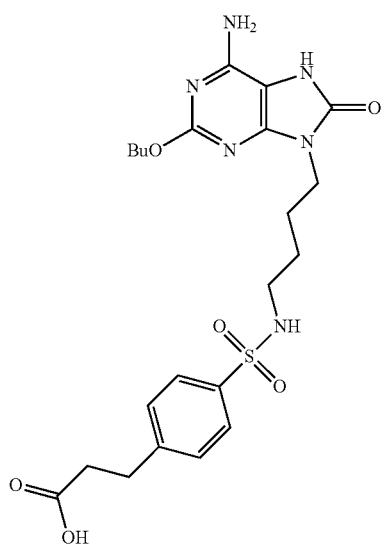

The compound obtained in Example 2-11 (100 mg) and lithium hydroxide (17 mg) were added to tetrahydrofuran (4 ml) and water (2 ml) and the mixture was stirred at room temperature for 16 hours. To the reaction solution was added acetic acid (2 ml) and the mixture was concentrated under reduced pressure. The residue was purified by RPHPLC and appropriate fractions were concentrated under reduced pressure to give the titled compound as a white solid. Yield: 40 mg (41%); mp 210-211° C., MS APCI+ve 507 (M+H).

$^1$H NMR δ (DMSO d$_6$) 7.66 (2H, d), 7.36 (2H, d), 6.31 (2H, s), 4.18 (2H, t), 3.69 (2H, t), 2.94 (2H, t), 2.78 (2H, t), 2.57-2.51 (5H, m), 1.75-1.62 (4H, m), 1.51-1.33 (4H, m), 0.95 (3H, t).

EXAMPLE 2-13

Methyl (3-{[[4-(6-amino-2-butoxy-8-oxo-7,8-dihydro-9H-purin-9-yl)butyl](2-pyrrolidin-1-ylethyl)amino]sulfonyl}phenyl)acetate

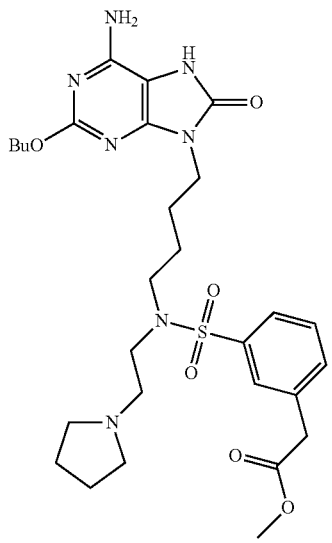

(i) 9-(4-Bromobutyl)-2-butoxy-8-methoxy-9H-purine-6-amine

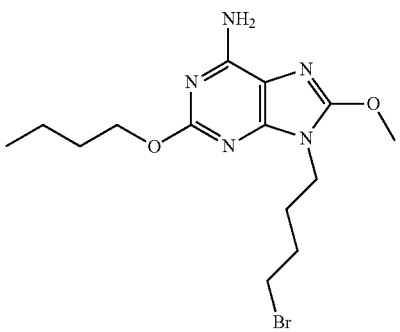 [SMILES: CCCCOc1nc(N)c2nc(OC)n(CCCCBr)c2n1]

The compound obtained in Example 2-1 step (v) (0.5 g) was added to potassium carbonate (0.92 g) and 1,4-dibromobutane (0.85 ml) in dimethylformamide (5 ml), and the mixture was stirred at room temperature for 16 hours. To the reaction solution was added brine and the mixture was extracted with ethyl acetate. The organic layer was washed with brine and concentrated to dryness. The residue was purified by flash column chromatography (ethyl acetate) to give the titled compound, as a white solid. Yield: 370 mg (70%).

$^1$H NMR δ (CDCl$_3$) 5.12 (2H, s), 4.28 (2H, t), 4.12 (3H, s), 3.97 (2H, t), 3.44 (2H, t), 2.01-1.69 (6H, m), 1.59-1.40 (2H, m), 0.96 (3H, t).

(ii) 2-Butoxy-8-methoxy-9-{4-[(2-pyrrolidin-1-yl-ethyl)amino]butyl}-9H-purine-6-amine

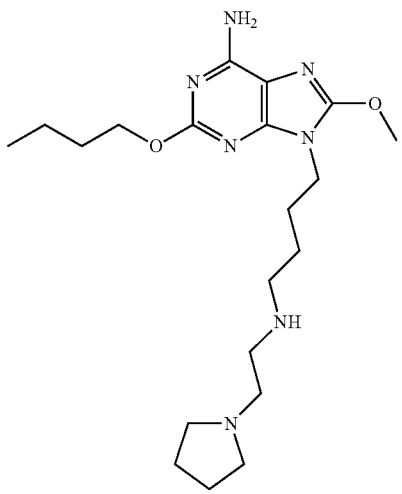 [SMILES: CCCCOc1nc(N)c2nc(OC)n(CCCCNCCN3CCCC3)c2n1]

The compound obtained in the step (i) (370 mg) and (2-pyrrolidin-1-ylethyl)amine (342 mg) were dissolved in dimethylformamide (5 ml) and the mixture was stirred at 70° C. for 1 hour. The reaction mixture was cooled, filtered and purified by RPHPLC. Appropriate fractions were concentrated under reduced pressure to give the titled compound as a white solid. Yield: 200 mg (50%); MS APCI+ve 406 (M+H).

$^1$H NMR δ (CDCl$_3$) 5.05 (2H, s), 4.27 (2H, t), 4.10 (3H, s), 3.94 (2H, t), 2.73-2.53 (6H, m), 2.50-2.44 (5H, m), 1.84-1.72 (6H, m), 1.56-1.43 (6H, m), 0.96 (3H, t).

(iii) Methyl (3-{[[4-(6-amino-2-butoxy-8-oxo-7,8-dihydro-9H-purin-9-yl)butyl](2-pyrrolidin-1-ylethyl)amino]sulfonyl}phenyl)acetate

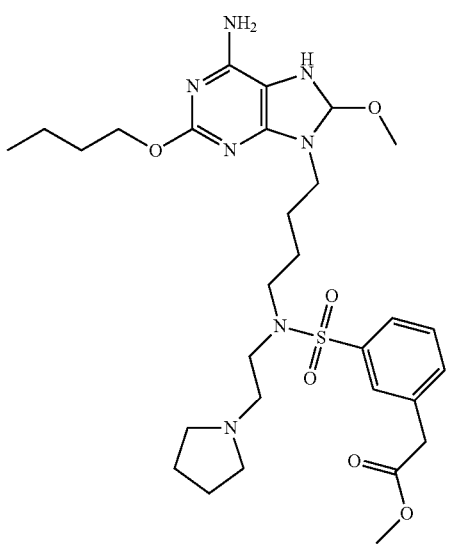 [SMILES: CCCCOc1nc(N)c2c(n1)N(CCCCN(CCN1CCCC1)S(=O)(=O)c1cccc(CC(=O)OC)c1)C(OC)N2]

The compound obtained in the step (ii) (232 mg), methyl [3-(chlorosulfonyl)phenyl]acetate (43 mg) and triethylamine (0.08 ml) were stirred in acetonitrile (10 ml) at 60° C. for 1 hour. The reaction mixture was cooled, concentrated under reduced pressure and purified by RPHPLC. Appropriate fractions were concentrated under reduced pressure to give a white solid 190 mg. The obtained solid was dissolved in methanol (5 ml) and 4M hydrochloric acid-dioxane (2 ml) was added thereto. The mixture was stirred at room temperature overnight. The reaction mixture was concentrated under reduced pressure and purified by RPHPLC, and appropriate fractions were concentrated under reduced pressure to give the titled compound as a white solid. Yield: 100 mg (29%); MS APCI+ve 602 (M+H).

$^1$H NMR δ (DMSO d$_6$) 9.84 (1H, s), 7.73-7.71 (1H, m), 7.68-7.63 (1H, m), 7.54-7.50 (2H, m), 6.39 (2H, s), 4.13 (2H, t), 3.83 (2H, s), 3.66 (2H, t), 3.62 (3H, s), 3.13-3.05 (4H, m), 2.44-2.26 (4H, m), 1.68-1.57 (9H, m), 1.49-1.32 (5H, m), 0.91 (3H, t).

EXAMPLE 2-14

(3-{[[4-(6-Amino-2-butoxy-8-oxo-7,8-dihydro-9H-purin-9-yl)butyl](2-pyrrolidin-1-ylethyl)amino]sulfonyl}phenyl)acetic acid

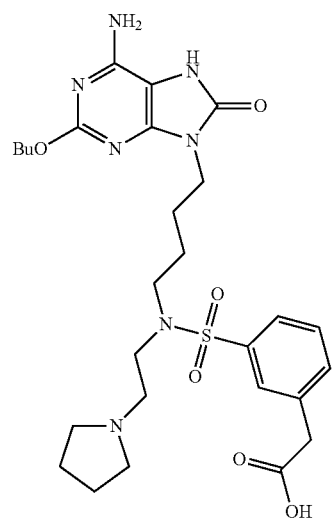

The compound obtained in Example 2-13 (70 mg) and lithium hydroxide (20 mg) were added to tetrahydrofuran (4 ml) and water (2 ml) and by the same manner to Example 2-12, the titled compound was obtained as a white solid. Yield: 35 mg (51%); mp 192-193° C., MS APCI-ve 588 (M-H).

$^1$H NMR δ (DMSO d$_6$) 7.69 (1H, s), 7.62 (1H, d), 7.55-7.43 (2H, m), 6.51 (2H, s), 4.13 (4H, t), 3.08 (4H, t), 2.43 (4H, t), 2.36-2.30 (4H, m), 1.69-1.55 (8H, m), 1.48-1.30 (6H, m), 0.91 (3H, t).

EXAMPLE 2-15

Methyl (3-{[[4-(6-amino-2-butoxy-8-oxo-7,8-dihydro-9H-purin-9-yl)butyl](2-methoxyethyl)amino]sulfonyl}phenyl)acetate

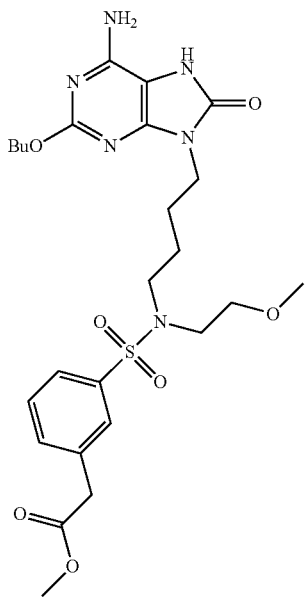

(i) 2-Butoxy-8-methoxy-9-{4-[(2-methoxyethyl)amino]butyl}-9H-purine-6-amine

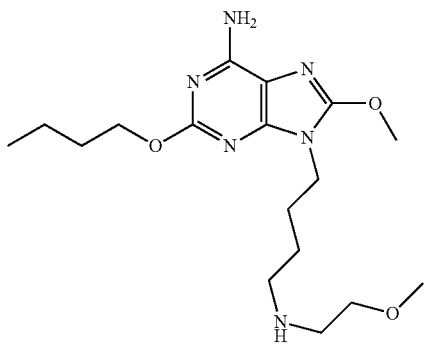 [SMILES: CCCCOc1nc(N)c2nc(OC)n(CCCCNCCOC)c2n1]

The compound obtained in Example 2-13 step (i) (500 mg) and (2-methoxyethyl)amine (303 mg) were dissolved in acetonitrile (5 ml) and stirred at 80° C. for 1 hour. The reaction mixture was cooled, filtered and purified by RPHPLC to give the titled compound as a white solid. Yield: 270 mg (55%); mp 99-100° C., MS APCI+ve 367 (M+H).

$^1$H NMR δ (DMSO $d_6$) 6.77 (2H, s), 4.16 (2H, t), 4.06 (3H, s), 3.83 (2H, t), 3.34-3.31 (3H, m), 3.21 (3H, s), 2.58 (2H, t), 1.75-1.58 (4H, m), 1.48-1.26 (6H, m), 0.92 (3H, t).

(ii) 2-Butoxy-8-oxo-9-{4-[(3-methoxycarbonylmethyl)phenylsulfonyl(2-methoxyethyl)amino]butyl}-9H-purine-6-amine

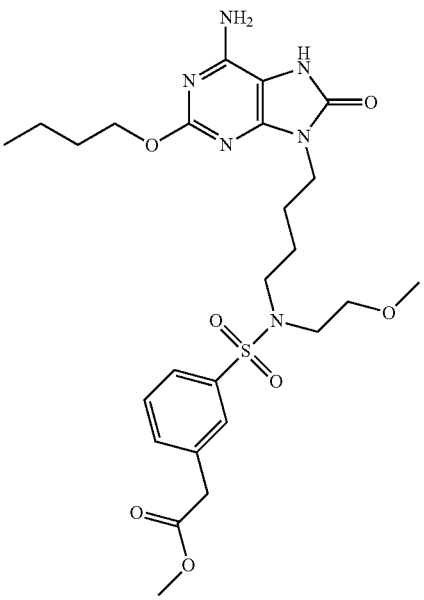 [SMILES: CCCCOc1nc(N)c2[nH]c(=O)n(CCCCN(CCOC)S(=O)(=O)c3cccc(CC(=O)OC)c3)c2n1]

Using the compound obtained in the step (i) (230 mg), methyl [3-(chlorosulfonyl)phenyl]acetate (157 mg) and triethylamine (0.09 ml), the titled compound was obtained as a white solid by the same manner to Example 2-13 step (iii). Yield: 170 mg (48%); mp 182-183° C., MS APCI+ve 565 (M+H).

$^1$H NMR δ (DMSO $d_6$) 9.86 (1H, s), 7.73 (1H, s), 7.68-7.64 (1H, m), 7.56-7.48 (2H, m), 6.41 (2H, s), 4.14 (2H, t), 3.83 (2H, s), 3.69-3.60 (5H, m), 3.38-3.30 (2H, m), 3.20 (2H, t), 3.17-3.06 (5H, m), 1.69-1.56 (4H, m), 1.52-1.32 (4H, m), 0.92 (3H, t).

EXAMPLE 2-16

(3-{[[4-(6-Amino-2-butoxy-8-oxo-7,8-dihydro-9H-purin-9-yl)butyl](2-methoxyethyl)amino]sulfonyl}phenyl)acetic acid

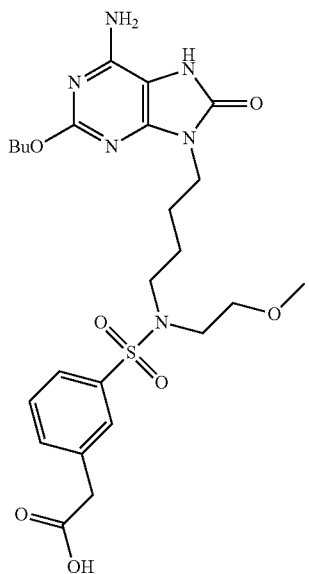

By the same manner to Example 2-12, using the compound obtained in Example 2-15 (100 mg) and a mixed solution of lithium hydroxide solution (20 mg) in tetrahydrofuran (4 ml) and water (2 ml), the titled compound was obtained as a white solid from diethyl ether/isohexane. Yield: 60 mg (61%); mp 171-172° C., MS APC-ve 549 (M−H).

$^1$H NMR δ (DMSO d$_6$) 7.67 (1H, s), 7.61-7.40 (4H, m), 6.57 (2H, s), 4.13 (2H, t), 3.69-3.60 (2H, m), 3.58 (2H, s), 3.37-3.30 (2H, m), 3.21-3.12 (5H, m), 3.08-2.99 (2H, m), 1.68-1.56 (2H, m), 1.48-0.99 (4H, m), 0.96-0.77 (6H, m).

EXAMPLE 2-17

Methyl (3-{[[4-(6-amino-2-butoxy-8-oxo-7,8-dihydro-9H-purin-9-yl)butyl](methyl)amino]sulfonyl}phenyl)acetate

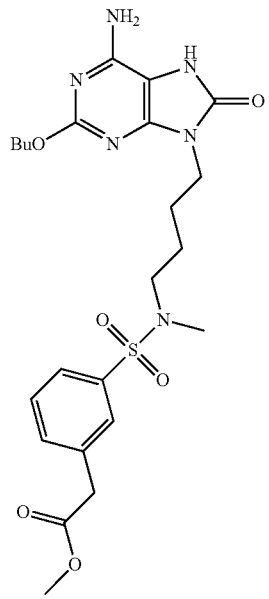

The compound obtained in Example 2-13 step (i) (417 mg) and a 40% aqueous methylamine solution (2 ml) were dissolved in acetonitrile (5 ml) and stirred at 80° C. for 1.5 hour. The reaction mixture was cooled, and concentrated under reduced pressure. The residue was dissolved in acetonitrile (5 ml), and using triethylamine (0.16 ml) and methyl [3-(chlorosulfonyl)phenyl]acetate (278 mg), the titled compound was obtained as a white solid by the same manner to Example 2-13 step (iii). Yield: 120 mg (21%); MS APCI+ve 521 (M+H).

$^1$H NMR δ (DMSO d$_6$) 7.69 (1H, s), 7.65-7.61 (2H, m), 7.57-7.53 (2H, m), 6.40 (2H, s), 4.14 (2H, t), 3.84 (2H, s), 3.67 (2H, t), 3.63 (3H, s), 2.96 (2H, t), 2.62 (3H, s), 1.69-1.58 (4H, m), 1.49-1.33 (4H, m), 0.91 (3H, t).

EXAMPLE 2-18

(3-{[[4-(6-Amino-2-butoxy-8-oxo-7,8-dihydro-9H-purin-9-yl)butyl](methyl)amino]sulfonyl}phenyl)acetic acid

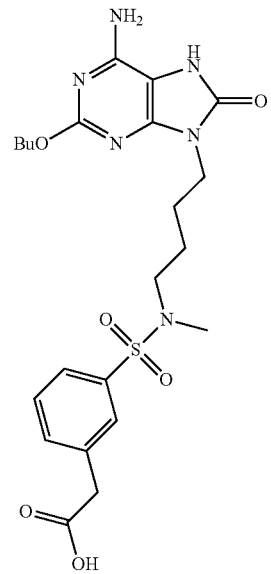

The compound obtained in Example 2-17 (100 mg) and lithium hydroxide (20 mg) were added to tetrahydrofuran (4 ml) and water (2 ml), followed by conducting a reaction by the same manner to Example 2-12, the titled compound was obtained as a white solid from diethyl ether/isohexane. Yield: 43 mg (64%); mp 171-172° C., MS APC+ve 507 (M+H).

$^1$H NMR δ (DMSO d$_6$) 7.63 (1H, s), 7.56-7.43 (3H, m), 6.61 (2H, s), 4.13 (2H, t), 3.67 (2H, t), 3.54 (2H, s), 2.88 (2H, t), 2.59 (3H, s), 1.70-1.57 (4H, m), 1.48-1.30 (4H, m), 0.91 (3H, t).

EXAMPLE 2-19

Methyl [3-({[4-(6-amino-2-butoxy-8-oxo-7,8-dihydro-9H-purin-9-yl)butyl][3-(dimethylamino)-2,2-dimethylpropyl]amino}sulfonyl)phenyl]acetate

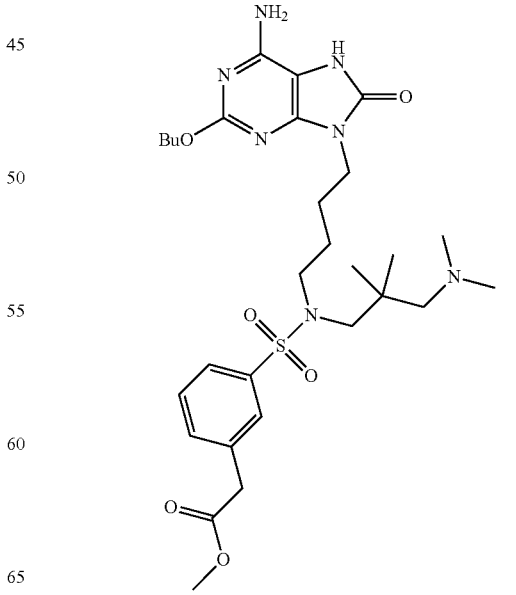

The compound obtained in Example 2-13 step (i) (417 mg), triethylamine (0.312 ml) and N,N,2,2-tetramethylpropane-1,3-diamine (146 mg) were dissolved in acetonitrile (5 ml) and stirred at 100° C. for 4 hours. The reaction mixture was cooled and concentrated under reduced pressure and purified by RPHPLC. Appropriate fractions were concentrated under reduced pressure to give a residue 190 mg. The residue was dissolved in acetonitrile (5 ml), and using triethylamine (0.13 ml) and methyl [3-(chlorosulfonyl)phenyl]acetate (112 mg), the titled compound was obtained as a white solid by the same manner to Example 2-13 step (iii). Yield: 83 mg (12%); MS APCI+ve 620 (M+H).

$^1$H NMR δ (DMSO d$_6$) 9.82 (1H, s), 7.71 (1H, s), 7.65-7.61 (1H, m), 7.52-7.45 (2H, m), 6.40 (2H, s), 4.13 (2H, t), 3.82 (2H, s), 3.62 (3H, s), 3.57 (2H, t), 3.07-3.01 (2H, m), 2.95 (2H, s), 2.17 (6H, s), 2.04 (2H, s), 1.68-1.57 (2H, m), 1.55-1.31 (6H, m), 0.91 (3H, t), 0.84 (6H, s).

EXAMPLE 2-20

[3-({[4-(6-Amino-2-butoxy-8-oxo-7,8-dihydro-9H-purin-9-yl)butyl][3-(dimethylamino)-2,2-dimethylpropyl]amino}sulfonyl)phenyl]acetic acid

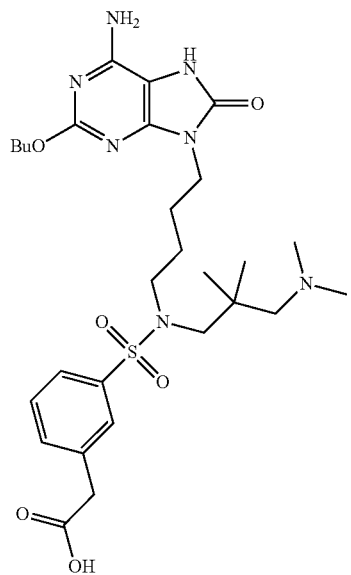

The compound obtained in Example 2-19 (0.165 g) and lithium hydroxide (45 mg) were added to tetrahydrofuran (4 ml) and water (2 ml). The same manner to Example 2-12 was conducted to give the titled compound as a white solid. Yield: 80 mg (51%); mp 175-176° C., MS APC-ve 604 (M−H).

$^1$H NMR δ (DMSO d$_6$) 7.74-7.71 (1H, m), 7.64-7.60 (1H, m), 7.58-7.53 (1H, m), 7.51-7.45 (1H, m), 6.63 (2H, s), 4.19 (3H, t), 3.67 (2H, s), 3.10-3.03 (2H, m), 2.99 (2H, s), 2.22 (6H, s), 2.10 (2H, s), 1.74-1.63 (2H, m), 1.62-1.38 (8H, m), 0.97 (3H, t), 0.90 (6H, s).

EXAMPLE 2-21

Methyl [3-({[3-(6-amino-2-butoxy-8-oxo-7,8-dihydro-9H-purin-9-yl)propyl]amino}sulfonyl)phenyl]acetate

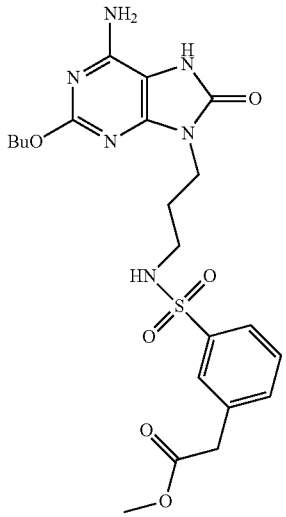

The compound obtained in Example 2-3 step (ii) (240 mg), triethylamine (0.12 ml) and methyl [3-(chlorosulfonyl)phenyl]acetate (204 mg) were dissolved in acetonitrile (5 ml), and the same manner to Example 2-13 step (iii) was conducted to give the titled compound as a white solid. Yield: 35 mg (9%); mp 218-219° C., MS APCI+ve 493 (M+H).

$^1$H NMR δ (DMSO d$_6$) 7.71-7.61 (2H, m), 7.54 (1H, s), 7.43-7.20 (3H, m), 6.73 (1H, s), 4.16-4.09 (1H, m), 3.84 (1H, s), 3.67 (3H, s), 2.81-2.71 (1H, m), 2.51 (2H, s), 1.83-1.69 (2H, m), 1.68-1.56 (2H, m), 1.45-1.30 (2H, m), 1.14-1.05 (2H, m), 0.95-0.84 (3H, m).

EXAMPLE 2-22

Methyl (3-{[[4-(6-amino-2-butoxy-8-oxo-7,8-dihydro-9H-purin-9-yl)butyl](2-hydroxy-2-methylpropyl)amino]sulfonyl}phenyl)acetate

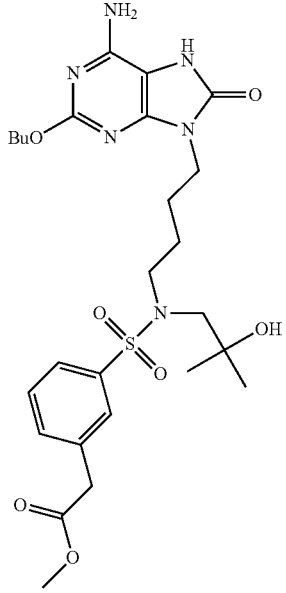

The compound obtained in Example 2-13 step (i) (371 mg) and 1-amino-2-methylpropane-2-ol (400 mg) were dissolved in acetonitrile (5 ml) and the same manner to Example 2-19 using triethylamine (0.055 ml) and methyl [3-(chlorosulfonyl)phenyl]acetate (93 mg) was conducted to give the titled compound as a white solid. Yield: 140 mg (24%); mp 192-193° C., MS APCI+ve 579 (M+H).

$^1$H NMR δ (DMSO d$_6$) 9.81 (1H, s), 7.71 (1H, s), 7.65-7.61 (1H, m), 7.50-7.42 (2H, m), 6.40 (2H, s), 4.46 (1H, s), 4.13 (2H, t), 3.81 (2H, s), 3.62 (3H, s), 3.58-3.52 (2H, m), 3.25-3.17 (2H, m), 1.71-1.54 (2H, m), 1.52-1.32 (7H, m), 1.10 (6H, s), 0.92 (3H, t).

EXAMPLE 2-23

(3-{[[4-(6-Amino-2-butoxy-8-oxo-7,8-dihydro-9H-purin-9-yl)butyl] (2-hydroxy-2-methylpropyl)amino]sulfonyl}phenyl)acetic acid

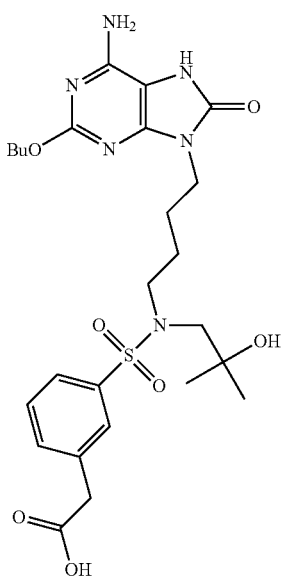

By the same manner to Example 2-12, the compound obtained in Example 2-22 (70 mg) and lithium hydroxide (20 mg) were added to tetrahydrofuran (4 ml) and water (2 ml) and the mixture was stirred at room temperature for 24 hours. The reaction mixture was concentrated under reduced pressure and partitioned between 2M hydrochloric acid and ethyl acetate. The aqueous layer was extracted with ethyl acetate and the combined organic layer was dried and concentrated under reduced pressure to give the titled compound as a white solid. Yield: 23 mg (34%); MS APCI+ve 565 (M+H).

$^1$H NMR δ (DMSO d$_6$) 10.08 (1H, s), 7.69 (1H, s), 7.64-7.59 (1H, m), 4.18 (2H, t), 3.69 (2H, s), 3.61-3.53 (2H, m), 3.24-3.16 (2H, m), 3.03 (2H, s), 1.70-1.59 (2H, m), 1.54-1.34 (8H, m), 1.09 (6H, s), 0.92 (3H, t).

EXAMPLE 2-24

Methyl [3-({[2-(6-amino-2-butoxy-8-oxo-7,8-dihydro-9H-purin-9-yl)ethyl]amino}sulfonyl)phenyl]acetate

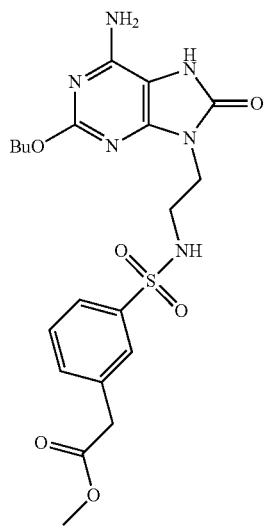

The compound obtained in Example 2-1 step (vii) (245 mg), triethylamine (0.13 ml) and methyl [3-(chlorosulfonyl)phenyl]acetate (217 mg) were dissolved in acetonitrile (5 ml) and the same manner to Example 2-13 step (iii) was conducted to give the titled compound as a white solid. Yield: 40 mg (9%); MS APCI+ve 479 (M+H).

$^1$H NMR δ (DMSO d$_6$) 7.83 (1H, t), 7.69-7.59 (2H, m), 7.52-7.47 (2H, m), 6.48 (2H, s), 4.15 (2H, t), 3.80 (5H, s), 3.61 (3H, s), 3.14-3.03 (2H, m), 1.70-1.57 (2H, m), 1.46-1.31 (2H, m), 0.92 (2H, t).

EXAMPLE 2-25

Methyl [3-({[4-(6-amino-2-butoxy-8-oxo-7,8-dihydro-9H-purin-9-yl)butyl][(2R)-2,3-dihydroxypropyl]amino}sulfonyl)phenyl]acetate

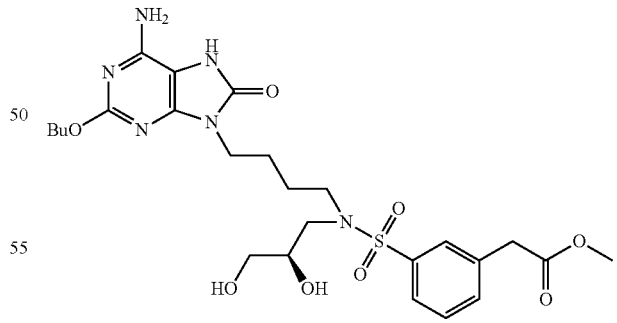

The compound obtained in Example 2-13 step (i) (400 mg), (2R)-3-aminopropane-1,2-diol (200 mg) were dissolved in acetonitrile (5 ml) and the gummy residue 230 mg was obtained by the same manner to Example 2-13 step (ii). The residue was dissolved in acetonitrile (10 ml) and the same manner to Example 2-13 step (iii) was conducted using triethylamine (0.090 ml) and methyl [3-(chlorosulfonyl)phenyl]acetate (150 mg) to give the titled compound as a white solid. Yield: 170 mg (27%); MS APCI+ve 581 (M+H).

$^1$H NMR δ (DMSO d$_6$) 9.83 (1H, s), 7.71 (1H, s), 7.66-7.64 (2H, m), 7.54-7.45 (2H, m), 6.40 (2H, s), 4.75 (1H, d), 4.57 (1H, t), 4.14 (2H, t), 3.82 (2H, s), 3.62 (3H, s), 3.30-3.05 (6H, m), 2.94-2.86 (1H, m), 1.67-1.32 (6H, m), 0.92 (3H, t).

EXAMPLE 2-26

[3-({[4-(6-Amino-2-butoxy-8-oxo-7,8-dihydro-9H-purin-9-yl)butyl][(2R)-2,3-dihydroxypropyl]amino}sulfonyl)phenyl]acetic acid

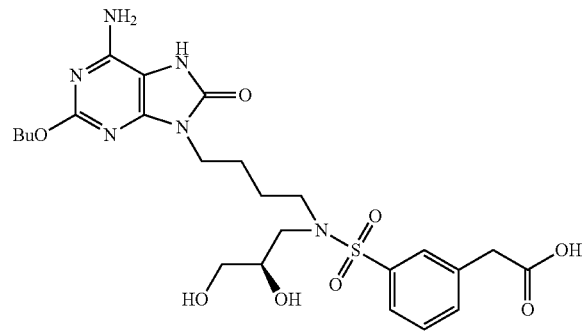

The compound obtained in Example 2-25 (100 mg) and lithium hydroxide (20 mg) were added to tetrahydrofuran (5 ml) and water (2 ml), and the same manner to Example 2-12 was conducted to give the titled compound as a white solid. Yield: 58 mg (60%); MS APCI+ve 567 (M+H).

$^1$H NMR δ (DMSO d$_6$) 7.66 (1H, s), 7.56-7.52 (1H, m), 7.50-7.47 (1H, m), 7.43-7.38 (1H, m), 6.55 (2H, s), 4.13 (2H, t), 3.63 (2H, t), 3.50 (2H, s), 3.39-3.02 (8H, m), 1.67-1.24 (8H, m), 0.91 (3H, t).

EXAMPLE 2-27

Methyl 3-({[4-(6-amino-2-butoxy-8-oxo-7,8-dihydro-9H-purin-9-yl)butyl][3-(dimethylamino)-2,2-dimethylpropyl]amino}sulfonyl)benzoate

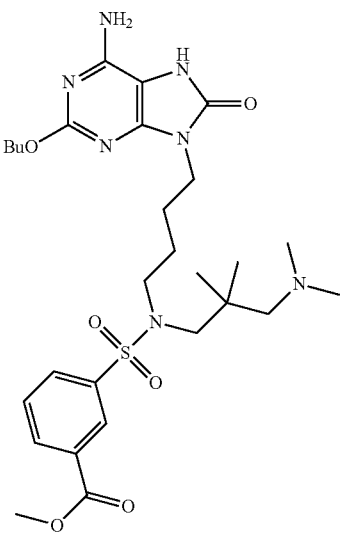

The compound obtained in Example 2-13 step (i) (500 mg) and N,N,2,2-tetramethylpropane-1,3-diamine (1.5 ml) were dissolved in acetonitrile (10 ml) and the reaction was conducted by the same manner to Example 2-13 step (ii) to give gummy residue 383 mg as trifluoroacetate. The residue was dissolved in acetonitrile (10 ml), and triethylamine (0.3 ml) and 3-(chlorosulfonyl)benzoic acid (158 mg) were added thereto and the mixture was stirred at 80° C. for 2 hours. The reaction mixture was cooled, concentrated under reduced pressure and purified by RPHPLC. Appropriate fractions were concentrated under reduced pressure to give a solid residue 170 mg. The residue was dissolved in methanol (5 ml) and 4M hydrochloric acid-dioxane (2 ml) was added and stirred at room temperature for 24 hours, and then trimethylsilyl chloride (2 ml) were added thereto and the mixture was stirred at room temperature for further 72 hours. The reaction mixture was concentrated under reduced pressure and purified by RPHPLC. Appropriate fractions were concentrated under reduced pressure to give the titled compound as a white solid. Yield: 8 mg (5%); MS APCI+ve 606 (M+H).

$^1$H NMR δ (DMSO d$_6$) 9.85 (1H, s), 8.21 (1H, t), 8.17-8.13 (1H, m), 8.05-8.01 (1H, m), 7.69 (1H, t), 6.41 (2H, s), 4.11 (2H, t), 3.90 (3H, s), 3.58 (2H, t), 3.12-3.06 (2H, m), 2.18 (6H, s), 2.04 (2H, s), 1.67-1.55 (2H, m), 1.52-1.28 (8H, m), 0.91 (3H, t), 0.85 (6H, s).

EXAMPLE 2-28

3-({[4-(6-Amino-2-butoxy-8-oxo-7,8-dihydro-9H-purin-9-yl)butyl][3-(dimethylamino)-2,2-dimethylpropyl]amino}sulfonyl)benzoic acid

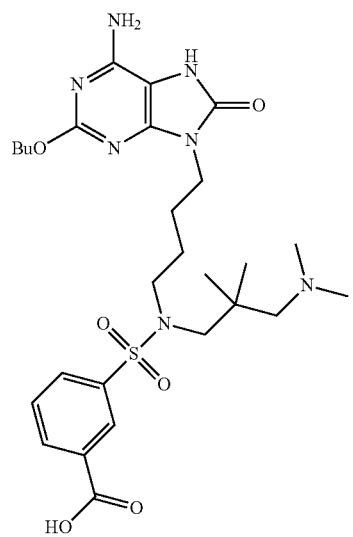

The titled compound was obtained as a white solid by the same manner to Example 2-27. Yield: 38 mg (23%); MS ESI+ve 592 (M+H).

$^1$H NMR δ (DMSO d$_6$) 9.86 (1H, s), 8.83 (1H, s), 7.70-7.60 (2H, m), 7.40-7.26 (2H, m), 6.41 (2H, s), 4.14-4.10 (2H, m), 4.12 (2H, t), 3.55-3.37 (4H, m), 3.05-2.96 (2H, m), 2.88-2.80 (6H, m), 1.68-1.58 (2H, m), 1.44-1.27 (6H, m), 1.10 (6H, s), 0.92 (3H, t).

EXAMPLE 2-29

Methyl (3-{[[4-(6-amino-2-butoxy-8-oxo-7,8-dihydro-9H-purin-9-yl)butyl](3-morpholin-4-ylpropyl)amino]methyl}phenyl)acetate

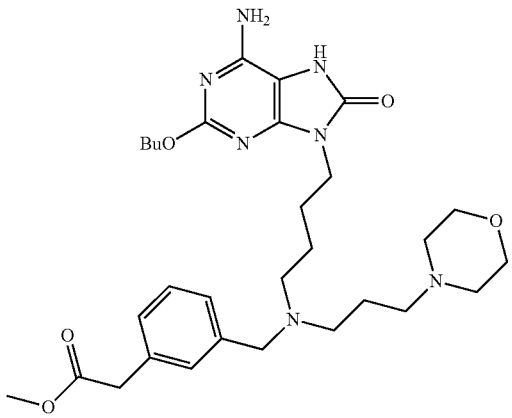

The compound obtained in Example 2-13 step (i) (830 mg) and (3-morpholin-4-ylpropyl)amine (3 ml) were dissolved in acetonitrile (10 ml) and stirred at 80° C. for 3 hours. The reaction mixture was cooled and concentrated under reduced pressure, and purified by RPHPLC. Appropriate fractions ware concentrated under reduced pressure to give colorless gummy residue 600 mg. The residue was dissolved in acetonitrile (20 ml), and potassium carbonate (380 mg) and methyl [3-(bromomethyl)phenyl]acetate (336 mg) were added thereto. The mixture was stirred at room temperature for 16 hours. The reaction mixture was partitioned between ethyl acetate and water. Further, an aqueous layer was extracted with ethyl acetate and the combined organic layer was dried and concentrated under reduced pressure. The resulting gummy residue was purified by RPHPLC. Appropriate fractions were concentrated under reduced pressure, and the obtained gummy residue was dissolved in methanol (5 ml) and 4M hydrochloric acid was added thereto and the mixture was stirred at room temperature for 24 hours. The reaction mixture was concentrated under reduced pressure and purified by RPHPLC. Appropriate fractions were concentrated under reduced pressure to give the titled compound as a white solid. Yield: 460 mg (57%); MS APCI+ve 584 (M+H).

$^1$H NMR δ (CDCl$_3$) 7.25-7.15 (3H, m), 7.14-7.10 (1H, m), 5.67 (2H, s), 4.26 (2H, t), 3.83 (2H, t), 3.69 (3H, s), 3.67 (2H, t), 3.61 (2H, s), 3.49 (2H, s), 2.46-2.23 (10H, m), 1.83-1.39 (12H, m), 0.96 (3H, t).

EXAMPLE 2-30

(3-{[[4-(6-Amino-2-butoxy-8-oxo-7,8-dihydro-9H-purin-yl)butyl](3-morpholin-4-ylpropyl)amino]methyl}phenyl)acetic acid

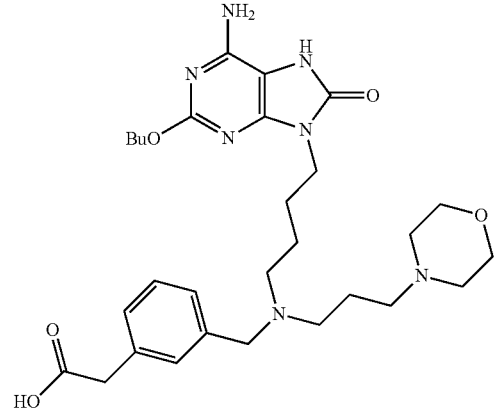

The compound obtained in Example 2-29 (200 mg) and lithium hydroxide (100 mg) were added to tetrahydrofuran (15 ml) and water (5 ml) and the same manner as Example 2-12 was conducted to give the titled compound as a white solid. Yield: 130 mg (66%); MS APCI+ve 570 (M+H).

$^1$H NMR δ (CDCl$_3$) 7.30 (1H, s), 7.15-7.08 (2H, m), 7.03-6.95 (1H, m), 6.10 (1H, s), 4.20 (2H, t), 3.74 (2H, s), 3.64 (2H, s), 2.62-2.32 (12H, m), 1.76-1.58 (8H, m), 1.54-1.37 (6H, m), 1.21 (2H, t), 0.94 (3H, t).

EXAMPLE 2-31

Methyl [3-({[4-(6-amino-2-butoxy-8-oxo-7,8-dihydro-9H-purin-9-yl)butyl][3-(dimethylamino)-2,2-dimethylpropyl]amino}methyl)phenyl]acetate

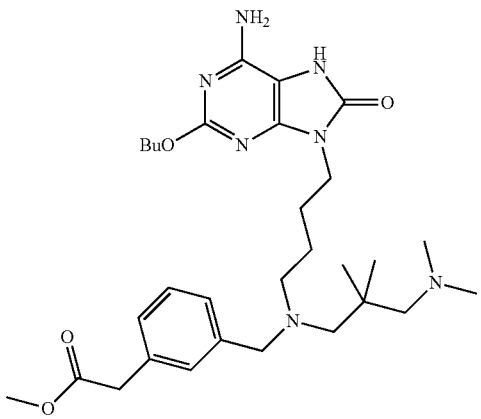

Using the compound obtained in Example 2-13 step (i) (350 mg), N,N,2,2-tetramethylpropane-1,3-diamine (1 ml), potassium carbonate (500 mg) and methyl[3-(bromomethyl)phenyl]acetate (200 mg), the same manner to Example 2-29 was conducted to give the titled compound as a white solid. Yield: 60 mg (13%); MS APCI+ve 570 (M+H).

$^1$H NMR δ (CDCl$_3$) 7.25-7.19 (3H, m), 7.13-7.08 (1H, m), 5.63 (2H, s), 5.63 (2H, s), 4.26 (2H, t), 3.78 (2H, t), 3.69 (3H, s), 3.62 (2H, s), 3.59 (2H, s), 2.38 (2H, t), 2.31 (2H, s), 2.24 (6H, s), 1.79-1.43 (8H, m), 0.96 (3H, t), 0.86 (6H, s).

EXAMPLE 2-32

[3-({[4-(6-Amino-2-butoxy-8-oxo-7,8-dihydro-9H-purin-9-yl)butyl][3-(dimethylamino)-2,2-dimethylpropyl]amino}methyl)phenyl]acetic acid

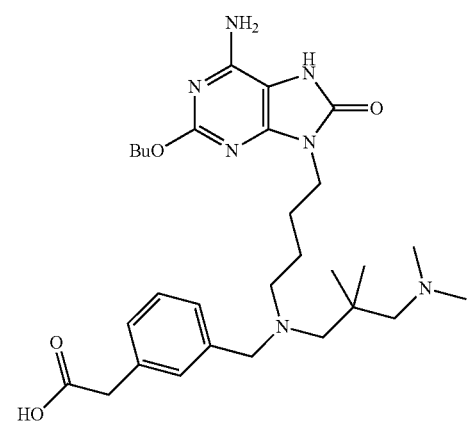

Using the compound obtained in Example 2-31 (50 mg) and lithium hydroxide (15 mg), the same manner to Example 2-12 was conducted to give the titled compound as a white solid. Yield: 10 mg (21%); mp 189-190° C., MS APCI+ve 556 (M+H).

$^1$H NMR δ (DMSO d$_6$) 7.78-7.56 (1H, m), 7.28-7.09 (3H, m), 5.90 (2H, s), 4.26-4.17 (2H, m), 3.77-3.68 (2H, m), 3.58 (2H, s), 3.54 (2H, s), 2.44-2.10 (13H, m), 1.81-1.55 (4H, m), 1.50-1.38 (5H, m), 0.95 (3H, t), 0.90 (6H, s).

EXAMPLE 2-33

Methyl [3-({[4-(6-amino-2-butoxy-8-oxo-7,8-dihydro-9H-purin-9-yl)butyl][3-(2-oxopyrrolidin-1-yl)propyl]amino}methyl)phenyl]acetate

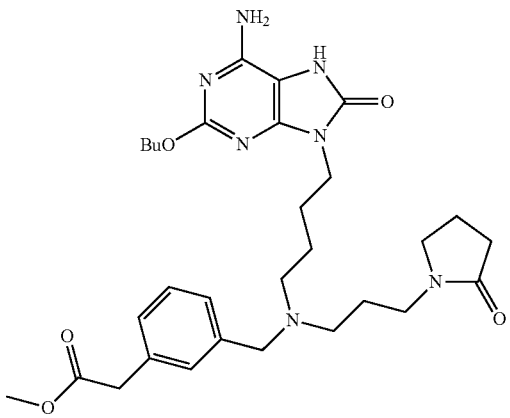

Using the compound obtained in Example 2-13 step (i) (400 mg), 1-(3-aminopropyl)pyrrolidin-2-on (1 ml), potassium carbonate (175 mg) and methyl [3-(bromomethyl)phenyl]acetate (175 mg), the same manner to Example 2-29 was conducted to give the titled compound as a white solid. Yield: 200 mg (48%); mp 115-116° C., MS APCI+ve 582 (M+H).

$^1$H NMR δ (CDCl$_3$) 10.46 (1H, s), 7.24-7.10 (4H, m), 5.88 (2H, s), 4.27 (2H, t), 3.87 (2H, t), 3.68 (3H, s), 3.61 (2H, s), 3.48 (2H, s), 3.27 (2H, t), 3.22-3.18 (2H, m), 2.41-2.32 (6H, m), 2.01-1.90 (2H, m), 1.82-1.55 (6H, m), 1.52-1.41 (4H, m), 0.96 (3H, t).

EXAMPLE 2-34

[3-({[4-(6-Amino-2-butoxy-8-oxo-7,8-dihydro-9H-purin-9-yl)butyl][3-(2-oxopyrrolidin-1-yl)propyl]amino}methyl)phenyl]acetic acid

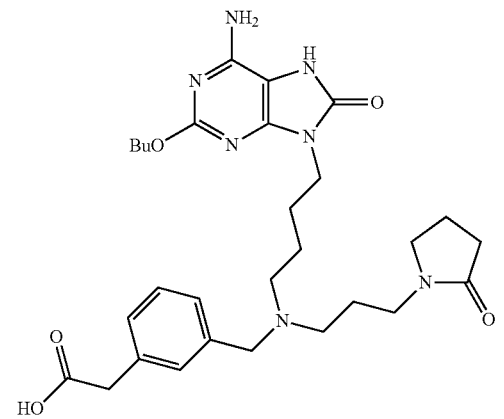

The compound obtained in Example 2-33 (50 mg) and lithium hydroxide (20 mg) were added to tetrahydrofuran (5 ml) and water (1 ml), and the same manner to Example 2-12 was conducted to give the titled compound as a white solid. Yield: 39 mg (80%); MS APCI+ve 568 (M+H).

$^1$H NMR δ (CDCl$_3$) 7.41-7.36 (1H, m), 7.22-7.06 (3H, m), 5.71 (2H, s), 4.23 (2H, t), 3.79 (2H, t), 3.58 (2H, s), 3.53 (2H, s), 3.29-3.21 (4H, m), 2.60-2.57 (1H, m), 2.49-2.38 (5H, m), 2.31 (2H, t), 1.97-1.89 (2H, m), 1.79-1.60 (6H, m), 1.53-1.39 (4H, m), 0.95 (3H, t).

EXAMPLE 2-35

Methyl (3-{[[4-(6-amino-2-butoxy-8-oxo-7,8-dihydro-9H-purin-9-yl)butyl](2-morpholin-4-ylethyl)amino]methyl}phenyl)acetate

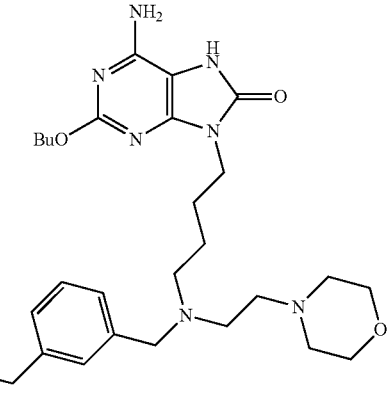

Using the compound obtained in Example 2-13 step (i) (500 mg), (2-morpholin-4-ylethyl)amine (1 ml), potassium carbonate (206 mg) and methyl [3-(bromomethyl)phenyl]acetate (180 mg), the same manner to Example 2-29 was conducted to give the titled compound as a white solid. Yield: 100 mg (13%); mp 189-190° C., MS APCI+ve 570 (M+H).

$^1$H NMR δ (DMSO d$_6$) 7.26-7.07 (4H, m), 6.38 (2H, s), 4.12 (2H, t), 3.72-3.61 (6H, m), 3.59 (3H, s), 3.51-3.45 (8H, m), 2.45-2.29 (2H, m), 2.25-2.14 (2H, m), 1.90-1.75 (2H, m), 1.68-1.26 (8H, m), 0.90 (3H, t).

EXAMPLE 2-36

(3-{[[4-(6-Amino-2-butoxy-8-oxo-7,8-dihydro-9H-purin-9-yl)butyl](2-morpholin-4-ylethyl)amino]methyl}phenyl)acetic acid

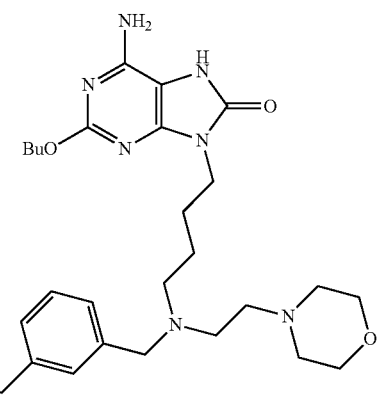

The compound obtained in Example 2-35 (50 mg) lithium hydroxide (20 mg) were added to tetrahydrofuran (5 ml) and water (1 ml), and the same manner to Example 2-12 was conducted to give the titled compound as a white solid. Yield: 35 mg (76%); MS APCI+ve 556 (M+H).

$^1$H NMR δ (DMSO d$_6$) 9.95 (1H, s), 7.25-7.07 (4H, m), 6.43 (2H, s), 4.14 (2H, t), 3.65 (2H, t), 3.53-3.46 (6H, m), 2.51 (2H, s), 2.47-2.37 (4H, m), 2.35-2.21 (6H, m), 1.70-1.59 (4H, m), 1.44-1.32 (4H, m), 0.91 (3H, t).

EXAMPLE 2-37

Methyl (3-{[[3-(6-amino-2-butoxy-8-oxo-7,8-dihydro-9H-purin-9-yl)propyl](3-morpholin-4-ylpropyl)amino]methyl}phenyl)acetate

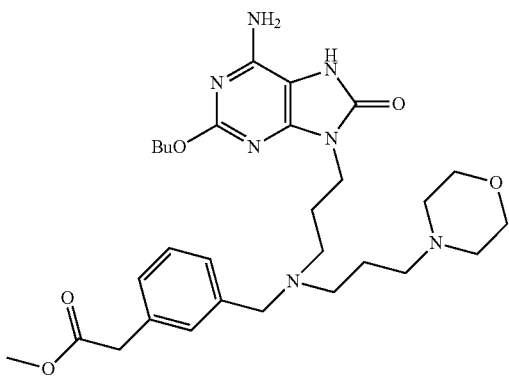

(i) 9-(3-bromopropyl)-2-butoxy-8-methoxy-9H-purine-6-amine

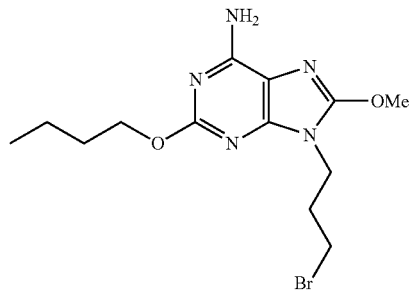 [SMILES: CCCCOc1nc(N)c2nc(OC)n(CCCBr)c2n1]

The compound obtained in Example 2-1 step (v) (2 g), potassium carbonate (3.7 g) and 1,3-dibromopropane (2.85 ml) were added to dimethylformamide (5 ml), and the same manner to Example 2-13 step (i) was conducted to give the titled compound as a white solid. Yield: 1.0 g (50%).

$^1$H NMR δ (CDCl$_3$) 5.18 (2H, s), 4.28 (2H, t), 4.12 (3H, s), 4.09 (2H, t), 3.38 (2H, t), 2.38-2.31 (2H, m), 1.80-1.73 (2H, m), 1.54-1.45 (2H, m), 0.96 (3H, t).

(ii) Methyl (3-{[[3-(6-amino-2-butoxy-8-oxo-7,8-dihydro-9H-purin-9-yl)propyl](3-morpholin-4-ylpropyl)amino]methyl}phenyl)acetate

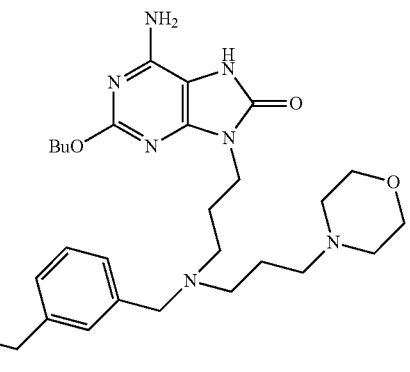

Using the compound obtained in the step (i) (481 mg), (3-morpholin-4-ylpropl)amine (1.5 ml), potassium carbonate (150 mg) and methyl [3-(bromomethyl)phenyl]acetate (125 mg), the same manner to Example 2-29 was conducted to give the titled compound as a white solid. Yield: 57 mg (7%); mp 200-201° C., MS APCI+ve 570 (M+H).

$^1$H NMR δ (DMSO d$_6$) 7.26-7.07 (4H, m), 6.38 (2H, s), 4.12 (2H, t), 3.72-3.61 (6H, m), 3.59 (3H, s), 3.51-3.45 (8H, m), 2.45-2.29 (2H, m), 2.25-2.14 (2H, m), 1.90-1.75 (2H, m), 1.68-1.26 (8H, m), 0.90 (3H, t).

EXAMPLE 2-38

Methyl [3-({[4-(6-amino-2-butoxy-8-oxo-7,8-dihydro-9H-purin-9-yl)butyl][2-(1H-tetrazol-5-yl)ethyl]amino}methyl)phenyl]acetate

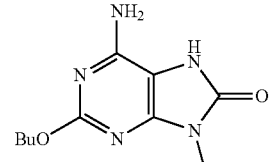

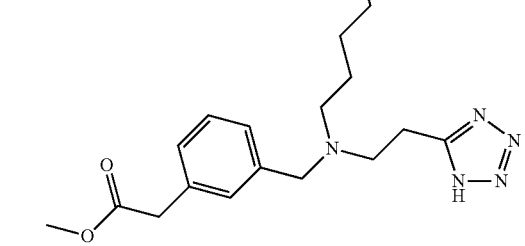

The compound obtained in Example 2-13 step (i) (500 mg) and 3-aminopropane nitrile (471 mg) were dissolved in acetonitrile (10 ml) and stirred at 80° C. for 2 hours. The reaction mixture was cooled, concentrated under reduced pressure and purified by RPHPLC. Appropriate fractions were concentrated under reduced pressure to give a white solid 220 mg. The residue was dissolved in methanol, (3-formylphenyl)acetate (109 mg) was added thereto and the mixture was stirred at room temperature for 1 hour. Sodium borohydride (28 mg) was added thereto and the mixture was stirred at room temperature for further 2 hours. To the reaction mixture was added acetic acid (2 ml) and the mixture was concentrated under reduced pressure and purified by RPHPLC.

Appropriate fractions were concentrated under reduced pressure to give a solid 170 mg. The obtained solid was dissolved in toluene (8 ml), and methylsilylazide (0.06 ml) and dibutyl tin oxide (72 mg) were added thereto, followed by stirring at 110° C. for 24 hours. The reaction mixture was cooled, concentrated under reduced pressure and purified by RPHPLC. Appropriate fractions were concentrated under reduced pressure to give a gummy substance. The gummy substance was dissolved in methanol (5 ml), and 4M hydrochloric acid-dioxane (2 ml) was added thereto, followed by stirring at room temperature for 24 hours. The reaction mixture was concentrated under reduced pressure and purified by RPHPLC. Appropriate fractions were concentrated under reduced pressure to give the titled compound as a white solid. Yield: 10 mg (2%); MS APCI+ve 553 (M+H).

$^1$H NMR δ (CDCl$_3$) 7.23-6.98 (4H, m), 4.24 (2H, t), 3.97-3.86 (2H, m), 3.67 (3H, s), 3.59 (2H, s), 3.22-3.10 (2H, m), 3.01-2.89 (2H, m), 2.77-2.60 (2H, m), 2.29-1.95 (2H, m), 1.86-1.66 (4H, m), 1.62-1.31 (4H, m), 0.94 (3H, t)

EXAMPLE 2-39

Methyl (3-{[2-(6-amino-2-butoxy-8-oxo-7,8-dihydro-9H-purin-9-yl)ethyl]thio}phenyl)acetate

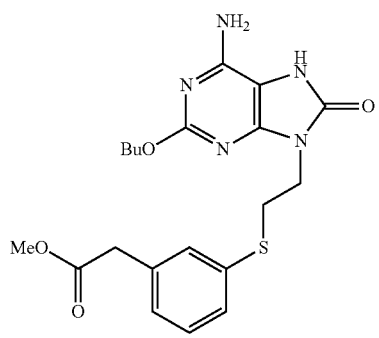

(i) 9-(2-Bromoethyl)-2-butoxy-8-methoxy-9H-purin-6-amine

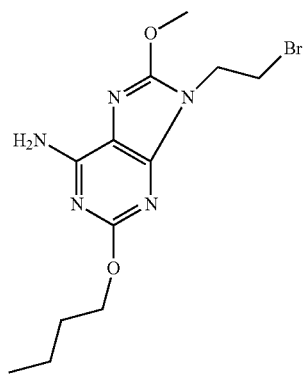 [SMILES: CCCCOc1nc(N)c2nc(OC)n(CCBr)c2n1]

The compound obtained in Example 2-1 step (v) (2 g), potassium carbonate (3.7 g) and 1,2-dibromoethane (0.6 ml) were added to dimethylformamide (20 ml), and the same manner to Example 2-13 step (i) was conducted to give the titled compound as a cream colored solid. Yield: 1.2 g (62%).

$^1$H NMR δ (CDCl$_3$) 5.15 (2H, s), 4.30 (4H, m), 4.13 (3H, s), 3.65 (2H, t), 1.82-1.72 (2H, m), 1.56-1.43 (2H, m), 0.97 (3H, t).

(ii) Methyl (3-{[2-(6-amino-2-butoxy-8-methoxy-9H-purin-9-yl)ethyl]thio}phenyl)acetate

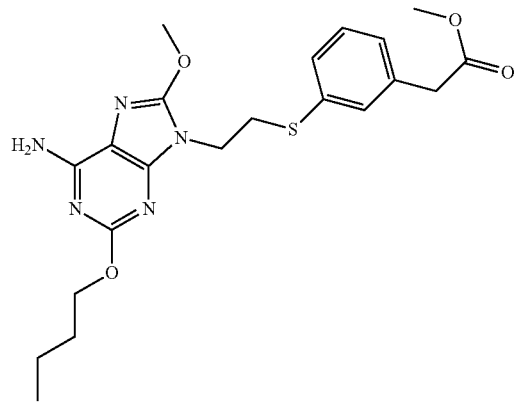 [SMILES: CCCCOc1nc(N)c2nc(OC)n(CCSc3cccc(CC(=O)OC)c3)c2n1]

The compound obtained in the step (i) (200 mg), methyl (3-mercaptophenyl)acetate (110 mg) and potassium carbonate (100 mg) were stirred in dimethylformamide (2 ml) at room temperature. After 1 hour, the reaction was completed and purification by RPHPLC was conducted to give the titled compound as a colorless solid. Yield: 150 mg (58%).

$^1$H NMR δ (DMSO d$_6$) 7.28-7.21 (3H, m), 7.11-7.06 (1H, m), 6.74 (2H, s), 4.13 (2H, t), 4.07-4.00 (2H, m), 4.00 (3H, s), 3.66 (2H, s), 3.61 (3H, s), 3.38-3.27 (2H, m), 1.64 (2H, quintet), 1.39 (2H, sextet), 0.91 (3H, t).

(iii) Methyl (3-{[2-(6-amino2-butoxy-8-oxo-7,8-dihydro-9H-purin-9-yl)ethyl]thio}phenyl)acetate

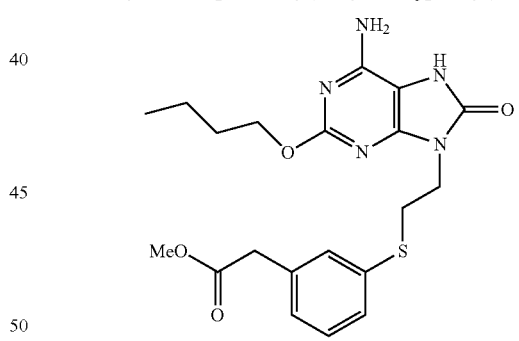

The compound obtained in the step (ii) (135 mg) and 6N hydrochloric acid solution (2 ml) in acetonitrile (10 ml) were stirred under heating for 17 hours. The reaction mixture was concentrated to dryness, and methanol (20 ml) and 4N hydrochloric acid-dioxane were added thereto. The mixture was heated under reflux for 1 hour, and then the solvent was removed by distillation under reduced pressure. The residue was partitioned between an aqueous saturated sodium hydrogen carbonate solution and ethyl acetate. The organic layer was dried and concentrated under reduced pressure and purified by RPHPLC to give the titled compound, as a colorless solid. Yield: 13 mg (10%); mp 232-233° C., MS APCI+ve 432 (M+H).

$^1$H NMR δ (DMSO d$_6$+CD$_3$OD) 7.24 (2H, m), 7.17 (2H, t), 7.04 (1H, d), 4.22 (2H, t), 4.06 (2H, t), 3.67 (3H, s), 3.58 (2H, s), 3.37 (2H, t), 1.73 (2H, quintet), 1.48 (2H, sextet), 0.98 (3H, t).

EXAMPLE 2-40

(3-{[2-(6-Amino-2-butoxy-8-oxo-7,8-dihydro-9H-purin-9-yl)ethyl]thio}phenyl)acetic acid

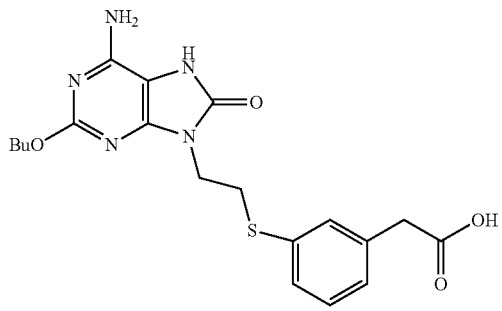

(i) (3-{[2-(6-Amino-2-butoxy-8-methoxy-9H-purin-9-yl)ethyl]thio}phenyl)acetic acid

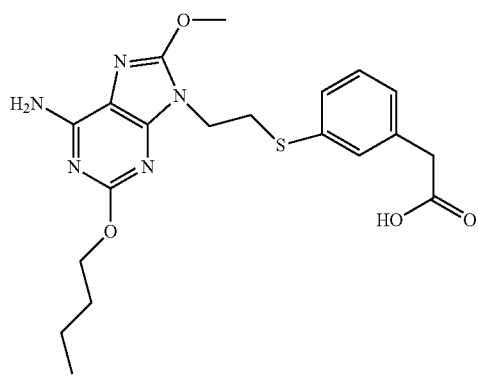 [SMILES: CCCCOc1nc(N)c2nc(OC)n(CCSc3cccc(CC(=O)O)c3)c2n1]

The same manner to Example 2-39 step (ii) using (3-mercaptophenyl)acetic acid (100 mg) was conducted to give the titled compound. Yield: 70 mg (28%); MS APCI+ve 432 (M+H).

$^1$H NMR δ (DMSO d$_6$) 7.28-7.22 (3H, m), 7.11-7.07 (1H, m), 6.77 (2H, s), 4.14 (2H, t), 4.04 (2H, t), 3.99 (3H, s), 3.55 (2H, s), 3.35 (2H, t), 1.64 (2H, quintet), 1.4 (2H, sextet), 0.92 (3H, t).

(ii) (3-{[2-(6-Amino-2-butoxy-8-oxo-7,8-dihydro-9H-purin-9-yl)ethyl]thio}phenyl)acetic acid

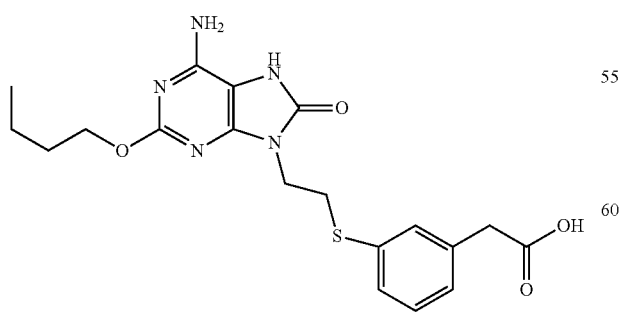

The compound obtained in the step (i) (70 mg) was added to tetrahydrofuran (10 ml) and 6N hydrochloric acid (2 ml)

and the mixture was heated under reflux for 3 hours. The solvent was removed by distillation under reduced pressure and purified by RPHPLC to give the titled compound as a solid. Yield: 40 mg (59%); mp 205-207° C., MS APCI-ve 416 (M−H).

$^1$H NMR δ (DMSO d$_6$) 12.33 (1H, s), 9.85 (1H, s), 7.31-7.20 (3H, m), 7.08 (1H, d), 6.40 (2H, s), 4.12 (2H, t), 3.89 (2H, t), 3.55 (2H, s), 3.30 (2H, t), 1.64 (2H, quintet), 1.38 (2H, sextet), 0.92 (3H, t).

EXAMPLE 2-41

Methyl (3-{[2-(6-amino-2-butoxy-8-oxo-7,8-dihydro-9H-purin-9-yl)ethyl]amino}phenyl)acetate

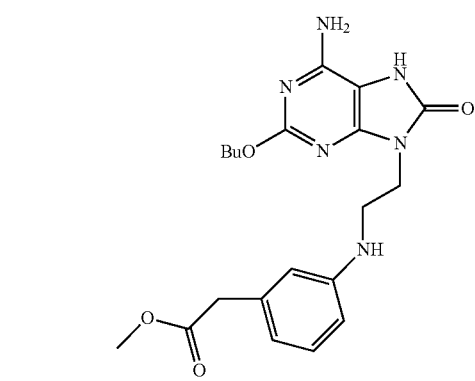

(i) Methyl {3-[(2-bromoethyl)amino]phenyl}acetate

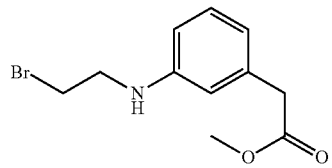

Methyl (3-aminophenyl)acetate (1 g) and 1,2-dibromoethane (5 ml) were heated at 100° C. for 5 hours. After cooling, the resultant was purified by column chromatography (ethyl acetate:isohexane 7:3) to give the titled compound as an oil. Yield: 280 mg (17%).

$^1$H NMR δ (CDCl$_3$) 7.14 (1H, t), 6.66 (1H, d), 6.59-6.52 (2H, m), 3.69 (3H, s), 3.58-3.53 (6H, m).

(ii) Methyl (3-{[2-(6-amino-2-butoxy-8-methoxy-9H-purin-9-yl)ethyl]amino}phenyl)acetate

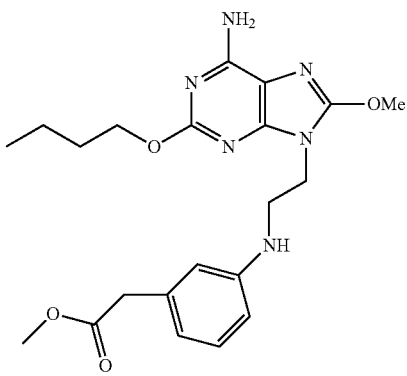 [SMILES: CCCCOc1nc(N)c2nc(OC)n(CCNc3cccc(CC(=O)OC)c3)c2n1]

To a solution of the compound obtained in Example 2-1 step (v) (0.2 g) in dimethylformamide (2 ml) was added potassium carbonate (236 mg) and then the compound obtained in the step (i) (160 mg) was further added thereto. The mixture was stirred at room temperature overnight. To the reaction mixture was added water and extracted with ethyl acetate. The organic layer was dried, concentrated and purified by RPHPLC to give the titled compound as a colorless solid. Yield: 200 mg (82%); mp 119-120° C., MS APCI+ve 429 (M+H).

$^1$H NMR δ (DMSO d$_6$) 7.01 (1H, t), 6.77 (2H, s), 6.52 (1H, d), 6.48 (1H, s), 6.43 (1H, d), 5.82 (1H, t), 4.15 (2H, t), 4.05-3.93 (5H, m), 3.60 (3H, s), 3.50 (2H, s), 3.39-3.33 (2H, m), 1.65 (2H, quintet), 1.40 (2H, sextet), 0.92 (3H, t).

(iii) Methyl (3-{[2-(6-amino-2-butoxy-8-oxo-7,8-dihydro-9H-purin-9-yl)ethyl]amino}phenyl)acetate

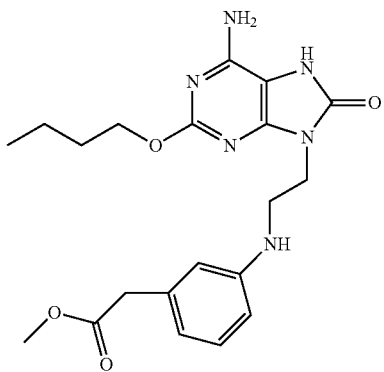 [SMILES: CCCCOc1nc(N)c2[nH]c(=O)n(CCNc3cccc(CC(=O)OC)c3)c2n1]

To the solution of the compound obtained in the step (ii) (200 mg) in methanol (15 ml) was added 4N dioxane (5 ml) under stirring, and stirred at room temperature for 24 hours, concentrated under reduced pressure and purified by RPHPLC to give the titled compound as a colorless solid. Yield: 13 mg (6.7%); mp 222-223° C., MS APCI+ve 415 (M+H).

$^1$H NMR δ (DMSO d$_6$+CD$_3$OD) 7.01 (1H, t), 6.59-6.43 (3H, m), 4.20 (2H, t), 4.01-3.91 (2H, m), 3.64 (3H, s), 3.49 (2H, s), 3.46-3.38 (2H, m), 1.70 (2H, quintet), 1.45 (2H, sextet), 0.96 (3H, t).

EXAMPLE 2-42

Methyl (3-{[3-(6-amino-2-butoxy-8-oxo-7,8-dihydro-9H-purin-9-yl)propyl]amino}phenyl)acetate

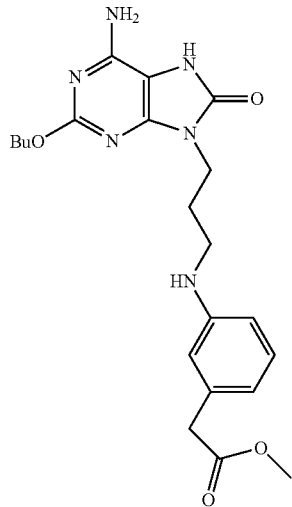

(i) Methyl {3-[(3-bromopropyl)amino]phenyl}acetate

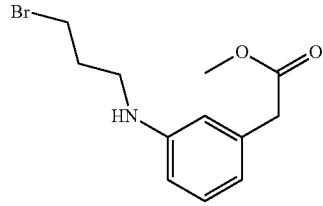 [SMILES: COC(=O)Cc1cccc(NCCCBr)c1]

Using 1,3-dibromopropane (1.7 ml) and methyl (3-aminophenyl)acetate (280 mg), the same manner to Example 2-41 step (i) was conducted to give the titled compound as a solid. Yield: 200 mg (70%).

$^1$H NMR δ (CDCl$_3$) 7.15-7.11 (1H, m), 6.62 (1H, d), 6.56-6.5 (2H, m), 3.69 (3H, s), 3.56-3.48 (4H, m), 3.33 (2H, t), 2.15 (2H, quintet).

(ii) Methyl (3-{[3-(6-amino-2-butoxy-8-methoxy-9H-purin-9-yl)propyl]amino}phenyl)acetate

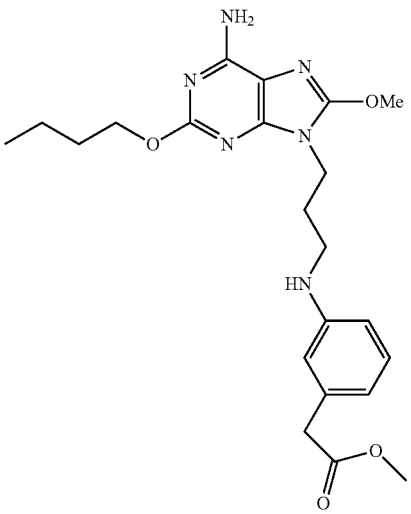 [SMILES: CCCCOc1nc(N)c2nc(OC)n(CCCNc3cccc(CC(=O)OC)c3)c2n1]

Using the compound obtained in the step (i) (170 mg), the same manner to Example 2-41 step (ii) was conducted to give the titled compound as a solid. Yield: 220 mg (87%); mp 129-130° C., MS APCI+ve 443 (M+H).

$^1$H NMR δ (DMSO d$_6$) 6.99 (1H, t), 6.44-6.38 (3H, m), 4.15 (2H, t), 4.02 (3H, s), 3.94 (2H, t), 3.59 (3H, s), 3.48 (2H, s), 2.96 (2H, t), 1.94 (2H, quintet), 1.64 (2H, quintet), 1.39 (2H, sextet), 0.91 (3H, t).

(iii) Methyl (3-{[3-(6-amino-2-butoxy-8-oxo-7,8-dihydro-9H-purin-9-yl)propyl]amino}phenyl)acetate

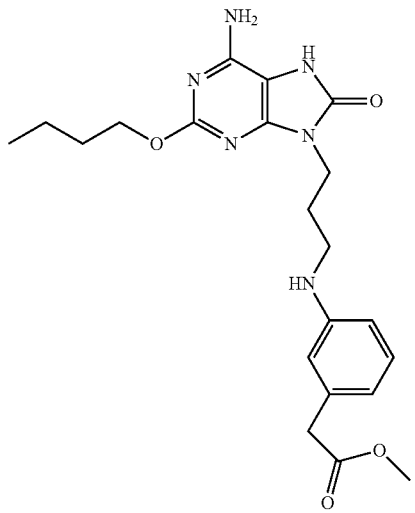 [SMILES: CCCCOc1nc(N)c2[nH]c(=O)n(CCCNc3cccc(CC(=O)OC)c3)c2n1]

Using the compound obtained in the step (ii), the same manner to Example 2-41 step (iii) was conducted to give the titled compound as a solid. Yield: 63 mg (31%); mp 208-209° C., MS APCI+ve 429 (M+H).
$^1$H NMR δ (DMSO d$_6$) 9.86 (1H, s), 6.98 (1H, t), 6.46-6.35 (5H, m), 5.61 (1H, t), 4.13 (2H, t), 3.76 (2H, t), 3.58 (3H, s), 3.47 (2H, s), 3.00 (2H, q), 1.90 (2H, quintet), 1.63 (2H, quintet), 1.38 (2H, sextet), 0.91 (3H, t).

EXAMPLE 2-43

(3-{[3-(6-Amino-2-butoxy-8-oxo-7,8-dihydro-9H-purin-9-yl)propyl]amino}phenyl)acetic acid

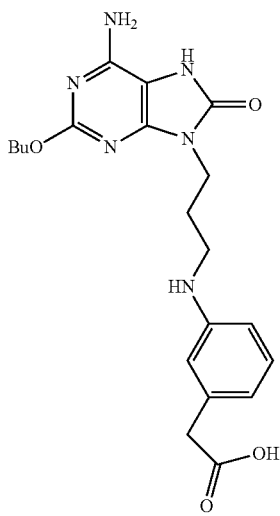

The compound obtained in Example 2-42 (70 mg) was dissolved in methanol (5 ml) and a lithium hydroxide solution (45 mg) in water (5 ml) was added thereto. The same manner to Example 2-12 was conducted to give the titled compound as a colorless solid. Yield: 14 mg (21%); mp 247° C., MS APCI-ve 413 (M−H).

$^1$H NMR δ (DMSO d$_6$) 6.85 (1H, t), 6.73-6.45 (2H, brs), 6.35 (2H, d), 6.28 (1H, d), 5.42 (1H, t), 4.11 (2H, t), 3.71 (2H, t), 3.08 (2H, s), 2.99-2.88 (2H, m), 1.92-1.80 (2H, m), 1.63 (2H, quintet), 1.39 (2H, sextet), 0.92 (3H, t).

EXAMPLE 2-44

Methyl [3-({[3-(6-amino-2-butoxy-8-oxo-7,8-dihydro-9H-purin-9-yl)propyl]amino}methyl)phenyl]acetate

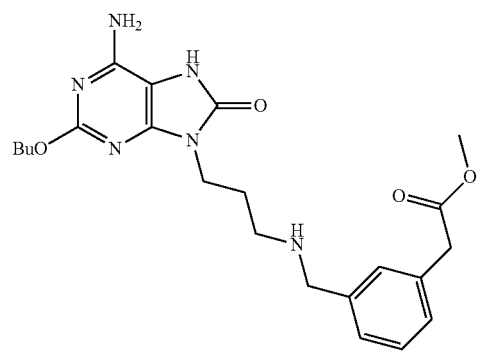

Using the compound obtained in Example 2-7 step (i) (180 mg), the same manner to Example 2-41 step (iii) was conducted to give the titled compound as a solid. Yield: 55 mg (32%); MS APCI+ve 443 (M+H).
$^1$H NMR δ (DMSO d$_6$) 7.29 (4H, m), 7.19 (1H, d), 6.58 (2H, s), 6.53 (3H, s), 4.13 (2H, t), 3.85 (2H, s), 3.73 (2H, t), 3.66 (2H, s), 3.60 (3H, s), 2.69 (2H, t), 1.90 (2H, quintet), 1.63 (2H, quintet), 1.38 (2H, sextet), 0.91 (3H, t).

EXAMPLE 2-45

([3-({[3-(6-Amino-2-butoxy-8-methoxy-9H-purin-9-yl)propyl]amino}methyl)phenyl]acetic acid

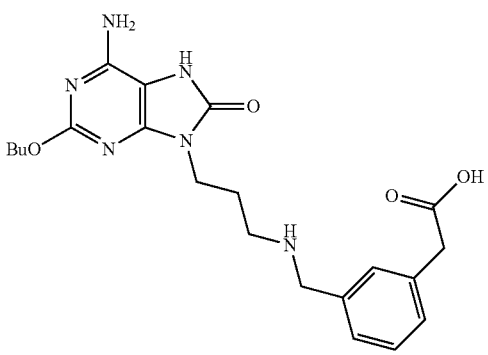

Using the compound obtained in Example 2-44 (30 mg), the same manner as Example 2-12 was conducted to give the titled compound. Yield: 26 mg (89%); MS APCI+ve 429 (M+H).
$^1$H NMR δ (DMSO d$_6$) 7.45 (1H, d), 7.40 (1H, s), 7.36 (1H, t), 7.30 (1H, d), 4.42 (2H, t), 4.08 (2H, s), 3.83 (2H, t), 3.58 (2H, s), 2.95 (2H, t), 2.16-2.05 (2H, m), 1.73 (2H, quintet), 1.42 (2H, sextet), 0.94 (3H, t).

EXAMPLE 2-46

Methyl (3-{[[2-(6-amino-2-butoxy-8-oxo-7,8-dihydro-9H-purin-9-yl)ethyl] (2-methoxyethyl)amino]methyl}phenyl)acetate

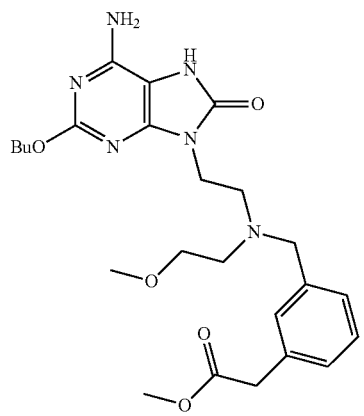

(i) Methyl (3-{[(2-methoxyethyl)amino]methyl}phenyl)acetate oxalate

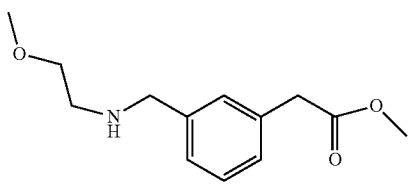

Under stirring at 0° C., to (2-methoxyethyl)amine (2.5 ml) was added methyl [3-(bromomethyl)phenyl]acetate (0.5 g) and the mixture was stirred for 5 minutes. The resultant was purified by column chromatography (dichloromethane:7N-ammonia-methanol, 9:1), and 1N oxalic acid in ethanol was added thereto to give the titled compound as a monooxalate. Yield: 630 mg (93%).

¹H NMR δ (DMSO d₆) 7.42-7.27 (4H, m), 4.11 (2H, s), 3.70 (2H, s), 3.62 (3H, s), 3.58 (2H, t), 3.28 (3H, s), 3.05 (2H, t).

(ii) Methyl (3-{[[2-(6-amino-2-butoxy-8-methoxy-9H-purin-9-yl)ethyl](2-methoxyethyl)amino]methyl}phenyl)acetate

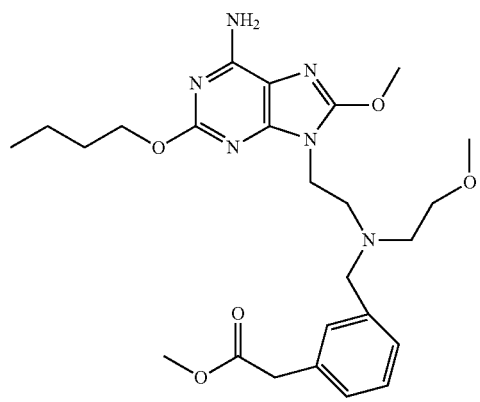 [SMILES: CCCCOc1nc(N)c2nc(OC)n(CCN(CCOC)Cc3cccc(CC(=O)OC)c3)c2n1]

A suspension of the compound obtained in the step (i) (571 mg), the compound obtained in Example 2-39 step (i) (300 mg) and potassium carbonate (730 mg) in dimethylformamide (4 ml) was stirred at 55° C. for 4 days. The resultant was cooled and filtrated, and the filtrate was purified by RPHPLC to give the titled compound as a colorless solid. Yield: 140 mg (32%); MS APCI+ve 501 (M+H).

¹H NMR δ (CDCl₃) 7.17-7.06 (2H, m), 6.98 (2H, d), 6.94 (2H, s), 5.13 (2H, s), 4.19 (2H, t), 4.01-3.96 (5H, m), 3.68 (3H, s), 3.63 (2H, s), 3.55 (2H, s), 3.38 (2H, t), 3.26 (3H, s), 2.86 (2H,t), 2.73 (2H, t), 1.72 (2H, quintet), 1.48 (2H, sextet), 0.95 (3H, t).

(iii) Methyl 3-{[[2-(6-amino-2-butoxy-8-oxo-7,8-dihydro-9H-purin-9-yl)ethyl](2-methoxyethyl)amino]methyl}phenyl)acetate

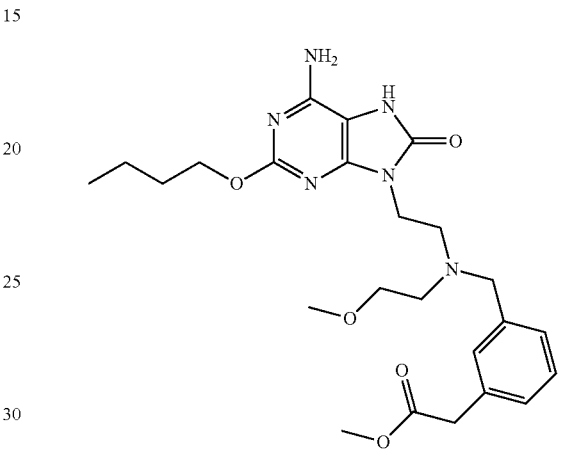

Using the compound obtained in the step (ii) (130 mg), the same manner to Example 2-41 step (iii) was conducted to give the titled compound as a solid. Yield: 120 mg (95%); MS APCI+ve 487 (M+H).

¹H NMR δ (DMSO d₆) 9.80 (1H, s), 7.15-7.10 (2H, m), 7.07-7.00 (2H, m), 6.36 (2H, s), 4.05 (2H, t), 3.76 (2H, t), 3.61 (2H, s), 3.58 (3H, s), 3.56 (2H, s), 3.30 (2H, s), 3.14 (3H, s), 2.76 (2H, t), 2.60 (2H, t), 1.59 (2H, quintet), 1.35 (2H, sextet), 0.89 (3H, t).

EXAMPLE 2-47

(3-{[[2-(6-Amino-2-butoxy-8-methoxy-9H-purin-9-yl)ethyl](2-methoxyethyl)amino]methyl}phenyl)acetic acid

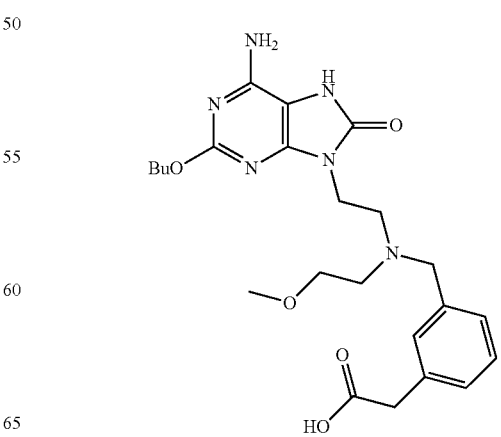

Using the compound obtained in Example 2-46 (40 mg), the same manner to Example 2-12 was conducted to give the titled compound. Yield: 35 mg (90%); MS APCI+ve 473 (M+H).

$^1$H NMR δ (DMSO d$_6$) 7.08 (1H, d), 7.02 (1H, t), 6.89-6.81 (2H, m), 6.64 (2H, s), 4.10 (2H, t), 3.72 (2H, t), 3.50 (2H, s), 3.31 (2H, t), 3.23 (2H, s), 3.15 (3H, s), 2.74 (2H, t), 2.61 (2H, t), 1.62 (2H, quintet), 1.38 (2H, sextet), 0.91 (3H, t).

EXAMPLE 2-48

Methyl (3-{[2-(6-amino-2-butoxy-8-oxo-7,8-dihydro-9H-purin-9-yl)ethyl]sulfonyl}phenyl)acetate

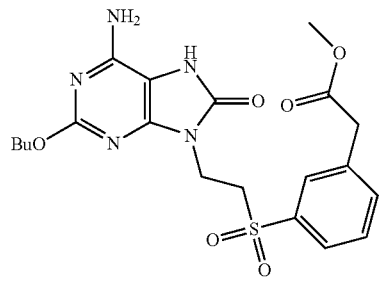

(i) Methyl (3-{[2-(6-amino-2-butoxy-8-methoxy-9H-purin-9-yl)ethyl]sulfonyl}phenyl)acetate

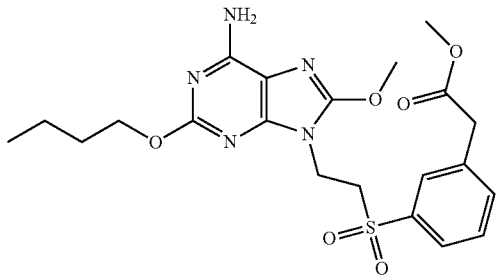 [SMILES: CCCCOc1nc(N)c2nc(OC)n(CCS(=O)(=O)c3cccc(CC(=O)OC)c3)c2n1]

The compound obtained in Example 2-39 step (ii) (200 mg) was dissolved in water (15 ml) and acetone (20 ml), and Oxone® (610 mg) was added together with sufficient sodium carbonate to maintain basic condition and stirred at room temperature for 0.5 hour. To the reaction solution was added water and the mixture was extracted with ethyl acetate. The organic layer was concentrated and the residue was purified by RPHPLC to give the titled compound as a colorless solid. Yield: 90 mg (42%); MS APCI+ve 478 (M+H).

$^1$H NMR δ (CD$_3$OD) 7.64-7.61 (1H, m), 7.60-7.58 (1H, m), 7.50-7.47 (1H, m), 7.40 (1H, t), 4.32 (2H, t), 4.26 (2H, t), 4.09 (3H, s), 3.91 (2H, t), 3.69 (3H, s), 3.67 (2H, s), 1.76 (2H, quintet), 1.51 (2H, sextet), 1.00 (3H, t).

(ii) Methyl (3-{[2-(6-amino-2-butoxy-8-oxo-7,8-dihydro-9H-purin-9-yl)ethyl]sulfonyl}phenyl)acetate

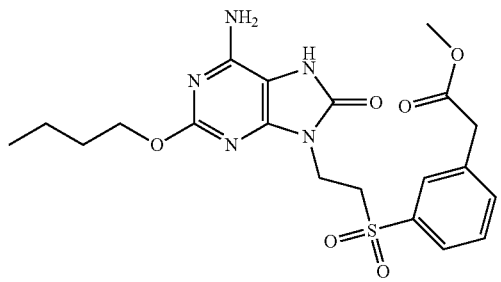 [SMILES: CCCCOc1nc(N)c2[nH]c(=O)n(CCS(=O)(=O)c3cccc(CC(=O)OC)c3)c2n1]

Using the compound obtained in the step (i) (80 mg), the same manner to Example 2-41 step (iii) was conducted to give the titled compound as a colorless solid. Yield: 30 mg (38%); mp 246-247° C., MS APCI+ve 464 (M+H).

$^1$H NMR δ (DMSO d$_6$) 9.78 (1H, s), 7.77-7.73 (2H, m), 7.60-7.58 (1H, m), 7.53 (1H, t), 6.38 (2H, s), 4.12 (2H, t), 3.98 (2H, t), 3.82 (2H, t), 3.78 (2H, s), 3.63 (3H, s), 1.65 (2H, quintet), 1.40 (2H, sextet), 0.93 (3H, t).

EXAMPLE 2-49

Methyl (3-{[[2-(6-amino-2-butoxy-8-oxo-7,8-dihydro-9H-purin-9-yl)ethyl](methyl)amino]methyl}phenyl)acetate

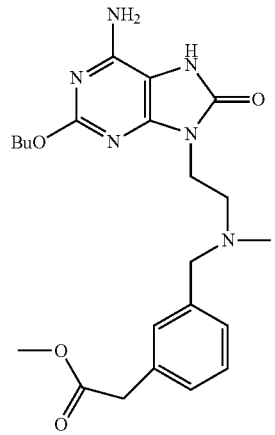

(i) Methyl {3-[(methylamino)methyl]phenyl}acetate oxalate

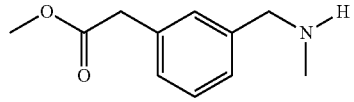

To a 40% aqueous methylamine solution (10 ml) was added methyl [3-(bromomethyl)phenyl]acetate (3 g). The mixture was stirred for 0.5 hour, extracted with ethyl acetate, and concentrated under reduced pressure. The residue was dissolved in ethanol (100 ml) and acetic acid (10 ml). The resulting solution was stirred at room temperature for 1 hour in the presence of a 10% palladium-carbon catalyst under hydrogen atmosphere, and then the catalyst was removed by filtration. The filtrate was concentrated under reduced pressure and the residue was partitioned between 2N hydrochloric acid and ethyl acetate. After collecting the aqueous layer, it was made alkaline by potassium carbonate and extracted with ethyl acetate. The extract was dried and concentrated to give an and oil (1 g). To the obtained oil in ethanol (5 ml) was added oxalic acid (467 mg) to give the titled compound as a colorless solid. Yield: 1.3 g (37%).

$^1$H NMR δ (DMSO d$_6$) 7.41-7.28 (4H, m), 4.09 (2H, s), 3.71 (2H, s), 3.62 (3H, s), 2.54 (3H, s).

(ii) Methyl (3-{[[2-(6-amino-2-butoxy-8-methoxy-9H-purin-9-yl)ethyl](methyl)-amino]methyl}phenyl)acetate

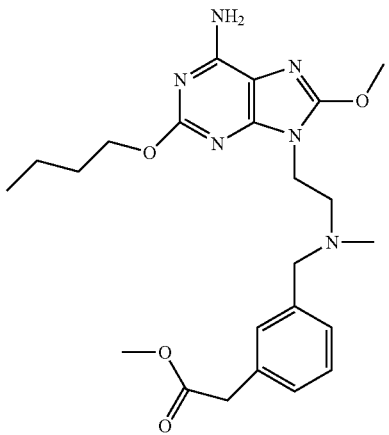 [SMILES: CCCCOc1nc(N)c2nc(OC)n(CCN(C)Cc3cccc(CC(=O)OC)c3)c2n1]

Using the compound obtained in the step (i) (500 mg) and the compound obtained in Example 2-39 step (i) (300 mg), the same manner as Example 2-46 step (ii) was conducted to give the titled compound as a colorless solid. Yield: 130 mg (33%); MS APCI+ve 457 (M+H).

$^1$H NMR δ (CD$_3$OD) 7.11-7.01 (2H, m), 6.89-6.84 (2H, m), 4.16 (2H, t), 4.06-3.99 (5H, m), 3.64 (3H, s), 3.51 (2H, s), 3.46 (2H, s), 2.68 (2H, t), 2.33 (3H, s), 1.68 (2H, quintet), 1.44 (2H, sextet), 0.95 (3H, t).

(iii) Methyl (3-{[[2-(6-amino-2-butoxy-8-oxo-7,8-dihydro-9H-purin-9-yl)ethyl](methyl)amino]methyl}phenyl)acetate

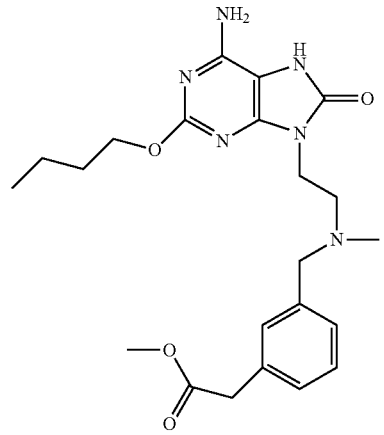 [SMILES: CCCCOc1nc(N)c2[nH]c(=O)n(CCN(C)Cc3cccc(CC(=O)OC)c3)c2n1]

Using the compound obtained in the step (ii) (125 mg), the same manner to Example 2-41 step (iii) was conducted to give the titled compound as a cream colored solid. Yield: 85 mg (97%); MS APCI+ve 443 (M+H).

$^1$H NMR δ (DMSO d$_6$) 9.84 (1H, s), 7.14 (1H, t), 7.06 (1H, d), 7.03-6.96 (2H, m), 6.39 (2H, s), 4.06 (2H, t), 3.80 (2H, t), 3.59 (3H, s), 3.56 (2H, s), 3.47 (2H, s), 2.63 (2H, t), 2.18 (3H, s), 1.59 (2H, quintet), 1.34 (2H, sextet), 0.89 (3H, t).

EXAMPLE 2-50

(3-{[[2-(6-Amino-2-butoxy-8-oxo-7,8-dihydro-9H-purin-9-yl)ethyl](methyl)amino]methyl}phenyl)acetic acid

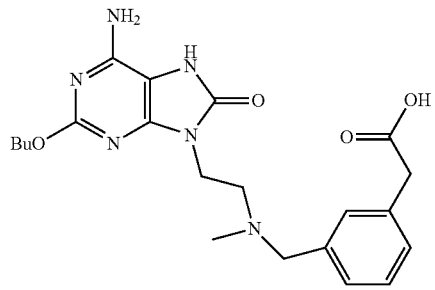

Using the compound obtained in Example 2-49 (60 mg), the same manner to Example 2-12 was conducted to give the titled compound as a solid. Yield: 35 mg (60%); mp 164-166° C., MS APCI-ve 427 (M−H).

$^1$H NMR δ (DMSO d$_6$) 9.90 (1H, s), 7.12 (1H, t), 7.06 (1H, d), 7.01-6.95 (2H, m), 6.39 (2H, s), 4.06 (2H, t), 3.80 (2H, t), 3.45 (4H, d), 2.64 (2H, t), 2.17 (3H, s), 1.59 (2H, quintet), 1.34 (2H, sextet), 0.89 (3H, t).

EXAMPLE 2-51

Methyl 4-[3-(6-amino-2-butoxy-8-oxo-7,8-dihydro-9H-purin-9-yl)-2-hydroxypropoxy]benzoate

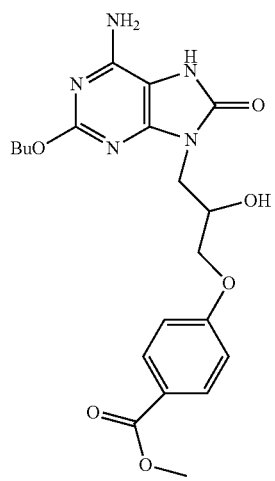

(i) tert-Butyl 4-[3-(6-amino-2-butoxy-8-methoxy-9H-purin-9-yl)-2-hydroxypropoxy]benzoate

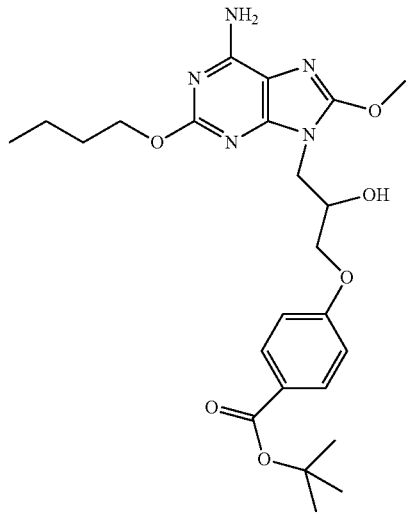 [SMILES: CCCCOc1nc(N)c2nc(OC)n(CC(O)COc3ccc(C(=O)OC(C)(C)C)cc3)c2n1]

A suspension of the compound obtained in Example 2-1 step (v) (330 mg), tert-butyl 4-(oxilan-2-ylmethoxy)benzoate (256 mg) and potassium carbonate (365 mg) in 2-methylpropane-2-ol (2.5 ml) was heated at 50° C. for 24 hours. The mixture was cooled and partitioned between water and ethyl acetate. The organic layer was dried, concentrated under reduced pressure and purified by flash column chromatography (ethyl acetate:isohexane, 8:2) to give the titled compound as a colorless oil. Yield: 260 mg (62%); Purity about 80%, MS APCI+ve 488 (M+H).

(ii) Methyl 4-[3-(6-amino-2-butoxy-8-oxo-7,8-dihydro-9H-purin-yl)-2-hydroxypropoxy]benzoate

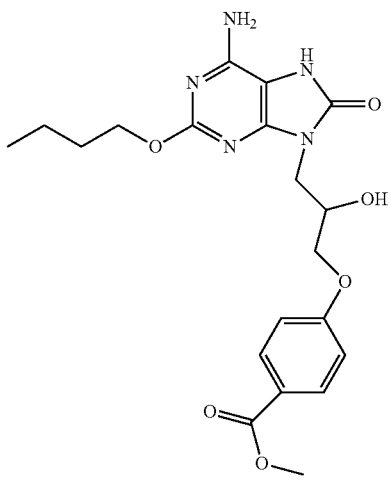 [SMILES: CCCCOc1nc(N)c2[nH]c(=O)n(CC(O)COc3ccc(C(=O)OC)cc3)c2n1]

Using the compound obtained in the step (i) (260 mg), the same manner to Example 2-41 step (iii) was conducted to give the titled compound, as a solid. Yield: 35 mg (15%); MS APCI+ve 432 (M+H).

$^1$H NMR δ (DMSO d$_6$) 9.88 (1H, s), 7.88 (2H, d), 6.96 (2H, d), 6.40 (2H, s), 5.39 (1H, d), 4.36-4.21 (1H, m), 4.10-3.95 (4H, m), 3.82 (1H, s), 3.81 (3H, s), 1.57 (2H, quintet), 1.34 (2H, sextet), 0.89 (3H, t).

EXAMPLE 2-52

Methyl (3-{[[2-(6-amino-2-butoxy-8-oxo-7,8-dihydro-9H-purin-9-yl)ethyl] (2-hydroxyethyl)amino]methyl}phenyl)acetate

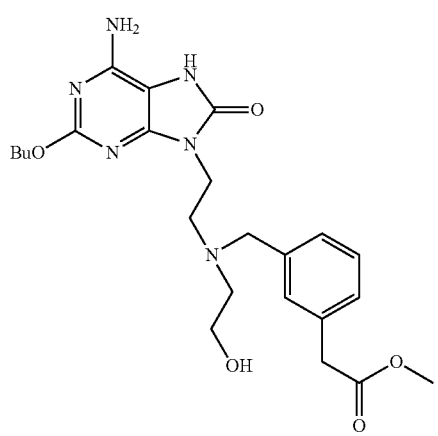

(i) 2-{[2-(6-Amino-2-butoxy-8-methoxy-9H-purin-yl)ethyl]amino}ethanol

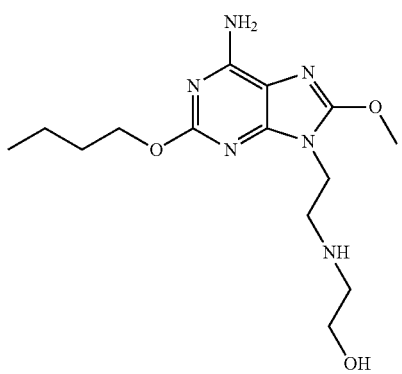 [SMILES: CCCCOc1nc(N)c2nc(OC)n(CCNCCO)c2n1]

To the compound obtained by Example 2-39 step (i) (300 mg) in acetonitrile (5 ml) was added 2-aminoethanol (265 mg) and heated at 70° C. for 24 hours. The reaction mixture was purified by column chromatography (ethyl acetate:7N ammonia-methanol 95:5) to give the titled compound. Yield: 295 mg (100%).

$^1$H NMR δ (CDCl$_3$) 5.20 (2H, s), 4.27 (2H, t), 4.11 (3H, s), 4.05 (2H, t), 3.60 (2H, t), 3.03 (2H, t), 2.82 (2H, t), 1.81-1.69 (2H, m), 1.49 (2H, sextet), 0.96 (3H, t).

(ii) Methyl (3-{[[2-(6-amino-2-butoxy-8-methoxy-9H-purin-9-yl)ethyl](2-hydroxyethyl)amino]methyl}phenyl)acetate

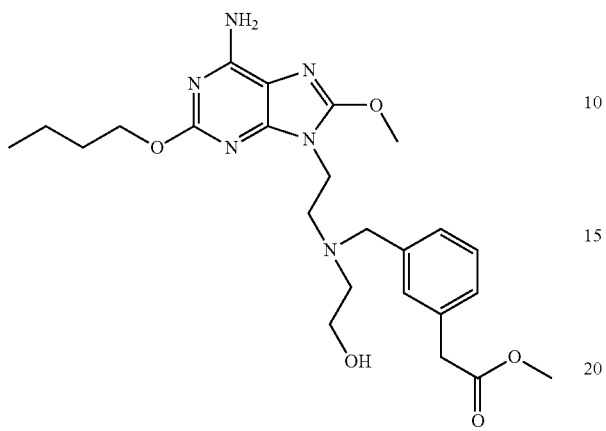

A suspension of the compound obtained in the step (i) (270 mg), methyl [3-(bromomethyl)phenyl]acetate (245 mg) and potassium carbonate (140 mg) in acetonitrile (3 ml) was stirred at room temperature for 24 hours. To the resultant was added water and the mixture was extracted with ethyl acetate. The organic layer was dried and concentrated under reduced pressure and purified by column chromatography (dichloromethane: 7N ammonia-methanol, 95:5) to give the titled compound as a colorless solid. Yield: 170 mg (42%); MS APCI+ve 487 (M+H).

$^1$H NMR δ (CDCl$_3$) 7.11-7.04 (2H, m), 6.88-6.82 (2H, m), 5.16 (2H, s), 4.24 (2H, t), 3.98 (3H, s), 3.95 (2H, t), 3.67 (3H, s), 3.62-3.56 (2H, m), 3.52 (2H, s), 3.51 (2H, s), 3.33-3.27 (1H, m), 2.84 (2H, t), 2.74 (2H, t), 1.75 (2H, quintet), 1.48 (2H, sextet), 0.96 (3H, t).

(iii) Methyl (3-{[[2-(6-amino-2-butoxy-8-oxo-7,8-dihydro-9H-purin-9-yl)ethyl](2-hydroxyethyl)amino]methyl}phenyl)acetate

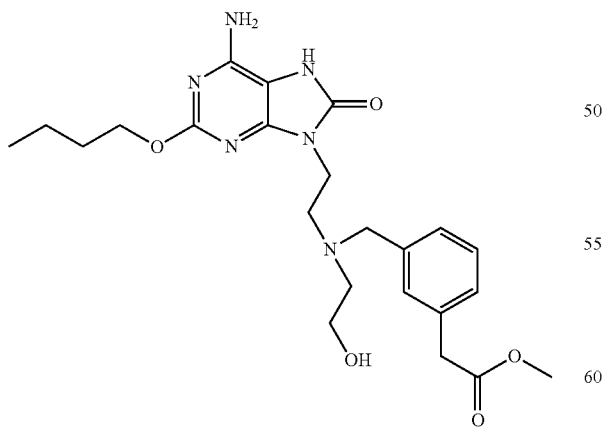

Using the compound obtained in the step (ii) (170 mg), the same manner to Example 2-41 step (iii) was conducted to give the titled compound as a colorless solid. Yield: 150 mg (91%); MS APCI+473 ve (M+H).

$^1$H NMR δ (DMSO d$_6$) 9.81 (1H, s), 7.09 (1H, t), 7.03-6.98 (3H, m), 6.36 (2H, s), 4.34 (1H, t), 4.05 (2H, t), 3.73 (2H, t), 3.59 (3H, s), 3.57 (2H, s), 3.54 (2H, s), 3.39 (2H, q), 2.73, (2H, t), 2.54 (2H, t), 1.58 (2H, quintet), 1.35 (2H, sextet), 0.89 (3H, t).

EXAMPLE 2-53

Methyl (3-{[[4-(6-amino-2-butoxy-8-oxo-7,8-dihydro-9H-purin-9-yl)butyl](2-hydroxyethyl)amino]methyl}phenyl)acetate

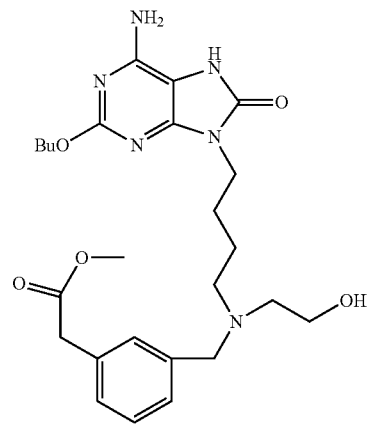

(i) Methyl (3-{[(2-hydroxyethyl)amino]methyl}phenyl)acetate oxalate

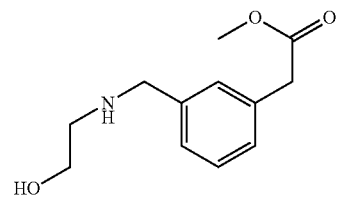

Using 2-aminoethanol (2.5 ml), the same manner to Example 2-46 step (i) was conducted to give the titled compound as a colorless solid. Yield: 250 mg (39%).

$^1$H NMR δ (DMSO d$_6$) 7.43-7.27 (4H, m), 4.13 (2H, s), 3.70 (2H, s), 3.65 (2H, t), 3.62 (3H, s), 2.94 (2H, t).

(ii) Methyl (3-{[[4-(6-amino-2-butoxy-8-oxo-7,8-dihydro-9H-purin-9-yl)butyl](2-hydroxyethyl)amino]methyl}phenyl)acetate fumarate

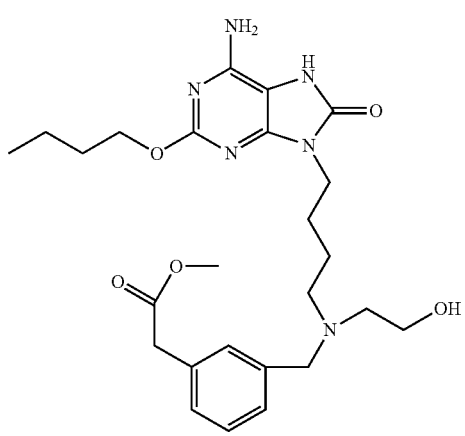 [SMILES: CCCCOc1nc(N)c2[nH]c(=O)n(CCCCN(CCO)Cc3cccc(CC(=O)OC)c3)c2n1]

A suspension of the compound obtained in Example 2-13 step (i) (200 mg), the compound obtained in the step (i) (170 mg) and potassium carbonate (300 mg) in dimethylformamide (5 ml) was stirred at 70° C. overnight, and to the resultant was added water. The mixture was extracted with ethyl acetate and the organic layer was dried and concentrated under reduced pressure. The residue was dissolved in methanol (10 ml) and 4N hydrochloric acid-dioxane (5 ml) was added thereto and the mixture was stirred at room temperature for 20 hours and concentrated under reduced pressure and purified by RPHPLC. Then the resultant was made into fumarate by using 1N fumaric acid in ethanol to give the titled compound. Yield: 19 mg (6%); MS APCI+50 1ve (M+H).

$^1$H NMR δ (DMSO d$_6$) 9.86 (1H, s), 7.25-7.09 (4H, m), 6.61 (2H, s), 6.39 (2H, s), 4.13 (2H, t), 3.65-3.61 (4H, m), 3.59 (3H, s), 3.56 (2H, s), 3.44 (2H, t), 2.49-2.45 (2H, m), 1.63 (4H, quintet), 1.45-1.32 (4H, m), 0.90 (3H, t).

EXAMPLE 3

Synthesis of 2-butoxy-8-oxo-9-[2-(2-methoxycarbonylphenoxy)ethyl]adenine

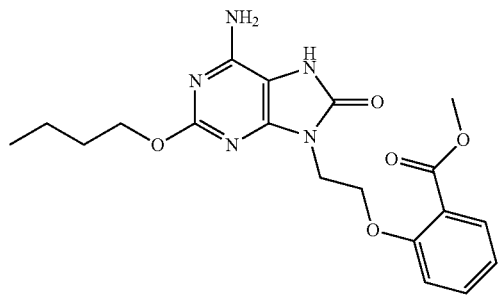 [SMILES: CCCCOc1nc(N)c2[nH]c(=O)n(CCOc3ccccc3C(=O)OC)c2n1]

The titled compound was obtained by the same manner to Example 1.

$^1$H NMR (DMSO-d$_6$) δ 9.91 (1H, brs), 7.55 (1H, dd, J=1.7, 7.6 Hz), 7.48 (1H, dt, J=1.7, 8.2 Hz), 7.17 (1H, d, J=8.2 Hz), 7.00 (1H, t, J=7.6 Hz), 6.41 (2H, brs), 4.35 (2H, t, J=5.7 Hz), 4.09 (2H, t, J=6.6 Hz), 4.05 (2H, t, J=5.7 Hz), 3.61 (3H, s), 1.64-1.58 (2H, m), 1.42-1.37 (2H, m), 0.89 (3H, t, J=7.4 Hz).

EXAMPLE 4

Synthesis of 2-butoxy-8-oxo-9-[2-(2-methoxycarbonylmethylphenoxy)ethyl]adenine

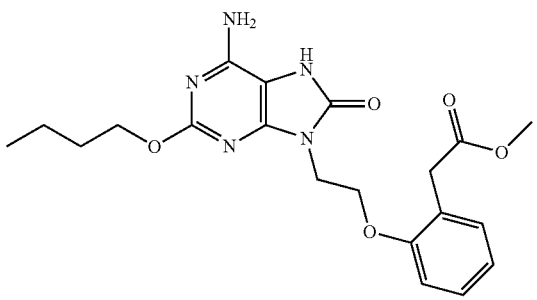 [SMILES: CCCCOc1nc(N)c2[nH]c(=O)n(CCOc3ccccc3CC(=O)OC)c2n1]

The titled compound was obtained by the same method as Example 1.

$^1$H NMR (DMSO-d$_6$) δ 9.89 (1H, brs), 7.19 (1H, dt, J=1.7, 8.1 Hz), 7.11 (1H, dd, J=1.5, 7.4 Hz), 6.98 (1H, d, J=7.6 Hz), 6.86 (1H, t, J=7.6 Hz), 6.41 (2H, brs), 4.23 (2H, t, J=5.7 Hz), 4.12 (2H, t, J=6.6 Hz), 4.03 (2H, t, J=5.7 Hz), 3.47 (2H, s), 3.46 (3H, s), 1.65-1.61 (2H, m), 1.41-1.36 (2H, m), 0.90 (3H, t, J=7.4 Hz).

EXAMPLE 5

Synthesis of 2-butoxy-8-oxo-9-[2-(4-methoxycarbonylphenoxy)ethyl]adenine

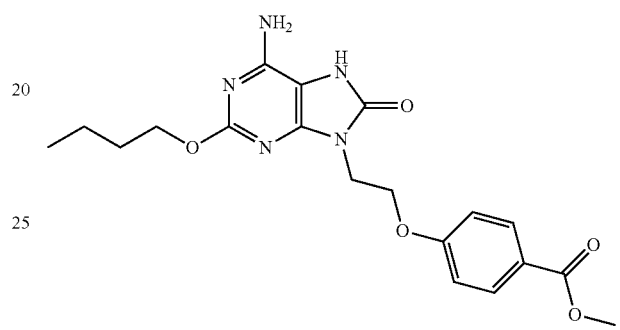

The titled compound was obtained by the same method as Example 1.

$^1$H NMR (DMSO-d$_6$) δ 9.78 (1H, brs), 7.87 (2H, d, J=8.9 Hz), 6.97 (2H, d, J=8.9 Hz), 6.43 (2H, brs), 4.37 (2H, t, J=5.0 Hz), 4.08-4.02 (4H, m), 3.80 (2H, s), 1.63-1.58 (2H, m), 1.35-1.30 (2H, m), 0.89 (3H, t, J=7.4 Hz).

EXAMPLE 6

Synthesis of 2-butoxy-8-oxo-9-[2-(4-methoxycarbonylmethylphenoxy)ethyl]adenine

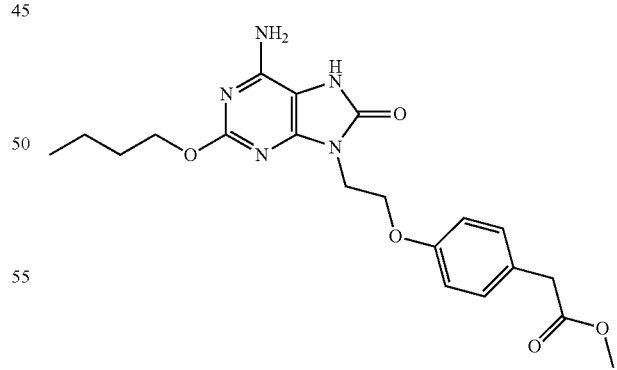

The titled compound was obtained by the same method as Example 1.

$^1$H NMR (DMSO-d$_6$) δ 9.90 (1H, s), 7.14 (2H, d, J=8.7 Hz), 6.84 (2H, d, J=8.7 Hz), 6.42 (2H, brs), 4.24 (2H, t, J=5.8 Hz), 4.12 (2H, t, J=6.6 Hz), 4.03 (2H, t, J=5.8 Hz), 3.58 (3H, s), 3.57 (2H, s), 1.65-1.61 (2H, m), 1.39-1.34 (2H, m), 0.90 (3H, t, J=7.4 Hz).

EXAMPLE 7

Synthesis of 2-butoxy-8-oxo-9-{2-[4-(2-methoxycarbonylethyl)phenoxy]ethyl}adenine

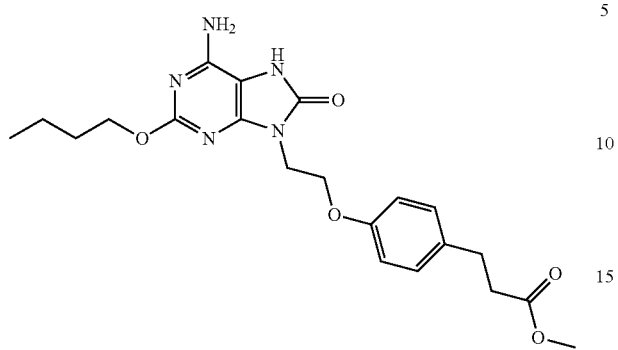

To 2-butoxy-8-bromo-9-{2-[4-(2-cyanoethyl)phenoxy]ethyl}adenine (948 mg, 2.1 mmol) obtained in Reference Example 16 were added water (20 ml) and 5N potassium hydroxide (20 ml) and the mixture was stirred at 95° C. for 6 hours. The resultant was adjusted to pH 5 with concentrated hydrochloric acid, and then the precipitated solid was collected by filtration. Methanol (25 ml) and sulfuric acid (400 μl) were added thereto, followed by stirring at 90° C. for 4 hours. The reaction solution was neutralized with saturated sodium hydrogencarbonate, and the precipitated solid was collected by filtration to give 750 mg (1.7 mmol) of the titled compound as a white solid. Yield: 85%.

$^1$H NMR (DMSO-$d_6$) δ 9.90 (1H, brs), 7.08 (2H, d, J=8.6 Hz), 6.80 (2H, d, J=8.6 Hz), 6.41 (2H, brs), 4.24 (2H, t, J=5.8 Hz), 4.11 (2H, t, J=6.6 Hz), 4.01 (2H, t, J=5.8 Hz), 3.67 (3H, s), 2.76 (2H, t, J=7.6 Hz), 2.55 (2H, t, J=7.6 Hz), 1.64-1.59 (2H, m), 1.41-1.36 (2H, m), 0.90 (3H, t, J=7.4 Hz).

EXAMPLE 8

Synthesis of 2-butoxy-8-oxo-9-[4-(3-methoxycarbonylbenzenesulfonamide)butyl]adenine

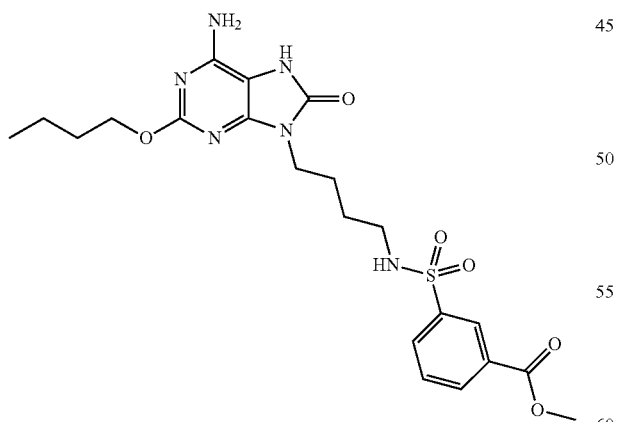

To 2-butoxy-8-methoxy-9-[4-(3-methoxycarbonylbenzenesulfonamide)butyl]adenine (64 mg, 0.13 mmol) obtained in Reference Example 22 were added methanol (10 ml) and sulfuric acid (300 μl), and the mixture was stirred at 85° C. for 3 hours. The mixture was neutralized with saturated sodium hydrogencarbonate, diluted with water and the precipitated solid was collected by filtration to give 54 mg (0.11 mmol) of the titled compound as a white solid. Yield: 87%.

$^1$H NMR (DMSO-$d_6$) δ 9.82 (1H, s), 8.30 (1H, dd, J=1.4, 1.7 Hz), 8.17 (1H, ddd, J=1.3, 1.4, 7.9 Hz), 8.01 (1H, ddd, J=1.3, 1.7, 7.9), 7.78 (1H, t, J=5.8 Hz), 7.72 (1H, t, J=7.9 Hz), 6.49 (2H, brs), 4.11 (2H, t, J=6.6 Hz), 3.89 (3H, s), 3.58 (2H, t, J=6.7 Hz), 2.77 (2H, dt, J=5.8, 6.6 Hz), 1.64-1.59 (4H, m), 1.41-1.36 (2H, m), 1.33-1.28 (2H, m), 0.89 (3H, t, J=7.4 Hz).

EXAMPLE 9

Synthesis of 2-butoxy-8-oxo-9-[4-(3-methoxycarbonylmethylbenzenesulfonamide)butyl]adenine

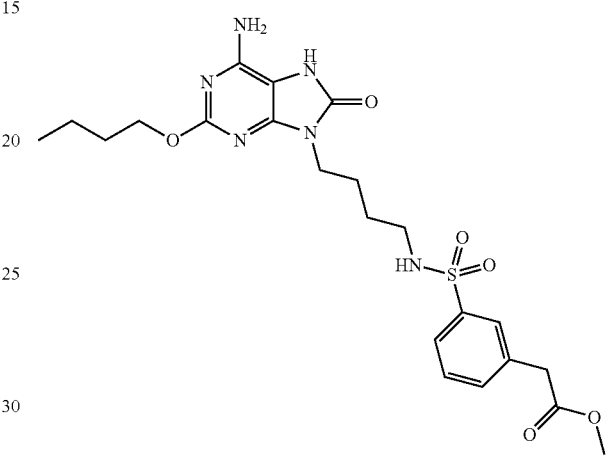

To 2-butoxy-8-oxo-9-[4-(3-hydroxycarbonylmethylbenzenesulfonamide)butyl]adenine (100 mg, 0.2 mmol) obtained in Comparison Example 9 were added methanol (15 ml) and sulfuric acid (200 μl) and the mixture was stirred at 80° C. for 3 hours. The mixture was and neutralized with an aqueous ammonium solution, and water was added thereto. Precipitated solid was collected by filtration to give 89 mg (0.2 mmol) of the titled compound, as a white solid. Yield: 91%.

$^1$H NMR (DMSO-$d_6$) δ 9.82 (1H, s), 7.68 (1H, s), 7.66-7.64 (1H, m), 7.59 (1H, t, J=5.8 Hz), 7.52-7.50 (1H, m), 6.40 (2H, brs), 4.12 (2H, t, J=6.6 Hz), 3.81 (3H, s), 3.59 (2H, t, J=6.6 Hz), 2.75 (2H, dt, J=5.8, 6.6 Hz), 1.65-1.58 (4H, m), 1.40-1.34 (2H, m), 1.36-1.29 (2H, m), 0.91 (3H, t, J=7.4 Hz).

EXAMPLE 10

Synthesis of 2-butoxy-8-oxo-9-[4-(3-methoxycarbonylphenylaminocarbonylamino)butyl]adenine

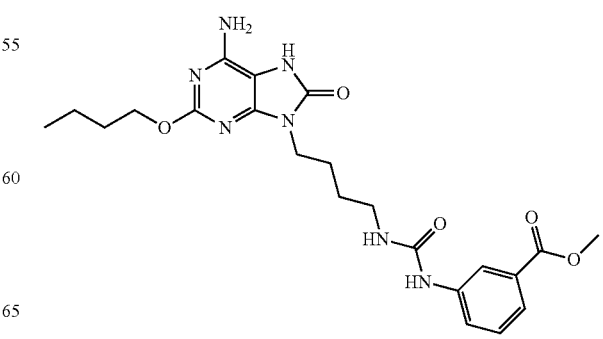

The titled compound was obtained by the same method as Example 8.

$^1$H NMR (DMSO-$d_6$) δ 9.85 (1H, brs), 8.67 (1H, s), 8.10 (1H, dd, J=1.5, 2.2 Hz), 7.56 (1H, ddd, J=1.0, 2.2, 8.2 Hz), 7.47 (1H, ddd, J=1.0, 1.5, 7.6 Hz), 7.34 (1H, dd, J=7.6, 8.2 Hz), 6.40 (2H, brs), 6.17 (1H, t, J=5.7 Hz), 4.13 (2H, t, J=6.6 Hz), 3.83 (3H, s), 3.67 (2H, t, J=6.8 Hz), 3.10 (2H, dt, J=5.7, 6.6 Hz), 1.69-1.63 (2H, m), 1.64-1.59 (2H, m), 1.44-1.37 (2H, m), 1.40-1.35 (2H, m), 0.88 (3H, t, J=7.4 Hz).

EXAMPLE 11

Synthesis of 2-butoxy-8-oxo-9-[4-(3-methoxycarbonylmethylphenylaminocarbonylamino)butyl]adenine

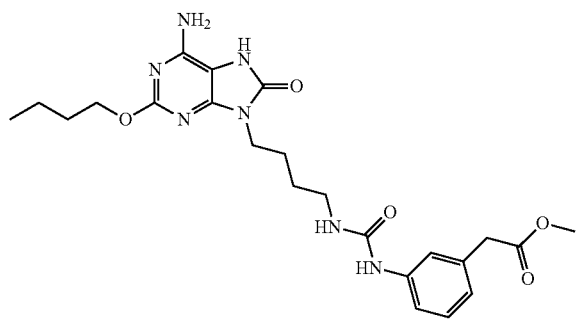 [SMILES: CCCCOc1nc(N)c2[nH]c(=O)n(CCCCNC(=O)Nc3cccc(CC(=O)OC)c3)c2n1]

To a solution of 2-butoxy-8-methoxy-9-[4-(3-hydroxymethylphenylaminocarbonylamino)butyl]adenine (300 mg, 0.66 mmol) obtained in Reference Example 27 in chloroform (7 ml) were added under ice-cooling triethylamine (1.08 ml, 7.86 mmol) and thionyl chloride (143 μl, 3.94 mmol), and the mixture was stirred for 5 minutes. Saturated sodium hydrogencarbonate was added thereto, and the mixture was diluted with water and extracted with chloroform (methanol 5%). The organic layer was washed with water and saturated brine, dried over sodium sulfate, and concentrated under reduced pressure. The residue was dissolved in DMF 10 ml, and sodium cyanide 96 mg (2.0 mmol) was added thereto at room temperature, followed by stirring at room temperature for 22 hours. To the reaction mixture was added saturated ammonium chloride, and the mixture was concentrated under reduced pressure. To the residue was added water and the mixture was extracted with chloroform (methanol 5%). The organic layer was washed with saturated brine, dried over sodium sulfate, and concentrated under reduced pressure. To the residue were added methanol (5 ml) and 5N potassium hydroxide (5 ml), followed by stirring at 90° C. for 6.5 hours. The resultant was neutralized with concentrated hydrochloric acid and concentrated under reduced pressure. To the residues were added methanol (20 ml) and the mixture was concentrated sulfuric acid (0.3 ml), followed by stirring at 90° C. for 2 hours. After cooling, the resultant was neutralized with an aqueous ammonium solution, and the precipitated solid was collected by filtration to give 140 mg (0.29 mmol) of the titled compound as a white solid. Yield: 44%.

$^1$H NMR (DMSO-$d_6$) δ 9.85 (1H, s), 8.39 (1H, s), 7.34 (1H, s), 7.26 (1H, d, J=8.2 Hz), 7.14 (1H, dd, J=7.5, 8.2 Hz), 6.76 (1H, d, J=7.5 Hz), 6.40 (2H, brs), 6.10 (1H, t, J=5.7 Hz), 4.13 (2H, t, J=6.6 Hz), 3.60 (3H, s), 3.58 (2H, s), 3.08 (2H, dt, J=5.7, 6.6 Hz), 1.68-1.60 (4H, m), 1.40-1.32 (4H, m), 0.89 (3H, t, J=7.4 Hz).

EXAMPLE 12

Interferon Inducing Activity of Rat Spleen Cells (in vitro)

Spleen was removed from CD(SD)IGS rat (male; 8-10 weeks old). A suspension of spleen cells of 1×10$^7$ cells/ml was prepared by using non serum MEN broth, and each 0.1 ml thereof was poured in a well of 96-well microplate. The test sample diluted with the broth (containing 0.2% DMSO) in each 0.1 ml was poured in the well and incubated in 5% $CO_2$ incubator at 37° C. for 24 hours. The culture broth was centrifuged to give a supernatant of the incubation. The interferon activity in the supernatant of the broth was quantitatively measured by the partially-improved bioassay method described in A. Armstrong, Methods in Enzymology 78, 381-7. Namely after mouse fibroblast L929 in 4×10$^4$ cells/50 μl was cultured in a 96-well culture plate for 7 hour, thereto was added 50 μl of the diluted culture supernatant and the mixture was further cultured for 17 hours. After the cultured broth in each well was removed, each 100 μl of vesicular stomatitis virus was added to each well and the effect of the cell denaturation 44 hours after the virus infection was confirmed by the neutral red stain. In Table 30, an interferon inducing activity (minimum effective concentration) on each compound was shown.

TABLE 30

| Compound | Minimum effective concentration (nM) |
|---|---|
| Example 1 | 0.3 |
| Example 2 | 3 |
| Example 3 | 1 |
| Example 4 | 1 |
| Example 6 | 10 |
| Example 8 | 3 |
| Example 9 | 3 |
| Example 10 | 1 |
| Example 11 | 10 |
| Comparison Example 1 | 10 |
| Comparison Example 2 | 30 |
| Comparison Example 3 | 100 |
| Comparison Example 4 | 100 |
| Comparison Example 6 | 100 |
| Comparison Example 8 | 100 |
| Comparison Example 9 | 300 |
| Comparison Example 10 | 300 |
| Comparison Example 11 | 100 |

EXAMPLE 13

Metabolic Stability Test Using Human Plasma

Plasma was prepared from fresh human blood and the test compound (containing 1% DMSO) of the final concentration of 1 μM was added thereto.

After a metabolic reaction by plasma esterase was conducted at 37° C. for 15 minutes, the test compound was extracted with ethyl acetate, and quantitatively analyzed by reverse phase HPLC. The metabolic stability of the test compound was shown by the residual amount (%) per the concentration of pre-metabolization as 100%. The result was shown in Table 31.

TABLE 31

| Compound | Residual rate (%) |
| --- | --- |
| Example 2 | 1.4 |
| Example 9 | <1.0 |

EXAMPLE 14

Metabolic Stability Test on Rat Liver S9

The reaction using liver S9 of rat was conducted on a 96-well plate by using a screening robot by Tecan Company. S9 solution was prepared by adding 250 mM Kpi (ph 7.4) 20 ml and deionized water 20 ml to 10 ml of liver S9 of rat, a Cofactor solution was prepared by dissolving NADPH 220 mg in deionized water 40.5 ml (Final 6 mM), and IS (Internal Standard) solution was prepared by adding IS solution (1 mM DMSO solution) 300 μl to acetonitrile 30 ml (100 times dilution). The test compound (1 μM DMSO solution) was dissolved in an incubator at 37° C. After each 35 μL was poured in a 96-well plate (24 samples/plate), plates (sample plates, 96-well plates for dilution, each Deep well plates for the reaction and the recovery, plates for extraction of a solid phase) and reagents (S9 solution, Cofactor solution, IS (Internal Standard) solution, Stop solution, acetonitrile for elution) were set to the specified position in the booth of the robot and the reaction started (the concentration of the test compounds was 1 μM). Incubation was conducted under shaking at 37° C., the solid phase was extracted (at the same time, the internal standard for analysis was added). To the recovered samples 200 μL/well was added 50 μL of acetonitrile per each well, and to 2 plates of FALCON Deep well were poured 100 μL/well of the solution per well. By subjecting to the LC/MS analysis, the chromatography of the test compound and the internal standard were described and the peak area was calculated. And then, the stability (residual rate after reaction) was calculated. The result was shown in Table 32.

TABLE 32

| Compound | Residual rate (%) |
| --- | --- |
| Example 1 | 0 |
| Example 2 | 1 |
| Example 3 | 0 |
| Example 4 | 0 |
| Example 5 | 0 |
| Example 6 | 0 |
| Example 7 | 0 |
| Example 8 | 0 |
| Example 9 | 0 |
| Example 10 | 1 |

COMPARISON EXAMPLE 1

Synthesis of 2-butoxy-8-oxo-9-[2-(3-hydroxycarbonylphenoxy)ethyl]adenine

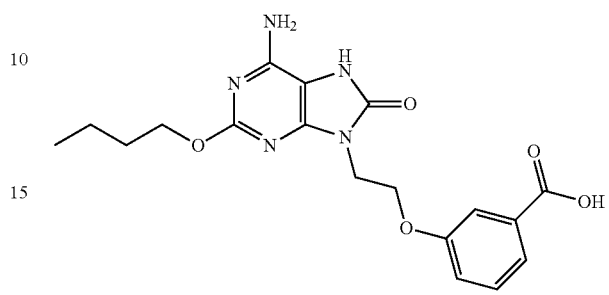

To 2-butoxy-8-oxo-9-[2-(3-methoxycarbonylphenoxy)ethyl]adenine (50 mg, 0.12 mmol) obtained in Example 1 were added methanol (2.5 ml) and 2.5N potassium hydroxide (5 m), and the mixture was stirred at 85° C. for 4.5 hours. After cooling, water was added and the resultant was made to pH 5 by concentrated hydrochloric acid. The precipitated crystal was collected by filtration to give 49 mg (0.12 mmol) of the titled compound as a white solid. Yield: 100%.

$^1$H NMR (DMSO-$d_6$) δ 13.02 (1H, br), 10.23 (1H, brs), 7.51 (1H, dd, J=1.2, 8.8 Hz), 7.38-7.36 (2H, m), 7.14 (1H, dd, J=0.8, 2.6 Hz), 6.57 (2H, brs), 4.32 (2H, t, J=5.7 Hz), 4.11-4.04 (4H, m), 1.65-1.60 (2H, m), 1.40-1.35 (2H, m), 0.89 (3H, t, J=7.4 Hz).

COMPARISON EXAMPLE 2

Synthesis of 2-butoxy-8-oxo-9-[2-(3-hydroxycarbonylmethylphenoxy)ethyl]adenine)

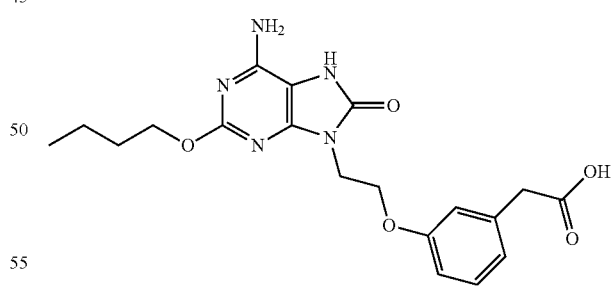

From 2-butoxy-8-oxo-9-[2-(3-methoxycarbonylmethylphenoxy)ethyl]adenine 15 mg (0.04 mmol) obtained in Example 2, 10 mg (0.03 mmol) of the titled compound was obtained as a white solid by the same method as Comparison Example 1. Yield: 70%.

$^1$H NMR (DMSO-$d_6$) δ 12.43 (1H, br), 9.93 (1H, s), 7.22-7.20 (1H, m), 6.81-7.78 (3H, m), 6.45 (2H, br), 4.24 (2H, t,

J=5.8 Hz), 4.12 (2H, t, J=6.6 Hz), 4.04 (2H, t, J=5.8 Hz), 3.50 (2H, s), 1.65-1.60 (2H, m), 1.39-1.35 (2H, m), 0.90 (3H, t, J=7.4 Hz).

COMPARISON EXAMPLE 3

Synthesis of 2-butoxy-8-oxo-9-[2-(2-hydroxycarbonylphenoxy)ethyl]adenine

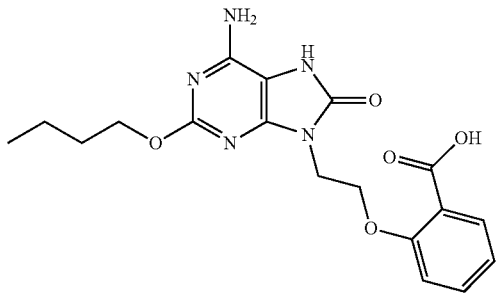 [SMILES: CCCCOc1nc(N)c2[nH]c(=O)n(CCOc3ccccc3C(=O)O)c2n1]

The titled compound was obtained by the same method as Comparison Example 1.

$^1$H NMR (DMSO-d$_6$) δ 12.46 (1H, br), 10.03 (1H, brs), 7.61 (1H, dd, J=1.7, 7.6 Hz), 7.45 (1H, dt, J=1.7, 8.2 Hz), 7.16 (1H, d, J=8.2 Hz), 7.00 (1H, t, J=7.6 Hz), 6.49 (2H, brs), 4.33 (2H, t, J=5.7 Hz), 4.09 (2H, t, J=6.6 Hz), 4.04 (2H, t, J=5.7 Hz), 1.64-1.59 (2H, m), 1.39-1.34 (2H, m), 0.89 (3H, t, J=7.4 Hz).

COMPARISON EXAMPLE 4

Synthesis of 2-butoxy-8-oxo-9-[2-(2-hydroxycarbonylmethylphenoxy)ethyl]adenine

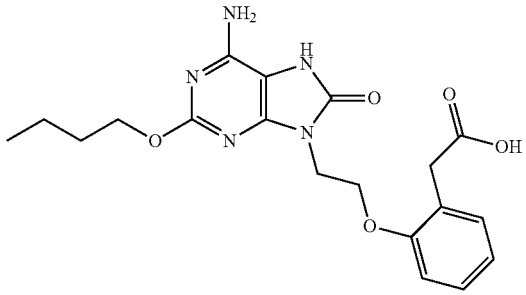 [SMILES: CCCCOc1nc(N)c2[nH]c(=O)n(CCOc3ccccc3CC(=O)O)c2n1]

The titled compound was obtained by the same method as Comparison Example 1.

$^1$H NMR (DMSO-d$_6$) δ 12.17 (1H, br), 10.35 (1H, br), 7.16-7.14 (1H, m), 6.97 (1H, d, J=7.6 Hz), 6.86 (1H, d, J=7.6 Hz), 6.58 (2H, brs), 4.21 (2H, t, J=5.7 Hz), 4.11 (2H, t, J=6.6

Hz), 4.02 (2H, t, J=5.7 Hz), 3.40 (2H, s), 1.65-1.60 (2H, m), 1.39-1.35 (2H, m), 0.88 (3H, t, J=7.4 Hz).

COMPARISON EXAMPLE 5

Synthesis of 2-butoxy-8-oxo-9-[2-(4-hydroxycarbonylphenoxy)ethyl]adenine

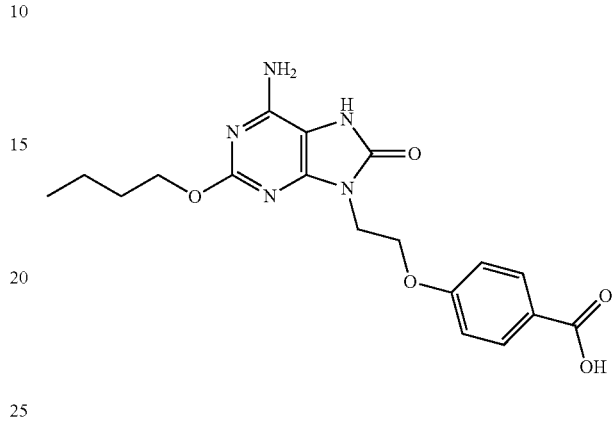

The titled compound was obtained by the same method as Comparison Example 1.

$^1$H NMR (DMSO-d$_6$) δ 12.62 (1H, br), 9.47 (1H, brs), 7.84 (2H, d, J=8.7 Hz), 6.97 (2H, d, J=8.7 Hz), 6.35 (2H, brs), 4.36 (2H, t, J=5.0 Hz), 4.11-4.08 (4H, m), 1.65-1.60 (2H, m), 1.37-1.32 (2H, m), 0.90 (3H, t, J=7.4 Hz).

COMPARISON EXAMPLE 6

Synthesis of 2-butoxy-8-oxo-9-[2-(4-methoxycarbonylmethylphenoxy)ethyl]adenine

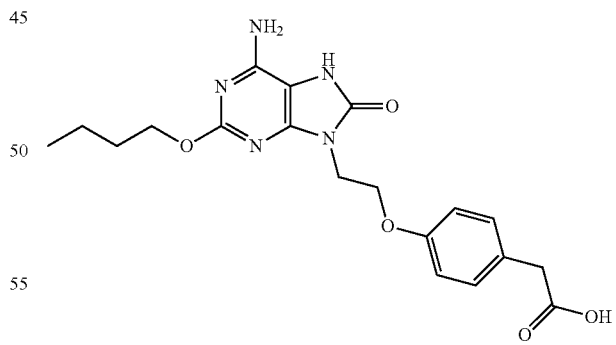

The titled compound was obtained by the same method as Comparison Example 1.

$^1$H NMR (DMSO-d$_6$) δ 12.25 (2H, br), 9.97 (1H, br), 7.12 (2H, d, J=8.7 Hz), 6.83 (2H, d, J=8.7 Hz), 6.44 (2H, brs), 4.24

(2H, t, J=5.8 Hz), 4.12 (2H, t, J=6.6 Hz), 4.03 (2H, t, J=5.8 Hz), 3.45 (2H, s), 1.65-1.60 (2H, m), 1.40-1.35 (2H, m), 0.90 (3H, t, J=7.4 Hz).

COMPARISON EXAMPLE 7

Synthesis of 2-butoxy-8-oxo-9-{2-[4-(2-hydroxycarbonylethyl)phenoxy]ethyl}adenine

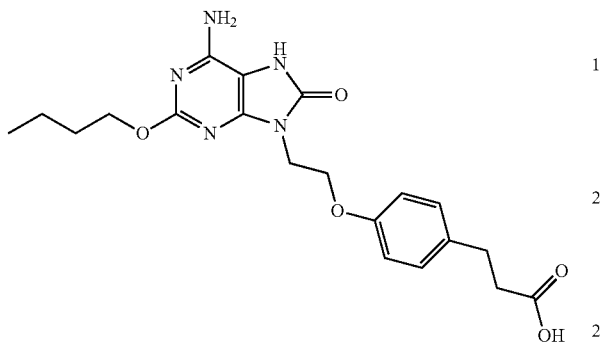

The titled compound was obtained by the same method as Comparison Example 1.

$^1$H NMR (DMSO-d$_6$) δ 12.12 (1H, br), 10.03 (1H, brs), 7.09 (2H, d, J=8.6 Hz), 6.79 (2H, d, J=8.6 Hz), 6.47 (2H, brs), 4.22 (2H, t, J=5.8 Hz), 4.11 (2H, t, J=6.6 Hz), 4.04 (2H, t, J=5.8 Hz), 2.72 (2H, t, J=7.6 Hz), 2.43 (2H, t, J=7.6 Hz), 1.64-1.59 (2H, m), 1.41-1.36 (2H, m), 0.90 (3H, t, J=7.4 Hz).

COMPARISON EXAMPLE 8

Synthesis of 2-butoxy-8-oxo-9-[4-(3-hydroxycarbonylbenzenesulfonamide)butyl]adenine

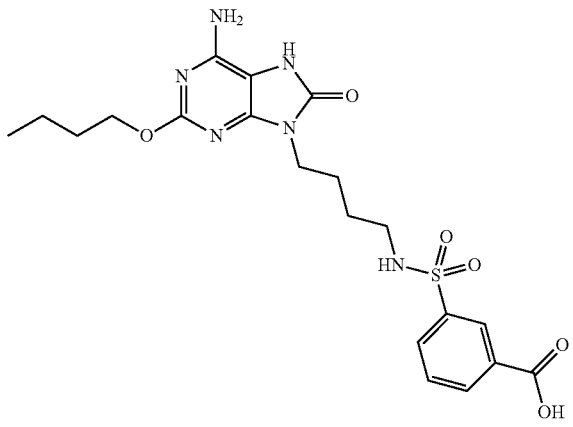 [SMILES: CCCCOc1nc(N)c2[nH]c(=O)n(CCCCNS(=O)(=O)c3cccc(C(=O)O)c3)c2n1]

The titled compound was obtained by the same method as Comparison Example 1.

$^1$H NMR (DMSO-d$_6$) δ 13.59 (1H, br), 10.06 (1H, brs), 8.29 (1H, dd, J=1.4, 1.7 Hz), 8.13 (1H, ddd, J=1.3, 1.4, 7.9 Hz), 7.92 (1H, ddd, J=1.3, 1.7, 7.9 Hz), 7.71 (1H, t, J=5.8 Hz), 7.66 (1H, t, J=7.9 Hz), 6.47 (2H, brs), 4.11 (2H, t, J=6.6 Hz), 3.60 (2H, t, J=6.6 Hz), 2.75 (2H, dt, J=5.8, 6.6 Hz), 1.63-1.58 (4H, m), 1.38-1.32 (4H, m), 0.89 (3H, t, J=7.4 Hz).

COMPARISON EXAMPLE 9

Synthesis of 2-butoxy-8-oxo-9-[4-(3-hydroxycarbonylmethylbenzenesulfonamide)butyl]adenine

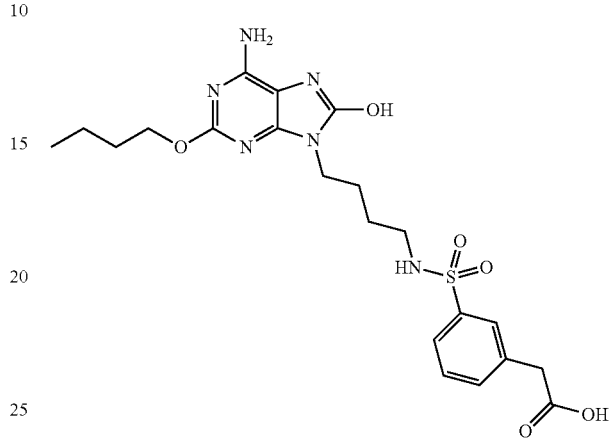

To 2-butoxy-8-methoxy-9-[4-(3-cyanomethylbenzenesulfonamide)butyl]adenine (190 mg, 0.4 mmol) obtained in Reference Example 25 were added methanol (3 ml) and 3.7N potassium hydroxide (3 ml) and the mixture was stirred at 90° C. for 3 hours. The resultant was adjusted to pH 5 by 1N hydrochloric acid, and the precipitated solid was collected by filtration. The obtained solid was dissolved in 1N sodium hydroxide and washed with chloroform. The aqueous layer was adjusted to pH 5 with 1N aqueous hydrochloric acid solution, and the precipitated solid was collected by filtration to give 145 mg (0.3 mmol) of the titled compound as a white solid. Yield: 73%.

$^1$H NMR (DMSO-d$_6$) δ 12.48 (1H, brs), 9.98 (1H, s), 7.68 (1H, s), 7.64-7.62 (1H, m), 7.58 (1H, t, J=5.9 Hz), 7.50-7.48 (1H, m), 7.48 (1H, d, J=1.0 Hz), 6.48 (2H, brs), 4.12 (2H, t, J=6.6 Hz), 3.69 (2H, brs), 3.59 (2H, t, J=6.6 Hz), 2.75 (2H, dt, J=5.9, 6.6 Hz), 1.65-1.58 (4H, m), 1.40-1.36 (2H, m), 1.35-1.29 (2H, m), 0.91 (3H, t, J=7.4 Hz).

COMPARISON EXAMPLE 10

Synthesis of 2-butoxy-8-oxo-9-[4-(3-hydroxycarbonylphenylaminocarbonylamino)butyl]adenine

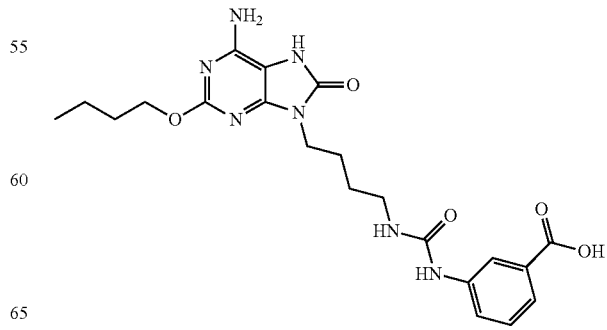

The titled compound was obtained by the same method as Comparison Example 1.

$^1$H NMR (DMSO-$d_6$) δ 12.82 (1H, brs), 9.86 (1H, s), 8.61 (1H, s), 8.01 (1H, dd, J=1.5, 2.2 Hz), 7.57 (1H, ddd, J=1.0, 2.2, 8.2 Hz), 7.45 (1H, ddd, J=1.0, 1.5, 7.6 Hz), 7.31 (1H, dd, J=7.6, 8.2 Hz), 6.41 (2H, brs), 6.16 (1H, t, J=5.7 Hz), 4.13 (2H, t, J=6.6 Hz), 3.68 (2H, t, J=6.8 Hz), 3.10 (2H, dt, J=5.7, 6.6 Hz), 1.70-1.64 (2H, m), 1.64-1.59 (2H, m), 1.44-1.37 (2H, m), 1.39-1.33 (2H, m), 0.88 (3H, t, J=7.4 Hz).

COMPARISON EXAMPLE 11

Synthesis of 2-butoxy-8-oxo-9-[4-(3-hydroxycarbonylmethylphenylaminocarbonylamino)butyl]adenine

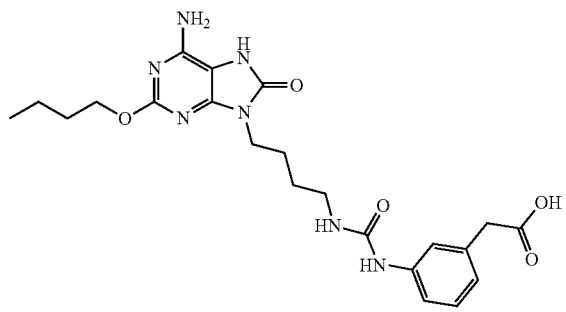 [SMILES: CCCCOc1nc(N)c2[nH]c(=O)n(CCCCNC(=O)Nc3cccc(CC(=O)O)c3)c2n1]

The titled compound was obtained by the same method as Comparison Example 1.

$^1$H NMR (DMSO-$d_6$) δ 12.29 (1H, br), 9.90 (1H, s), 8.38 (1H, s), 7.28 (1H, s), 7.25 (1H, d, J=8.2 Hz), 7.13 (1H, dd, J=7.5, 8.2 Hz), 6.76 (1H, d, J=7.5 Hz), 6.41 (2H, brs), 6.10 (1H, t, J=5.7 Hz), 4.14 (2H, t, J=6.6 Hz), 3.68 (2H, t, J=6.8 Hz), 3.46 (2H, s), 3.08 (2H, dt, J=5.7, 6.6 Hz), 1.68-1.59 (4H, m), 1.42-1.35 (4H, m), 0.89 (3H, t, J=7.4 Hz).

REFERENCE EXAMPLE 1

Synthesis of methyl 3-(2-bromoethoxy)benzoate

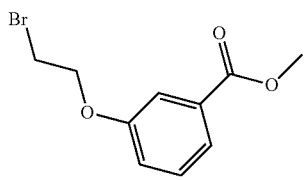

To a solution of methyl 3-hydroxybenzoate (2.00 g, 13.1 mmol) in acetone (50 ml) were added potassium carbonate (3.18 g, 23.0 mmol) and 1,2-dibromoethane (6.4 ml, 74.1 mmol) and the mixture was stirred at 85° C. for 24 hours. After cooling, the resultant was concentrated under reduced pressure. To the residue was added 75 ml of water and the mixture was extracted with ethyl acetate. The organic layer was washed with 1N aqueous sodium hydroxide solution, water and saturated brine in this order, dried over sodium sulfate and concentrated under reduced pressure. The residue was purified by silica gel column chromatography to give 1.79 g (6.9 mmol) of the titled compound as an yellow oil. Yield: 53%.

$^1$H NMR (CDCl$_3$) δ 7.67 (1H, dt, J=1.5, 7.8 Hz), 7.56 (1H, dd, J=1.5, 2.6 Hz), 7.36 (1H, t, J=7.8 Hz), 7.15-7.13 (1H, m), 4.34 (2H, t, J=6.2 Hz), 3.92 (3H, s), 3.66 (2H, t, J=6.2 Hz).

REFERENCE EXAMPLE 2

Synthesis of 2-butoxy-9-[2-(3-methoxycarbonylphenoxy)ethyl]adenine

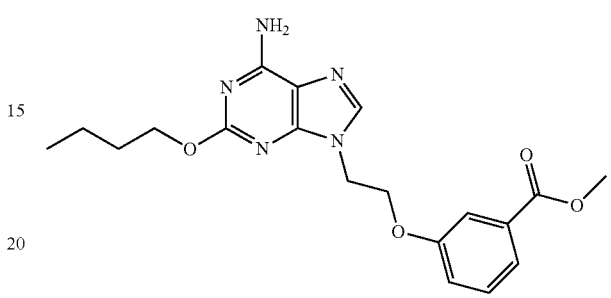

To 2-butoxyadenine (727 mg, 3.5 mmol) and potassium carbonate (727 mg, 5.3 mmol) was added DMF (35 ml), and the mixture was stirred at 70° C. for 2 hours. Then a solution of methyl 3-(2-bromoethoxy)benzoate obtained in Reference Example 1 (1.0 g, 3.9 mmol) in DMF (2 ml) was added thereto under ice-cooling, followed by stirring at room temperature for 3 hours. The solvent was removed under reduced pressure, and to the residue was added water. The mixture was neutralized with concentrated hydrochloric acid and extracted with chloroform (methanol 5%). The organic layer was washed with water and saturated brine, dried over sodium sulfate and concentrated under reduced pressure. The residue was purified by silica gel column chromatography to give, as white crystal, 1.1 g (2.9 mmol) of the titled compound. Yield: 81%.

$^1$H NMR (CDCl$_3$) δ 7.83 (1H, s), 7.65 (1H, dt, J=1.5, 8.0 Hz), 7.51 (1H, dd, J=1.5, 2.6 Hz), 7.31 (1H, t, J=8.0 Hz), 7.07 (1H, ddd, J=0.9, 2.6, 8.0 Hz), 5.88 (2H, br), 4.53 (2H, t, J=4.8 Hz), 4.33 (4H, m), 3.90 (3H, s), 1.83-1.73 (2H, m), 1.53-1.47 (2H, m), 0.97 (3H, t, J=7.4 Hz).

REFERENCE EXAMPLE 3

Synthesis of 2-butoxy-9-[2-(3-methoxycarbonylmethylphenoxy)ethyl]adenine

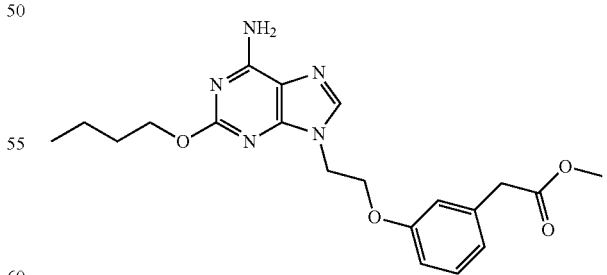

To a suspension of lithium aluminum hydride (150 mg, 4.0 mmol) in THF (15 ml) was added a solution of 2-butoxy-9-[2-(3-methoxycarbonylphenoxy)ethyl]adenine (540 mg, 1.4 mmol) obtained in Reference Example 2 in THF (5 ml) under ice-cooling, and the mixture was stirred at room temperature for 3 hours. 1N Aqueous sodium hydroxide solution was added thereto, followed by filtration through celite pad and concentration under reduced pressure. The residue was dissolved in chloroform (10 ml), and thionyl chloride (336 μl, 4.62 mmol) was added thereto at room temperature, followed by stirring at 60° C. for 10 minutes. To the reaction mixture was added 1N aqueous sodium hydroxide solution, and the mixture was diluted with water and extracted with chloroform (methanol 5%). The organic layer was washed with water and brine, dried over sodium sulfate and concentrated under reduced pressure to give chloromethyl product as a pale yellow crystal, 380 mg. To a solution of the chloromethyl product (380 mg) in DMF (10 ml) was added sodium cyanide (99 mg, 2.02 mmol) at room temperature, followed by stirring at room temperature for 1 hour. To the reaction mixture was added saturated ammonium chloride and the mixture was concentrated under reduced pressure. To the residue was added water and the mixture was extracted with chloroform (methanol 5%). The organic layer was washed with water and saturated brine, dried over sodium sulfate and concentrated under reduced pressure. To the residue were added methanol (7 ml) and 5N aqueous potassium hydroxide solution (7 ml) and the mixture was stirred at 95° C. for 3.5 hours. The reaction solution was neutralized with concentrated hydrochloric acid, and concentrated under reduced pressure. Methanol (20 ml) and concentrated sulfuric acid (0.3 ml) were added thereto, followed by stirring at 90° C. for 3.5 hours. After cooling, the resultant was concentrated under reduced pressure, and to the residue was added water. The solution was extracted with chloroform (methanol 5%). The organic layer was washed with water and saturated brine, dried over sodium sulfate and concentrated under reduced pressure. The residue was purified by silica gel column chromatography to give 160 mg (0.40 mmol) of the titled compound as a pale yellow oil. Yield: 29%.

$^1$H NMR (DMSO-d$_6$) δ 7.22 (1H, t, J=7.8 Hz), 6.87 (1H, d, J=7.8 Hz), 6.80-6.77 (2H, m), 5.51 (2H, brs), 4.56 (2H, t, J=4.8 Hz), 4.31-4.27 (4H, m), 3.68 (3H, s), 3.58 (2H, s), 1.82-1.78 (2H, m), 1.53-1.48 (2H, m), 0.97 (3H, t, J=7.4 Hz).

REFERENCE EXAMPLE 4

Synthesis of methyl 2-(2-bromoehyoxy)benzoate

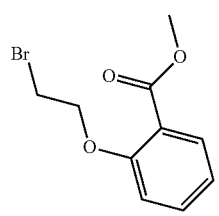

The titled compound was obtained by the same method as Reference Example 1.

$^1$H NMR (CDCl$_3$) δ 7.60 (1H, dd, J=1.6, 7.6 Hz), 7.46-7.44 (1H, m), 7.04-7.02 (1H, m), 6.97 (1H, dt, 0.6, 8.3 Hz), 4.36 (2H, t, J=6.5 Hz), 3.90 (3H, s), 3.68 (2H, t, J=6.5 Hz).

REFERENCE EXAMPLE 5

Synthesis of 2-butoxy-9-[2-(2-methoxycarbonylphenoxy)ethyl]adenine

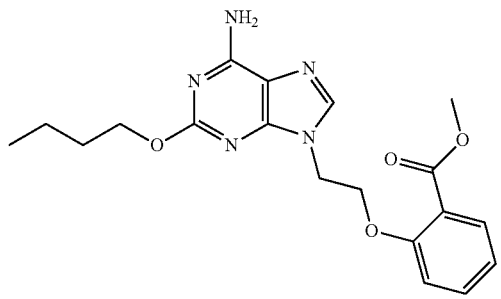 [SMILES: CCCCOc1nc(N)c2ncn(CCOc3ccccc3C(=O)OC)c2n1]

The titled compound was obtained by the same method as Reference Example 2.

$^1$H NMR (DMSO-d$_6$) δ 8.01 (1H, s), 7.64 (1H, dd, J=1.8, 7.7 Hz), 7.51-7.50 (1H, m), 7.19 (2H, brs), 7.15 (1H, d, J=8.1 Hz), 7.02-7.00 (1H, m), 4.47-4.42 (2H, m), 4.38-4.34 (2H, m), 4.18 (2H, t, J=6.6 Hz), 3.73 (3H, s), 1.67-1.76 (2H, m), 1.41-1.38 (2H, m), 0.89 (3H, t, J=7.4 Hz).

REFERENCE EXAMPLE 6

Synthesis of 2-butoxy-9-[2-(2-hydroxymethylphenoxy)ethyl]adenine

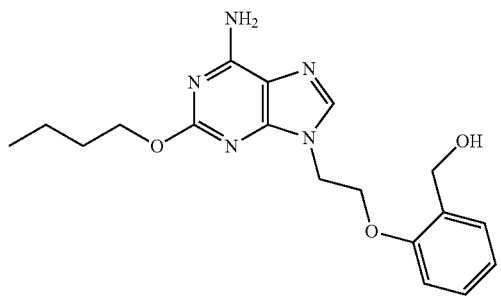 [SMILES: CCCCOc1nc(N)c2ncn(CCOc3ccccc3CCl)c2n1]

To a suspension of lithium aluminum hydride (74 mg, 1.9 mmol) in THF (10 ml) was added a solution of 2-butoxy-9-[2-(2-methoxycarbonylphenoxy)ethyl]adenine (500 mg, 1.4 mmol) obtained by Reference Example 5 in THF (2 ml) under ice-cooling, and the mixture was stirred at room temperature for 1 hour. 1N Aqueous sodium hydroxide solution was added thereto, followed by filtration through celite pad, and the filtrate was concentrated under reduced pressure to give 500 mg (1.4 mmol) of the titled compound as a white solid. Yield: 99%.

$^1$H NMR (DMSO-d$_6$) δ 7.98 (1H, s), 7.32 (1H, d, J=7.6 Hz), 7.18 (2H, brs), 7.15-7.13 (1H, m), 6.94-6.92 (1H, m), 6.91-6.89 (1H, m), 4.96 (1H, t, 4.9 Hz), 4.44 (2H, t, J=5.1 Hz), 4.33 (2H, d, J=4.9 Hz), 4.29 (2H, t, J=5.1 Hz), 4.19 (2H, t, J=6.6 Hz), 1.67-1.62 (2H, m), 1.41-1.37 (2H, m), 0.92 (3H, t, J=7.4 Hz).

REFERENCE EXAMPLE 7

Synthesis of 2-butoxy-9-[2-(2-chloromethylphenoxy)ethyl]adenine

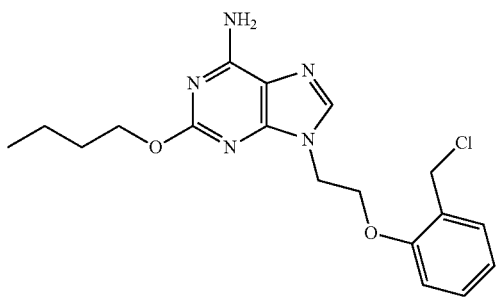

To a solution of 2-butoxy-9-[2-(2-hydroxymethylphenoxy)ethyl]adenine (500 ml, 1.4 mmol) obtained in Reference Example 6 in chloroform (10 ml) was added thionyl chloride (510 μl, 7.0 mmol) at room temperature, and the mixture was stirred at 60° C. for 1 hour. 1N Aqueous sodium hydroxide solution was added to the resultant, followed by dilution with water and extraction with chloroform (methanol 5%). The organic layer was washed with water and saturated brine, dried over sodium sulfate and concentrated under reduced pressure to give 529 mg (1.3 mmol) of the titled compound as a pale yellow solid. Yield: 93%.

$^1$H NMR (DMSO-$d_6$) δ 8.07 (1H, s), 7.33-7.31 (4H, m), 7.04 (1H, d, J=8.1 Hz), 6.93 (1H, t, J=7.2 Hz), 4.59 (2H, s), 4.50-4.48 (2H, m), 4.38-4.36 (2H, m), 4.21 (2H, t, J=6.6 Hz), 1.69-1.64 (2H, m), 1.45-1.40 (2H, m), 0.92 (3H, t, J=7.4 Hz).

REFERENCE EXAMPLE 8

Synthesis of 2-butoxy-9-[2-(2-cyanomethylphenoxy)ethyl]adenine

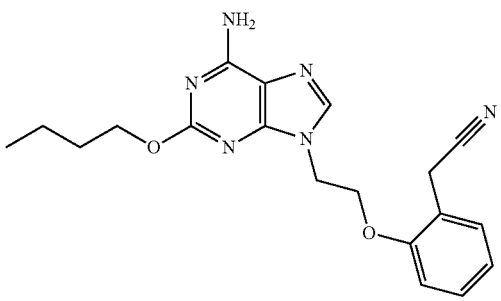 [SMILES: CCCCOc1nc(N)c2ncn(CCOc3ccccc3CC#N)c2n1]

To a solution of 2-butoxy-9-[2-(2-chloromethylphenoxy)ethyl]adenine (529 mg, 1.3 mmol) obtained in Reference Example 7 in DMF (14 ml) was added sodium cyanide (207 mg, 4.2 mmol) at room temperature and the mixture was stirred at room temperature for 1 hour. Saturated ammonium chloride was added thereto and concentrated under reduced pressure. To the residue was added water and the solution was extracted with chloroform (methanol 5%). The organic layer was washed with water and an aqueous saline solution, dried over sodium sulfate and concentrated under reduced pressure to give 436 mg (1.2 mmol) of the titled compound as pale a yellow solid. Yield: 84%.

$^1$H NMR (DMSO-$d_6$) δ 8.32 (1H, s), 7.32-7.30 (2H, m), 7.20 (2H, br), 7.06 (1H, d, J=8.0 Hz), 7.97 (1H, t, J=7.1 Hz), 4.47 (2H, t, J=5.0 Hz), 4.36 (2H, t, J=5.0 Hz), 4.19 (2H, t, J=6.6 Hz), 3.73 (2H, s), 1.69-1.64 (2H, m), 1.45-1.40 (2H, m), 0.92 (3H, t, J=7.4 Hz).

REFERENCE EXAMPLE 9

Synthesis of 2-butoxy-9-[2-(2-methoxycarbonylmethylphenoxy)ethyl]adenine

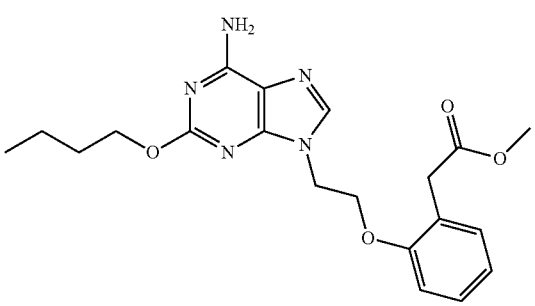 [SMILES: CCCCOc1nc(N)c2ncn(CCOc3ccccc3CC(=O)OC)c2n1]

To 2-butoxy-9-[2-(2-cyanomethylphenoxy)ethyl]adenine (436 mg, 1.2 mmol) obtained in Reference Example 8 were added methanol (12 ml) and 5N aqueous potassium hydroxide solution (12 ml), and the mixture was heated at 95° C. for 6.5 hours. The reaction solution was neutralized with concentrated hydrochloric acid and the precipitated solid was collected by filtration. Methanol (15 ml) and concentrated sulfuric acid (0.3 ml) were added thereto and the mixture was stirred at 75° C. for 5 hours. After cooling, the resultant was neutralized with saturated sodium hydrogencarbonate solution, and methanol was removed by distillation. The precipitated solid was collected by filtration to give 384 mg (1.0 mmol) of the titled compound as a white solid. Yield: 81%.

$^1$H NMR (DMSO-$d_6$) δ 8.01 (1H, s), 7.22-7.20 (3H, m), 7.14 (1H, dd, J=1.6, 7.4 Hz), 6.98 (1H, d, J=6.5 Hz), 6.88 (1H, dt, J=0.8, 7.4 Hz), 4.41 (2H, t, J=5.0 Hz), 4.28 (2H, t, J=5.0 Hz), 4.19 (2H, t, J=6.6 Hz), 3.53 (3H, s), 3.50 (2H, s), 1.69-1.64 (2H, m), 1.42-1.37 (2H, m), 0.90 (3H, t, J=7.4 Hz).

REFERENCE EXAMPLE 10

Synthesis of methyl 4-(2-bromoethoxy)benzoate

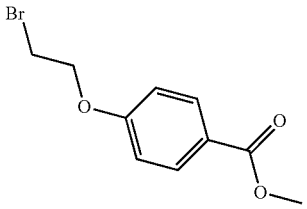

The titled compound was obtained by the same method as Reference Example 1.

$^1$H NMR (CDCl$_3$) δ 7.99 (2H, d, J=9.0 Hz), 6.92 (2H, d, J=9.0), 4.35 (2H, t, J=6.2 Hz), 3.89 (3H, s), 3.66 (2H, t, J=6.2 Hz).

REFERENCE EXAMPLE 11

Synthesis of 2-butoxy-9-[2-(4-methoxycarbonylphenoxy)ethyl]adenine

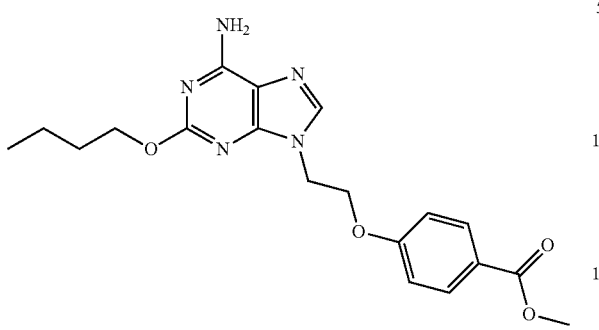

The titled compound was obtained by the same method as Reference Example 2.

$^1$H NMR (DMSO-d$_6$) δ 7.97 (2H, d, J=8.6 Hz), 7.27 (1H, s), 6.90 (2H, d, J=8.6 Hz), 5.84 (2H, brs), 4.54 (2H, m), 4.38-4.34 (2H, m), 4.18 (2H, t, J=6.6 Hz), 3.73 (3H, s), 1.67-1.76 (2H, m), 1.41-1.38 (2H, m), 0.89 (3H, t, J=7.4 Hz).

REFERENCE EXAMPLE 12

Synthesis of methyl 4-(2-bromoethoxy)phenylacetate

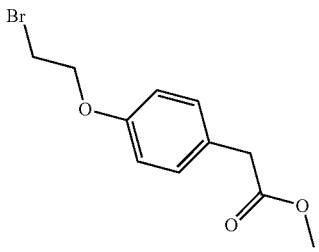

The titled compound was obtained by the same method as Reference Example 1.

$^1$H NMR (CDCl$_3$) δ 7.21 (2H, d, J=8.7 Hz), 6.88 (2H, d, J=8.7 Hz), 4.30 (2H, t, J=6.3 Hz), 3.71 (3H, s), 3.65 (2H, t, J=6.3 Hz), 3.59 (2H, s).

REFERENCE EXAMPLE 13

Synthesis of 2-butoxy-9-[2-(4-methoxycarbonylmethylphenoxy)ethyl]adenine

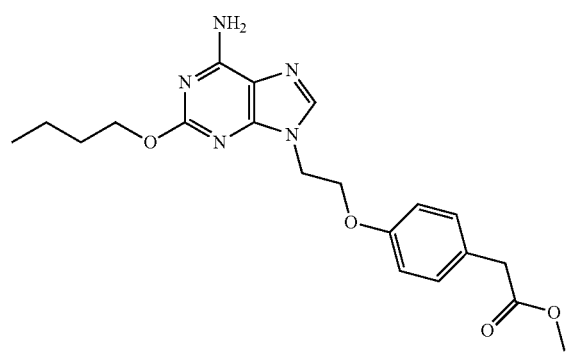 [SMILES: CCCCOc1nc(N)c2ncn(CCOc3ccc(CC(=O)OC)cc3)c2n1]

The titled compound was obtained by the same method as Reference Example 2.

$^1$H NMR (DMSO-d$_6$) δ 7.96 (1H, s), 7.18 (2H, brs), 7.14 (2H, d, J=8.7 Hz), 6.86 (2H, d, J=8.7 Hz), 4.42 (2H, t, J=5.4 Hz), 4.32 (2H, t, J=5.4 Hz), 4.19 (2H, t, J=6.6 Hz), 3.58 (5H, s), 1.68-1.63 (2H, m), 1.41-1.36 (2H, m), 0.91 (3H, t, J=7.4 Hz).

REFERENCE EXAMPLE 14

Synthesis of 2-butoxy-9-{2-[4-(2-hydroxyethyl)phenoxy]ethyl}adenine

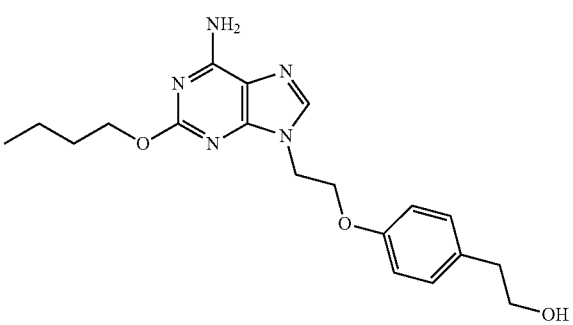 [SMILES: CCCCOc1nc(N)c2ncn(CCOc3ccc(CCO)cc3)c2n1]

The titled compound was obtained by the same method as Reference Example 6.

$^1$H NMR (DMSO-d$_6$) δ 7.95 (1H, s), 7.18 (2H, brs), 7.08 (2H, d, J=8.6 Hz), 6.81 (2H, d, J=8.6 Hz), 4.58 (2H, t, J=5.3 Hz), 4.40 (2H, t, J=5.2 Hz), 4.29 (2H, t, J=5.2 Hz), 4.19 (2H, t, J=6.6 Hz), 3.51 (2H, dt, J=5.3, 7.2 Hz), 2.62 (2H, t, J=7.2 Hz), 1.67-1.62 (2H, m), 1.40-1.35 (2H, m), 0.91 (3H, t, J=7.4 Hz).

REFERENCE EXAMPLE 15

Synthesis of 2-butoxy-9-{2-[4-(2-chloroethyl)phenoxy]ethyl}adenine

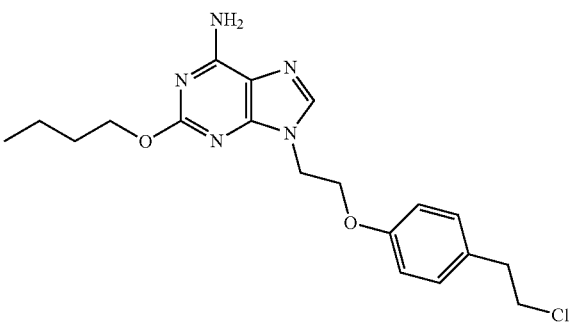 [SMILES: CCCCOc1nc(N)c2ncn(CCOc3ccc(CCCl)cc3)c2n1]

The titled compound was obtained by the same method as Reference Example 7.

$^1$H NMR (DMSO-d$_6$) δ 8.05 (1H, s), 7.43 (2H, br), 7.16 (2H, d, J=8.6 Hz), 6.87 (2H, d, J=8.6 Hz), 4.43 (2H, t, J=5.2 Hz), 4.32 (2H, t, J=5.2 Hz), 4.23 (2H, t, J=6.6 Hz), 3.77 (2H, t, J=7.1 Hz), 2.93 (2H, t, J=7.1 Hz), 1.69-1.64 (2H, m), 1.43-1.38 (2H, m), 0.90 (3H, t, J=7.4 Hz).

REFERENCE EXAMPLE 16

Synthesis of 2-butoxy-8-bromo-9-{2-[4-(2-cyanoethyl)phenoxy]ethyl}adenine

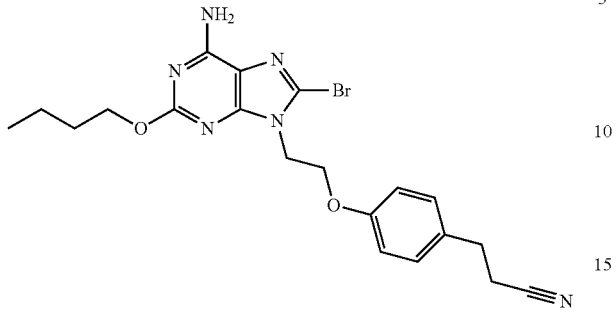

To a solution of 2-butoxy-9-{2-[4-(2-chloroethyl)phenoxy]ethyl}adenine (985 mg, 2.6 mmol) obtained in Reference Example 15 in DMF (20 ml) was added sodium cyanide (3085 mg, 7.9 mmol) at room temperature, and the mixture was stirred at room temperature for 18 hours and at 50° C. for 2 hours. 1N Hydrochloric acid was added to the resultant and the mixture was concentrated under educed pressure. To the residue was added water and the mixture was extracted with chloroform (methanol 5%). The organic layer was washed with water and saturated brine, dried over sodium sulfate and concentrated under reduced pressure to give a cyano product. To a solution of the obtained cyano product in chloroform (25 ml) were added sodium acetate (653 mg, 3.6 mmol) and bromine (180 μl, 3.6 mmol) under ice-cooling, followed by stirring at room temperature for 3 hours. Saturated sodium hydrogencarbonate and saturated sodium thiosulfate were added to the resultant, followed by stirring for 10 minutes. The reaction solution was diluted with water and extracted with chloroform (methanol 5%). The organic layer was washed with water and saturated brine, dried over sodium sulfate and concentrated under reduced pressure. The resulting crude crystal was recrystallized from methanol to give 948 mg (2.1 mmol) of the titled compound as a pale yellowish white solid. Yield: 82%.

$^1$H NMR (DMSO-$d_6$) δ 7.11 (2H, d, J=8.6 Hz), 6.81 (2H, d, J=8.6 Hz), 5.46 (2H, br), 4.53 (2H, t, J=5.7 Hz), 4.31 (2H, t, J=5.7 Hz), 4.30 (2H, t, J=6.6 Hz), 2.89 (2H, t, J=7.3 Hz), 2.56 (2H, t, J=7.3 Hz), 1.81-1.76 (2H, m), 1.52-1.47 (2H, m), 0.97 (3H, t, J=7.4 Hz).

REFERENCE EXAMPLE 17

Synthesis of (2-butoxy-9-(4-phthalimidobutyl)adenine

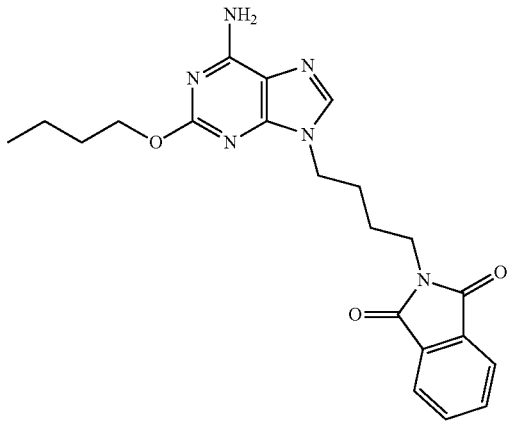 [SMILES: CCCCOc1nc(N)c2ncn(CCCCN3C(=O)c4ccccc4C3=O)c2n1]

The titled compound was obtained by the same method as Reference Example 2.

$^1$H NMR (DMSO-$d_6$) δ 7.90 (1H, s), 7.85-7.84 (4H, m), 7.14 (2H, brs), 4.14 (2H, t, J=6.6 Hz), 4.05 (2H, t, J=7.8 Hz), 3.60 (2H, t, J=6.9 Hz), 1.79-1.72 (2H, m), 1.65-1.60 (2H, m), 1.58-1.52 (2H, m), 0.89 (3H, t, J=7.4 Hz).

REFERENCE EXAMPLE 18

Synthesis of (2-butoxy-8-bromo-9-(4-phthalimidobutyl)adenine

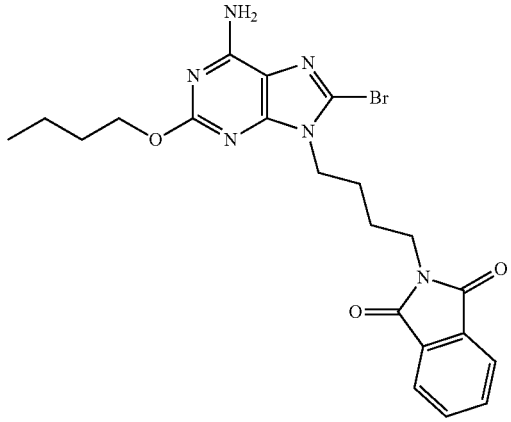 [SMILES: CCCCOc1nc(N)c2nc(Br)n(CCCCN3C(=O)c4ccccc4C3=O)c2n1]

To a solution of 2-butoxy-9-(4-phthalimide butyl)adenine (500 mg, 1.2 mmol) obtained in Reference Example 17 in chloroform (13 ml) were added sodium acetate (334 mg, 1.8 mmol) and bromine (92 μl, 1.8 mmol) under ice-cooling, and the mixture was stirred for 2 hours. Saturated sodium hydrogencarbonate and saturated sodium thiosulfate were added to the resultant, followed by stirring for 10 minutes. The reaction solution was diluted with water and extracted with chloroform (methanol 5%). The organic layer was washed with water and saturated brine, dried over sodium sulfate and concentrated under reduced pressure. The residue was purified by silica gel column chromatography to give, as a pale yellow solid, 575 mg (1.2 mmol) of the titled compound. Yield: 96%.

$^1$H NMR (DMSO-$d_6$) δ 7.84-7.82 (4H, m), 7.35 (2H, brs), 4.14 (2H, t, J=6.6 Hz), 4.04 (2H, t, J=6.6 Hz), 3.60 (2H, t, J=6.7 Hz), 1.79-1.75 (2H, m), 1.60-1.55 (2H, m), 1.37-1.32 (2H, m), 0.88 (3H, t, J=7.4 Hz).

REFERENCE EXAMPLE 19

Synthesis of 2-butoxy-8-methoxy-9-[4-(2-hydroxycarbonylbenzamide)butyl]adenine

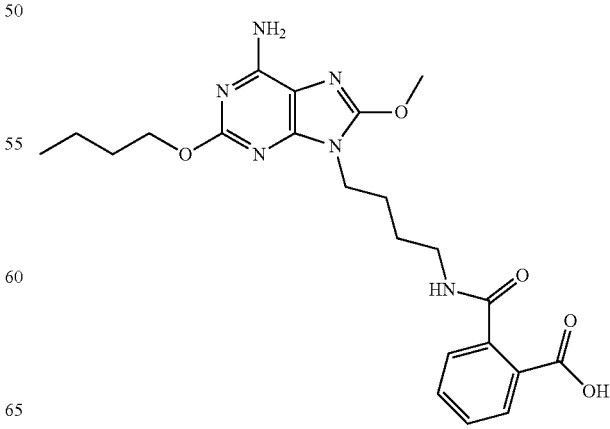

To 2-butoxy-8-bromo-9-(4-phthalimidebutyl)adenine (258 mg, 0.53 mmol) obtained in Reference Example 18 were added methanol (3 ml) and 3N potassium hydroxide (3 ml) and the mixture was stirred at 90° C. for 4 hour. The resultant was adjusted to pH 5 by concentrated hydrochloric acid and the precipitated solid was collected by filtration to give 230 mg (0.51 mmol) of the titled compound as a pale yellow solid. Yield: 95%.

$^1$H NMR (DMSO-$d_6$) δ 12.91 (1H, brs), 8.33 (1H, brs), 7.72 (1H, d, J=7.6 Hz), 7.50 (2H, m), 7.35 (1H, d, J=7.4 Hz), 6.80 (2H, brs), 4.15 (2H, t, J=6.5 Hz), 4.05 (3H, s), 3.86 (2H, t, J=6.8 Hz), 3.23-3.17 (2H, m), 1.78-1.73 (2H, m), 1.66-1.61 (2H, m), 1.41-1.36 (2H, m), 0.91 (3H, t, J=7.3 Hz).

REFERENCE EXAMPLE 20

Synthesis of 2-butoxy-8-methoxy-9-(4-aminobutyl)adenine

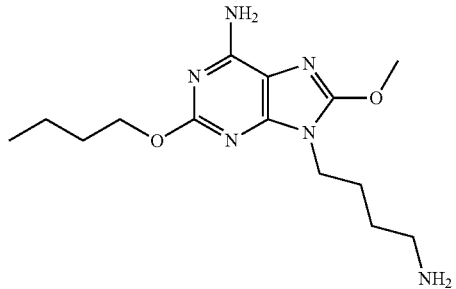 [SMILES: CCCCOc1nc(N)c2nc(OC)n(CCCCN)c2n1]

To a solution of 2-butoxy-8-methoxy-9-{4-(2-hydroxycarbonylbenzamide)butyl}adenine (682 mg, 1.5 mmol) obtained in Reference Example 19 in ethanol (20 ml) was added hydrazine (3 ml) and the mixture was stirred at 90° C. for 4.5 hours. After cooling, the resultant was filtered and the filtrate was concentrated under reduced pressure, followed by addition of water and extraction with chloroform (methanol 5%). The organic layer was washed with water and saturated brine, dried over sodium sulfate and concentrated under reduced pressure. The residue was purified by silica gel column chromatography to give 461 mg (1.5 mmol) of the titled compound as a pale yellow solid. Yield: 99%.

$^1$H NMR (DMSO-$d_6$) δ 6.79 (2H, brs), 4.15 (2H, t, J=6.6 Hz), 4.03 (3H, s), 3.82 (2H, t, J=7.0 Hz), 1.73-1.68 (2H, m), 1.67-1.61 (4H, m), 1.43-1.39 (2H, m), 1.28-1.23 (2H, m), 0.92 (3H, t, J=7.4 Hz).

REFERENCE EXAMPLE 21

Synthesis of 3-methoxycarbonylbenzenesulfonyl chloride

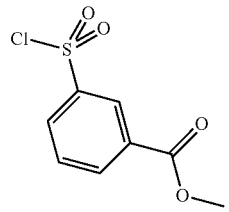

To a solution of 3-chlorocarbonylbenzenesulfonyl chloride (5.0 g, 21 mmol) in THF (100 ml) was added methanol 1.7 ml (42 mmol) and the mixture was stirred at room temperature for 13 hours. After the reaction was completed, the resultant was concentrated under reduced pressure to give 5.14 g (21 mmol) of the titled compound as a pale purple solid. Yield: 100%.

$^1$H NMR (CDCl$_3$) δ 8.70 (1H, dd, J=1.4, 1.9 Hz), 8.42 (1H, dt, J=1.4, 7.9 Hz), 8.22 (1H, ddd, J=1.2, 1.9, 7.9 Hz), 7.74 (1H, t, J=7.9 Hz), 4.00 (3H, s).

REFERENCE EXAMPLE 22

Synthesis of 2-butoxy-8-methoxy-9-[4-(3-methoxycarbonylbenzenesulfonamide)butyl]adenine

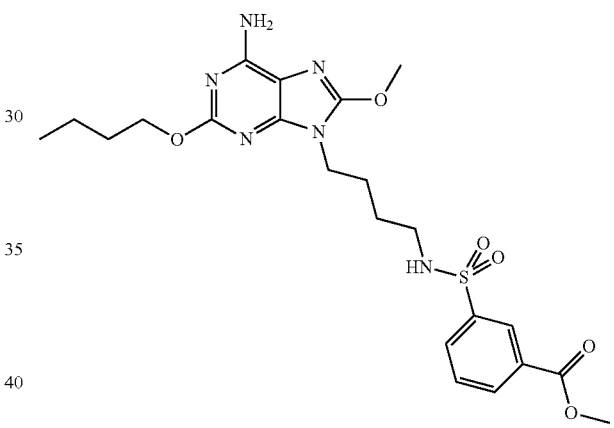

To a solution of 2-butoxy-8-methoxy-9-(4-aminobutyl)adenine (440 mg, 1.4 mmol) obtained in Reference Example 20 in THF (20 ml) were added 3-chlorocarbonylbenzenesulfonyl chloride (502 mg, 2.1 mmol) obtained in Reference Example 22 and triethylamine (312 μl, 2.3 mmol) and the mixture was stirred at room temperature for 1.5 hour. To the resultant was added water, and the mixture was concentrated under reduced pressure and purification by silica gel column chromatography to give 724 mg (1.4 mmol) of the titled compound as a white solid. Yield: 100%.

$^1$H NMR (DMSO-$d_6$) δ 8.30 (1H, dd, J=1.4, 1.7 Hz), 8.15 (1H, ddd, J=1.3, 1.4, 7.9 Hz), 8.00 (1H, ddd, J=1.3, 1.7, 7.9 Hz), 7.79 (1H, t, J=5.8 Hz), 7.73 (1H, t, J=7.9 Hz), 6.81 (2H, brs), 4.13 (2H, t, J=6.6 Hz), 4.02 (3H, s), 3.90 (3H, s), 3.77 (1H, t, J=6.7 Hz), 2.75 (1H, dt, J=5.8, 6.6 Hz), 1.65-1.60 (4H, m), 1.42-1.37 (2H, m), 1.27-1.22 (2H, m), 0.89 (3H, t, J=7.4 Hz).

REFERENCE EXAMPLE 23

Synthesis of 2-butoxy-8-methoxy-9-[4-(3-hydroxymethylbenzenesulfonamide)butyl]adenine

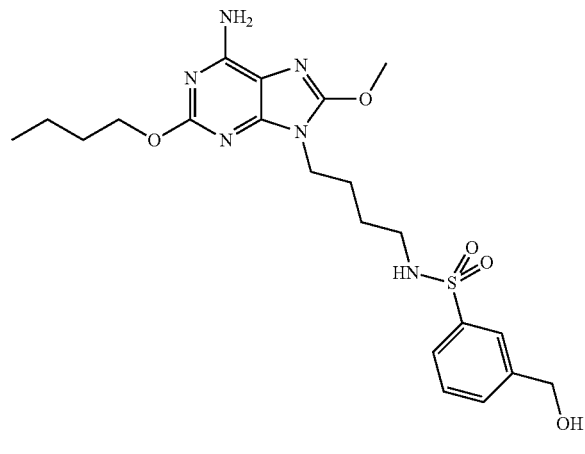

The titled compound was obtained by the same method as Reference Example 6.

$^1$H NMR (DMSO-d$_6$) δ 7.74 (1H, s), 7.61-7.62 (1H, m), 7.57-7.56 (2H, m), 7.53-7.51 (2H, m), 6.78 (2H, brs), 5.41 (2H, t, J=5.7 Hz), 4.56 (1H, t, J=6.6 Hz), 4.14 (2H, t, J=6.6 Hz), 4.02 (3H, s), 3.76 (2H, t, J=6.6 Hz), 2.74 (2H, dt, J=5.8, 6.6 Hz), 1.67-1.63 (4H, m), 1.40-1.36 (2H, m), 1.31-1.27 (2H, m), 0.91 (3H, t, J=7.4 Hz).

REFERENCE EXAMPLE 24

Synthesis of 2-butoxy-8-methoxy-9-[4-(3-chloromethylbenzenesulfonamide)butyl]adenine

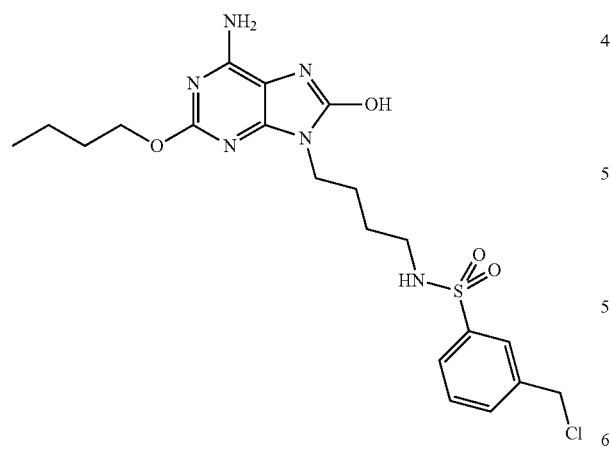 [SMILES: CCCCOc1nc(N)c2nc(OC)n(CCCCNS(=O)(=O)c3cccc(C(=O)OC)c3)c2n1]

The titled compound was obtained by the same method as Reference Example 7.

$^1$H NMR (DMSO-d$_6$) δ 10.36 (1H, br), 7.84 (1H, dd, J=1.4, 1.7 Hz), 7.67-7.65 (2H, m), 7.57 (1H, t, J=7.9 Hz), 7.01 (2H, br), 4.86 (2H, s), 4.21 (2H, t, J=6.6 Hz), 3.62 (2H, t, J=6.6 Hz), 2.78 (2H, dt, J=5.8, 6.6 Hz), 1.65-1.61 (4H, m), 1.41-1.36 (2H, m), 1.35-1.28 (2H, m), 0.91 (3H, t, J=7.4 Hz).

REFERENCE EXAMPLE 25

Synthesis of 2-butoxy-8-methoxy-9-[4-(3-cyanomethylbenzenesulfonamide)butyl]adenine

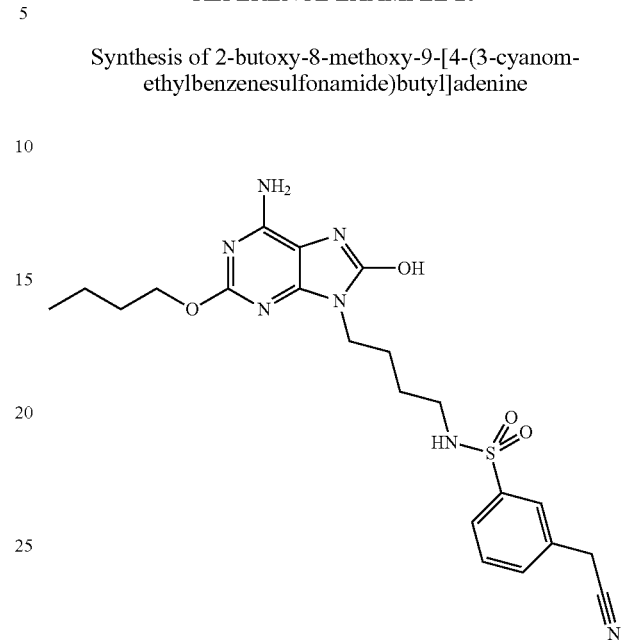

The titled compound was obtained by the same method as Reference Example 8.

$^1$H NMR (DMSO-d$_6$) δ 9.83 (1H, s), 7.77 (1H, s), 7.72-7.70 (2H, m), 7.59-7.57 (2H, m), 6.40 (2H, br), 4.18 (2H, s), 4.12 (2H, t, J=6.6 Hz), 3.60 (2H, t, J=6.6 Hz), 2.76 (2H, dt, J=5.8, 6.6 Hz), 1.66-1.61 (4H, m), 1.38-1.30 (4H, m), 0.91 (3H, t, J=7.4 Hz).

REFERENCE EXAMPLE 26

Synthesis of 2-butoxy-8-methoxy-9-[4-(3-methoxycarbonylphenylaminocarbonylamino)butyl]adenine

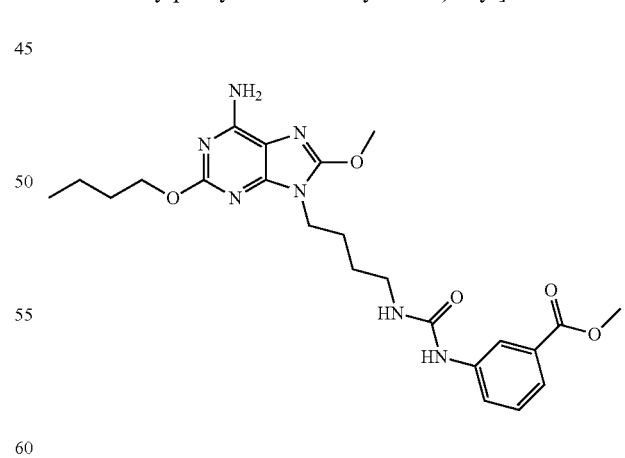

To a solution of 2-butoxy-8-methoxy-9-(4-aminobutyl)adenine solution (1143 mg, 3.71 mmol) obtained in Reference Example 20 in THF (37 ml) was added 3-methoxycarbonylphenyl isocyanate (689 mg, 3.9 mmol) under ice-cooling and the mixture was stirred for 5 minutes. The precipitated solid was collected by filtration to give 1550 mg (2.4 mmol) of the titled compound as a white solid. Yield: 86%.

$^1$H NMR (DMSO-d$_6$) δ 8.67 (1H, s), 8.10 (1H, dd, J=1.5, 2.2 Hz), 7.57 (1H, ddd, J=1.0, 2.2, 8.2 Hz), 7.48 (1H, ddd, J=1.0, 1.5, 7.6 Hz), 7.34 (1H, dd, J=7.6, 8.2 Hz), 7.68 (2H, brs), 6.17 (1H, t, J=5.7 Hz), 4.15 (2H, t, J=6.6 Hz), 4.05 (3H, s), 3.86 (2H, t, J=6.8 Hz), 3.82 (3H, s), 3.10 (2H, dt, J=5.7, 6.6 Hz), 1.73-1.66 (2H, m), 1.66-1.59 (2H, m), 1.42-1.35 (4H, m), 0.88 (3H, t, J=7.4 Hz).

REFERENCE EXAMPLE 27

Synthesis of 2-butoxy-8-methoxy-9-[4-(3-hydroxymethylphenylaminocarbonylamino)butyl]adenine

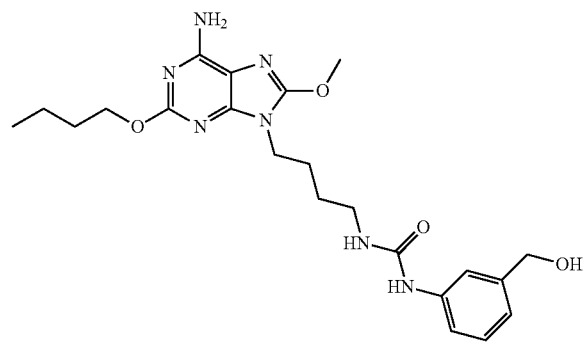 [SMILES: CCCCOc1nc(N)c2nc(OC)n(CCCCNC(=O)Nc3cccc(CO)c3)c2n1]

The titled compound was obtained by the same method as Reference Example 6.

$^1$H NMR (DMSO-d$_6$) δ 8.36 (1H, s), 7.32 (1H, s), 7.25 (1H, d, J=8.0 Hz), 7.13 (1H, dd, J=7.6, 8.0 Hz), 6.81 (1H, d, J=7.6 Hz), 6.78 (2H, brs), 6.08 (1H, t, J=5.7 Hz), 5.11 (1H, t, J=5.7 Hz), 4.41 (2H, d, J=5.7 Hz), 4.17 (2H, t, J=6.6 Hz), 4.05 (3H, s), 3.84 (2H, t, J=6.8 Hz), 3.09 (2H, dt, J=5.7, 6.6 Hz), 1.72-1.66 (2H, m), 1.67-1.60 (2H, m), 1.41-1.35 (4H, m), 0.91 (3H, t, J=7.4 Hz).

An Example of a Pharmaceutical Preparation

There was prepared an aerosol containing per 1 g of the aerosol, the compound of Example 9 (0.641 mg, 0.06%), ethanol (26.816 mg, 2.68%) and 1,1,1,2-tetrafluoroethane (972.543 mg, 97.25%).

Industrial Applicability

By the present invention, it has become possible to provide an 8-oxoadenine compound effective as a therapeutic or prophylactic agent for diseases including allergic diseases such as asthma and atopic dermatitis, viral diseases such as herpes and cancers. Further, in a case where the compound of the present invention is externally applied (topical administration) in a form of spray, etc., systemic adverse effects caused by an interferon inducing activity is suppressed and the strong effect is exhibited in the applied region.

The invention claimed is:

1. A method for treating asthma or allergic rhinitis comprising:
administering to a patient a therapeutic effective amount of 8-oxoadenine compound shown by formula (1):

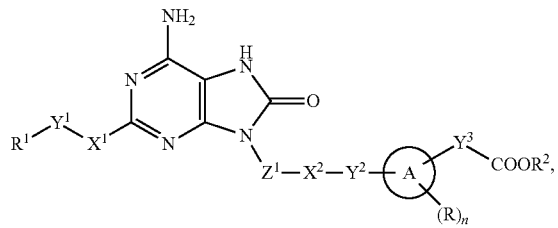

wherein ring A represents a 6-10 membered aromatic carbocyclic ring or a 5-10 membered heteroaromatic ring;
R represents a halogen atom, an alkyl group, a hydroxyalkyl group, a haloalkyl group, an alkoxy group, a hydroxyalkoxy group, a haloalkoxy group, amino group, an alkylamino group, a dialkylamino group, or a 4-7 membered cyclic group containing in the ring 1-2 hetero atoms selected from 1-2 nitrogen atoms and optionally 0-1 oxygen atom or 0-1 sulfur atom;
n represents an integer of 0-2, and when n is 2, the Rs may be the same or different;
$Z^1$ represents a substituted or unsubstituted alkylene group or a substituted or unsubstituted cycloalkylene group;
$X^2$ represents oxygen atom, sulfur atom, $SO_2$, $NR^5$, CO, $CONR^5$, $NR^5CO$, $SO_2NR^5$, $NR^5SO_2$, $NR^5CONR^6$ or $NR^5CSNR^6$ (in which $R^5$ and $R^6$ are each independently hydrogen atom, a substituted or unsubstituted alkyl group, or a substituted or unsubstituted cycloalkyl group);
$Y^1$, $Y^2$ and $Y^3$ represent each independently a single bond or an alkylene group;
$X^1$ represents oxygen atom, sulfur atom, $SO_2$, $NR^4$ (wherein $R^4$ is hydrogen atom or an alkyl group) or a single bond;
$R^2$ represents hydrogen atom, a substituted or unsubstituted alkyl group, a substituted or unsubstituted alkenyl group, a substituted or unsubstituted alkynyl group or a substituted or unsubstituted cycloalkyl group; and
$R^1$ represents hydrogen atom, hydroxy group, an alkoxy group, an alkoxycarbonyl group, a haloalkyl group, a haloalkoxy group, a substituted or unsubstituted aryl group, a substituted or unsubstituted heteroaryl group or a substituted or unsubstituted cycloalkyl group,
or its pharmaceutically acceptable salt.

2. A method for modulating immune response comprising administering to a patient a therapeutically effective amount of 8-oxoadenine compound shown by formula (1):

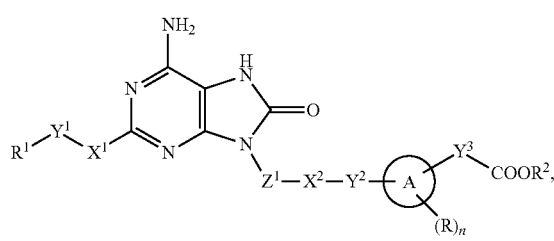

wherein ring A represents a 6-10 membered aromatic carbocyclic ring or a 5-10 membered heteroaromatic ring;

R represents a halogen atom, an alkyl group, a hydroxyalkyl group, a haloalkyl group, an alkoxy group, a hydroxyalkoxy group, a haloalkoxy group, amino group, an alkylamino group, a dialkylamino group, or a 4-7 membered cyclic group containing in the ring 1-2 hetero atoms selected from 1-2 nitrogen atoms and optionally 0-1 oxygen atom or 0-1 sulfur atom;

n represents an integer of 0-2, and when n is 2, the Rs may be the same or different;

$Z^1$ represents a substituted or unsubstituted alkylene group or a substituted or unsubstituted cycloalkylene group;

$X^2$ represents oxygen atom, sulfur atom, $SO_2$, $NR^5$, CO, $CONR^5$, $NR^5CO$, $SO_2NR^5$, $NR^5SO_2$, $NR^5CONR^6$ or $NR^5CSNR^6$ (in which $R^5$ and $R^6$ are each independently hydrogen atom, a substituted or unsubstituted alkyl group, or a substituted or unsubstituted cycloalkyl group);

$Y^1$, $Y^2$ and $Y^3$ represent each independently a single bond or an alkylene group;

$X^1$ represents oxygen atom, sulfur atom, $SO_2$, $NR^4$ (wherein $R^4$ is hydrogen atom or an alkyl group) or a single bond;

$R^2$ represents hydrogen atom, a substituted or unsubstituted alkyl group, a substituted or unsubstituted alkenyl group, a substituted or unsubstituted alkynyl group or a substituted or unsubstituted cycloalkyl group; and $R^1$ represents hydrogen atom, hydroxy group, an alkoxy group, an alkoxycarbonyl group, a haloalkyl group, a haloalkoxy group, a substituted or unsubstituted aryl group, a substituted or unsubstituted heteroaryl group or a substituted or unsubstituted cycloalkyl group, or its pharmaceutically acceptable salt.

3. The method according to claim 1, wherein:

ring A represents a 6-10 membered aromatic carbocyclic ring, or a 5-10 membered heteroaromatic ring containing 1-4 hetero atoms selected from 0-4 nitrogen atoms, 0-2 oxygen atoms, and 0-2 sulfur atoms;

R represents a halogen atom, an alkyl group of 1-6 carbons, a hydroxyalkyl group of 1-6 carbons, a haloalkyl group of 1-6 carbons, an alkoxy group of 1-6 carbons, a hydroxyalkoxy group of 1-6 carbons, a haloalkoxy group of 1-6 carbons, amino group, an alkylamino group of 1-6 carbons, a dialkylamino group in which each alkyl moiety has 1-6 carbons, or a 4-7 membered cyclic group containing in the ring 1-2 hetero atoms selected from 1-2 nitrogen atoms and optionally 0-1 oxygen atom or 0-1 sulfur atom;

$Z^1$ represents an alkylene group of 1-6 carbons or a cycloalkylene group of 3-8 carbons, which is optionally substituted by hydroxy group;

$X^2$ represents oxygen atom, sulfur atom, $SO_2$, $NR^5$, CO, $CONR^5$, $NR^5CO$, $SO_2NR^5$, $NR^5SO_2$, $NR^5CONR^6$ or $NR^5CSNR^6$ (in which $R^5$ and $R^6$ are each independently hydrogen atom, a substituted or unsubstituted alkyl group of 1-6 carbons, or a substituted or unsubstituted cycloalkyl group of 3-8 carbons, wherein the substituents of the alkyl group or cycloalkyl group are selected from a halogen atom, hydroxy group, an alkoxy group of 1-6 carbons, carboxy group, an alkoxycarbonyl group of 2-5 carbons, carbamoyl group, amino group, an alkylamino group of 1-6 carbons, an dialkylamino group in which each alkyl moiety has 1-6 carbons, a cyclic group, and tetrazolyl group which may be substituted by an alkyl group of 1-6 carbons);

$Y^1$, $Y^2$ and $Y^3$ represent each independently a single bond or an alkylene group of 1-6 carbons;

$R^2$ represents a substituted or unsubstituted alkyl group of 1-6 carbons, a substituted or unsubstituted alkenyl group of 2-6 carbons, a substituted or unsubstituted alkynyl group of 2-6 carbons, or a substituted or unsubstituted cycloalkyl group of 3-8 carbons (wherein the substituent in the alkyl group, alkenyl group and alkynyl group is selected from a halogen atom, hydroxy group, an alkoxy group of 1-6 carbons, an acyloxy group of 2-10 carbons selected from the group consisting of a substituted or unsubstituted alkylcarbonyloxy group of 2-5 carbons, a substituted or unsubstituted alkenylcarbonyloxy group of 2-5 carbons, a substituted or unsubstituted alkynylcarbonyloxy group of 2-5 carbons, a substituted or unsubstituted arylcarbonyloxy group and a substituted or unsubstituted heteroarylcarbonyloxy group, amino group, an alkylamino group of 1-6 carbons, a dialkylamino group in which the each alkyl moiety has 1-6 carbons, and a cyclic group); and $R^1$ represents hydrogen atom, hydroxy group, an alkoxy group of 1-6 carbons, an alkoxycarbonyl group of 2-5 carbons, a haloalkyl group of 1-6 carbons, a haloalkoxy group of 1-6 carbons, a substituted or unsubstituted aryl group of 6-10 carbons, a substituted or unsubstituted 5-10 membered heteroaryl group containing 1-4 hetero atoms selected from 0-4 nitrogen atoms, 0-2 oxygen atoms and 0-2 sulfur atoms, or a substituted or unsubstituted cycloalkyl group of 3-8 carbons;

and the said substituent in the aryl group, the heteroaryl group, and the cycloalkyl group is selected from a halogen atom, hydroxy group, an alkyl group of 1-6 carbons, a haloalkyl group of 1-6 carbons, an alkoxy group of 1-6 carbons, a haloalkoxy group of 1-6 carbons, an alkylcarbonyl group of 2-5 carbons, amino group, an alkylamino group of 1-6 carbons and a dialkylamino group (wherein the each alkyl group has 1-6 carbons), and the said cyclic group represents a 4-7 membered saturated cyclic group containing in the ring 1-2 hetero atoms selected from 1-2 nitrogen atoms and optionally 0-1 oxygen atom or 0-1 sulfur atom, which may be substituted with a halogen atom, hydroxy group, oxo group, an alkyl group of 1-6 carbons, an alkoxy group of 1-6 carbons, an alkylcarbonyl group of 2-5 carbons, or an alkoxycarbonyl group of 2-5 carbons, or its pharmaceutically acceptable salt.

4. The method according to claim 1, wherein $X^2$ is oxygen atom, sulfur atom, $NR^5$, $SO_2$, $NR^5SO_2$, or $NR^5CONR^6$.

5. The method according to claim 1, wherein $Y^3$ is a single bond, methylene, or ethylene.

6. The method according to claim 1, wherein $Z^1$ is a straight chained alkylene group of 1-6 carbons which may be substituted with hydroxy group.

7. The method according to claim 1, wherein $X^1$ is oxygen atom or sulfur atom.

8. The method according to claim 1, wherein $Y^1$ is a single bond or an alkylene group of 1-6 carbons.

9. The method according to claim 1, wherein $R^1$ is hydrogen atom, an alkoxycarbonyl group, hydroxy group, or an alkoxy group.

10. The method according to claim 1, wherein in the formula (1), a group shown by the formula (2):

(wherein ring A, R, n, $Y^3$ and $R^2$ have the same meaning as in claim 1) is a group shown by the formula (3) or the formula (4):

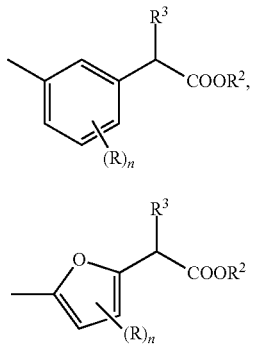

(wherein R, n and $R^2$ have the same meaning as in claim 1, and $R^3$ is hydrogen atom or an alkyl group).

11. The method according to claim 1, wherein $R^2$ is methyl group or an alkyl group of 2-6 carbons substituted by a dialkylamino group or a cyclic group.

12. The method according to claim 10, wherein $R^3$ is hydrogen atom.

13. The method according to claim 1, wherein the compound shown by formula (1) is chosen from:
   Methyl (3-{[[4-(6-amino-2-butoxy-8-oxo-7,8-dihydro-9H-purin-9-yl)butyl](3-morpholin-4-ylpropyl)amino]methyl}phenyl)acetate, its pharmaceutically acceptable salts,
   Methyl [3-({[4-(6-amino-2-butoxy-8-oxo-7,8-dihydro-9H-purin-9-yl)butyl][3-(dimethylamino)-2,2-dimethylpropyl]amino}methyl)phenyl]acetate, its pharmaceutically acceptable salts,
   Methyl (3-{[[4-(6-amino-2-butoxy-8-oxo-7,8-dihydro-9H-purin-9-yl)butyl](2-morpholin-4-ylethyl)amino]methyl}phenyl)acetate, its pharmaceutically acceptable salts, and
   Methyl (3-{[[3-(6-amino-2-butoxy-8-oxo-7,8-dihydro-9H-purin-9-yl)propyl](3-morpholin-4-ylpropyl)amino]methyl}phenyl)acetate, and its pharmaceutically acceptable salts.

14. The method according to claim 1, wherein the compound shown by formula (1) is Methyl (3-{[[3-(6-amino-2-butoxy-8-oxo-7,8-dihydro-9H-purin-9-yl)propyl](3-morpholin-4-ylpropyl)amino]methyl}phenyl)acetate or its pharmaceutically acceptable salts.

15. The method according to claim 2, wherein:
   ring A represents a 6-10 membered aromatic carbocyclic ring, or a 5-10 membered heteroaromatic ring containing 1-4 hetero atoms selected from 0-4 nitrogen atoms, 0-2 oxygen atoms, and 0-2 sulfur atoms;
   R represents a halogen atom, an alkyl group of 1-6 carbons, a hydroxyalkyl group of 1-6 carbons, a haloalkyl group of 1-6 carbons, an alkoxy group of 1-6 carbons, a hydroxyalkoxy group of 1-6 carbons, a haloalkoxy group of 1-6 carbons, amino group, an alkylamino group of 1-6 carbons, a dialkylamino group in which each alkyl moiety has 1-6 carbons, or a 4-7 membered cyclic group containing in the ring 1-2 hetero atoms selected from 1-2 nitrogen atoms and optionally 0-1 oxygen atom or 0-1 sulfur atom;
   $Z^1$ represents an alkylene group of 1-6 carbons or a cycloalkylene group of 3-8 carbons, which is optionally substituted by hydroxy group;
   $X^2$ represents oxygen atom, sulfur atom, $SO_2$, $NR^5$, CO, $CONR^5$, $NR^5CO$, $SO_2NR^5$, $NR^5SO_2$, $NR^5CONR^6$ or $NR^5CSNR^6$ (in which $R^5$ and $R^6$ are each independently hydrogen atom, a substituted or unsubstituted alkyl group of 1-6 carbons, or a substituted or unsubstituted cycloalkyl group of 3-8 carbons, wherein the substituents of the alkyl group or cycloalkyl group are selected from a halogen atom, hydroxy group, an alkoxy group of 1-6 carbons, carboxy group, an alkoxycarbonyl group of 2-5 carbons, carbamoyl group, amino group, an alkylamino group of 1-6 carbons, an dialkylamino group in which each alkyl moiety has 1-6 carbons, a cyclic group, and tetrazolyl group which may be substituted by an alkyl group of 1-6 carbons);
   $Y^1$, $Y^2$ and $Y^3$ represent each independently a single bond or an alkylene group of 1-6 carbons;
   $R^2$ represents a substituted or unsubstituted alkyl group of 1-6 carbons, a substituted or unsubstituted alkenyl group of 2-6 carbons, a substituted or unsubstituted alkynyl group of 2-6 carbons, or a substituted or unsubstituted cycloalkyl group of 3-8 carbons (wherein the substituent in the alkyl group, alkenyl group and alkynyl group is selected from a halogen atom, hydroxy group, an alkoxy group of 1-6 carbons, an acyloxy group of 2-10 carbons selected from the group consisting of a substituted or unsubstituted alkylcarbonyloxy group of 2-5 carbons, a substituted or unsubstituted alkenylcarbonyloxy group of 2-5 carbons, a substituted or unsubstituted alkynylcarbonyloxy group of 2-5 carbons, a substituted or unsubstituted arylcarbonyloxy group and a substituted or unsubstituted heteroarylcarbonyloxy group, amino group, an alkylamino group of 1-6 carbons, a dialklylamino group in which the each alkyl moiety has 1-6 carbons, and a cyclic group); and
   $R^1$ represents hydrogen atom, hydroxy group, an alkoxy group of 1-6 carbons, an alkoxycarbonyl group of 2-5 carbons, a haloalkyl group of 1-6 carbons, a haloalkoxy group of 1-6 carbons, a substituted or unsubstituted aryl group of 6-10 carbons, a substituted or unsubstituted 5-10 membered heteroaryl group containing 1-4 hetero atoms selected from 0-4 nitrogen atoms, 0-2 oxygen atoms and 0-2 sulfur atoms, or a substituted or unsubstituted cycloalkyl group of 3-8 carbons;
   and the said substituent in the aryl group, the heteroaryl group, and the cycloalkyl group is selected from a halogen atom, hydroxy group, an alkyl group of 1-6 carbons, a haloalkyl group of 1-6 carbons, an alkoxy group of 1-6 carbons, a haloalkoxy group of 1-6 carbons, an alkylcarbonyl group of 2-5 carbons, amino group, an alkylamino group of 1-6 carbons and a dialkylamino group (wherein the each alkyl group has 1-6 carbons), and the said cyclic group represents a 4-7 membered saturated cyclic group containing in the ring 1-2 hetero atoms selected from 1-2 nitrogen atoms and optionally 0-1 oxygen atom or 0-1 sulfur atom, which may be substituted with a halogen atom, hydroxy group, oxo group, an alkyl group of 1-6 carbons, an alkoxy group of 1-6 carbons, an alkylcarbonyl group of 2-5 carbons, or an alkoxycarbonyl group of 2-5 carbons, or its pharmaceutically acceptable salt.

16. The method according to claim 2, wherein $X^2$ is oxygen atom, sulfur atom, $NR^5$, $SO_2$, $NR^5SO_2$, or $NR^5CONR^6$.

17. The method according to claim 2, wherein $Y^3$ is a single bond, methylene, or ethylene.

18. The method according to claim 2, wherein $Z^1$ is a straight chained alkylene group of 1-6 carbons which may be substituted with hydroxy group.

19. The method according to claim 2, wherein $X^1$ is oxygen atom or sulfur atom.

20. The method according to claim 2, wherein $Y^1$ is a single bond or an alkylene group of 1-6 carbons.

21. The method according to claim 2, wherein $R^1$ is hydrogen atom, an alkoxycarbonyl group, hydroxy group, or an alkoxy group.

22. The method according to claim 2, wherein in the formula (1), a group shown by the formula (2):

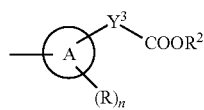
(2)

(wherein ring A, R, n, $Y^3$ and $R^2$ have the same meaning as in claim 2) is a group shown by the formula (3) or the formula (4):

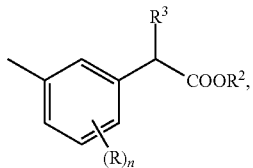
(3)

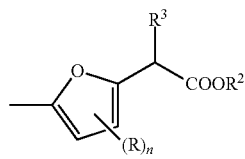
(4)

(wherein R, n and $R^2$ have the same meaning as in claim 2, and $R^3$ is hydrogen atom or an alkyl group).

23. The method according to claim 2, wherein $R^2$ is methyl group or an alkyl group of 2-6 carbons substituted by a dialkylamino group or a cyclic group.

24. The method according to claim 22, wherein $R^3$ is hydrogen atom.

25. The method according to claim 2, wherein the compound shown by formula (1) is chosen from:
Methyl (3-{[[4-(6-amino-2-butoxy-8-oxo-7,8-dihydro-9H-purin-9-yl)butyl]3-morpholin-4-ylpropyl)amino]methyl}phenyl)acetate, its pharmaceutically acceptable salts,
Methyl [3-({[4-(6-amino-2-butoxy-8-oxo-7,8-dihydro-9H-purin-9-yl)butyl][3-(dimethylamino)-2,2-dimethylpropyl]amino}methyl)phenyl]acetate, its pharmaceutically acceptable salts,
Methyl (3-{[[4-(6-amino-2-butoxy-8-oxo-7,8-dihydro-9H-purin-9-yl)butyl](2-morpholin-4-ylethyl)amino]methyl}phenyl)acetate, its pharmaceutically acceptable salts, and
Methyl (3-{[[3-(6-amino-2-butoxy-8-oxo-7,8-dihydro-9H-purin-9-yl)propyl](3-morpholin-4-ylpropyl)amino]methyl}phenyl)acetate, and its pharmaceutically acceptable salts.

26. The method according to claim 2, wherein the compound shown by formula (1) is Methyl (3-{[[3-(6-amino-2-butoxy-8-oxo-7,8-dihydro-9H-purin-9-yl)propyl](3-morpholin-4-ylpropyl)amino]methyl}phenyl)acetate or its pharmaceutically acceptable salt.

* * * * *

UNITED STATES PATENT AND TRADEMARK OFFICE
CERTIFICATE OF CORRECTION

PATENT NO.       : 8,969,362 B2
APPLICATION NO.  : 14/058064
DATED            : March 3, 2015
INVENTOR(S)      : Ayumu Kurimoto et al.

Page 1 of 1

It is certified that error appears in the above-identified patent and that said Letters Patent is hereby corrected as shown below:

In the Claims,

Claim 3, col. 151, line 46, "a dia kylamino group" should read -- a diakylamino group --.

Claim 15, col. 154, line 15, "an diakylamino group" should read -- a diakylamino group --.

Signed and Sealed this
Thirtieth Day of June, 2015

Michelle K. Lee
*Director of the United States Patent and Trademark Office*

UNITED STATES PATENT AND TRADEMARK OFFICE
CERTIFICATE OF CORRECTION

PATENT NO.        : 8,969,362 B2
APPLICATION NO.   : 14/058064
DATED             : March 3, 2015
INVENTOR(S)       : Ayumu Kurimoto et al.

It is certified that error appears in the above-identified patent and that said Letters Patent is hereby corrected as shown below:

Title page, Item 22, line 1, "Filed: Oct. 21, 2013" should read --Filed: Oct. 18, 2013--

Signed and Sealed this
Twenty-fifth Day of August, 2015

Michelle K. Lee
*Director of the United States Patent and Trademark Office*